(12) United States Patent
Bzik et al.

(10) Patent No.: US 8,673,289 B2
(45) Date of Patent: *Mar. 18, 2014

(54) ATTENUATED URACIL AUXOTROPH OF AN APICOMPLEXAN AND USE THEREOF

(75) Inventors: David J. Bzik, Grantham, NH (US); Barbara A. Fox, Grantham, NH (US)

(73) Assignee: Trustees of Dartmouth College, Hanover, NH (US)

( * ) Notice: Subject to any disclaimer, the term of this patent is extended or adjusted under 35 U.S.C. 154(b) by 1 day.

This patent is subject to a terminal disclaimer.

(21) Appl. No.: 12/808,273

(22) PCT Filed: Dec. 17, 2008

(86) PCT No.: PCT/US2008/087081
§ 371 (c)(1),
(2), (4) Date: Jun. 15, 2010

(87) PCT Pub. No.: WO2009/082651
PCT Pub. Date: Jul. 2, 2009

(65) Prior Publication Data
US 2010/0260804 A1  Oct. 14, 2010

Related U.S. Application Data

(63) Continuation of application No. 11/962,584, filed on Dec. 21, 2007.

(51) Int. Cl.
*A01N 63/00* (2006.01)
*A61K 39/00* (2006.01)
*A61K 48/00* (2006.01)

(52) U.S. Cl.
USPC .... 424/93.1; 424/93.2; 424/93.21; 424/184.1

(58) Field of Classification Search
None
See application file for complete search history.

(56) References Cited

U.S. PATENT DOCUMENTS

| 5,869,248 | A * | 2/1999 | Yuan et al. | 435/6.12 |
| 6,440,730 | B1 * | 8/2002 | Von Laer et al. | 435/325 |
| 2002/0164754 | A1 * | 11/2002 | Bzik et al. | 435/196 |
| 2004/0013689 | A1 | 1/2004 | Kadurugamuwa et al. | 424/200.1 |
| 2007/0172502 | A1 * | 7/2007 | Bzik et al. | 424/273.1 |

OTHER PUBLICATIONS

Loimas et al (Cancer Gene Ther. vol. 8 (2), pp. 137-144, 2001).*
Asai et al. "Enzymes of the De Novo Pyrimidine Biosynthetic Pathway in *Toxoplasma gondii*" Molecular and Biochemical Parasitology 1983 vol. 7: 89-100.
Black et al. "Genetics" Proc. Natl. Acad. Sci. USA 1996 vol. 93: 3525-3529.
Bzik et al. "Molecular Cloning and Sequence Analysis of the *Plasmodium falciparum* Dihydrofolate Reductase-thymidylate Synthase Gene" Proc. Natl. Acad. Sci USA 1987 vol. 84: 8360-8364.

Charest et al. "Recombinant Attenuated *Toxoplasma gondii* Expressing the *Plasmodium yoelii* Circumsporozoite Protein Provides Highly Effective Priming for CD8+ T Cell-Dependent Protective Immunity Against Malaria" Journal of Immunology 2000 vol. 165: 2084-2092.
Davis R. H. "Compartmental and Regulatory Mechanisms in the Arginine Pathways of *Neurospora crassa* and *Saccharmoyecs cerevisiae*" Microbiological Reviews 1986 vol. 50 (3): 280-313.
Donald, R. G. K. and Roos, D. S. "Insertional Mutagenesis and Marker Rescue in a Protozoan Parasite: Cloning of the Uracil Phosphoribosyltransferase Locus from *Taxoplasma gondii*" Proc. Natl. Acad. Sci. USA 1995 vol. 92: 685-5753.
Flores et al. "Characterisation of the Carabamoyl Phosphate Synthetase Gene from *Plasmodium falciparum*" Molecular and Biochemical Parasitology 1994 vol. 68: 315-318.
Hill et al. "The enzyme of Pyrimidine Biosynthesis in a Range of Parasitic Protozoa and Helminths" Molecular and Biochemical Parasitology 1981 vol. 2: 123-134.
Iltzsch et al. "Pyrimidine Salvage Pathways in *Taxoplasma gondii*" J. Euk. Microbiol. 1993 vol. 40 (1): 24-28.
Jones M. E. "Pyrimidine Nucleotide Biosynthesis in Animals: Genes, Enzymes, and Regulation of UMP Biosynthesis" Ann. Rev. Biochem. 1980 vol. 49: 253-279.
Mergeay et al. "Physiology and Genetics of Carbamoylphosphate Synthesis in *Escherichia coli* K12" Molec. Gen. Genet. 1974 vol. 133: 229-316.
Pfefferkorn, E. R. and Pfefferkorn L. C. "*Toxoplasma gondii*: Isolation and Preliminary Characterization of Temperature-Sensitive Mutants" Experimental Parasitology 1976 vol. 39: 365-376.
Pfefferkorn, E. R. "*Toxoplasma gondii*: The Enzymic Defect of a Mutant Resistant to 5-Flurodeoxyuridine" Experimental Parasitology 1978 vol. 44: 26-35.
Schwartzman, J. D. and Pfefferkorn, E. R. "Pyrimidine Synthesis by Intracellular *Toxoplasma gondii*" J. Parasitol. 1981 vol. 67 (2): 150-158.
Sullivan et al. "Insertional Tagging of At Least Two Loci Associated with Resistance to Adenine Arabinoside in *Toxoplasma gondii*, and Cloning of the Adenosine Kinase Locus" Molecular and Biochemical Parasitology 1999 vol. 103: 1-14.
NCBI Genbank Accession No. XP_763067 [gi:71026847] with Revision History Jul. 19, 2005-Apr. 21, 2006.
NCBI Genbank Accession No. AAC47302 [gi:619743] with Revision History Jan. 10, 1995-Oct. 15, 1996.
NCBI Genbank Accession No. CAD52216 [gi:23615226] with Revision History Oct. 3, 2002-Apr. 16, 2005.
NCBI Genbank Accession No. BAA74521 [gi:4210453] with Revision History Feb. 2-Jul. 16, 1999.

(Continued)

*Primary Examiner* — Albert Navarro
(74) *Attorney, Agent, or Firm* — Licata & Tyrrell P.C.

(57) ABSTRACT

Uracil auxotroph mutants of apicomplexans are provided which lack a functional carbamoyl phosphate synthase II (CPSII) enzyme. Also provided are *T. gondii* autoxtroph mutants which express exogenous antigens, and methods of protecting an animal against a *T. gondii* and non-*T. gondii* disease.

8 Claims, 25 Drawing Sheets

(56) References Cited

OTHER PUBLICATIONS

Mercier et al. "Targeted Disruption of the GRA2 Locus in *Toxoplasma gondii* Decreases Acute Virulence in Mice" Infection and Immunity 1998 vol. 66 (9): 4176-4182.

Wang et al. "Rapid Positive Selection of Stavle Integrants Following Transfection of *Plasmodium falciparum*" Molecular & Biochemical Parasitology 2002 vol. 123: 1-10.

Office Communication dated Aug. 20, 2008 from U.S. Appl. No. 11/962,584, filed Dec. 21, 2007.

Office Communication dated Nov. 28, 2008 from U.S. Appl. No. 11/962,584, filed Dec. 21, 2007.

Office Communication dated Aug. 6, 2009 from U.S. Appl. No. 11/962,548, filed Dec. 21, 2007.

Office Communication dated Dec. 1, 2009 from U.S. Appl. No. 11/962,584, filed Dec. 21, 2007.

* cited by examiner

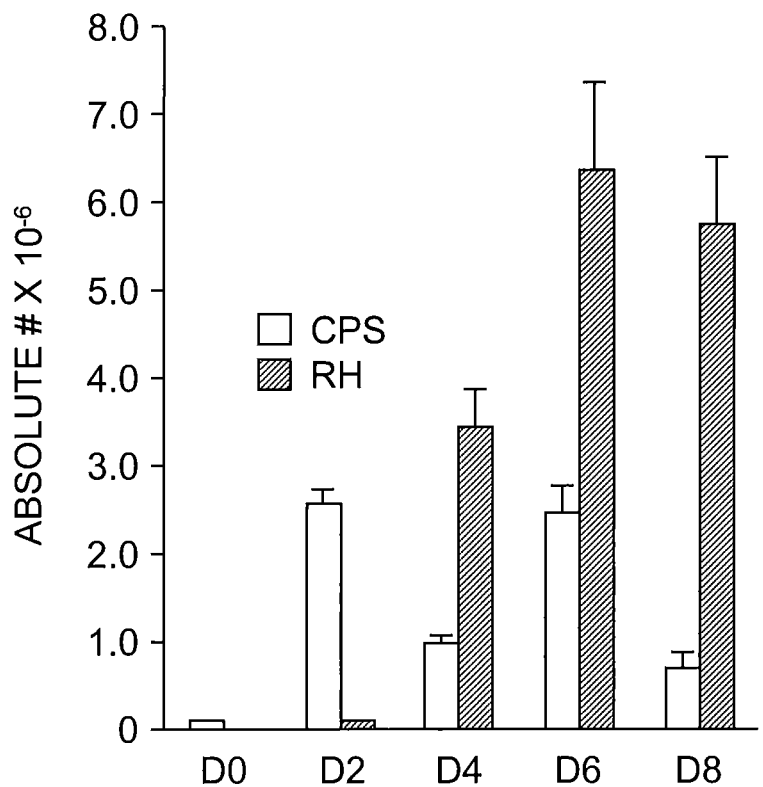
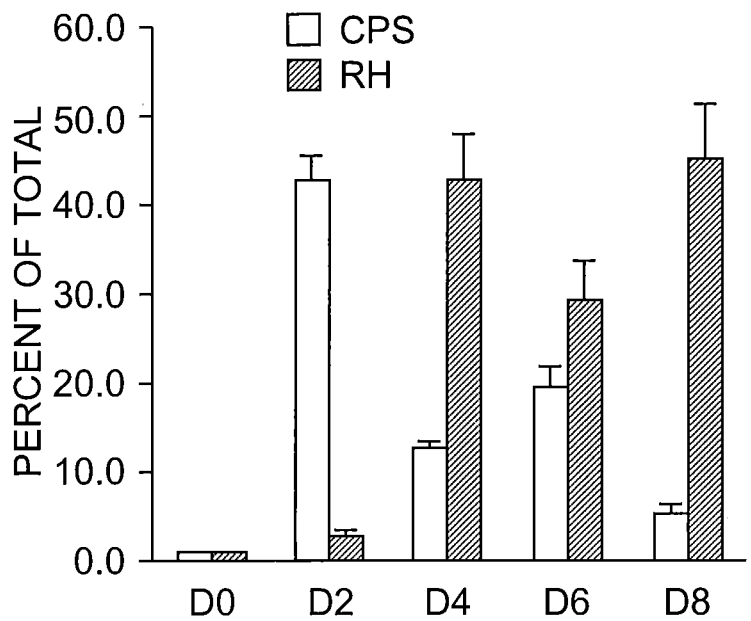
FIG. 4D

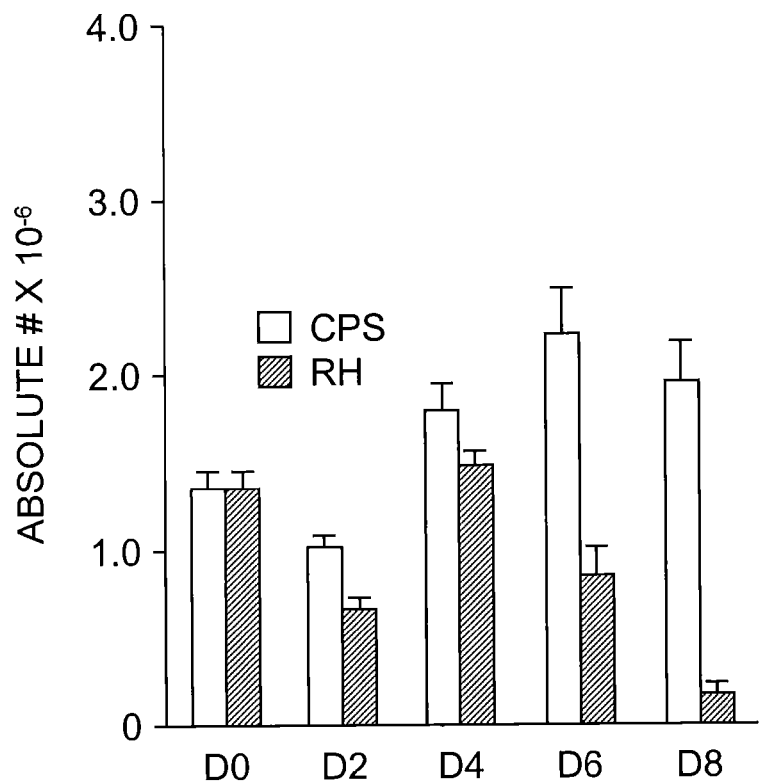
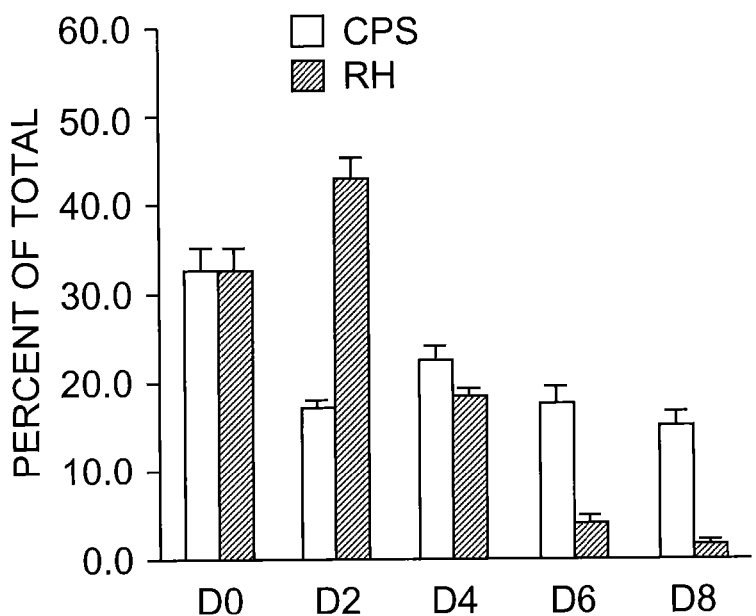
FIG. 4E

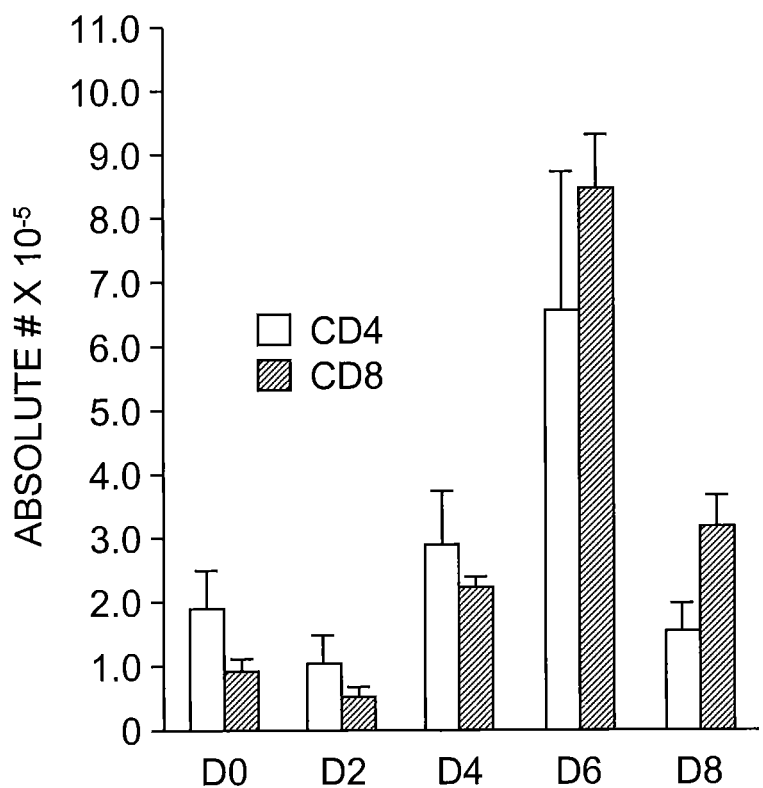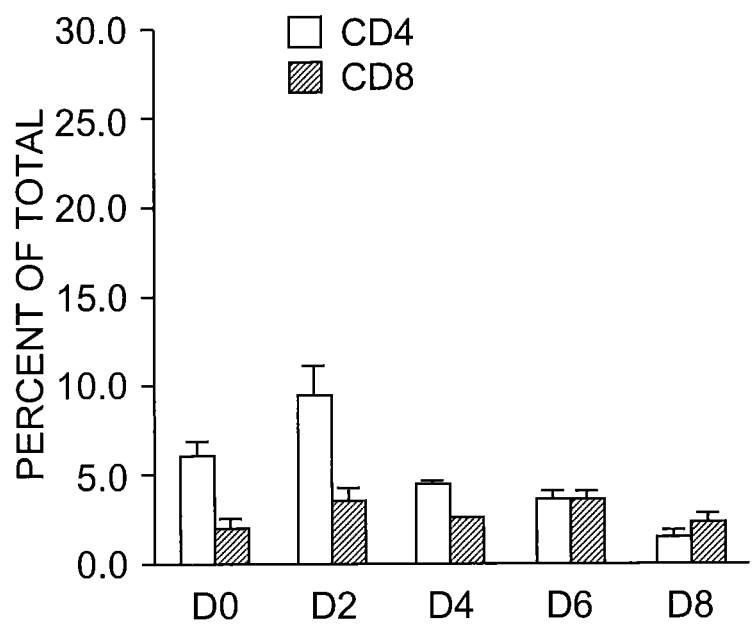
FIG. 4H

FIG. 7A

```
Ec   .................T. gondii GATase Indel.........................................                                          -AALALEKARAFPGLNGM-----------------
Tg   ---------------------ALPSATAAEQRGENDATVTPDKAEARLRVERRQAALTMWEEAIRNKAKNLPWEDPNKD-----------------
Pf   PGNIDTLKYVCNHFIRVIKLNNITYNYKNKEEFNYTNEMITNDSSMEDHDNEINGSISNFNNCPSISSFDKSESKNVINHTLLRD
Bb   ----------------------------------------------------------GLVSPRLLESSSFYDTNNP-----------------
Tc   ----------------------------------------------------------------------PFFDPNVR-----------------
Lm   ----------------------------------------------------------------------PFMDPNTR-----------------
Sc   --------------------------------------------DRTISRSRSSWRSAFDVPEWVDPNVQ-----------------
Hs   ----------------------------------------------------------------SSLPFLDPNAR-----------------
                                                                              * *

Ec   --DLAKEVT----------TAEAYSWTQGSWTLTG-----------------------------------------------
Tg   --NLVALVS----------RKEVRVYKS--------------------------------------------------
Pf   KMNLITSSEEYLKDLHNCNFSNSSDKNDSFFKLYGICEYDKYLIDLEENASFHYNNVDEYGYDVNKNTNILSNNKIEQNNNNEN
Bb   --DLMRSLP----------DPHPVLYTMSEIDGERYVTSYEFTVAELDDILSRDPCACHSSDLDVHFASKKKFCGYP
Tc   --HLVAEVS----------TKTRSTYG---------------------------------------------------
Lm   --NLVAEVS----------TKTRVTHG---------------------------------------------------
Sc   --NLVSKVS----------INEPKLYVPPADNKH--------------------------------------------
Hs   --PLVPEVS----------IKTPRVFN---------------------------------------------------
         *

Ec   -----------------------------------------------GIPEAKKEDELPFHVVAYDFG
Tg   -----------------------------------------------TVVDPNLRDVLILCVDCG
Pf   NKNNKNNNNNEVDYIKKDEDNNVNSKVFYSQYNNNAQNNEHTEFNLNNDYSTYIRKKMKNEEFLNLVNKRKVDHKEKIIVIVDCG
Bb   NKPVNDCASG---------------------------------------SGSLYSSSLSLKGVTLVVIVDCG
Tc   -----------------------------------------------------HGTLVILVIDMG
Lm   -----------------------------------------------------HGTLRILVIDMG
Sc   -----------------------------------------------IELQTGPDGKVLRILAIDVG
Hs   -----------------------------------------------------TGGAPRILALDCG
```

FIG. 7B

```
Ec  AKRNILRMIVDRGCR-----LTIVPAQTSAEDVLKMNPDGIFLSNGPGDPAPCDYAITTAIQKFL--ETDIPVFGICLGHQLLALA
Tg  MKYNIYRQLLHSKFEHCNI ILKVVPWDFDFG---NDEFDGLFISNGPGDPERCEKTVANIRRVM--ERKIPIFGICLGNQLLALA
Pf  IKNSIIKNLIRHGMDLP-LTYIIVPYYNFN---HIDYDAVLLSNGPGDPKKCDFLIKNLKDSLT--KNKIIFGICLGNQLLGIS
Bb  IKSNIIRLFLRMSPVQVR--ALVVPHNFDFN---RIPYDGLIISNGPGDPSDATVTIANLRRAM--ERTTPIFGICLGHQLMGLA
Tc  VKLNSLRCLLKYDVT-----LIVVPHDWDIT---KETYDGLFISNGPGNPQMCTKTIEHVRWAIT--QDKPIFGICMGNQIIALA
Lm  VKLNQLRCLLKHDVT-----LIVVPHDWDIT---TELYDGLFITNGPGNPQMCTSTIRSVRWALQ--QDKPIFGICMGNQMLCPP
Sc  MKYNQIRCFIKRGVE-----LKVVPWNYDFT---KEDYDGLFISNGPGDPSVLDDLSQRLSNVL-EAKKTPVFGICIGHQLIARA
Hs  LKYNQIRCLCQRGAE-----VTVVPWDHALD---SQEYEGLFLSNGPGDPASYPSVVSTLSRVLSEPNPRPVFGICLGHQLLALA
                     *                   *   *  *    *            *              *

Ec  SGAKTVKMKFGHHGGNHPVKDVEKNVVMITAQNHGFAVDEATLPAN--LRVTHKSLFDGTLQGIHRTDKPAFSFQGHPEASPGPH
Tg  AGARTYKMKYGNRGMNQPVIDLRTSRCYITPQNHGFAVDESTLPRD--FLPLFVNANDRSNEGIIHRTLPFFSAQFHPEASGGPT
Pf  LGCDTYKMKYGNRGVNQPVIQLVDNICYITSQNHGYCLKKKSILKRKELAISYINANDKSIEGISHKNGRFYSVQFHPEGNNGPE
Bb  AGAKTYKMRYGHRGFNQPCVDLRTSKCYMTSQNHGYAIDEETLPSE--WLRYCDANDGCVEGIIHMTYPWFSLQFHPEASGGPT
Tc  AGGSTYKMKYGHRGQNQPSTSRSDGHVFITTQNHGFAVDFKSVSQDE-WEEECFYNPNDDSNEGLRHRTKPFFSVQFHPEGRCGPQ
Lm  AGGTTYKMKYGHRGQNQPCKCNIDDRVVITTQKPGFAVDFKTLPSDE-WEEYFTNSNDGSNEGLWHKTKPFCSVQFHPEGRCGPQ
Sc  AGASTLKLKFGNRGHNIPCTSTISGRCYITSQNHGFAVDVDTLTSG--WKPLFVNANDDSNEGIYHSELPYFSVQFHPESTPGPR
Hs  IGAKTYKMRYGNRGHNQPCLLVGSGRCFLTSQNHGFAVETDSLPAD--WAPLFTNANDGSNEGIVHNSLPFFSVQFHPEHQAGPS
     *  *  *    *            *            *                          *       ***  *

Ec  DAAPLFDHFIELIEQYRKTAK                     MPKRTDIKSILILGAGPIVIGQACEFDYSGAQACKALREE
Tg  DTFYLFGDFIASIMKAQTLK------QVHTTPFSFPQKF-------QKVLLLGSGGLSIGQAGEFDYSGSQAIKALKEQ
Pf  DTSFLFKNFLLDIFNKKKQ------YREYLGYNIIYIK---------KKVLLLGSGGLCIGQAGEFDYSGTQAIKSLKEC
Bb  DTLFLMRDFIYSLGKSGSIP---LHIRRHFTSRSMEG---------GILILLSSGGISIGQAGEFDYSGSQAILALKES
Tc  DTEYLFGGVIAHVKESKVK-------EAS-KYKP--------------RKVLVLGAGGIVIAQAGEFDYSGSQCLKALSEE
Lm  DTEYLFSEYVCRVKGSKVK-------BVA-KFKP--------------RKVLVLGAGGIVIAQAGEFDYSGSQCLKSLREE
Sc  DTEFLFDVFIQAVKEFKYT------QVLK-PIAFPGGLLEDNVKAHPRIEAKKVLVLGSGGLSIGQAGEFDYSGSQAIKALKEE
Hs  DMELLFDIFLETVKEATAGNPGGQTVRERLITERLCPPGIPTPGSLPP---PRKVLILGSGGLSIGQAGEFDYSGSQAIKALKEE
                                                       *** ****** ***************** *
              GATase Linker
              ****
```

FIG. 7C

```
Ec  GYRVILVNSNPATIMTDPEMADATYIEPIHWEVVRKIIEKERPDAVLPTMGGQTALNCALELERQGVLEEFGVTMIGATADAIDK
Tg  NIFVVVVNPNIATVQTSQHMADRVYFLPVTDEFVTKVIEKEMPDGILCTFGGQTALNCAVKLHEQGVLAKFGCKILGSPIEAIIA
Pf  GIYVILVNPNIATVQTSKGLADKVYFLPVNCEFVEKIIKKEKPDFILCTFGGQTALNCALMLDQKKVLKKNNCQCLGTSLESIRI
Bb  GAEVILVNPNVATVQTNHGLADVVYFE-LLLLIVSNIIEKERPDGIMCSFGGQTALNCGIDLYKSGILSKYNCEVLGTPIETIIN
Tc  GIETVLVNPNIATVQTDDEMADQIYFVPITAEAVERVIEKERPDGIMLAWGGQTALNCGLEMDRLGILKKYNQVLGTPISTITV
Lm  GMETVLINPNIATVQTDDEMADHIYFVPLITVEAVERVIEKERPDGILLGWGGQTALNCGVKLDELGVLKKYNVQVLGTPVSVIAV
Sc  GIYTILINPNIATIQTSKGLADKVYFVPVTAEFVRKVILHERPDAIYVTFGGQTALSVGIAMKDE--FEALGVKVLGTPIDTIIT
Sc  NIQTLLINPNIATVQTSQGLADKVYFLPITPHYVTQVIRNERPDGVLLTFGGQTALNCGVELTKAGVLARYGVRVLGTTVETIEL
    *:  : **** ***:**.  :*:*  : : .* :.  *:*:***:::.*  :  *  :  ..*   .*:. *::*  * :*

Ec  AEDRRRFDVAMKKIGLETARSGIAHTMEEALAVAADVGFPCIIRPSFTMGGSGGIAYNREEFEEICARGLDLSPT----------
Tg  TEDRKVFAAKLEEIGEKVAESAAATNTEEAVQAAKAIGYPVLIRAAFALGGLGSGFAEDEETVRRICKEAFSHSSQ---------
Pf  TENRTLFAEKLKEINERIAPYGSAKNVNQAIDIANKIGYPILVRTTFSLGGLNSSFINNEEELIEKCNKIFLQTDN---------
Bb  TEDRALFNRKLAEIGERCAPSKVGTDVGSCISAAQELGYPVLVRTNYALGGFGSGLASDESELRSILSNIFSTSSCRKGGSDTTE
Tc  TEDRDLFRNALLQINEHVAKSLAVTSIEEAVGASKVIGFPLMLRAAYCLGGQGSGIVYNEEELRHKVGVALAVSPQ---------
Lm  TEDRELFRDTLLQINEQVAKSAAVTSVEEAVVASKDIGFPMMVRAAYCLGGQGSGIVENMAELRHKVEVALAASPQ---------
Sc  TEDRELFSNAIDEINEKCAKSQAANSVDEALAAVKEIGFPVIVRAAYALGGLGSGFANNEKELVDLCNVAFSSSPQ---------
Hs  TEDRRAFAARMAEIGEHVAPSEAGNSLEQAQAAAERLGYPVLVRAAFAVGGLGSGFASNREELSALVAPAFAHTSQ---------
    ::*  :    :: *   . .  . :.:   ..   :*:* ::*::  ** . .:  :  :       *

Ec  ----------------KELLIDESLIGWKEYEMEVVRDKNDNCIIVCSIENFDAMGIHTGDSIVVAPAQTLTDKEYQIMRNASMAVLREI
Tg  -----------------VFVDKSLKGWKEYEVEYEVVRDCKNNCITVCNMENLDPLGIHTGDSIVVAPSQTLSNEDYYRLRDTALKVIRHF
Pf  -----------------EIFIDKSLQGWKEIEYELLRDNKNNCIAICNMENIDPLGIHTGDSIVVAPSQTLSNYEYKFREIALKVITHL
Bb  AGSGSSFPVEDVCVYIDKALKGWKEIEFEIIRDNNDNCISPASMENFDPLGIHTGDSIVVAPAQTLTNGELYKYREIAFKIVRYL
Tc  ----------------VLLEESVAGWKEYEVEYEVVRDIYDNCITVCNMENFDPMGTHTGESIVVAPLQTLTSDEYHMLRSASIKIIRHL
Lm  ----------------VLLEESVAGWKEIEYEVVRDIYDNCITVCNMENFDPMGVHTGESIVVAPSQTLSNDEFHHLRSASIKIIRHL
Sc  ----------------VLVEKSMKGWKEVEVEYEVVRDAFDNCITVCNMENFDPLGIHTGDSIVVAPSQTLSDEDYNMLRTTAVNVIRHL
Hs  ----------------VLVDKSLKGWKEIEYEVVRDAYGNCVTVCNMENLDPLGIHTGESIVVAPSQTLNDREYQLLRQTAIKVTQHL
                   .:   :  ****  ::: **      :  .: **:** ***:*****       *  :    *

FIG. 7D
```

```
Ec  GVETGGSNVQFAVNPKNGRLIVIEMNPRVSRSSALASKATGFPIAKVAAKLAVGYTLDELMNDITGGRTPASFEPSIDYVVTKIP
Tg  GIVG-ECNIQYALDPNSEKYYIVEVNARLSRSSALASKATGYPLAYIAAKLALGSTLVELSNSVTKET-TACFEPSLDYVVTKVP
Pf  NIIG-ECNIQFGINPQTGEYCIIEVNARLSRSSALASKATGYPLAYISAKIALGYDLISLKNSITKKT-TACFEPSLDYITTKIP
Bb  GSVG-ECNVQFAVNPDTDDYFIVELNARLSRSSALASKATGYPLAYFAARIALGFDLVQMRNAITLVT-TACFEPSLDYIVVKIP
Tc  GIVG-ECNIQYGLDPTSHRYVVIEVNARLSRSSALASKATGYPLALVAAKIALGKGLFEIANGVTKTT-MACFEPSLDYIVVKVP
Lm  GIVG-ECNIQYGLDPFSHRYVVIEVNARLSRSSALASKATGYPLAHVATKIALGKGLFEITNGVTKTT-MACFEPSMDYIAVKMP
Sc  GVVG-ECNIQYALNPVSKDYCIIEVNARLSRSSALASKATGYPLAYTAAKLGLNIPLNEVKNSVTKST-CACFEPSLDYCVVKMP
Hs  GIVG-ECNVQYALNPESEQYYIIEVNARLSRSSALASKATGYPLAYVAAKLALGIPLPELRNSVTGG---TAAFEPSVDYCVVKIP
    *    *  *          *  * ********************* **  *  **                 ** ** **  ** *
                                              [...T.gondii oligomerization indel Ec  RFNFEKFAGANDRLTTQMKSVGEVMAIGRTQQESLQKALRGLEVGATGFDPKV----------------------------------
Tg  RWDLRKFESCDPLMGSAMKSVGEVMAIGRTFEESLQKALRMVDEKAGGFDESVCHFFSTDEDCAPSLPGSDFKTSSGECMRGGC
Pf  RWDLNKFEFASNTMNSSMKSVGEVMSIGRTFEESIQKSLRCIDDNYLGFSNTY----------------------------------
Bb  KWDLRKFEYADNLLGSSMKSVGEVMSIGRTFEEAMQKALRMQVR-VLGFNSGV----------------------------------
Tc  RWDLSKFNMVSQNIGSMMKSVGEVMAIGRTFEEALQKALRMVDPSHTGFDVPP----------------------------------
Lm  RWDLHKFNMVSQEIGSMMKSVGEVMSIGRTFEEAMQKAIRMVDPSYTGFSIPD----------------------------------
Sc  RWDLKKFTRVSTELSSSMKSVGEVMSIGRTFEEAIQKAIRSTEYANLGFNETD----------------------------------
Hs  RWDLSKFLRVSTKIGSCMKSVGEVMGIGRSFEEAFQKALRMVDENCVGFDHTV----------------------------------
    ** *                ******* ***  **  *  *
           .....]

Ec  ---SLDDPEALTKIRRELKDAGADRIWYIADAFRAG-LSVDGVFNLTNIDRWFLVQIEELVRLEEKVAEVG---ITGLNADFLRQ
Tg  GRTDSGAERQAALLEAELRRPSPNRIWALALAFQLG-WTVDALHEKTKIDKWFLSKLQNINDIKRQLTQLT---LDDLTRADFFY
Pf  -----CIDWDEKKIIEELKNPSPKRIDAIHQAFHLN-MPMDKIHELTHIDYWFLHKFYNIYNLQNKLKTLK---LEQLSFNDLKY
Bb  -----MSGADSEAITEALRHPTPDHVAAIARAFELG-MTVSDIHGLTKIDPWFLHRLHHLILNAHLSILPS---LSSFTPAMRY
Tc  ----RLEAKKNWDHMQDLKVPTPDRIFAICRALHEG-VSVETIHEMTRINLFFLNKLIHKLILLQNHMLGQYKGKMNTMPRDCLLK
Lm  ----RFAGADFDYMEHIRHPTPYRLFAICRALLDG-HSAEELYQMTKITRVFLYKLEKLVRLSMATSTLYANRLTEMPRENLLS
Sc  ----LDIDYELNNPTDMRVFAIANAFAKKGYSVDKVWEMTRIDKWFLNKLHDLVQFAEKISSFGT--KEELPSLVLRQ
Hs  ----KPVSDMELETPTDKRIFVVAAALWAG-YSVDRLYELTRIDRWFLHRMKRIIAHAQLLEQHR---GQPLPPDLLQQ
                                *  *
```

FIG. 7E

```
Ec  LKRKGFADARLAKLAGVR----------------EAEIRKLRDQYDLHPVYKRVDTCAAEFATDTA-YMYSTYEEECEANPSTD
Tg  IKKYGFSDRQIAQYLMNSPSAAA-----------LSQFDVRRRLHLGVRPSVKQIDTLAAEFPAHTN-YLYLTYQGIDDDVSPLA
Pf  FKKHGFSDKQIAHYLSFNTSDNNNNNNNISSCRVTENDVMKYREKLGLFPHIKVIDTLSAEFPALTN-YLYLTYQGQEHDVLPLN
Bb  YKVYGFSDRQISREIVKSTVS-------------EDDVRELRKSWGIVPFVKVIDTMAAEYPAKTN-YCYLTYNGIESDVLPCG
Tc  MKANGFSDAQIAKYFLCT----------------ADDVRESRMELKITPKVKQIDTVAGEIPASQCGFLYTSYNAYHDDVEFTE
Lm  MKAHGFSDRQLAQLLNTT----------------AADVRARRVELNVMPLIKQIDTVAGEYPAAQCCYLYSTYNAQRDDVPFTE
Sc  AKQLGFDDRQIARFLDSN----------------EVAIRRLRKEYGITPFVKQIDTVAAEFPAYTN-YLYMTYNADSHDLSFDD
Hs  AKCLGFSDKQIALAVLST----------------ELAVRKLRQELGICPAVKQIDTVAAEWPAQTN-YLYLTYWGTTHDLTFRT
                                                     *       *              ** *

Ec  REK-
Tg  ATPSVSAVFAGARAEKRE-
Pf  MKRKKICTLNNKRNANKKKVHVKNHLYNEVVDDKDTQLHKENNNNNNMNSGNVENKCKLNKESYGYNNSSNCINTNNINIENNIC
Bb  PIDSK-
Tc  RM-
Lm  RM-
Sc  HG-
Hs  PH-

Ec
Tg
Pf  HDISINKNIKVTINNSNNSISNNENVETNLNCVSERAGSHHIYGKEEKSIGSDDTNILSAQNSNNNFSCNNENMNKANVDVNVLE
Bb
Tc
Lm
Sc
Hs
```

FIG. 7F

```
Ec  ----------------------------------------------------------------
Tg  ----------------------------------------------------------------
Pf  NDTKKREDINTTTVFMEGQNSVINNKKENSSLLKGDEEDIVMVNLKKENNYNSVINNVDCRKKDMDGKNINDECKTYKKNKYKD
Bb  ----------------------------------------------------------------
Tc  ----------------------------------------------------------------
Lm  ----------------------------------------------------------------
Sc  ----------------------------------------------------------------
Hs  ----------------------------------------------------------------

Ec  ----------------------------------------------------------------
Tg  ----------------------------------------------------------------
Pf  MGLNNNIVDELSNGTSHSTNDHLYLDNFNTSDEEIGNNKNMDMYLSKEKSISNKNPGNSYYVVDSVYNNEYKINMKELIDNENL
Bb  ----------------------------------------------------------------
Tc  ----------------------------------------------------------------
Lm  ----------------------------------------------------------------
Sc  ----------------------------------------------------------------
Hs  ----------------------------------------------------------------

Ec  ----------------------------------------------------------------
Tg  ----------------------------------------------------------------
Pf  NDEYNNNVNMNCSNYNNASAFVNGKDRNDNLENDCIEKNMDHTYKHYNRLNNRRSTNERMLMVNNEKESNHEKGHRRNGLNKKN
Bb  ----------------------------------------------------------------
Tc  ----------------------------------------------------------------
Lm  ----------------------------------------------------------------
Sc  ----------------------------------------------------------------
Hs  ----------------------------------------------------------------
```

FIG. 7G

```
Ec   ------------------------------------------------------------
Tg   ------------------------------------------------------------
Pf   KEKNMEKNKGKNKDKKNYHYVNHKRNNEYNSNNIESKFNNYVDDINKKEYYEDENDIYYFTHSSQGNNDDLSNDNYLSSEELNTD
Bb   ------------------------------------------------------------
Tc   ------------------------------------------------------------
Lm   ------------------------------------------------------------
Sc   ------------------------------------------------------------
Hs   ------------------------------------------------------------

Ec   ------------------------------------------------------------
Tg   ------------------------------------EENAETCRDDEDESLLRRLSKSSSARLRT
Pf   EYDDDYYDEDEEDDYDDDNDDDDDDDGEDEEDNDYYNDDGYDSYNSLSSSRISDVSSVIYSGNENIFNEKYNDIGFKIIDNR
Bb   ------------------------------------------------------------
Tc   ------------------------------------------------------------
Lm   ------------------------------------------------------------
Sc   ------------------------------------------------------------
Hs   ------------------------------------------------------------

Ec   --------IMVLGGGPNRIGQGIEFDYCCVHASLALREDGYETIMVNCNPETVSTDYDTSDRLYFEPVTLEDVLEIVRIEKPK
Tg   GEGDAPGKQCFVVLGCGCYRIGSSVEFDWSAVSCVRTLRSLGHHAIVVNCNPETVSTDYDVSDRLYFEDLSLETVLNIWDIEAPA
Pf   NEKEKEKKKCFIVLGCGCYRIGSSVEFDWSAIHCVRTIRKLNHKAILNCNPETVSTDYDESDRLYFDEITTEVIKFIYNFENSN
Bb   ---DSVSATSIVVLGCGPYRIGSSIEFDWVCCSCVKALRSLGHAAVIVNCNPETVSTDYDVRDRLYFDELTVEIVDAIYHFENPK
Tc   -------YAVFGCGVYRIGNSVEFDYGGVLVARELRRLGKKVILINYNPETVSTDYDECDRLYFEEVSEETVLDILLKERIQ
Lm   -------YAVLGCGVYRIGNSVEFDYGGVLVARELRRLGNKVILINYNPETVSTDYDECDRLYFDEVSEETVLDILTKERVR
Sc   -------VMVLGSGVYRIGSSVEFDWCAVTAVRTLRANNIKTIMVNYNPETVSTDYDEADRLYFETINLERVLDIYEIENSS
Hs   -------VLVLGSGVYRIGSSVEFDWCAVGCIQQLRKMGYKTIMVNYNPETVSTDYDMCDRLYFDEISFEVVMDIYELENPE
             *  ***  ****    *    *   *       * ***********  **** *   *  *  *     *
```

```
Ec  VKEVVLPFNKFPGVDPLLGPEMRSTGEVMGVGRTFAEAFAKAQLGSNSTMKKHGRALLSVREGDKER--VVDLAAKLLKQGFELD
Tg  VKVPVFSFARLRGCDPVLGVEMRSTGEVACFGASKHEAFLKALISAGVPLPLEKRTILISAGPLWSKMELEPYFKILLDLGFTIY
Pf  VKAPIFSFNRLHGSDCILGVEMKSTGEVACFGLNKYEALLKSLIATGMKLP--KKSILISIKNLNKLAFEEPFQLLFLMGFTIY
Bb  VKVPVFSFHRLSPSHPVVGVDMKSTGEVVGFGANKYEALLKAMMASNVRLP--TSGMLISLDSDVRQVFDFSYCKDDIGIRLRRL
Tc  CKASVFSFNRLAGADPILGVEMASTGEIGVFGRDKKEVFLKAMLCQNFRYP--QRGVFISCDVDAMAEDLCPTLS--ASDRFPVF
Lm  CKASMFSFIPLAGADPILGVEMASTGEIGVFGRDKHEVFLKAMLCQNFRIP--KKGVFFSIDVDSQTEALCPYIQHLVGRGLKVY
Sc  VKVPQFSFPRLAGADPVLGVEMASTGEVATFGHSKYEAYLKSLLATGFKLP--KKNILLSIGSYKEKQELLSSVQKLYNMGYKLF
Hs  VKVPQFSFSRLAGADVVLGVEMTSTGEVAGFGESRCEAYLKAMLSTGFKIP--KKNILLTIGSYKNKSELLPTVRLLESLGYSLY
           *     *                *                   *
Ec  ATHGTAIVLGEAGINPRLVNKVHEGRP---------HIQDRIKNGEYTYINTTSGRR-----AIE----------[......T. gondii
Tg  ATEGTYRFLMNSVVRGQGTHLPGNASPASDS------GLRTPTTAESDADACIRAKYASRIIRVRKPIVGSNESHNGGHQSPHAL
Pf  ATEGTYDFYSKFLESFNVNKGSKFHQRLIK------VHNKNAENISPNTTDLIMNHKVEMVINITDTLKT-----
Bb  CYKGYIRIPFLINEVPASGASITKGLDVQS-----LLACSLQFFEDTIGDSLLHVGSSHKCGRLLCCTNLVRKVS-----PRPV
Tc  TSKQTSRVLADYGIPHTVLTQRHEDSE--------PTFDTAVAVKEKFDLVIQLRDKRQDFMLRRCTQ-----
Lm  GTANTAAVLHEYGIECEVLLQRSELPSGDACESNRPAVYDEEVAKKEKFDLVIQLRDKRRDFVLRRCTR-----
Sc  ATSGTADFLSEHGIAVQYLEVLNKDDDQKS------EYSLTQHLANNEIDLYINLPSANR-FRRPASYV-----
Hs  ASLGTADFYTEHGVKVTAVDWHFEEAVDGECP---PQRSILEQIAEKNFELVINLSMRGAGGRRLSSFV-----
    Regulatory domain indel
                  →
Ec  -------------------------------DSRVIRRSALQYKVHYDTTLNGGFATAMALNADATEKVISVQEMHAQIK
Tg  SLIESGKVEMVINVPDSMNHRAGTNGYLMRRTATDCGVPLLTNVKVASMFVEALNKKEAQGRSFWDIRSWDEYWPQKN
Pf  --------------------------------KVSSNGYKIRRLASDFQVPLITNMKLCSLFIDSLYRKFSRQKERKSFYTIKSYDEYISLV
Bb  ELMKSVVHMFINAAGCAIPNRLSDGYVMRRAAVDNKVTLITCMKLAKLFIDALVMRHIRTSKGKLFFHNKSQQEYLN
Tc  ------------ENATADYIWIRRLAVDYNHSLLTEPNVVRMFCETLDVDVKEIEIEPFRLYVPRVYNKMENDNYTML
Lm  -----ETAPPDYWVRRLAVDYNIPLLTEPSLVKMFCEFMDLPASSIEVEPFRHYVPKIYHKVENNNCAML
Sc  -----------SKGYKTRRLAVDYSVPLVTNVKCAKLLEAISRNITLDVSER---DAQT
Hs  -------------TKGYRTRRLAADFSVPLIIDIKCTKLFVEALGQIGPAPPLKV---HVDC
                 * **                                  *   *
```

FIG. 7J

Tc  HRHKVGLCITSTNDSKVLAISLREEKIALTCFHACLGGIKNNSEEIAEQFRSIGSTSRAHRPPH
Lm  RCHKVGLMITDNNGSKVLALRLSQEGLNITCFHGYLGGS--------D-----IGQFEQAFQRP

FIG. 7K

ATTENUATED URACIL AUXOTROPH OF AN APICOMPLEXAN AND USE THEREOF

INTRODUCTION

This patent application is the National Stage of International Application No. PCT/US2008/087081 filed Dec. 17, 2008, which claims the benefit of priority from U.S. Ser. No. 11/962,584 filed Dec. 21, 2008, teachings of each of which are herein incorporated by reference in their entirety.

This invention was supported in part by funds from the U.S. government (NIH Grant No. R01 AI41930) and the U.S. government may therefore have certain rights in the invention.

BACKGROUND OF THE INVENTION

*Toxoplasma gondii* is an obligate intracellular parasite capable of infecting most warm-blooded vertebrates and many nucleated cell types. Parasite transmission occurs orally through ingestion of tissue cysts or sporozoites from feline feces in contaminated soil, food, and water. Infection typically results in an asymptomatic primary infection that leads to a chronic latent infection affecting 30% of the world's population (Carruthers (2002) *Acta Trop.* 81:111-122). Following oral ingestion of tissue or oocyst cysts, parasites are released into the gut mucosa where they infect host cells and transform into the rapidly replicating tachyzoite stage. Rapidly replicating tachyzoites disseminate widely throughout the host reaching most organs and the brain. Host immune pressure is thought to trigger differentiation of tachyzoites into slow growing bradyzoites and development of tissue cysts. Despite the potent Th-1 acquired immunity that is elicited by primary infection, tissue cysts persist in immune privileged sites such as the brain for the life of the host. The reactivation of bradyzoites to tachyzoite differentiation in brain cysts leads to recrudescent and life threatening Toxoplasmic encephalitis in AIDS patients (Luft and Remington (1992) *Clin. Infect. Dis.* 15:211-222). *T. gondii* primary infections in pregnancy also lead to spontaneous abortion or severe CNS damage in neonates. As *T. gondii* is the $3^{rd}$ leading cause of food-born illness in the U.S., it is a significant human pathogen and therefore understanding the mechanisms underlying the development of protective immunity in response to infection is of high importance to development of vaccines.

*T. gondii* is now a widely recognized model for host response mechanisms. During active infection, *T. gondii* induces a potent systemic Th-1 inflammatory response that results in life long $CD8^+$ T cell-mediated immune control of the infection. Infection triggers the innate response through a MyD88-dependent pathway resulting in IL-12-independent production of IFN-γ by NK and T cells leading to the recruitment of neutrophils and macrophages to the site of infection (Scanga, et al. (2002) *J. Immunol.* 168:5997-6001; Mun, et al. (2003) *Int. Immunol.* 15:1081-1087; Scharton-Kersten, at al. (1996) *Exp. Parasitol.* 84:102-114). Concomitant with the innate response, the development of the acquired Th-1 response is driven by secretion of IL-12 from neutrophils, macrophages and DCs that increases inflammatory cell infiltration, activates APCs and enhances production of IFN-γ by T cells and NK cells leading to the cell-mediated immune control (Bennouna, et al. (2003) *J. Immunol.* 171:6052-6058; Gazzinelli, et al. (1994) *J. Immunol.* 153:2533-2543).

Certain mechanisms of the immune response and key mediators of host immune control have been defined. Previous studies of host responses have typically used replicating and infectious strains of *T. gondii* that widely disseminate and cause extensive host tissue destruction and associated host-derived inflammatory responses. Other immune response models are based on studies using whole parasite antigen or parasite components (Scanga, et al. (2002) supra; Mun, et al. (2003) supra; Scharton-Kersten, et al. (1996) supra; Bennouna, et al. (2003) supra; Gazzinelli, et al. (1994) supra; Aliberti, et al. (2000) *Nat. Immunol.* 1:83-87). These host response and vaccine models reveal that immunization with weakened, but living and invasive *T. gondii* parasites results in complete protection against lethal challenge infections (Waldeland and Frenkel (1983) *J. Parasitol.* 69:60-65; Snzuki and Remington (1988) *J. Immunol.* 140:3943-3946; Bourguin, et al. (1998) *Infect. Immun.* 66:4867-4874; Kasper, et al. (1985) *J. Immunol.* 134:3426-3431). However, there is a need in the art for live attenuated vaccines to *T. gondii* and other apicomplexans. The present invention meets this need in the art.

SUMMARY OF THE INVENTION

The present invention features an attenuated uracil auxotroph mutant of *Toxoplasma gondii* containing a nucleic acid molecule encoding an exogenous protein. In certain embodiments, the mutant lacks a functional carbamoyl phosphate synthetase II enzyme.

In some embodiments, the exogenous protein is a non-*Toxoplasma gondii* antigen, such as a bacterial, viral, fungal, parasitic or tumor antigen, or the exogenous protein produces a non-*Toxoplasma gondii* antigen such as a lipid or polysaccharide. A vaccine for protection against infection by *T. gondii* and a non-*T. gondii* disease is also provided, as is the use of the mutants and vaccines of the invention to generate an immune response in an animal to *Toxoplasma gondii* and/or a non-*T. gondii* antigen.

In other embodiments the exogenous protein is a therapeutic antibody, protein, enzyme or peptide; or a human therapeutic target protein or enzyme. Use of mutant expressing human therapeutic target protein or enzyme in a live, whole-cell screening assay for identifying effectors of the human therapeutic target protein or enzyme is also provided.

The present invention also features the use of a mutant of the invention for sensing the host cell environment or specific molecules present or absent in the host cell environment. In particular embodiments, the molecule is a pyrimidine.

An addition feature of the present invention is an attenuated uracil auxotroph mutant of *Toxoplasma gondii* having a mutation at one or more amino acid residues selected from amino acid residue 171-229, 345, 348, 385, 435, 454-470, 533, 873-910, 1316, 1318, 1336, 1430, 1530, 1592-1628, and 1649 of SEQ ID NO:2, and a vaccine containing the same for generating an immune response in an animal to *Toxoplasma gondii*.

The present invention further pertains to an attenuated uracil auxotroph mutant of an apicomplexan, wherein said mutant lacks a functional CPSII enzyme comprising the amino acid sequence set forth in SEQ ID NO:8, and a vaccine containing the same. In one embodiment, the attenuated pyrimidine auxotroph mutant features the replacement of all or a portion of the coding sequence of the CPSII enzyme with a nucleic acid encoding a marker protein. In another embodiment, the apicomplexan is *Toxoplasma gondii*. In particular embodiment, the *Toxoplasma gondii* CPSII mutant is used in a method for generating an immune response in an animal to *Toxoplasma gondii*

BRIEF DESCRIPTION OF THE DRAWINGS

FIG. 2 shows the percent survival of mice immunized with cps1-1 knock-out via different routes of administration. In FIGS. 2B and 2C, statistical significance was calculated using Kaplan-Meier product limit test.

FIG. 4 shows peritoneal excudate inflammatory cell recruitment in response to infection with cps1-1 knock-out as compared to highly virulent strain RH. C57Bl/6 mice were infected i.p. with $1\times10^6$ cps1-1 knock-out or $1\times10^3$ RH parasites and total PECs were harvested at Days 0, 2, 4, 6, and 8. FIGS. 4B-4F respectively show numbers of granulocytes (GR-1$^+$ CD68$^+$ in R3), macrophages (CD68$^+$), inflammatory macrophages (GR-1$^+$ CD68$^+$), and B lymphocytes (CD19$^+$), and T lymphocytes (CD3$^+$) upon cps1-1 vaccination and RH infection, whereas FIGS. 4F and 4G show CD3$^+$ CD4$^+$ and CD3$^+$ CD8$^+$ T lymphocyte numbers upon cps1-1 vaccination (FIG. 4F) or RH infection (FIG. 4G). The data are mean absolute numbers (upper panel) or percentages of total events recorded (lower panel) and are representative of two experiments that had similar outcomes. P values are based on unpaired two tailed Students T test.

FIG. 5 shows systemic Th-1 cytokine production in response to infection with cps1-1 or RH. C57Bl/6 mice were infected i.p. with $1\times10^6$ cps1-1 or $1\times10^3$ RH parasites and sera were taken at Days 0, 2, 4, 6, and 8. Serum levels of cps1-1- and RH-induced production of IFN-γ (FIG. 5A), IL-12p40 (FIG. 5B), and IL-12p70 (FIG. 5C) were measured by ELISA. The data presented are representative of three experiments with similar results and indicate the mean±SEM. P values are based on unpaired two tailed Students t-test and are as follows.

FIG. 6 shows PEC and splenocyte Th-1 cytokine production in response to infection with cps1-1 or RH. C57Bl/6 mice were infected i.p. with $10^6$ cps1-1 or $10^3$ RH and whole PECs or splenocytes were harvested at Day 0, 2, 4, 6, and 8. PECs (FIGS. 6A-6C) were plated at $1\times10^6$ cells/ml and splenocytes (FIGS. 6D-6F) were plated at $5\times10^6$ cells/ml. All cells were cultured for 24 hours. Supernatants were then assayed for IFN-γ (FIGS. 6A and 6D), IL-12p40 FIGS. 6B and 6E), and Il-12p70 (FIGS. 6C and 6F) by ELISA. Day 0 controls represent control injection of PBS i.p. All experiments were performed with n=4 mice per group. The data presented are representative of two experiments with similar results and indicate the mean±SEM. P values are based on the unpaired two tailed Students t-test and are as follows.

FIG. 7 shows a sequence alignment of CPSII genes from *Escherichia coli* (Ec; SEQ ID NO:26), *Toxoplasma gondii* (Tg; SEQ ID NO:2), *Plasmodium falciparum* (Pf; SEQ ID NO:27), *Babesia bovis* (Bb; SEQ ID NO:28), *Trypanosoma cruzi* (Tc; SEQ ID NO:29), *Leishmania major* (Lm; SEQ ID NO:30), *Saccharomyces cerevisiae* (Sc; SEQ ID NO:31), *Homo sapiens* (Hs; SEQ ID NO:32). Locations of indels in *Toxoplasma gondii* and locations where point mutations were constructed are underlined.

DETAILED DESCRIPTION OF THE INVENTION

Figure 1:
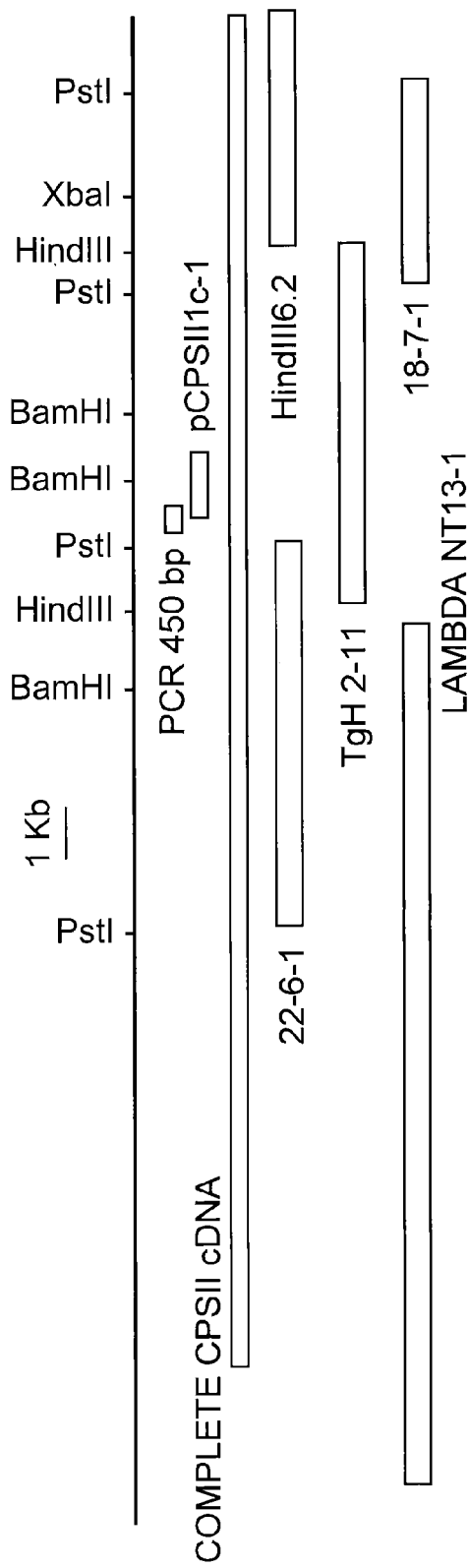
FIG. 1 shows the genomic DNA and cDNA derived clones obtained from the CPSII locus of *T. gondii*. Genomic DNA clones and their names are shown in solid, uniformly-sized boxes, cDNA clones are shown in solid boxes, which alternate in size. The complete *T. gondii* CPSII cDNA is encoded on 37 exons spanning about 24 kb of the genomic DNA.

*T. gondii* has a complete pathway for the de novo biosynthesis of pyrimidines (Schwartzmann and Pfefferkorn (1981) *J. Parasitol.* 67:150-158; Asai, et al. (1983) *Mol. Biochem. Parasitol.* 7:89-100). UMP, the first major end-product of the pathway, is synthesized from bicarbonate, glutamine, ATP, aspartate, and phosphoribosyl pyrophosphate (P-rib-PP) is catalyzed by six major enzymes: carbamoyl phosphate synthase (CPS), aspartate transcarbamylase (ATC), dihydroorotase (DHO), dihydroorotase dehydrogenase (DHOD), orotate phosphoribosyl transferase (OPT), and orotidylate decarboxylase (ODC or URA3). The pathway begins with CPS which combines glutamine, ATP and bicarbonate to form carbamoyl phosphate. The glutamine-specific CPS activity involved in de novo pyrimidine biosynthesis is referred to as CPSII and the enzyme is typically localized in the nucleolus of eukaryotic cells (Davis (1986) *Microbiol. Reviews* 50:280-313). ATC then combines carbamoyl phosphate and aspartate to form carbamoyl aspartate. The third reaction, catalyzed by DHO, yields dihydroorotate. DHOD then oxidizes dihydroorotate to orotate with the reduction of NAD. OPT then phosphoribosylates orotate to OMP. The sixth step, catalyzed by OMP Decarboxylase (URA3), converts OMP to UMP. UMP is the precursor of all pyrimidine nucleotides and deoxyribonucleotides.

In the Urea Cycle of ureotelic animals, carbamoyl phosphate is combined with ornithine, derived from ammonia, to form citrulline during de novo arginine biosynthesis. The CPS involved in arginine biosynthesis is referred to as CPSI. In some eukaryotes such as yeast, where CPSI is cytosolic, mutants of CPSII are a bit leaky because of some "mixing" of these two pools of carbamoyl phosphate. In many eukaryotes, CPSI is confined to the mitochondrial matrix and carbamoyl phosphate produced from CPSI in the Urea Cycle is unavailable to the carbamoyl phosphate "pool" which feeds into de novo pyrimidine biosynthesis (Davis (1986) supra). There is no mixing of CPSI and CPSII in *T. gondii* due to either sequestering of CPSI to a compartment such as the mitochondria or a lack of CPSI type activity in *T. gondii*. Thus, the CPSII involved in the de novo biosynthesis of pyrimidines is the first committed step of the de novo pathway of pyrimidine synthesis in *T. gondii*.

Comparative studies across many genera demonstrate extensive diversity in the de novo pathway's regulatory mechanisms, in the structure of its enzymes, and in the organization of the genes which encode the enzymes (Jones (1980) *Ann. Rev. Biochem.* 49:253-279). In many organisms, including man, the first three enzymes of de novo pyrimidine biosynthesis are found as multifunctional polypeptides. Typically, in higher eukaryotes the CPS, ATC, and DHO activities are encoded on a single gene, CAD, that specifies a single multifunctional polypeptide chain. In lower eukaryotes such as *S. cerevisiae*, the CAD-homologue gene specifies functional CPS and ATC domains, but a non-functional DHO domain. The organization of these CAD activities has evolved differently in various parasitic protozoa. In protozoan parasites of phylum Apicomplexa, including *Babesia* and *Plasmodium* species, the CPS activity is specified as an individual gene specifying a polypeptide with a single CPSII enzyme activity comprising the glutamine amido transferase (GAT) activity and the CPS activity; GAT+CPS=CPSH (Chansiri and Bagnara (1995) *Mol. Biochem. Parasitol.* 74:239-243; Flores, et al. (1994) *Mol. Biochem. Parasitol.* 68:315-318). This peculiar protozoan parasite gene organization is more similar to bacteria where CPS is monofunctional (Mergeay, et al. (1974) *Mol. Gen. Genet.* 133:299-316). *T. gondii* is also an apicomplexan and it also specifies the CAD enzyme activities on individual polypeptides (Asai, et al. (1983) *Mol. Biochem. Parasitol.* 7:89-100). This difference in CAD gene organization between man and apicomplexan parasites is reminiscent of the situation with DHFR and TS where these enzyme activities are present on a single polypeptide in apicomplexan parasites (Bzik, et al. (1987) *Proc. Natl. Acad. Sci. USA* 84:8360-8364) and on individual polypeptides in man. The difference in DHFR-TS gene structure between parasites and man has provided significant opportunity for chemotherapy using compounds such as pyrimethamine.

The difference in the CAD gene structure for pyrimidine synthesis between parasites and man also provides a unique chemotherapeutic opportunity. Further, blocking the accumulation of UMP by attacking one of the de novo pyrimidine biosynthetic enzymes should have a more profound anti-parasite effect than, for example, blocking accumulation of dTMP via pyrimethamine and sulfonamide treatment which is the standard chemotherapy for recrudescent toxoplasmosis. The latter strategy primarily blocks tachyzoite DNA replication with little apparent effect on bradyzoites, whereas the former strategy is predicted to block both parasite RNA synthesis as well as DNA replication.

In addition to the novel protozoan gene organization of CAD, the CAD-encoded enzymes have unique properties and regulation that make them attractive targets for chemotherapy. The CPSII activity detected in *T. gondii* is primarily involved in de novo pyrimidine biosynthesis based on substrate preference (Asai, et al. (1983) supra). While the mammalian CPSI involved in the Urea Cycle is activated by N-acetyl glutamate, the CPSII activity found in *T. gondii* is not affected by this treatment. The *T. gondii* CPSII activity is inhibited by UTP, suggesting a pyrimidine-controlled regulatory circuit. While the CPSII activity of man is activated by P-rib-PP, the *T. gondii* CPS activity is not. In contrast to CPSII, other enzymes of the de novo biosynthetic pathway were broadly characterized to behave similarly to their higher eukaryotic counterpart. The *T. gondii* CPSII appears to have markedly different properties from mammalian CPSII (Asai, at al. (1983) supra).

While *T. gondii* has a complete system for de novo pyrimidine biosynthesis, it only has a limited capacity to salvage pyrimidine bases. A biochemical survey of pyrimidine salvage enzymes supports the theory that all *T. gondii* pyrimidine salvage is funneled through uracil (Iltzsch (1993) *J. Euk. Micro.* 40:24-28). *T. gondii* has only three enzymes that are involved in salvage of pyrimidine nucleobases and nucleosides: cytidine/deoxycytidine deaminase, which deaminates cytidine and deoxycytidine; uridine phosphorylase, which catalyzes the reversible phosphorolysis of uridine, deoxyuridine, and thymidine; and uracil phosphoribosyltransferase (UPRT), which catalyzes the formation of UMP from uracil. The uridine phosphorylase and UPRT activities are the key salvage enzymes since pyrimidine salvage funnels all pyrimidine compounds first to uracil and then the UPRT activity yields UMP (Pfefferkorn (1978) *Exp. Parasitol.* 44:26-35; Iltzsch, (1993) *J. Euk. Micro.* 40:24-28). The limited *T. gondii* pyrimidine salvage pathway is not required for viability. Mutations that abolish UPRT activity are tolerated and are equally viable to wild-type parasites in vitro and in vivo (Pfefferkorn (1978) supra; Donald and Roos (1995) *Proc. Natl. Acad. Sci. USA* 92:5749-5753). Furthermore, there is no available evidence that *T. gondii* actually salvages any pyrimidine bases from the host cell under normal in vivo or in vitro growth conditions.

The nucleic acid molecule encoding *T. gondii* carbamoyl phosphate synthetase II (CPSII) has now been identified. Furthermore, an attenuated non-replicating uracil auxotroph strain, cps1-1, was generated which induces long lasting immunity against a low dose lethal challenge with hypervirulent *T. gondii* strain RH. The cps1-1-induced immunity was mediated by $CD8^+$ T cells and an early rapid influx of $Gr-1^+$ granulocytes and $Gr-1^+$ $CD68^+$ inflammatory macrophages were observed at the sight of inoculation. $CD19^+$ B cells and $CD4^+$ T cells infiltrated the site of inoculation 4 days after exposure to cps1-1. Unexpectedly, $CD8^+$ T cells responded earlier than $CD4^+$ T cells. Immunization with cps1-1 was marked by low early systemic IFN-γ, IL-12p40, and IL-12p70 production with higher levels of these inflammatory cytokines occurring locally at the site of cps1-1 inoculation. Advantageously, production of IL-12 and IFN-γ is the basis for protection against a large number of different intracellular pathogens. Moreover, the production of IL-12p70 is particularly relevant given that is thought that is protein is the single molecule that is needed to signal dendritic cells (DCs) to produce the optimum immune responses. As conventional adjuvants can not induce such strong and controlled levels of IL-12p70, cps1-1 is a desirable vector for delivering vaccine antigens. Given that the cps1-1 mutant induces immune responses solely to cps1-1 without the complication of dead host cells and host-derived inflammation, antigens expressed by the cps1-1 mutant can be delivered in a defined dose of non-replicating parasites.

Accordingly, the present invention relates to an isolated nucleic acid molecule encoding an apicomplexan CPSII protein and use thereof to generate an attenuated uracil auxotroph mutant which lacks a functional CPSII enzyme. Said attenuated uracil auxotroph mutant finds application as a vaccine against an apicomplexan as well as a delivery vector for exogenous proteins (e.g., antigens), thus resulting in a multivalent vaccine against the apicomplexan and the disease associated with the exogenous antigen.

An isolated nucleic acid molecule encoding an apicomplexan CPSII protein is intended to encompass nucleic acid molecules encoding CPSII protein from the parasitic Apicomplexa organisms, *P. falciparum*, *B. bovis*, *T. gondii*, *T. cruzi*, *Theileriai annulata*, and *T. parva*. It was found that *T. gondii* RH genomic DNA clones encoding CPSII exhibited significant sequence homology with amino acid residues 304-1400 of the *T. cruzi* CPSII protein. Alignment of the derived amino acid sequence of *T. gondii* CPSII as set forth in SEQ ID NO:2 was highest with the corresponding sequences of CPSII from the parasitic Apicomplexa organisms, *P. falciparum*, *B. bovis*, *T. cruzi*, *Theileria annulata*, and *T. parva*. Regions of amino acid sequence identity amongst the CPSII proteins of *P. falciparum* (GENBANK Accession No. CAD52216), *B. bovis* (GENBANK Accession No. AAC47302), *T. gondii*, *Theileria annulata* (GENBANK Accession No. CAI75289), *T. parva* (GENBANK Accession No. XP_763067) and *T. cruzi* (GENBANK Accession No. BAA74521) included, Glu-Xaa-Asn-Ala-Arg-Leu-Ser-Arg-Ser-Ser-Ala-Leu-Ala-Ser-Lys-Ala-Thr-Gly-Tyr-Pro-Leu-Ala (SEQ ID NO:7), wherein Xaa is an aliphatic amino acid (i.e., Ile, Leu or Val); Met-Lys-Ser-Val-Gly-Glu-Val-Met-Xaa$_1$-Ile-Gly-Xaa$_2$-Thr-Phe-Glu-Glu-Xaa$_3$ (SEQ ID NO:8), wherein Xaa$_1$ and Xaa$_3$ are independently Ser or Ala and Xaa$_2$ is positively charged amino acid residue (e.g., Lys, Arg, or His); and Leu-Xaa$_1$-Arg-Pro-Ser-Tyr-Val-Leu-Ser-Gly-Xaa$_2$-Xaa$_2$-Met (SEQ ID NO:9), wherein Xaa$_1$ is Val or Ala and Xaa$_2$ is Ser or Ala. Accordingly, certain embodiments embrace a nucleic acid molecule encoding an apicomplexan CPSII protein having the amino acid sequence set forth in SEQ ID NO:7, SEQ ID NO:8, and SEQ ID NO:9. In other embodiments, the nucleic acid molecule encodes a CPSII protein from a *Toxoplasma* species. In one embodiment, the nucleic acid molecule encodes a CPSII protein as set forth in SEQ ID NO:2. In another embodiment, the nucleic acid molecule has the sequence as set forth in SEQ ID NO:1.

An attenuated uracil auxotroph mutant of an apicomplexan is defined herein as a mutant apicomplexan, which lacks a functional CPSII enzyme. The mutant apicomplexan can be generated using any suitable method. For example, the mutant can be obtained by the single cross-over integration approach disclosed herein or using a double-crossover gene replacement, e.g., as disclosed by Mercier, et al. ((1998) *Infect. Immun.* 66:4176-82). See also Wang, et al. (2002) *Mol. Biochem. Parasitol.* 123(1):1-10. In general, the generation of a mutant apicomplexan includes isolating the nucleic acid molecule encoding the CPSII enzyme from the apicomplexan of interest; replacing, mutating, substituting or deleting all or a portion (e.g., 1 bp to 27 kb) of the CPSII gene to disrupt the promoter (e.g., nucleotides 1-2429 of SEQ ID NO:1) regulatory sequence(s) and/or open reading frame of the CPSII enzyme (e.g., nucleotides 2430-26452 of SEQ ID NO:1); and integrating the disrupted molecule (e.g., via single- or double-crossover homologous recombination events) into the genome of the apicomplexan of interest. Upon selection, i.e., marker protein expression or genomic DNA analysis, an uracil auxotrophic mutant which lacks a functional CPSII enzyme is obtained. Disruption of all or a portion of the CPSII gene can be achieved by, e.g., replacing the CPSII coding sequence with a nucleic acid molecule encoding selectable marker, replacing the CPSII coding sequence with a nucleic acid molecule encoding an exogenous protein, replacing the CPSII coding sequence with a nucleic acid molecule encoding a mutant CPSII protein, substituting the CPSII promoter with a mutated CPSII promoter which can no longer be recognized by *T. gondii* transcription proteins, etc. In particular embodiments, the uracil auxotroph has one or more of the mutations in CPSII as set forth herein, including but not limited mutations at amino acid residues 171-229, 345, 348, 385, 435, 454-470, 533, 873-910, 1316, 1318, 1336, 1430, 1530, 1592-1628, or 1649 of SEQ ID NO:2.

An attenuated uracil auxotroph mutant which lacks a functional CPSII enzyme can also be achieved by replacing (e.g., by double-crossover gene replacement) the wild-type CPSII enzyme with a mutant CPSII enzyme having one or more point mutations at active site or ATP binding domains. Selection of residues to be mutated can be based upon, e.g., the crystal structure of CPS from *E. coli* (Thoden, et al. (1997) *Biochemistry* 36:6305-6316) or biotin carboxylase which has been shown to have functionally equivalent ATP binding domains with CPS enzymes (see, e.g., Kothe, et al. (1997) *Proc. Natl. Acad. Sci. USA* 94:12348-12353).

Given that the sequences obtained from the cDNA and gDNA clones of *T. gondii* CPSII indicate that *T. gondii* has a CPSII genomic locus organized like other apicomplexan CPSII loci, it is contemplated that methods used to produce the *T. gondii* mutants disclosed herein are applicable to the generalized construction of uracil auxotroph mutants in other apicomplexan parasites including, but not limited to, parasitic species of *Theileria*, *Babesia*, *Plasmodium* and other species of *Toxoplasma* (e.g., *T. cruzi*) which encode a CPSII enzyme containing the common amino acid sequences set forth in SEQ ID NOs:7-9. In one embodiment, the mutant apicomplexan is a species of *Toxoplasma*. In another embodiment, mutant apicomplexan is *T. gondii*.

As will be appreciated by the skilled artisan, any suitable marker-encoding nucleic acid can be used to identify a cpsII mutant so long as it can be phenotypically detected in the mutant strain. Suitable marker proteins include, but are not limited, positive and negative selectable markers such as thymidine kinase, hygromycin resistance, cytosine deaminase, DHFR, bleomycin, chloramphenicol acetyl transferase and the like. It is contemplated that the nucleic acid molecule encoding the marker protein can be used to replace or substitute all or a portion of the promoter or coding sequence of the CPSII locus to generate a mutant which lacks a functional CPSII enzyme.

A mutant is said to lack a functional CPSII enzyme when there is no detectable CPSII enzyme activity and the mutant is completely dependent on pyrimidine supplementation for replication (e.g., as determined by a plaque assay in the presence between 200 and 400 µM uracil). In this regard, a "leaky" mutant (i.e., a mutant which expresses a detectable amount of protein, exhibits a detectable amount of CPSII activity, or is not completely dependent upon pyrimidine supplementation for replication) is not encompassed within the definition of an apicomplexan mutant which lacks a functional CPSII enzyme.

Having demonstrated that an attenuated uracil auxotroph mutant of *T. gondii* provides protection against infection by parasitic *T. gondii* and induces a Th-1 immune response which is specific to *T. gondii* antigens without the complication of dead host cells and host-derived inflammation, the present invention also embraces the use of an attenuated *T. gondii* uracil auxotroph mutant for intracellular vaccination by delivering exogenous antigens from non-*T. gondii* disease agents (i.e., antigens not naturally expressed by the *T. gondii*). In one embodiment, the exogenous antigen is expressed by *T. gondii*, secreted into the parasite vacuole and eventually into the cytosol of the mammalian host cell. The *T. gondii*-expressed exogenous antigen subsequently enters the mammalian antigen presenting cell's (APC) antigen processing and presenting pathway as a substrate for generation of class I and class II peptides which generate CD8 and CD4 T cell responses. Accordingly, in one embodiment of the present invention, the attenuated *T. gondii* uracil auxotroph mutant harbors a nucleic acid molecule encoding an exogenous antigen. In this regard, the inventive *T. gondii* uracil auxotrophic can be used to vaccinate against both *T. gondii* and against any non-*T. gondii* antigen(s) encoded by gene(s) expressed in the *T. gondii* uracil auxotroph. This includes both protein antigens and also non-protein antigens that could be produced by genes within the *T. gondii* carrier, such as polysaccharides and lipids. While certain embodiment embrace the expression of antigens from pathogenic organisms, e.g., bacteria, fungi, viruses, and parasites, other embodiments include any other antigen to which an immune response would be desired, e.g., host antigens such as tumor antigens.

It is further contemplated that an attenuated or non-attenuated mutant of *T. gondii* can be used to express any other genes one would want to express within a mammalian host cell. This could include genes encoding therapeutic peptides or proteins, e.g., therapeutic antibodies (e.g., Trastuzumab) proteins (e.g., interferons, blood factors, insulin, erythropoietin, and blood clotting factors), or enzymes (e.g., asparaginase, catalase, lipase, and tissue plasminogen activator) used in the treatment of diseases or conditions; as well as proteins, enzymes or peptides of use in screening assays to identify inhibitors or activators (i.e., effectors) of the same. Such proteins are routinely expressed in other systems, e.g., yeast, mammalian cells lines, bacteria or insect cells, such that one skilled in the art could readily obtain nucleic acids encoding such proteins and express them in a mutant *T. gondii*.

The *T. gondii* uracil auxotroph of the present invention can accommodate multiple expression constructs. Therefore, nucleic acid molecules encoding exogenous antigens from a non-*T gondii* disease can be integrated into the *T. gondii* genome, e.g., as part of the nucleic acid molecule used to disrupt the promoter, regulatory sequences, or open reading frame of the CPSII enzyme or at any other suitable location in the genome (e.g., at non-essential loci). Examples of exogenous antigens include tetanus toxoid (tetC); malarial antigens such as circumsporozoite protein (CSP) and merozoite surface protein-1 (MSP-1); *Bacillus anthracis* protective antigen; *Yersinia pestis* antigens (e.g., Fl+V and Fl–V fusion); antigens from intracellular bacterial pathogens such as *Francisella tularensis*, Mycobacteria, *Legionella, Burkholderia* (e.g., *B. pseudomallei* and *B. mallei*), *Brucella* species and *Coxiella*; antigens from viruses, particularly intracellular invaders such as HIV; other toxoids such as botulinum toxoid or Epsilon toxin; tumor antigens; multi-agent biodefense antigens; antigens from non-biothreat infectious agents; plague antigens; and combinations of any of these. As indicated above, it is also contemplated that exogenous genes encoding enzymes which synthesize non-protein antigenic products, e.g., lipids or polysaccharides, can be expressed in the *T. gondii* platform. Care should be taken to ensure that antigens being expressed in *T. gondii* are not functional virulence factors. Therefore, it may be desirable to use known protective antigens not representing virulence factors or use mutated genes that do not encode complete toxin or virulence factors.

The basic criteria for exogenous antigen expression are that the gene is a non-*T. gondii* gene or coding sequence and the gene or coding sequence is able to be expressed directly or indirectly from a recombinant molecule in a *T. gondii* cell. In this regard, it is desirable that the promoter employed is recognizable by *T. gondii*. Moreover, is desirable that the promoter promotes transcription of the antigen coding sequence when the *T. gondii* is inside mammalian cells. To this end, particular embodiments embrace the use of a *T. gondii* promoter. Known promoter and other regulatory elements (e.g., 5' UTR, 3' UTR, etc.) which can be operably linked to the coding sequence of an exogenous antigen of interest so that the exogenous antigen is expressed in *T. gondii* include, but are not limited to, sequences from the *T. gondii* SAG1 gene (Striepen, et al. (1998) *Mol. Biochem. Parasitol.* 92(2):325-38) or the *T. gondii* NTPase gene (Robibaro, et al. (2002) *Cellular Microbiol.* 4:139; Nakaar, et al. (1998) *Mol. Biochem. Parasitol.* 92(2):229-39). Alternatively, suitable regulatory sequences can be obtained by known trapping techniques. See, e.g., Roos, et al. (1997) *Methods* 13(2):112-22. Promoters of use in accordance with the present invention can also be stage-specific promoters, which selectively express the exogenous antigen(s) of interest at different points in the obligate intracellular *T. gondii* life cycle. Moreover, it is contemplated that an endogenous promoter can be used to drive expression of the exogenous antigen by, e.g., site-specific integration at the 3' end of a known promoter in the *T. gondii* genome.

One advantage of such multivalent vaccines is that protection against multiple disease agents can be attained with a single vaccine formulation. The protective immune response to *T. gondii* uracil auxotroph clearly involves both a humoral (antibody) response and the cell-mediated component of immunity, thus a diverse immune response to any expressed antigen is possible. In this regard, the instant *T. gondii*-based vaccine can serve as an agent of protection and of adjuvancy for any exogenous antigen(s) expressed.

When employed as a vaccine for protection against infection by *T. gondii* and/or a non-*T. gondii* disease, particular embodiments provide that the attenuated *T. gondii* uracil auxotroph mutant is in admixture with a pharmaceutically acceptable carrier. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000. Furthermore, it has now been shown that ex vivo loading of dendritic cells, macrophages, and peritoneal cells with cps1-1, then immunizing an animal with these loaded cells leads to successful immunization. Dendritic cells loaded with cps1-1 provide the strongest immune response in animals and produce long lasting CD8 T cell responses and long lasting immune memory. Accordingly, it is contemplated that the attenuated *T. gondii* uracil auxotroph or vaccine of the same can be administered via loading of dendritic cells, macrophages, and/or peritoneal cells.

Administration of a composition disclosed herein can be carried out by any suitable means, including parenteral injection (such as intraperitoneal, subcutaneous, or intramuscular injection), orally, or by topical application (typically carried in a pharmaceutical formulation) to an airway surface. Topical application to an airway surface can be carried out by intranasal administration (e.g., by use of dropper, swab, or inhaler which deposits a pharmaceutical formulation intranasally). Oral administration can be in the form of an ingestible liquid or solid formulation. In particular embodiments, administration is via intraperitoneal or intravenous routes.

An attenuated *T. gondii* uracil auxotroph or vaccine containing the same can be employed in various methods for protecting a subject against infection by *T. gondii* and/or a non-*T. gondii* disease. Such methods generally involve administering to a subject in need of treatment (e.g., a subject at risk of being exposed to an infectious disease or at risk of developing cancer) an effective amount of a *T. gondii* uracil auxotroph or vaccine of the present invention thereby protecting the subject against infection by *T. gondii* and/or the non-*T. gondii* disease. An effective amount, as used in the context of the instant invention, is an amount which produces a detectable Th-1 immune response or antibody response to an antigen thereby generating protective immunity against the pathogen or disease from which the antigen was derived or associated. As such, an effective amount prevents the signs or symptoms of a disease or infection, or diminishes pathogenesis so that the disease or infection is treated. Responses to administration can be measured by analysis of subject's vital signs, monitoring T cell or antibody responses, or monitoring production of IFN-γ, IL-12p40, and/or IL-12p70 according to the methods disclosed herein or any suitable method known in the art.

Administration can be given in a single dose schedule, or a multiple dose schedule in which a primary course of treatment can be with 1-10 separate doses, followed by other doses given at subsequent time intervals required to maintain and or reinforce the response, for example, at 1-4 months for a second dose, and if needed, a subsequent dose(s) after several months.

The exact dosage for administration can be determined by the skilled practitioner, in light of factors related to the subject that requires prevention or treatment. Dosage and administration are adjusted to provide sufficient levels of the composition or to maintain the desired effect of preventing or reducing signs or symptoms of the disease or infection, or reducing severity of the disease or infection. Factors which may be taken into account include the severity of the disease state, general health of the subject, age, weight, and gender of the subject, diet, time and frequency of administration, drug combination(s), reaction sensitivities, and tolerance/response to therapy.

While the instant composition and methods find application in the prevention and treatment of diseases or infections of mammals, in particular humans, the invention should be construed to include administration to a variety of animals, including, but not limited to, cats, dogs, horses, cows, cattle, sheep, goats, birds such as chickens, ducks, and geese. In this regard, the instant invention is also useful against potential bioterrorism aimed at agriculture and populace, e.g., *Brucella* and anthrax. As such, the instant *T. gondii* vector platform can be employed by both pharmaceutical and agribusiness to produce multivalent vaccines with intracellular delivery to create commercial multiagent vaccines for people and livestock. The disclosed *T. gondii* vector platform also can be employed more broadly in the development of new treatments or preventions (vaccines) against a wide variety of human diseases such as cancer, autoimmune disorders, vascular disorders, and musculoskeletal disorders.

Moreover, as the demonstrated herein, there are particular regions of the *T. gondii* CPSII which can be used in screening assays to identify parasite-selective drugs for preventing or treating a *T. gondii* infection. For example, deletion of the GATase indel as well as the C-terminal regulatory indel completely abolished complementation activity of a CPSII minigene showing these indels to be necessary for CPSII function and parasite growth in vivo. Furthermore, the results presented herein demonstrate a functional and essential role for a number of C-terminal amino acids known to transmit the allosteric regulatory signals in *E. coli* CPS or mammalian CPSII. *T. gondii* CPSII is dependent on GATase for production of ammonia in vivo, and an ammonia tunnel potentially analogous to the described ammonia tunnel in *E. coli* CPS is present. Therefore, these results reveal unique features of *T. gondii* CPSII that provide parasite-selective drug targets to inhibit CPSII thereby starving the parasite of essential pyrimidines required for RNA and DNA synthesis. Thus, conventional in vitro or in vivo drug screening assays can be employed to identify agents which modulate the activity of CPSII by targeting one or more of the essential amino acid residues or regions of *T. gondii* CPSII disclosed herein. Agents which can be screened in accordance with such an assay can include compounds such as antibodies, proteins, peptides, nucleic acids, small organic molecules, etc.

In so far as mutant *T. gondii* of the present invention can be modified to express any protein of interest, particular embodiments of this invention feature the use of a transgenic *T. gondii* strain expressing a human therapeutic target protein or enzyme in live, whole-cell screening assays for identifying effectors (i.e., inhibitors or activators) of said target protein or enzyme. Such whole-cell screening assays are routinely practiced in the art using other systems, e.g., yeast, mammalian cell lines, or bacteria, and can be readily adapted for use with *T. gondii*-infected cells. For the purposes of the present invention, a human therapeutic target protein or enzyme is any human protein, which is known to be involved in the manifestation of a disease or condition. In this regard, inhibition or activation of the human therapeutic target protein or enzyme results in the prevention or treatment of the disease or condition. Human therapeutic target proteins or enzymes are well-known to those skilled in the art.

The addition to the above-described uses, the mutants of this invention also find application as "sensors" of the intracellular mammalian cell environment. The cellular events inside of living mammalian cells during drug treatments for cancer, autoimmune disease and any other disease state or treatment state is typically difficult to measure, but is of major commercial interest. Many conventional treatments work by starving cells of pyrimidines or purines, or by adding pyrimidines (5-fluorouracil for cancer) or purines (mercaptopurine for cancer) derivatives. In this regard, uracil auxotroph mutants of the invention can be used to sense the concentration of pyrimidines and pyrimidine analogs present in the host cell.

For example, the pyrimidine auxotrophs disclosed herein rely on host cell uracil and uridine (and deoxyuridine) for growth. Thus, these mutants can both "sense" the host cell environment for these compounds measured by parasite growth rate, and also "sense" cytotoxic concentrations of 5-flurouracil or 5-fluorouridine (or deoxyuridine) concentrations based on stasis and/or death of the intracellular parasite.

The following non-limiting examples are provided to further illustrate the present invention.

Example 1

Materials, Assays, and Molecular Methods

Parasitic Material. Most of the work described herein used the RH strain of *Toxoplasma gondii* which is the most commonly used laboratory strain amongst *Toxoplasma* researchers (Pfefferkorn, et al. (1976) *Exp. Parasitol.* 39:365-376). Due to its long history of continuous passage in the laboratory, this strain is highly virulent in animals and grows rapidly in culture making it ideal for obtaining large amounts of material. However, it has lost the ability to go through the complete sexual cycle in cats.

Tachyzoites of the virulent Type I strain RH and the high-passage in vitro cultivated Type II parasite PLK were obtained by serial passage in human foreskin fibroblast (HFF) cell monolayers in EMEM, 1% FBS at 37° C. in 95% air/5% $CO_2$. Typically, infected cultures were maintained by seeding uninfected monolayers at about a 1:50 dilution every 48-72 hours. This yielded about $10^9$ parasites from three T175 flasks of infected cultures.

Tachyzoites were isolated from freshly lysed HFF monolayers by filtration through 3.0 μm nuclepore membranes, washed with phosphate-buffered saline (PBS), centrifuged, and then resuspended in PBS at defined numbers. Viability of tachyzoite preparations was tested in plaque assays to confirm that 30-50% of tachyzoites were infectious.

Detailed methods for growth, harvesting, passage, purification of tachyzoite parasites, storage, and replication assays of *T. gondii* are routine and well-known, for example, Roos, at al. (1994) *Meth. Microb. Path.* 45:23-65; Fox, et al. (1999) supra. All media reagents were purchased from GIBCO-BRL (Rockville, Md.), Bio Whittaker (Walkersville, Md.) and Sigma (St. Louis, Mo.).

Chemicals and Enzyme Assays. Most chemical or biochemical reagents were purchased from Sigma (St. Louis, Mo.). Ganciclovir was obtained from Roche Labs (Nutley, N.J.). The linked assay system for CPSII activity was performed in accordance with known methods, for example, Asai, et al. (1983) *Mol. Biochem. Parasitol.* 7:89-100 and Hill, et al. (1981) *Mol. Biochem. Parasitol.* 2:123-134. For CPSII assays parasites were lysed in M-PER extraction buffer (Pierce Inc., Rockford, Ill.) or by osmotic shock in 4 volumes (w/v) of 10 mM potassium phosphate (pH 7), 0.05 mM dithiothreitol and protease inhibitors antipain, leupeptin, chymostatin, and pepstatin A, each at 0.1 mM. After 1 to 2 minutes of lysis, glycerol 7.5% (w/v) was added to the extracts. The lysed parasite extracts were centrifuged at 20,000×g for 15 minutes and the supernatants used in CPSII enzyme assay. CPSII reaction assays contained 50 mM HEPES (pH 7.2), 10% (w/v) glycerol, 20 mM $MgCl_2$, 20 mM ATP, 3 mM L-glutamine, 0.5 mM L-ornithine, 10 mM KCl, 0.05 mM dithiothreitol, 1 unit ornithine carbamyl transferase, 10 mM bi[$^{14}C$]carbonate (1 μCi/μM) and extracted in a final volume of 0.1 ml. Sodium bi[$^{14}C$]carbonate was 30-60 mCi/mmol and obtained from ICN. Reactions were run for 30 minutes at 37° C. and then terminated by addition of 10 μl of 5 M formic acid. A small piece of solid $CO_2$ was dropped into the stopped reaction and excess $CO_2$ was removed by standing the open solution in a fume hood. Reaction volumes were removed, dried and redissolved in 0.1 ml water prior to addition of liquiscint scintillant and counting of [$^{13}C$] in a Beckman scintillation counter.

Thymidine kinase assays were performed in accordance with known methods, for example, Maga, at al. ((1994) *Biochem. J.* 302:279-282). Briefly, parasite extracts were lysed by sonication (1 minute, kontes microtip) or in M-PER extraction buffer plus a cocktail of protease inhibitors (antipain, leupeptin, chymostatin, and pepstatin A; 10 μg each) and 1 mM phenylmethylsulfonyl fluoride. TK assays were run in a 50 μl volume at 37° C. for 30 minutes in a mixture containing 30 mM potassium HEPES (pH 7.5), 6 mM ATP, 6 mM $MgCl_2$, 0.5 mM dithiothreitol and 3.3 μM [$^3H$]Thymidine (20-40 Ci/mmol from ICN). The reaction was terminated by transferring 25 μl of the incubation mixture to DE81 ion exchange paper (Whatman, Clifton, N.J.). The spotted paper was washed in 1 mM ammonium formate (pH 3.6) to remove unconverted nucleoside, distilled water, and then a final ethanol wash prior to drying of the paper and scintillation counting in liquiscint. Protein determination for parasite protein extracts was determined using BIO-RAD protein assay reagents and bovine serum albumin in accordance with standard procedures (BIO-RAD, Hercules, Calif.).

Molecular Methods. Molecular methods including DNA isolation, restriction, Southern blot analysis, hybridization, and PCR reactions used herein are all well-known, for example, Bzik, at al. (1987) *Proc. Natl. Acad. Sci. USA* 84:8360-8364 and Fox, et al. (1999) supra. Transfection of *T. gondii* was also performed in accordance with routine procedures (Roos, et al. (1994) supra and Fox et al. (1999) supra). The gene libraries were developed from HindII- or PstI-digested genomic DNA cloned into BLUESCRIPT KSII digested with the same enzyme and treated with alkaline phosphatase prior to ligation with *T. gondii* DNA fragments. Libraries were manipulated in accordance with known methods (Bzik, et al. (1987) supra). Total mRNA was isolated from *T. gondii* using TRIZOL-LS reagent (GIBCO-BRL, Rockville, Md.) and mRNA was converted to cDNA using a cDNA kit from Pharmacia (Piscataway, N.J.) with polydT or random hexamers primers. DNA sequencing was done using classical dideoxy chain termination or automated sequencing using fluorescent dyes (ABI sequencer, Foster City, Calif.). DNA sequences were analyzed using the MACVECTOR suite of programs (Oxford Molecular, Beaverton, Oreg.) and resources at NCBI, such as blast search. The DHFRm2m3-TS allele was obtained from the NIH AIDS Reference and Reagent Center (Rockville, Md.). The TK75 allele which was described by Black, et al. (1996) supra was obtained from Darwin (Seattle, Wash.). BLUESCRIPT plasmid was from STRATAGENE (La Jolla, Calif.). Restriction enzymes, nucleic acid modifying enzymes and transfer membranes were from Boehringer Mannheim, Indianapolis, Ind.

Flow Cytometric Differential Cell Analysis. Peritoneal excudate cells (PECS) from uninfected wild-type mice for day 0 controls and infected wild-type mice on days 2, 4, 6, and 8 post-infection were obtained by peritoneal lavage with 5-7 ml of ice-cold PBS. PECS were depleted of erythrocytes by treatment with buffered ammonium chloride (Obar, et al. (2004) *J. Immunol.* 173:2705-2714), washed in PBS, then counted to determine total viable cell numbers recovered by trypan blue exclusion. Differential cell analysis via flow cytometry was then performed using either single or dual color staining of $2-5\times10^5$ PECS per animal, PECS were stained using standard procedures in SWB buffer containing 2% FBS in 1×PBS and 5% normal mouse serum (SIGMA, St. Louis, Mo.) and Mouse FC Block (BD Biosciences, San Jose, Calif.) to block Fc receptors. Single-cell suspensions were initially fixed in SWB 1% paraformaldehyde then stained in primary reactions for either the surface markers PE-conjugated anti-mouse CD3 (17A2) or anti-mouse Gr-1 (RB6-8C5) alone or with one of each of the following FITC-conjugated antibodies anti-mouse CD45R/B220 (RA3-6B2), anti-mouse CDllb (Ml/70) (BD Biosciences), anti-mouse CD19, anti-mouse F4/80, or the intracellular stain anti-mouse CD68 (Serotec, Raleigh, N.C.). For the intracellular stain (CD68), fixed PECs were permeabilized using SWB 0.5% saponin then stained for anti-mouse CD68 using SWB 0.5% saponin as stain buffer. Flow cytometric data were acquired and analyzed using the FACS CALIBUR flow cytometer and CELLQUEST software (BD Immuncytometry Systems, San Jose, Calif.). Percentage of total events were based on $2-5\times10^4$ total events per sample and are the sum of the gates R1, R2 and R3. Granulocyte percentages were calculated from Gr-1$^+$ CD68$^-$ events in R3. Each percentage was verified by total event analysis. Absolute numbers were the product of percentage of total events multiplied by total cell number per mouse. Non-specific Ig isotype specific antibodies were used as negative controls for all samples (BD Biosciences).

Cytokine Assays. The concentrations of the mouse cytokines were measured by ELISA in the serum and in vitro culture supernatants of whole PECs or splenocytes harvested from wild-type mice injected i.p. with either 1×PBS, $1\times10^6$ cps1-1 tachyzoites at various times post-infection. Serum was obtained from whole blood by incubation at room temperature for 2 hours and coagulated blood was centrifuged for 10 minutes at 14,000 rpm at 4° C. and serum was frozen at −80° C. Immediately after obtaining blood, mice were euthanized via $CO_2$ overdose then PECS and spleen harvested. Single cell suspensions of splenocytes and PECs were depleted of RBCs and counted as described above, then resuspended in DMEM with 10% FBS and 1× antimicrobe/antimycotic (GIBCO BRL). Cells were seeded in 24-well trays at either $1×10^6$ or $5×10^6$ PECs or splenocytes, respectively, per well and cultured for 24 hours at 37° C., 5% $CO_2$ (Mordue & Sibley (2003) *J. Leukoc. Biol.* 74:1015-1025). Cells in 24-well trays were freeze-thawed 3 cycles (−80° C. to +37° C.), debris was removed from the supernatants by centrifugation at 14,000 rpm at 4° C. for 10 minutes and the supernatants were stored at −80° C. Concentrations of the mouse cytokines IFN-γ, IL-12p40, and IL-12p70 were then determined using OPTELA ELISA sets (BD Biosciences) (Robben, et al. (2004) *J. Immunol.* 172:3686-3694) following the manufacturer's instructions. Serum was used at a 1:4 dilution in assay diluent whereas supernatant from PECs or splenocytes was not diluted.

Tg Lysate Preparation and Serum IgG Assay. Total tachyzoite lysate antigen was prepared from in vitro HFF cultures of RH (Nguyen, et al. (2003) *Magn. Reson. Med.* 50:235-241). Tachyzoites were purified by nucleopore filtration, counted then pelleted at 1500 g for 6 minutes at 4° C. Tachyzoites were washed once, resuspended in 1× PBS, then disrupted by sonication on ice four times for 20 seconds (Gazzinelli, et al. (1991) *J. Immunol.* 146:286-292; El-Malky, et al. (2005) *Microbiol. Immunol.* 49:639-646). TLA was then filtered through a 0.22 μm pore filter and stored at −80° C. Anti-*toxoplasma*-specific serum IgG responses were measured in cps1-1 immunized mice by coating each well of a 96-well plate with 100 μl of TLA at a concentration of 10 μg/ml in 1×PBS overnight at 4° C. (El-Malky, et al. (2005) supra). Plates were washed three times with 1×PBS then blocked with 1×PBS/1% BSA. Sera were serially diluted three-fold in PBS 0.1% BSA and applied to each well in triplicate then plates were incubated overnight at 4° C. Plates were washed with PBS to remove non-specifically bound Ig and secondary anti-mouse Ig-specific HRP-conjugated antibody was used to detect the *toxoplasma*-specific antibodies. Conjugated secondary Ig was either anti-mouse IgG H+L or isotype-specific anti-IgG1 and IgG2a. TMB substrate was used to detect secondary antibodies followed by stopping the reaction with 0.2N $H_2SO_4$ (Bourguin, et al. (1998) *Infect. Immun.* 66:4867-4874). Plates were then read at 405 nm on an ELISA plate reader.

Adoptive Transfer and T Lymphocyte Antibody Depletion. For adoptive transfers, spleens were harvested three weeks after final immunization with $1×10^6$ cps1-1 tachyzoites, and used as a source for either *toxoplasma*-specific memory T or B lymphocytes. Spleens were disrupted immediately after removal from mice by grinding between microscope slides, pelleting, then depleting RBCs as described. $CD19^+$, $CD8^+$, or $CD4^+$ T cells were purified using EASYSEP Mouse positive selection kits and purity was confirmed as per manufacturer's instructions (StemCell Technologies Inc.) (Obar, et al. (2004) supra). Naive recipient wild-type mice were given either $1×10^7$ $CD8^+$ T cells, $1×10^6$ $CD4^+$ T cells, $1×10^6$ $CD4^+$ and $1×10^6$ $CD8^+$ T cells, or $5.0×10^6$ $CD19^+$ B cells via tail vein injection. Twenty-four hours after transfer of purified cell populations, mice were high dose i.p.-challenged with $1×10^3$ RH tachyzoites (Ely, et al. (1999) *J. Immunol.* 162: 5449-5454). To deplete specific T cell populations immunized mice were injected i.p. with 500 μg of either control Rat IgG, anti-CD4 antibody (GK1.5), anti-CD8 antibody (TIB210), or both anti-CD4/CD8 antibody on days −3, −2, −1, 0 then every other day until day 21 post-challenge (Obar, et al. (2004) *J. Virol.* 78:10829-10832). On Day 0 of antibody treatment, T cell depletion was continued by flow cytometry of peripheral blood. Percent survival was measured of groups of four mice per condition and experiments were repeated twice.

Statistical Analysis. The Kaplan-Meier product limit test was used to measure significant differences between survival curves of i.v. and ex vivo loaded cell type route experiments (GRAPHPAD PRISM software). All other samples were subject to a Students t-test and are represented as the mean±SEM.

Example 2

Isolation of Gene Encoding CPSII

The DNA encoding *T. gondii* carbamoyl phosphate synthetase II (CPSII) has now been cloned. To clone the CPSII gene from the RH strain of *T. gondii*, a forward degenerate primer: CCN YTN GGN ATH CAY CAN GGN GAY (SEQ ID NO:3) and a reverse degenerate primer: YTC YTC MAA NGT YCT NCC KAT NGA CAT NAC (SEQ ID NO:4), were designed from two stretches of amino acid sequence, Pro-Leu-Gly-Ile-His-Thr-Gly-Asp-Ser-Ile (SEQ ID NO:5) and Gly-Glu-Val-Met-Ser-Ile-Gly-Arg-Thr-Phe-Glu-Glu (SEQ ID NO:6), respectively, which were well-conserved in the CPSII domain from various species. With these two primers, PCR amplification of strain RH single stranded cDNA derived from RH mRNA was performed in accordance with known procedures (Fox, et. al (1999) *Mol. Biochem. Parasitol.* 98:93-103). A PCR product of the expected length, PCR 450 bp (see FIG. 1) was obtained. The 450 bp amplicon was excised from agarose, purified and cloned into the SS phage vector M13 mp9 in both orientations, for single-stranded sequencing using the dideoxy termination method.

The purified amplicon was then reamplified and used to probe lambda phage cDNA libraries from the NIH AIDS Reference and Reagent Center and a 1.2 Kb cDNA phagemid clone (pCPSII lc-1) was identified and transduced into BLUESCRIPT plasmid (STRATAGENE) for analysis via the manufacturer's protocol. A 1.0 Kb EcoRI fragment from pCPS lc-1 was shot-gun cloned into M13 mp9 and SS dideoxy sequenced. The sequences were found to align to those of the original 450 bp M13 mp9 clone and to have high homology to CPSII of other species. Separately, Southern blot analysis of *T. gondii* genomic restriction digests were probed with the gel-purified 450 bp fragment. This probe hybridized to several restriction fragments derived from RH parasite DNA including a unique band generated by Hind= (6.5 Kb) (see FIG. 1). Genomic libraries were then constructed in BLUESCRIPT SKII* phagemid vector that would contain the 6.5 Kb HindIII fragment and these genomic libraries were screened with the labeled 450 bp PCR-derived CPSII cDNA. Positive clones containing the desired insert in both orientations were isolated. The ends of TgH 2-11 6.5 Kb clone were then dideoxy double-strand sequenced using T3 and T7 primers. Primers from the ends of the sequenced sections were used to sequence the remainder. The 6.5 Kb HindIII fragment was also used to screen additional *T. gondii* genomic Southern blots and three PstI fragments were identified. Subsequently, a PstI *T. gondii* genomic library was constructed using standard methods and probed with fragments from either end of TgH 211 plasmid to yield 7.5 Kb, 4.9 Kb, and 3.8 Kb PstI clones that matched the corresponding sizes on the Southern blot. Locations of these clones within the genomic DNA and cDNA of *T. gondii* are depicted in FIG. 1.

The remainder of the CPSII genomic DNA clones were sequenced using a "walking" primer approach (see FIG. 1). For example, fragments of DNA at the 5' end of clone 22-6-1 and the 3' end of clone 18-7-1 (see FIG. 1) were used to identify additional fragments on Southern blot to obtain appropriate clones encoding the full genomic CPSII coding region plus flanking regulatory sequences. The full length genomic DNA sequence of *T. gondii* CPSII locus is set forth herein as SEQ ID NO:1. The coding sequence for *T. gondii* CPSII is obtained by joining nucleotides 2430 to 2487, 3053 to 3157, 3626 to 3732, 4323 to 4479, 5607 to 5962, 6417 to 6521, 7019 to 7125, 7754 to 7860, 8051 to 8131, 9015 to 9131, 9934 to 10062, 10519 to 10667, 11403 to 11492, 11860 to 11943, 12274 to 12433, 12698 to 12777, 13222 to 13333, 13944 to 13984, 14240 to 14371, 14907 to 14994, 15288 to 15381, 15875 to 15991, 16224 to 16615, 17103 to 17495, 17948 to 18045, 18484 to 18578, 19356 to 19587, 20384 to 20545, 21071 to 21207, 21930 to 21979, 22441 to 22570, 22860 to 23004, 23374 to 23476, 23844 to 23924, 24759 to 25001, 25582 to 25677, and 26322 to 26452 of SEQ ID NO:1.

Mutant *T. gondii* were also prepared wherein CPSII activity was knocked out. Knock out of this enzymatic activity or any other de novo pyrimidine synthesis enzyme was expected to produce a pyrimidine auxotroph that would be attenuated in mammals due to the inability of mammalian cells to provide the abundant pyrimidines needed by the parasite for growth. However, salvaging the growth of *T. gondii* purely by feeding pyrimidine compounds to the parasite in the growth medium was uncertain. Thus, pyrimidine salvage in *T. gondii* was examined.

Initial experiments primarily involved an enzymatic analysis of drug resistant mutants and the incorporation of various pyrimidine analogs into *T. gondii* RNA and DNA as an indication of pyrimidine salvage when parasites were grown in either normal host or mutant host cells. All biochemical communications between the parasite and host cells cross the vacuolar membrane which is now known to contain "pores" that permit the passage of nucleobases ranging in molecular mass from 112 daltons up to 244 daltons. The size of the pores is estimated to be approximately 1500 daltons. A *T. gondii* mutant resistant to 5-fluorodeoxyuridine (FUDR-1) had lost uracil phosphoribosyltransferase (UPRT), an enzyme which is absent in normal host cells (Pfefferkorn (1978) *Expt. Parasitol.* 44:26-35). Labeling of wild-type parasites or FUDR-1 parasites with [$^3$H]deoxyuridine, [$^3$H]uridine, and [$^3$H]uracil revealed a striking pattern of pyrimidine incorporation into host or parasite nucleic acids. [$^3$H]deoxyuridine was incorporated into wild-type *T. gondii* and labeled the host cell nucleus (DNA only since deoxyuridine is mainly converted into TTP by host cell enzymes). FUDR-1 mutant parasites were not labeled with [$^3$H]deoxyuridine. [$^3$H]uridine was incorporated into wild-type parasites and labeled host DNA (nucleus) and host RNA (cytoplasm) (uridine is incorporated into the host cell UTP pool by host cell UTP pool by host enzymes). FUDR-1 mutant parasites were not labeled with [$^3$H]uridine. [$^3$H]uracil was incorporated into wild-type *T. gondii* and did not label either host DNA or RNA. FUDR-1 (UPRT knock-out) parasites were not labeled with [$^3$H]uracil.

In addition to the labeling patterns observed, wild-type RH parasites did not incorporate labeled orotic acid, orotate, cytosine, cytidine, thymine, or thymidine nucleobases. These results indicate that none of the host pyrimidine nucleotide pool is available to the parasite. Similarly, since uracil only labels the parasite, due to the parasite UPRT, which is absent in the host, the pyrimidine pools of the parasite are also unavailable to the host. Thus, there is no detectable pyrimidine traffic detected between the parasite and host.

Experiments to evaluate the feasibility of constructing pyrimidine auxotrophs of *T. gondii* were performed. Pyrimidine auxotrophy relies on the ability to feed mutant parasites a pyrimidine nucleobase, such as uracil, in culture medium in amounts that will restore parasite growth to near normal levels. Experiments were therefore conducted to measure whether uracil incorporation into parasites in culture could account for normal replication and normal growth rates. In these experiments, biochemically saturating amounts of [$^3$H] uracil (25 μg/ml) were added to the growth medium and the quantitative incorporation of label into parasite RNA and DNA was determined over a four hour interval. It was calculated using known values that about 82% of the pyrimidines incorporated into parasite nucleic acids were derived from the uracil which was added to the growth medium as a supplement.

The uracil incorporation assay, results and calculation of uracil incorporation were carried out as follows. Parasites ($2.09 \times 10^7$) were labeled for 4 hours in medium containing [$^3$H]uracil at 25 μg per ml or 0.223 μmole per ml, wherein the specific activity of uracil was 34.3 CPM per pmole (CPM=counts per minute). The results of this analysis indicated that the parasite culture incorporated $2.27 \times 10^5$ CPM in 4 hours based upon the following parameters: 1) actual incorporation per parasite 0.11 CPM per tachyzoite=0.00032 pmoles pyrimidine per tachyzoite per 4 hours; 2) tachyzoites contain 0.10 pg DNA per cell; 3) tachyzoites contain 0.50 pg nucleic acid per cell (RNA:DNA ratio is 4:1); 4) *Toxoplasma* nucleic acids contain 112:760 pyrimidine by weight, thus, tachyzoites contain 0.50×0.1476=0.074 pg of pyrimidines; 5) pyrimidine molecular weight=112; 6) tachyzoites contain 0.074 pg/112/pg/pmole=0.00066 pmoles pyrimidine in nucleic acid; 7) tachyzoites double in 6 hours representing a 1.6-fold increase in the 4 hour labeling period, which equals the synthesis of 60% of nucleic acids in 4 hours; 8) theoretical 100% incorporation=60% of 0.00066 pmoles=0.00039 pmole pyrimidine incorporated per tachyzoite per 4 hours; and 9) actual incorporation (0.00032 pmoles) therefore represents 82% of the theoretical maximum incorporation (0.00039 pmoles). Based upon these parameters, it was concluded that 82% of incorporated pyrimidines originate from uracil when it is added to medium.

An 82% efficiency of incorporation of exogenously added uracil into parasite nucleic acid was detected. However, the same pathway mediating this incorporation (UPRT) can be completely abolished with no effect on parasite growth rates in vitro or in vivo. These results indicate that the parasite may activate the uracil salvage pathway to obtain near normal levels of uracil directly from growth medium when it is available or when uracil is needed, or alternatively to completely rely upon de novo biosynthesis when uracil is unavailable extracellularly. These biochemical measurements supported the feasibility of constructing stable pyrimidine auxotrophs of *T. gondii* by constructing a knock out of a gene and enzyme activity of the de novo pathway.

Example 3

Experimental Infection and Animal Studies

Animal Studies. Adult 6-8 week old C57BL/6 and C57BL/6 B cell-deficient mice (μMT) (Kitamura, et al. (1991) *Nature* 350:423-426) were obtained from Jackson Labs Bar Harbor, ME) as were Balb/c inbred mice and balb/c mice bearing a homozygous knock-out of interferon gamma (gko). Mice were maintained in Tecniplast Seal Safe mouse cages on vent racks. µMT mice were maintained in sterile conditions.

Tachyzoite parasites were aseptically handled and purified from freshly lysed monolayers of infected HFF cells through a sterilized 3 micron polycarbonate membrane (Nucleopore, Cambridge, Mass.). Parasite concentration was scored microscopically in a hemocytometer. Purified parasites were pelleted at 1500 g for 10 minutes and washed in sterile EMEM media with no supplements and without disturbing the parasite pellet. The centrifuge tube was centrifuged once more for 2 minutes and the supernatant removed and replaced with EMEM media containing no supplements in a volume of EMEM to give a 10 times higher concentration (per/ml) of parasites than the highest dose. This was done so inoculation of 0.1 ml of this solution would equal the highest parasite dose. Parasites were gently resuspended in sterile EMEM (no additions).

Mice were immunized with $1 \times 10^6$ cps1-1 tachyzoites i.p, s.c, or i.v. once respectively or twice 14 days later with the same tachyzoite dose. At indicated times following the last immunization, mice were challenged with either low $1 \times 10^2$ or high ($1 \times 10^3$ or $1 \times 10^4$) doses of viable RH or PLK Tachyzoites i.p. (Villegas, et al. (1999) *J. Immunol.* 163:3344-3353).

Following inoculation of mice the residual volume of unused tachyzoite parasites was returned to the sterile hood and dilutions were made to represent 200 and 400 parasite plaques on 25 cm² HFF flasks assuming 100% recovery of parasites after centrifugation/resuspension and 100% percent viability. Then, following a 7 day plaque assay, actual plaques were counted, post-inoculation of mice, and the percent viable PFU ratio to parasite counts in the hemocytometer were determined microscopically in every experimental infection. Uniformly, all of the mutants described herein as well as RH parasites always fell in the range of 0.4 to 0.6 viable PFU per parasite counted using these conditions. Following inoculation of mice, mice were observed daily for signs of infection (or distress) or death.

Ex vivo Infection. Dendritic cells (DCs) were obtained from the spleens of wild-type mice and purified using EASY-SEP CDllc positive selection per the manufacturer's instructions. Briefly, spleens were harvested and injected with 1-2 ml of DNAse I/Liberase CI (Roche, Indianapolis, Ind.) followed by incubation at 37° C. for 30 minutes. Spleens were then ground through a 70-µm mesh nylon strainer and collected. DCs were then purified by CDllc magnetic positive selection and purity was verified as per manufacturer's instructions (StemCell Technologies Inc., Vancouver, BC). PECs were obtained from naïve mice and from a portion of those cells peritoneal-derived macrophages were obtained. PECs were plated at $4 \times 10^6$ cells/ml in DMEM with 10% FBS and 1× antimicrobe/antimycotic and incubated for 4 hours at 37° C. Non-adherent cells were physically removed by washing gently with medium and remaining adherent cells were examined for macrophage purity via flow cytometry for percentage of CDl1b+ cells (>90%) (Da Gama, et al. (2004) *Microbes Infect.* 6:1287-1296). The DCs, PECs, and PEC-derived macrophages obtained were plated at $2 \times 10^6$ cells/ml in infection medium consisting of EMEM with 1% FES, 1× antimicrobic/antimycotic and supplemented with 250 nM uracil (SIGMA, St. Louis, Mo.). Purified cps1-1 tachyzoites were inoculated into the wells containing specific cell populations at $5 \times 10^5$ parasites/ml and infected cultures were incubated for 12 hours at 37° C. Infected cells were examined by light microscopy and at the time of harvest typically contained 4-8 cps1-1 tachyzoites. DCs, macrophages and PECs were washed to remove any residual extracellular tachyzoites, harvested and resuspended in PBS at $5 \times 10^5$ cells/ml followed by inoculation into naïve recipient mice via tail vein injection.

Example 4

Generation of cps1-1 Mutant

A modified hit and run mutagenesis was devised for knocking out the *T. gondii* gene encoding CPSII. First, a new plasmid vector was developed for positive and negative selection analogous to the plasmid described by Fox, et al. ((1999) *Mol. Biochem. Parasitol.* 98:93-103), except using the herpes simplex virus type I thymidine kinase (TK) gene instead of bacterial cytosine deaminase in the linker region of DHFR-TS. To create this plasmid two primers, a forward primer GGG AGA TCT ATG GCT TCG TAC CCC GGC CAT CAA (SEQ ID NO:10) and a reverse primer GGG GAT CCT CAG TTA GCC TCC CCC ATC TCC CG (SEQ ID NO:11) were used to PCR amplify, via standard conditions, the ganciclovir hypersensitive TK75 HSVTK allele (Black, et al. (1996) *Proc. Natl Acad. Sci. USA* 93:3525-3529). The forward primer contains a BglII site and the reverse primer a BamHI site. Following BamHI and BglII digestion of the ~1130 bp PCR product, the TK allele was ligated into plasmid pDHFRm2m3-FLG-TS which was digested at the unique BamHI site in the FLAG epitope linker. The TK PCR primers were designed to join with pDHFRm2m3-FLG-TS to produce an in-frame insertion of TK between DHFR and TS in a plasmid called pDHFRm2m3-TK-TS, similar to previously described pDHFRm2m3-CD-TS plasmid (Fox, et al. (1999) supra). The trifunctional enzyme plasmid with TK was tested to confirm function of all three enzymes. Transfection of *T. gondii* with pDHFRm2m3-TK-TS and selection in 1 µM pyrimethamine produced parasites resistant to pyrimethamine. All subclones of *T. gondii* transfected with pDHFRm2m3-TK-TS (more than 100 clones of *T. gondii*) that are pyrimethamine resistant uniformly and concomitantly become sensitive to minute concentrations of ganciclovir. All *T. gondii* carrying a single allele of TK (or more than one allele) from pDHFRm2m3-TK-TS do not form plaques in 0.5 µm ganciclovir.

The TgH 2-11 clone of *T. gondii* CPSII was fused with the pDHFRm2m3-TK-TS plasmid to create a new plasmid suitable for modified hit and run mutagenesis. First, a 0.5 Kb segment of TgH 2-11 was removed from the 3' end by digestion with BglII and BamHI. Resulting 2.6 and 1.2 kb DNA fragments were resolved in agarose and the 2.7 kb 3' BamHI/BglII fragment was religated with the large DNA fragment from the same digest which contained the 5' side of the HindIII fragment and the plasmid DNA. The correct orientation was mapped by restriction digestion. This created a modified HindIII fragment of the CPSII gene (i.e., nucleotide positions 14622 and 21190 of SEQ ID NO:1) with a central 1.2 Kb BamHI fragment deleted (i.e., nucleotides 16882 to 17973 of SEQ ID NO:1), resulting in the removal of amino acids 723 and 1070 based on numbering of the *T. cruzi* CPSII protein (see also FIG. 1). Finally, the trifunctional DHFR-TK-TS enzyme from pDHFRm2m3-TK-TS was added into the deleted HindIII (delta 1.2 Kb BamHI) plasmid by digestion of pDHFRm2m3-TK-TS with NheI and XbaI and ligation into the unique XbaI site of the deleted 1.2 Kb BamHI HindIII TgH 2-11 plasmid. A clone with inverted directionality of DHFR-TK-TS and CPSII expression was obtained and this plasmid was called p53KOX3-1R. The targeted disruption of the endogenous *T. gondii* CPSII gene with p53KOX3-1R involved insertion of this plasmid by a single cross-over recombination to yield a C-terminal truncated CPSII with the 1.2 Kb BamHI deletion described above with a normal endogenous promoter but no untranslated 3' regulatory region, and a duplicated CPSII allele with a N-terminal truncated (deleting everything before the HindII site at amino acid 663) CPSII and a normal non-translated 3' regulatory region but no *T. gondii* promoter. Thus, single homologous crossover between truncated and deleted CPSII contained in p53KOX3-1R and the endogenous *T. gondii* locus generated 5'- and 3'-truncated cpsII alleles at the CPSII genomic locus which failed to produce a functional CPSII protein.

Wild-type RH parasites were transfected with p53KOX3-1R and selected in the presence of 1 µM pyrimethamine and 200 µM uracil. Following lysis of the primary flask with p53KOX3-1R transfected parasites after 4 days of growth in 1 µM pyrimethamine plus 200 µM uracil, parasites were diluted 1:100 and inoculated into a second flask of fresh HFF cells under the same growth conditions. The second growth cycle is necessary for efficient selection of stable plasmid integration under pyrimethamine selection. Thus, transfected parasites must undergo approximately 25 cycles of replication prior to subcloning and screening for potential mutants. It is obvious that any mutant with any moderate or significant defect in growth rate would be quickly diluted in number by rapidly growing parasite in the mixed cultures. Following the second growth cycle of the primary transfection of p53KOX3-1R in pyrimethamine plus uracil medium, parasites were subcloned into a duet of 96-well trays with or without uracil supplementation. Individual wells were scored microscopically at 4-5 days post subcloning to mark wells with one viable parasite (a subclone) based on the presence of a single zone of parasite growth in that well. Typically 10 to 20 wells of a 96-well tray were successful subclones. Successful subclone wells were individually mixed by washing up and down with a 50 µl pipette to mix parasites to infect the whole HIFF monolayer in that well. Typically 3 further days of incubation produced total well lysis and many free infectious extracellular parasites. From these wells parasites were individually picked and inoculated (separate additions) into parallel wells of HFF cells in 96-well trays that contained the same growth medium (pyrimethamine plus uracil 200 µM) or trays only containing pyrimethamine 1 µM. If the CPSII locus failed to produce a functional CPSII protein in any of the *T. gondii* subclones a difference in growth rate could be detected by visual microscopic examination of identically inoculated wells. No less than 1 µl was tested at this point due to reliability of transfer and parasite number of inoculum. Thus, the concentration of residual uracil in the "no uracil" tray was actually still ~1 µM. More than 800 subclones of *T. gondii* were eventually screened using the above assays, with more than 200 subclones being generated in each of four independent selections and transfection experiments with p53KOX3-1R. Following an initial assessment of growth rate estimate in the plus uracil or "minus uracil" condition, a number of putative clones were evaluated in a second test of uracil growth dependence. Following a second positive test of uracil growth dependence, a third test using 25 $cm^2$ HFF flask was performed under conditions of a uracil concentration less than 0.1 µM. From these selections four *T. gondii* mutants were obtained which had a quantitative assessment of at least a detectable growth dependency on addition of uracil to the growth medium. These were putative *T. gondii* uracil auxotrophs. One independent transfection produced mutant cps1, a second independent transfection produced mutant cps2, and a third independent transfection produced mutants cps3 and cps4. Each of these mutants was found to be highly sensitive to ganciclovir, loosing ability to form plaques in only 0.5 µM ganciclovir. The mutants were grown and genomic DNA was isolated from each mutant and wild-type RH parasites from the contents of 2 or more 25 $cm^2$ flasks for each DNA isolation to document integration of targeting disruption plasmid p53KOX3-1R into the endogenous CPSII locus by homologous recombination. The plasmid p53KOX3-IR could form two general patterns of integration based on recombination either 5' of the BamHI deletion, or recombination 3' of the BamHI deletion. HindII digested cps1, cps2, cps3, cps4 and RH parasite genomic DNA was subjected to Southern blot analysis and hybridized to labeled gel-purified 6.6 Kb HindIII fragment of TgH 2-11 encoding *T. gondii* CPSII sequences. A 5' cpsII integration would produce at least fragment sizes of ~6.5 Kb and 7.8 Kb following digestion with HindIII, whereas a 3' cpsII integration site would produce at least fragments of 5.0 Kb and 7.8 Kb when digested with HindIII. If the plasmid were duplicated at the time of integration, which is seen frequently with the pDHFRm2m3-TS plasmid backbone (Sullivan, et al. (1999) *Mol. Biochem. Parasitol.* 103:1-14), then an additional fragment at 7.8 or 9.5 Kb could be generated by integration at endogenous CPSII. Each of the selected putative cpsII mutants had undergone an integration of plasmid p53KOX3-1R at either the 5' location (cps1, cps2, cps3, or the 3' location, cps4). Mutant cps4 had multiple bands between 7.8 and 9.5 Kb and additional bands at higher molecular weights suggesting integration of plasmid at CPSII and other loci. In contrast, mutants cps1, cps2 and cps3, obtained in independent transfections and selection, had identical patterns of hybridization to CPSII DNA suggesting that the targeting plasmid p53KOX3-IR only integrated into the 5' site of the CPSII target region and each mutant had duplicated the plasmid DNA upon integration (the 9.5 Kb DNA band). Thus, successful targeting to and disruption of the *T. gondii* CPSII locus was demonstrated.

Each of the mutants (cps1, cps2, cps3, and cps4) had a phenotype of uracil growth dependence. However, all of these mutants are somewhat "leaky" in that there was not an absolute growth (replication) dependence on uracil addition to the growth medium for replication. Each of these mutants grows at a moderate (½ of normal) growth rate for the first 2 days following infection of a host cell producing vacuoles that contained 16 to 32 parasites by 3 days post infection. In contrast, RH parasites are lysed out of their primary vacuoles at this time (3 days, >64 parasites). However, the cps mutants slow after 3 days and many parasites never (about ⅓) break out of their primary vacuole. If the primary vacuole breaks, a few parasites can be detected at the site of infection but the infection site always involves a small zone of infection that never forms a visible plaque in a standard 7 day plaque assay. To quantitate growth of these mutants, HFF flasks were inoculated with opal or cps2 parasites (about a multiplicity of infection (MOI) of 1 parasite per 20 HFF cells). After 2 hours of attachment and invasion (all of these mutants have normal attachment and invasion phenotypes as scored by counting percent entered parasites into host cells as a function of time post-inoculation), different concentrations of different pyrimidine compound was added to parallel infected HFF flasks. As a function of time post pyrimidine addition (t=0 hour) the number of parasites per vacuole was scored for 50 vacuoles as described by Fox et al. ((1999) supra). The number of parasite doublings was calculated based on 1 parasite entering each primary vacuole. Thus, 1 doubling=2 parasites per vacuole, 3 doublings=8 parasites per vacuole, and 5 doublings=32 parasites per vacuole. The pyrimidine dependence of cps1 and cps2 replication (doublings of parasites in the vacuole) was plotted graphically. Relatively low concentrations of uracil, uridine, deoxyuridine, cytidine, and deoxycytidine completely rescued the growth rate of cps1 and cps2 mutants to wild-type RH levels. This pattern of rescue is precisely consistent with the limited set of salvage enzymes available to *T. gondii* suggesting that these mutants have a defect in de novo pyrimidine synthesis that can be corrected by salvage of pyrimidines from exogenously supplied pyrimidines in growth medium in vitro. Cytosine, as expected, did not rescue at all. The response to thymine and thymidine was additionally informative about the cause of the growth defect in cps1 and cps2. Moderate concentrations of thymine or thymidine partially rescued the replication of cps1 and cps2, whereas very high concentrations of these pyrimidines did not rescue replication. This is believed to be caused by the putative defect in the cps1 and cps2 mutants which is a reduced "pool" size of UMP. If UMP pools (ultimately used for RNA and DNA synthesis) are lowered it follows that a resulting decrease in TMP pools is expected since UMP is the precursor of TMP in *T. gondii* and all other apicomplexan parasites which normally lack TK activity. However, since cps1 and cps2 now express a TK activity carried into the parasite by the p53KOX3-1R plasmid, exemplified by sensitivity of these mutants to ganciclovir (specific to HSV TK), feeding parasites either thymine or thymidine is expected to increase TMP pools. Thus, it appears that moderate levels of thymine or thymidine partially rescue growth of cps1 and cps2 by restoring TMP pools. These data indicate that there is indeed a defect in accumulation of UMP and TMP pools in the cps1 and cps2 mutants. The defect is most easily rescued by feeding the parasite pyrimidines that can be incorporated (uracil, uridine, deoxyuridine, cytidine, deoxycytidine) and can be partially rescued with thymine or thymidine (the TMP pool). Since the parasite has no mechanism to convert TMP back to UMP there is still a defect in the UMP pool in cps1 and cps2 even with added thymine or thymidine and rescue is never complete. The ability of cps1 and cps2 mutants to form plaques on HFF monolayers in the standard 7 day assay paralleled the pyrimidine dependence of parasite replication in vacuoles.

The cps1 and cps2 mutants were inoculated intraperitoneally (i.p.) into balb/c mice to measure parasite virulence compared to virulent RH parasites. Both mutant cps1 and cps2 had equal virulence as RH parasites in balb/c mice (Jackson Labs), killing all mice within 10 days of i.p. inoculation (group size was four mice per parasite strain). Only 100 parasites (~50 PFU) of each parasite strain was needed to kill all mice in each group. This pattern of virulence can be understood by re-examining the pyrimidine dependence of cps1 and cps2 growth. Uridine is believed to be the pyrimidine responsible for virulence of cps1 and cps2 in mice. Only 5 μM uridine completely rescues normal plaque size of cps1 and cps2 in vitro. Plasma concentrations of uridine in mice are approximately 5 to 10 μM. Thus, as suggested by the "leaky" phenotype, cps1 and cps2 are not pyrimidines auxotrophs and therefore grow normally in mice and are not attenuated.

It is believed that the single recombination into the CPSII locus only partially disrupted expression of CPSII activity in cps1 and cps2. Accordingly, cps1 and cps2 mutants were not "complete" pyrimidine auxotrophs and did not lack a functional CPSII protein. Cps1 and cps2 were thus utilized as the parent strain background in which to select a more highly attenuated pyrimidine auxotroph mutant. Both the cps1 and cps2 mutants express a TK allele which was inserted into the CPSII locus. Hence, cps1 and cps2 mutants were grown for several generations in the absence of pyrimethamine and in the presence of 200 μM uracil. Then, approximately $1-2 \times 10^5$ cps1 or cps2 parasites was inoculated into a 25 cm$^2$ HFF flask and selected negatively in the presence of 10 μM ganciclovir plus 200 μM uracil. This is 20 times the dose of ganciclovir necessary to completely block plaque formation of these mutants. After approximately 10 days, an outgrowth of viable parasites was observed for both the cps1 and cps2 selections. The parasites which were growing in ganciclovir plus uracil were subcloned in ganciclovir and uracil (same conditions) and individual clones, cps1-1 and cps2-1, were identified from each parent, respectively, for further analysis. The cps1-1 and cps2-1 subclones were first tested for their sensitivity to pyrimethamine. The theory of negative selective in only ganciclovir is that a mutant that disrupts expression of the TK allele should simultaneously acquire sensitivity to pyrimethamine due to loss of the expression of the fused trifunctional DHFR-TK-TS transgene(s) inserted into the CPSII locus of cps1 and cps2. Indeed, loss of sensitivity to ganciclovir (10 μM) in cps1-1 and cps2-2 correlated perfectly with a gain of sensitivity to pyrimethamine (1 μM) in both replication and plaque assays.

Evaluation of the pyrimidine dependence of growth of cps1-1 and cps2-1 compared to the cps1 and cps2 parents, respectively, revealed that the newly selected mutants (cps1-1 and cps2-1) were absolute pyrimidine auxotrophs and lacked a functional CPSII protein. No pyrimidine compound at less than 25 μM could rescue plaque formation of cps1-1 or cps2-1. Further, only uracil and deoxyuridine provided significant growth rescue, and only in relatively high doses. Uridine was quite poor at rescue of plaque formation in cps1-1 and cps2-1. In pyrimidine concentrations up to 200 μM only uracil completely rescued plaque formation of cps1-1 and cps2-1. In addition, as expected from ganciclovir resistance (no TK expression) phenotype, no response was detected to thymine or thymidine.

A more detailed growth response to pyrimidine, measured as parasite replications (doublings) was performed for cps1-1 and cps2-1 and compared to the results previously obtained for cps2 and cps2. In the absence of added pyrimidines or the presence of even high concentrations of thymine, thymidine, deoxycytidine, cytidine, or cytosine, a cps1-1 or cps2-1 parasite that entered a vacuole in a host HFF cell remained as a single non-replicated parasite, not only in a 36-hour replication assay, but also upon continued incubation of infected cultures in vitro. Uridine rescue was poor, with a slow restoration of growth at very high amounts, >400 μM. Deoxyuridine rescue was significant, but again, full growth rate was not restored at any concentration of deoxyuridine. Rescue with uracil was robust, but only in a limited range of concentration. Full restoration of growth rate in cps1-1 and cps2-1 was possible only with uracil added between 200 and 400 μM. Lower concentrations of uracil rescued poorly and concentrations of uracil higher than ~500 μM reduced the growth rate of cps1-1 and cps2-1 significantly. In fact, cps1-1 and cps2-1, as well as cps1 and cps2, do not even form plaques in 2000 or 4000 μM uracil, conditions with no effect on RH parasite plaques. This result is dichotomous and suggests that there is an intimate, regulatory loop in *T. gondii* pyrimidine salvage that is down-regulated by very high concentrations of uracil. This phenotype can only be observed in *T. gondii* pyrimidine auxotroph mutants, not in wild-type parasites with intact de novo pyrimidine synthesis pathways.

The cps1-1 and cps2-1 mutants were examined for virulence in balb/c mice. An i.p. administered inoculum of 100 parasites of either cps1-1 or cps2-1 had no measured virulence in balb/c mice, compared to the same dose of RH, cps1 or cps2 which were virulent. The avirulence of cps1-1 and cps2-1 correlates well with the pyrimidine dependence of parasite growth in vitro. The high concentrations of pyrimidines needed for growth of mutant cps1-1 and cps2-1 are simply not available in mammals such as mice. Other mammals including humans and other vertebrates are also not expected to have sufficiently high pyrimidine concentration to support growth of these mutants.

Higher dose virulence studies were also performed for the mutant cps1-1. Pyrimidine auxotroph cps1-1 was completely avirulent in Balb/c mice at doses equal to or greater than $10^7$ parasites delivered by i.p. inoculation.

The ability of the pyrimidine auxotroph mutants of the present invention to protect against infections was demonstrated. After 40 days i.p. inoculation of cps1-1 in balb/c mice, the same group of 4 mice were challenged with 200 parasites of the virulent RH strain (a 100% lethal dose) Mice originally inoculated with $10^7$ or $10^5$ cps1-1 parasites were completely protected from RH challenge. In contrast, mice receiving only the lowest dose of $10^3$ cps1-1 parasites were completely unprotected from this RH parasite challenge. Thus, the pyrimidine auxotroph mutant given at appropriate dose is capable of protecting mice from lethal RH parasite challenge.

Safety of the pyrimidine auxotroph mutants of the present invention was also evaluated. A group of balb/c mice were inoculated with $10^8$ cps1-1 parasites and all survived at least 24 days post inoculation. A more rigorous test of safety was performed in immunocompromised mammals. Before the present invention, no *T. gondii* mutant had been isolated that would itself not kill gamma interferon homozygous knock-out mice (gko mice) (Jackson Labs, strain JR2286) (Radke and White (1999) *Infect. Immun.* 67:5292-5297). Gamma interferon homozygous knock-out mice were inoculated with various doses of the pyrimidine auxotroph cps1-1 or a lethal low dose of RH parasites. Doses of cps1-1 (i.p. administered) at $10^2$, $10^4$ and $10^6$ did not kill any of the 4 gamma interferon homozygous knock-out mice in each group, whereas all mice receiving RH parasites died within 8 days. Mutant cps2-1, was also avirulent in homozygous gamma interferon knock-out mice. Thus, the pyrimidine auxotroph mutants of the present invention are the first described *T. gondii* parasite isolates that are completely attenuated even in severely immunocompromised mice. The cps1-1 and cps2-1 mutants attach and invade as efficiently as wild-type RH parasites in the absence or presence of pyrimidine in vitro in HFF cells. Thus the growth defect seen in immunocompromised mice is due to a block in intracellular replication only.

The pyrimidine growth dependence of mutant cps1-1 on the pyrimidine salvage pathway was further documented in thymidine interference experiments. Mutant cps1-1 plaques well in 250 μM uracil or deoxyuridine, but not in 1000 μM thymidine. Since thymidine at 1000 μM is known to inhibit approximately 90% of the parasite nucleoside phosphorylase activity specific for cleavage of deoxyuridine (Iltzsch, (1993) *J. Euk. Micro.* 40:24-28), growth of cps1-1 was tested in combinations of 1000 μM thymidine and 250 μM uracil or 250 μM deoxyuridine. All pyrimidine salvage in *T. gondii* must pass through uracil and UPRT conversion of uracil to UMP. In contrast, thymidine has no effect on UPRT activity. Thus, if growth of cps1-1 were dependent on deoxyuridine supplementation then replication in this condition may be inhibited by co-supplementing with 1000 μM thymidine. It was found that thymidine did block deoxyuridine-dependent growth of cps1-1 in these experiments by inhibiting nucleoside phosphorylase. However, thymidine did not affect UPRT or uracil dependent growth of cps1-1. Thus, when cps1-1 is grown in deoxyuridine the parasite strictly requires nucleoside phosphorylase activity to cleave deoxyuridine for growth. These data show cps1-1 and cps2-1 to have a marked defect in de novo pyrimidine synthesis and depleted UMP pools. Thus, cps1-1 and cps2-1 rely strictly on pyrimidine salvage enzymes for growth and further, the HFF host cell in vitro cannot supply sufficient pyrimidines for growth of cps1-1 or cps2-1. These data indicate that the pyrimidine auxotroph mutants cps1-1 and cps2-1 can be used in screening assays to identify compounds as inhibitors of various salvage enzymes when the replication of *T. gondii* is dependent on salvage pathways. Such potential inhibitors can only be identified using a pyrimidine auxotroph such as provided in the instant invention.

Survival, persistence, and reversion potential of pyrimidine auxotroph mutants cps1-1 and cps2-1 were also assessed. Ability of *T. gondii* mutants cps1-1 and cps2-1 to survive and persist intracellularly was determined in an in vitro survivability assay. From microscopic examination of cps1-1 and cps2-1, it is known that in the absence of pyrimidine addition the mutants attach and invade at normal efficiency and a single parasite can be observed in a small vacuole. With no pyrimidines added to growth medium the single parasite in the small vacuole remains as a non-replicated single parasite indefinitely. After 2 days of pyrimidine starvation, typically one bright blue (translucent) circular structure or 2 structures about 1 micron in diameter become apparent in many parasites and in most parasites by day 3 to day 4 of pyrimidine starvation. Thus, an assay was devised to measure whether the single non-replicating parasites inside the host cells were viable or non-viable. HFF flasks were inoculated with various parasite doses. At t=0 hours medium was changed, and pyrimidine starvation started. Then, at various time points (in days), cultures of pyrimidine starved cps1-1 and cps2-1 parasites were "rescued" by addition of 300 μM uracil. Incubation of rescued cultures was performed for 7 days in a plaque assay. All cultures were then examined for evidence of small micro-plaques by microscopic examination. Cultures were also stained for normal plaques and plaques were counted. The data from this assay indicates that parasites rapidly lose viability (loss of pyrimidine rescue). This loss roughly correlates with the appearance of the small bright blue circular structure in the intracellular non-replicating parasite that is starved of pyrimidines. Thus, simple culture of cps1-1 and cps2-1 in normal growth medium results in a pyrimidine starvation that efficiently kills intracellular cps1-1 and cps2-1 parasites. Thirty-two days of pyrimidine starvation was sufficient to kill at least $10^6$ PFU which was added to a single 25 cm$^2$ HFF flask. In these experiments it was also shown that addition of more than $2 \times 10^7$ cps1-1 or cps2-1 parasites (MOI>10 parasites per HFF cell) to a single 25 cm$^2$ HFF flask resulted in all HFF cells becoming multiply infected with parasites each being a single parasite in an individual vacuole. Unexpectedly, even at these high MOI's of infection of HFF the host cell appeared perfectly normal, other than having 5 to 10 parasites within each cell on average. Thus, cps1-1 and cps2-1 also provide a useful strain of *T. gondii* to further analyze host-parasite interaction biology of obligate intracellular parasites. As demonstrated herein, these strains are particularly useful in further cell biological evaluation of the pyrimidine starvation phenotype or death phenotype.

To assess reversion, $10^6$ to $10^7$ cps1-1 or cps2-1 parasites were periodically inoculated into HFF flasks supplemented with 5 μM uridine. This concentration of uridine is sufficient to rescue the parent strains (cps1 and cps2) of cps1-1 and cps2-1. However, it is insufficient to support any growth of cps1-1 or cps2-1. In multiple experiments involving a total of $5 \times 10^8$ to $1 \times 10^9$ parasites of cps1-1 and cps2-1, no revertants were observed.

CPSII enzyme activity and thymidine kinase activity in parasite protein extracts derived from mutant or wild-type parasites were also assessed. In these experiments, parasites were grown under appropriate conditions in multiple 25 cm² flasks or in 150 cm² flasks until lysis of the host monolayer. Extracellular parasites were purified through 3 micron nucleopore filters and parasites in parasite pellets were lysed in the presence of protease inhibitors to generate protein extracts for enzyme assays. The CPSII and TK enzyme activities in the various parasite extracts was determined in enzyme assays. The enzyme activity data indicates that the cps1 and cps2 mutants are partial knock-outs of CPSII activity compared to the activity measured in the wild-type RH strain. Furthermore, as the bulk of data from pyrimidine rescue experiments indicated, no CPSII activity was detected in pyrimidine auxotroph mutants cps1-1 and cps2-1. Measurement of TK activity corresponded with previously determined sensitivity to ganciclovir. Parasites that were sensitive to ganciclovir had TK activity, whereas parasites that became resistant to ganciclovir lost TK activity. These measurements of CPSII enzyme activity confirm that cps1-1 and cps2-1 mutants lack a functional cpsII enzyme which results in blocking de novo synthesis of pyrimidines.

Example 5

*T. gondii* Vaccine to Elicit Cell-Mediated Immunity

This example describes the host immune response to cps1-1 using various routes of immunization, as well as APC cell-dependence of immune control of infection, the type of immunity responsible for long lasting protection and, the dynamics of cell and cytokine profiles during the first eight days of exposure to cps1-1.

Cps1-1 Tachyzoites Induce a Completely Protective Long Lasting Immune Response Against High Dose Lethal Challenge with Hypervirulent RH Tachyzoites. Having demonstrated herein that live attenuated cps1-1 tachyzoites protect Type II *T gondii* resistant BALB/C mice against a low dose lethal challenge in a single inoculation dose, immunization with live attenuated cps1-1 and mechanisms of immune protection elicited in the priming phase of the highly sensitive C57BL/6 mouse background was analyzed. Live attenuated cps1-1 tachyzoites were effective in producing immunological protection against high dose lethal challenge in C57Bl/6 mice. C57BL/6 mice were immunized intraperitoneally twice with $1 \times 10^6$ cps1-1 tachyzoites, 14 days apart, then challenged i.p. 4 weeks after the final immunization with a high $1 \times 10^3$ lethal dose of RH tachyzoites. Mice immunized with the cps1-1 vaccine were completely protected (100%) when followed up to 30 days post-challenge, whereas naïve mice uniformly succumbed to infection by day 10 post-challenge. Cps1-1 immunized mice were continuously monitored over 18 months post-challenge and uniformly survived challenge infection to old age, indicting that the cps1-1 vaccine induces long lasting protective immunity.

Intravenous Immunization with cps1-1 Tachyzoites Alone or ex vivo cps1-1 Infected DCs or PECs Induce Long Lasting Protective Immunity. Numerous studies have reported that the route of immunization is a critical factor in determining vaccine effectiveness (Bourquin, et al. (1998) *Infect. Immun.* 66:4867-4874; McLeod, et al. (1988) *J. Immunol.* 140:1632-1637; Aline, et al. (2004) *Infect. Immun.* 72:4127-4137). To explore the importance of the route of vaccination to the development of long lasting immunity in the cps1-1 model, C57Bl/6 mice were immunized either once i.p., or subcutaneously (s.c.), or twice i.p, or s.c. with $1 \times 10^6$ cps1-1 tachyzoites. Four weeks post-immunization, mice were challenged i.p. with a high $5 \times 10^4$ dose of high in vitro passaged hypervirulent Type II strain PLK tachyzoites and percent survival was monitored to 30 days post-challenge (Howe, et al. (1996) *Infect. Immun.* 64:5193-5198; Sibley & Howe (1996) *Curr. Top. Microbiol. Immunol.* 219:3-15). Mice immunized twice i.p. were completely protected against this high dose PLK challenge while mice immunized once i.p. showed lower survival (FIG. 2). Unexpectedly, mice immunized s.c. did not survive challenge infection (FIG. 2). The previously observed protection conferred by immunization with temperature-sensitive strain ts-4 tachyzoites (McLeod, et al. (1988) supra) must require parasite replication which does not occur in the non-replicating cps1-1 vaccine.

Figure 2A:
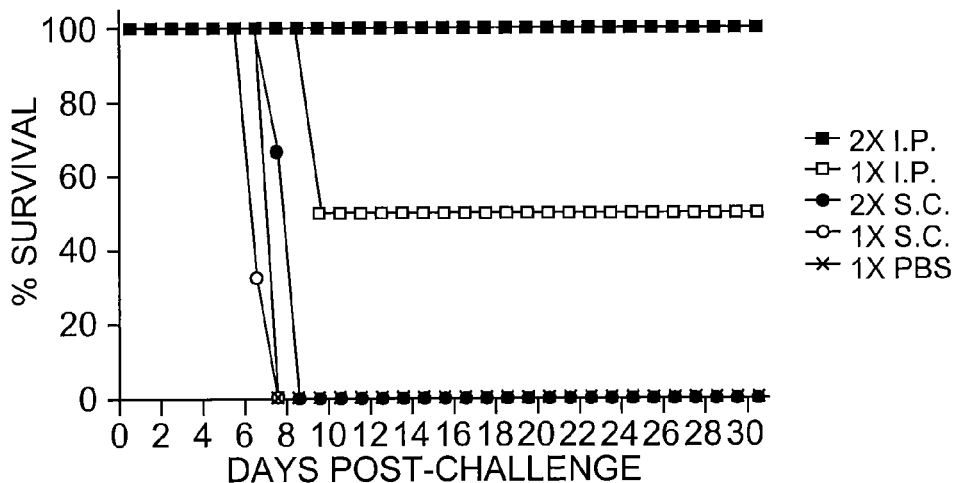
FIG. 2A, C57Bl/6 mice were unimmunized or immunized with either 1×s.c., 2×s.c., 1×i.p. or 2×i.p. and challenged 1 month after final immunization with $10^3$ RH and percent survival was measured.
Figure 2B:
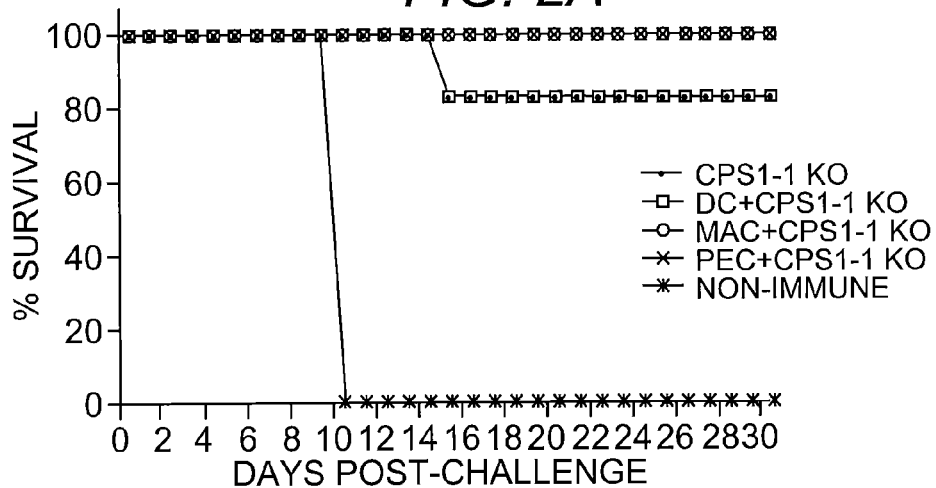
FIGS. 2B and 2C, C57BL/6 mice were unimmunized or immunized once with either cps1-1 knock-out alone or DC, pMAC, or PEC loaded ex vivo for 12 hours with cps1-1 knock-out. Two months (FIG. 2B) or 6 months (FIG. 2C) post-i.v. immunization, mice were challenged with $10^2$ tachyzoites of RH i.p. and percent survival was measured out to 30 days post-challenge. Data represents one experiment performed with 6 mice per immunization group.
Figure 2C:
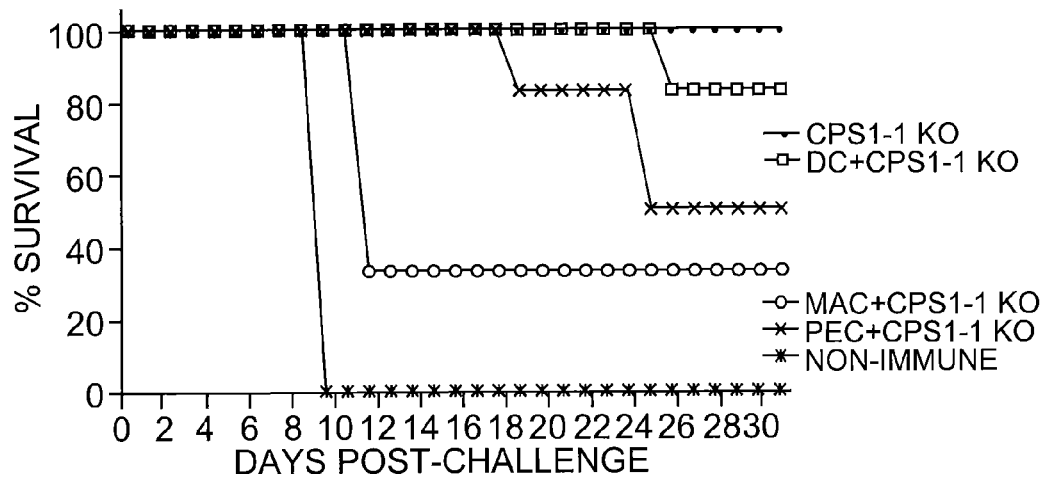

To further elucidate effective routes of cps1-1 immunization, it was determined whether immunizations given intravenously (i.v.) were capable of inducing protective immunity against lethal RH challenge. Mice were immunized once with $1 \times 10^6$ cps1-1 tachyzoites i.v. then challenged 2 months (FIG. 2A) or 6 months (FIG. 2B) post-immunization with a low dose ($1 \times 10^6$) of RH tachyzoites i.p. and survival was monitored. All mice immunized i.v. with cps1-1 survived challenge whereas all naïve control mice given PBS alone succumbed to challenge infection. Unexpectedly, naïve mice infected i.v. with RH tachyzoites succumbed 2 days earlier than naïve mice injected i.p., indicating that parasitemia is critical to lethal pathogenesis. Since the i.v. route was effective in inducing long lasting protective immunity in a single inoculation dose and previous studies exploring the use of professional APCs loaded ex vivo with antigen have achieved protection against lethal challenge, the effectiveness of specific host APC types in the development of protective immunity was examined (Bourguin, et al. (1998) *Infect. Immun.* 66:4867-4874; Aline, et al. (2004) *Infect. Immun.* 72:4127-4137). Mice were immunized once with ex vivo cps1-1 infected DCs, PECs and macrophages derived from resident PECs i.v. and then were challenged at 2 (FIG. 2A) or 6 months (FIG. 2B) post-immunization with a low dose of RH tachyzoites and survival was monitored. Immunization with ex vivo cps1-1 infected DCs, PECS, or PEC-derived macrophages resulted in nearly complete survival of RH challenged mice at 2 months post-immunization and was not significantly different from mice immunized with cps1-1 i.v. (FIG. 2A). When lethal challenge was administered at 6 months (FIG. 2C), differences in percent survival of mice immunized with ex vivo cps1-1 infected DCs (83% survival), PECs (50% survival), and PEC-derived macrophages (33% survival) were observed and all cps1-1 immunized mice survived longer than PBS naïve control mice (all p-values=0.0009). Percent survival of mice immunized with ex vivo cps1-1 infected DCs and PECs was of similar statistical significance to mice immunized i.v. with cps1-1 tachyzoites, indicating that although peritoneal macrophages were effective at inducing protection at 2 months, this protection was not as long lasting as that induced by ex vivo cps1-1 infected DCs and PECs (compare FIGS. 2B and 2C)

The Potent Long Lasting Protective Immune Response Elicited by Immunization with Live Attenuated cps1-1 Vaccine is Primarily CD8⁺ T Cell-Mediated and Can Re Adoptively Transferred. The paradigm of a Th-1 inflammatory response inducing cell-mediated immunity providing long term protection involving both CD4+ and CD4+ T cells for resistance to active *T. gondii* infection is well-established (Suzuki and Remington (1988) *J. Immunol.* 140:3943-3946; Gazzinelli, et al. (1991) *J. Immunol.* 146:286-292). Although during the innate response NK cells may play a role in controlling the initial parasite infection, the primary effector cell population responsible for the adaptive cell-mediated protective response is CD8⁺ T cells (Subauste, et al. (1991) *J. Immunol.* 147:3955-3959; Hakim, et al. (1991) *J. Immunol.*

Figure 3A:
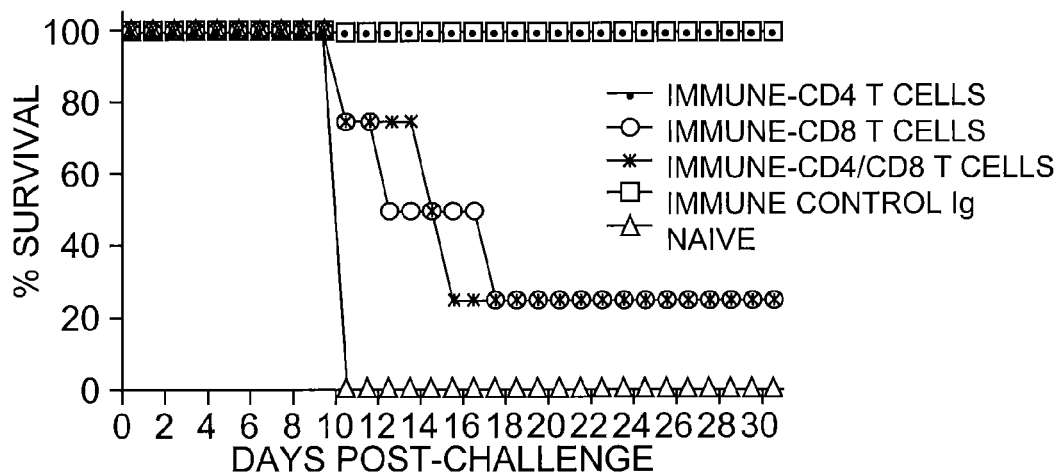
FIG. 3 shows the effect of antibody depletion of T cells, lack of B cells, and adoptive transfer of immune cells on survival against lethal challenge. C57Bl/6 wild-type and μMT mice were immunized following an established protocol. One month after final immunization, wild-type mice were treated with either control Ig or antibody specific for CD4, CD8, or both CD4 and CD8 (FIG. 3A).
FIG. 3B, both immunized and unimmunized μMT mice were left untreated, simultaneously challenged with $10^3$ RH parasites i.p. and percent survival was measured.
FIG. 3C, C57Bl/6 mice were immunized as described above, then three weeks post-final immunization whole splenocytes, CD19$^+$ and CD8$^+$ splenocytes were harvested and either $4\times10^7$ whole splenocytes, $1\times10^7$ CD8$^+$ T cells, or $5\times10^6$ CD19$^+$ B cells were transferred to naïve recipient mice. Twenty-four hours after transfer mice were challenged with $10^3$ RH parasites and monitored for survival. All experiments were performed with n=4 per group and repeated twice with similar results. The data are representative of the two experiments with similar results.
Figure 3B:
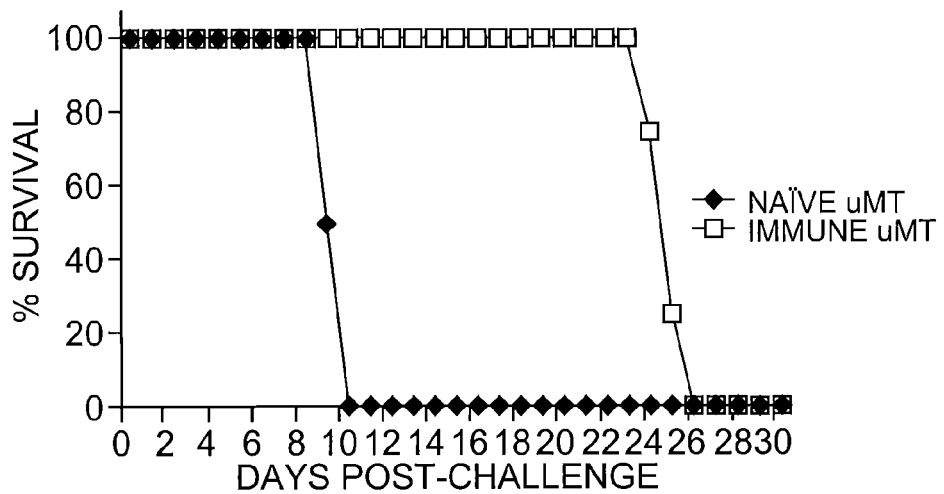

147:2310-2316). To determine whether CD8+ T cells are the primary effector cells responsible for the adaptive immune response after i.p. immunization with cps1-1, antibody depletion of specific T cell populations from immunized mice was used and survival of T cell-depleted mice was measured against lethal challenge. As a control for determining if T cells are the primary effector arm of adaptive immunity responsible for long lasting protection in the present vaccine model, B cell-deficient (μMT) mice were also immunized to assess whether B cells are required for immune responses leading to protective immunity. Wild-type C57Bl/6 and μMT mice were immunized i.p. with cps1-1. C57Bl/6 mice were then antibody depleted of either CD8+ T cells, CD4+ T cells, or both CD4+ and CD8+ T cells whereas μMT mice were not treated. All immunized mice were high dose challenged with $1 \times 10^3$ RH tachyzoites i.p. and monitored for survival. It was observed that 100% of CD4+ T cell-depleted mice survived whereas only 25% of either CD8+- or CD8+/CD4+-depleted mice survived the challenge infection (FIG. 3A). Although cps1-1 immunized μMT mice survived longer than non-immunized naïve μMT mice, all immunized μMT mice succumbed to infection by day 27 post-challenge (FIG. 3B). This result indicates that B cells may adopt a subordinate role as effector cells via antibody production, or that during host response to immunization a deficiency occurs in the development of an effective memory CD8+ T cell population leading to a less potent protective response (Sayles, et al. (2000) Infect. Immun. 68:1026-1033; Langhorne, et al. (1998) Proc Natl. Acad. Sci. USA 95:1730-1734; Matter, et al. (2005) Eur. J. Immunol. 35:3229-3239). These results demonstrate that CD8+ T cells are the main effector cell involved in the protective immunity induced by immunization with cps1-1.

Figure 3C:
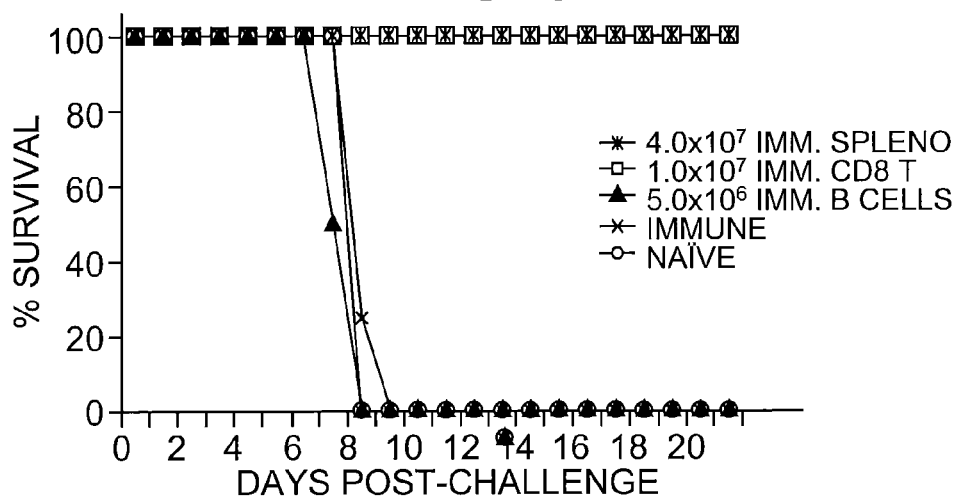

Adoptive transfer was also carried out to confirm that CD8+ T cells were the primary effector mechanism against T gondii infection that develop in response to immunization with cps1-1. Splenocytes were harvested 30 days after cps1-1 immunization and purified CD8+ T cells, B cells, or whole splenocytes were adoptively transferred into naïve recipients. Recipient naïve mice were then challenged with $1 \times 10^3$ RH tachyzoites and percent survival was monitored. Mice receiving $1 \times 10^7$ whole splenocyte-derived cells or $5 \times 10^6$ B cells succumbed to infection by day 10 post-challenge. In contrast, all naïve mice receiving $1 \times 10^7$ purified CD8+ T cells or $4 \times 10^7$ whole spleen cells survived challenge infection (FIG. 3C). These results confirm that T. gondii-pecific CD8+ T cells induced by immunization with cps1-1 are the primary effector cells required for adaptive immunity and long lasting protective immunity.

IgG2a is Present in Serum from cps1-1 Immunized Mice Indicative of a Th-1 Immune Response. Specific antibody subclasses are one indicator of the type of T helper cell response induced by infection. A T helper type I cell-biased population induces the production of the immunoglobulin subclass IgG2a (Snapper & Paul (1987) Science 236:944-947; Sornasse, et al. (1992) J. Exp. Med. 175:15-21). Infection with virulent T gondii parasites, as well as immunization with an attenuated temperature sensitive mutant (ts-4) or DCs pulsed with T. gondii antigens, result in IgG positive serum titers that predominantly include the IgG2a subclass (Bourguin, et al. (1998) supra; Waldeland, et al. (1983) J. Parasitol. 69:171-175; Johnson & Sayles (2002) Infect. Immun. 70:185-191). C57Bl/6 mice were immunized with cps1-1 and sera were collected four weeks after the final immunization and examined for titers of whole IgG, IgG1 and IgG2a. Anti-toxoplasma serum titers of total IgG and subclasses IgG1 and IgG2a were nearly equivalent (Table 1). These results for serum IgG titers were similar to those previously reported in response to immunization with ts-4 (Waldeland, et al. (1983) supra). The presence of significant levels of IgG2a in sera from cps1-1 immunized mice indicates the induction of a Th-1-biased T helper cell response.

TABLE 1

| IgG | Mean Titer | SEM | Mean A450 | SEM |
| --- | --- | --- | --- | --- |
| IgG H + L | 14103.8 | 781.8 | 0.546 | 0.011 |
| IgG1 | 12020.3 | 2921.9 | 0.095 | 0.009 |
| IgG2a | 13616.1 | 1126.3 | 0.398 | 0.027 |

Titers were calculated via dilution at which samples from immunized mice were equivalent to unimmunized control sera. Absorbance at 450 nm was recorded for 1:100 dilutions. All experiments were performed with n = 4 mice per group. The data are representative of two experiments with similar results and indicate the mean ± SEM.

Figure 4A:
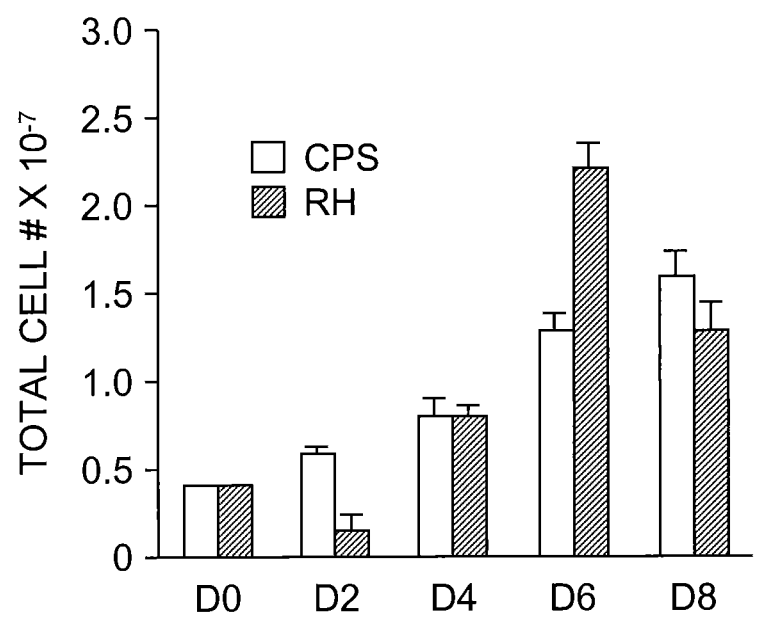
FIG. 4A, total PECs were analyzed by flow cytometry and total cell numbers recovered are presented.

Inflammatory Cell Infiltrate Response to cps1-1, in the Absence of Replication and Growth Associated Host Tissue Destruction is Faster and Less Potent Than Response to RH Infection. During T gondii infection, inflammatory cells infiltrate into the site of infection, indicate the type and magnitude of an immune response, and potentially relevant mechanisms in directly or indirectly controlling the infection (Bennouna, et al. (2003) J. Immunol. 171:6052-6058; Mordue & Sibley (2003) J. Leukoc. Biol. 74:1015-1025; Kelly, et al. (2005) Infect. Immun. 73:617-621; Robben, et al. (2005) J. Exp. Med. 201:1761-1769; Scharton-Kersten, et al. (1996) J. Immunol. 157:4045-4054). Knowledge regarding inflammation, such as cellular infiltrates in response to T gondii infection, has been elucidated with replication-competent strains that induce extensive growth-associated host tissue destruction (Scharton-Kersten, et al. (1996) Exp. Parasitol. 84:102-114; Gavrilescu, et al. (2001) J. Immunol. 167:902-909). Therefore, the magnitude and kinetics of inflammatory cell infiltrates was examined in the absence of parasite replication-associated host tissue destruction after immunization with cps1-1. For comparison, the inflammatory cell infiltrate response to RH infection, which causes significant levels of replication associated host tissue destruction, was measured. C57BL/6 mice were inoculated i.p. with either $1 \times 10^6$ cps1-1 or $1 \times 10^3$ RH tachyzoites intraperitoneally, and total PECs were isolated on days 0, 2, 4, 6, and 8 post-inoculation as described herein and enumerated (FIG. 4A). A significant (p=0.005) increase in cell numbers occurred by Day 2 post-cps1-1 inoculation followed by a steady and 3-fold significant increase (p=0.0001) by Day 6 and Day 8 as compared to Day 0 naïve controls (FIG. 4A). In contrast, RH infection induced an unexpected significant decrease (p=0.024) in total PEC numbers on Day 2 post-infection (FIG. 4A). This decrease in cell number was quickly resolved by Day 4 and the highest cell numbers were seen by Day 6 then declined by Day 8 post-infection, most likely due to significant necrosis and tissue destruction. The overall magnitude of inflammatory cell infiltrate into the site of infection was greater during RH infection than with cps1-1 immunization. While the level of cellular infiltrate was significantly greater at Day 2 post-infection with cps1-1 (p=0.003) than with RH infection, this was reversed by Day 6 post-infection, where RH PECs were 1.5-fold greater (p=0.002) than seen in cps1-1-treated mice. Total cell numbers of PECs measured at Day 8 were not significantly different between RH and cps1-1. These results reveal that i.p. inflammatory cellular infiltrate response to cps1-1 was earlier than with RH, indicating an inactivation or inhibition of the early innate immune response induced by the rapidly replicating RH parasite allowing it to gain a foothold and contribute to its lethal virulence. Moreover, the overall level of PEC infiltrate in response to cps1-1 inoculation was significantly lower than RH infection, indicating that replication-associated host tissue destruction contributed to the magnitude of the inflammatory response.

Recruitment of Specific Inflammatory Cells into the Site of Infection Occurs Earlier and is Less Potent in the Absence of Rapid Replication and Growth-Associated Host Tissue Destruction. As inflammatory cell types such as granulocytes (PMNs), macrophages, and B and T lymphocytes are important for the development of protective immunity and for direct control of primary *T. gondii* infection, it was of significant interest to investigate the absolute numbers and percent composition of the specific cell types contained in PECs infiltrating in response to the protective cps1-1 vaccine compared to virulent (RH) infection to examine which cell populations contribute to the control and development of long term protective immunity in the absence of rapid replication and growth-associated host tissue destruction (Mordue & Sibley (2003) *J. Leukoc. Biol.* 74:1015-1025; Scharton-Kersten, et al. (1996) *J. Immunol.* 157:4045-4054; Bliss, et al. (2000) *J. Immunol.* 165:4515-4521). Initial flow cytometric analysis of total PECs identified three general cell populations when using forward scatter (FSC) and side scatter (SSC) analyses. $FSC^{low} SSC^{low}$ were classified as lymphocytes (gate R1), $FSC^{high} SSC^{low-mid}$ were classified as macrophages/monocytes (gate R2), and $FSC^{mid} SSC^{high}$ were classified as granulocytes/neutrophils (gate R3) (Bliss, et al. (2000) *J. Immunol.* 165:4515-4521; Schleicher, et al. (2005) *Blood* 105:1319-1328; Henderson, et al. (2003) *Blood* 102:328-335). Based on these criteria three individual gates were drawn to isolate each region for analysis and whose sum of data were verified and found to be equivalent to results of total events.

Figure 4B:
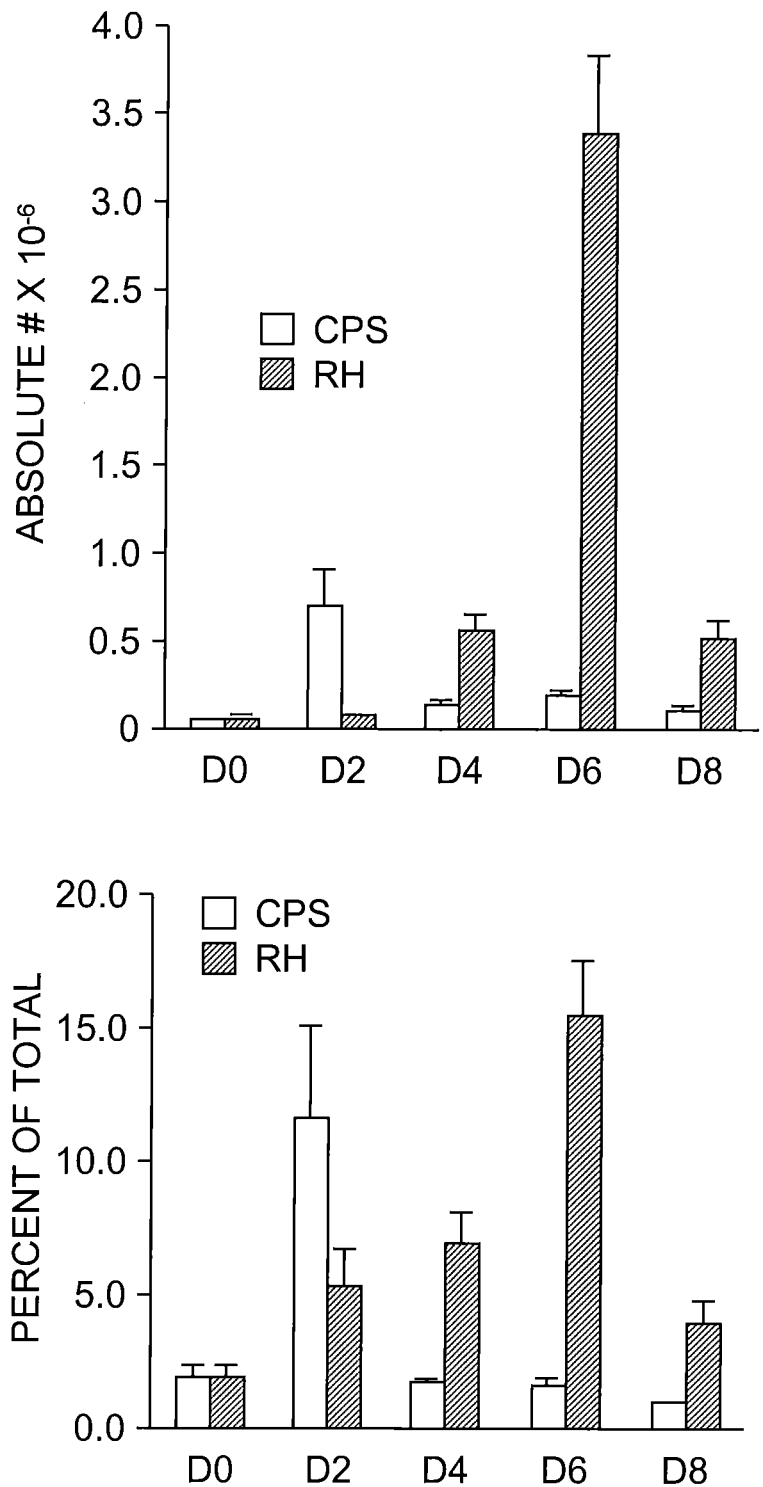
Figure 4C:
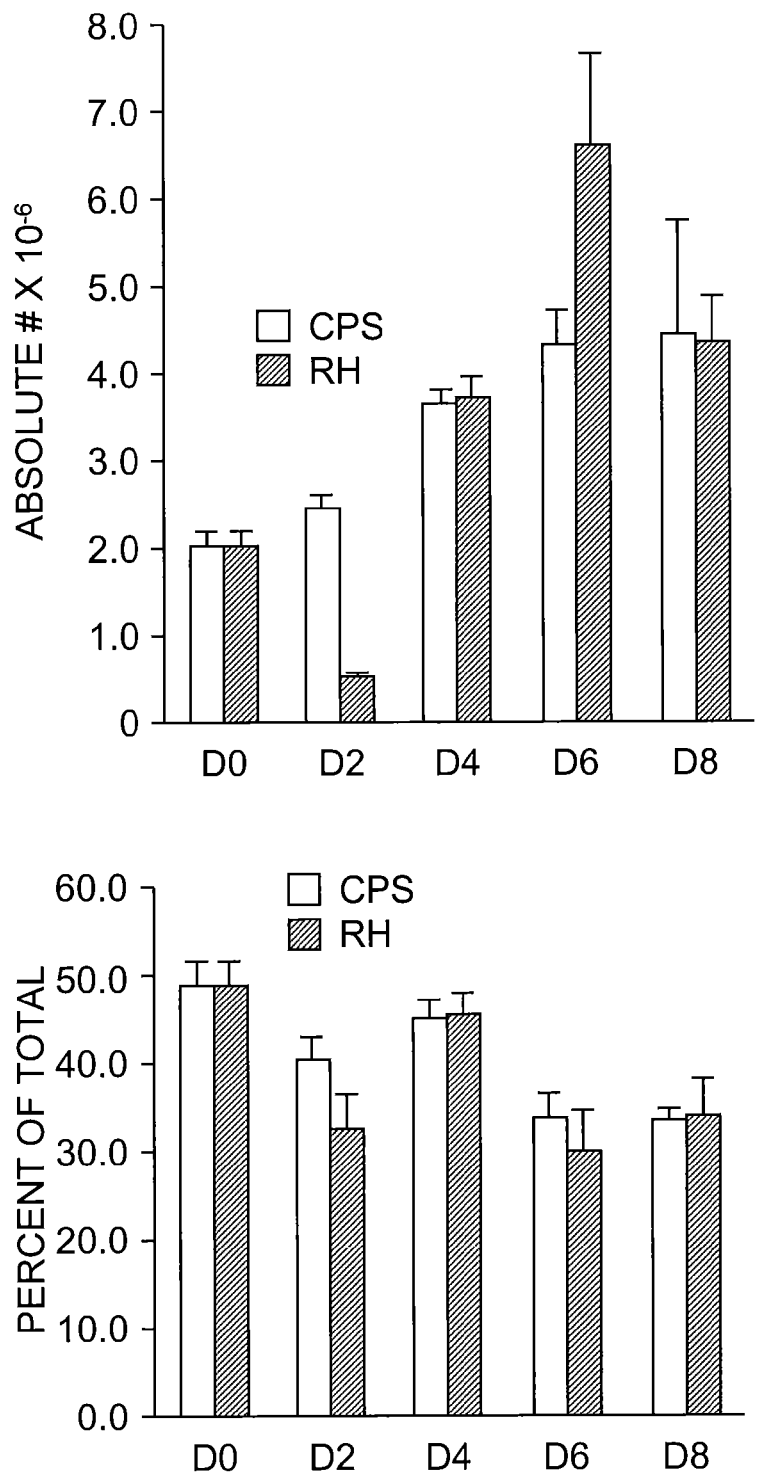

Granulocytes. Granulocytes are rapid responders and quickly infiltrate after *T. gondii* infection. These cells are required for early control of infection and are an early source of IL-12, which may set the stage for a Th-1-skewed response and early IFN-γ production (Bliss, et al. (2000) *J. Immunol.* 165:4515-4521; Khan, et al. (2001) *J. Immunol.* 166:1930-1937; Bliss, et al. (2001) *Infect. Immun.* 69:4898-4905; Del Rio, at al. (2001) *J. Immunol.* 167:6503-6509). To carry out this analysis, a double stain of Gr-1 and CD68 was used and the percent of total events in the granulocyte (R3) region were measured. The results from R3 were confirmed by back-gating from all three gates for $Gr-1^+ CD68^-$ cells and by staining for Gr-1 alone. From this analysis it was determined that R3 contained 95% of the granulocytes detected (Bliss, et al. (2000) *J. Immunol.* 165:4515-4521). After cps1-1 vaccination i.p. a significant 9-fold increase in the absolute number of granulocytes (p=0.026) was observed by Day 2 post-inoculation. After Day 2 the total numbers of granulocytes returned to uninfected control levels (FIG. 4B, upper panel). When the percent of $Gr-1^+ CD68^-$ cells in total events was measured, the identical pattern of granulocyte infiltration was observed with a significant increase by Day 2 post-infection (p=0.033) from 1.8% to 11.5% followed by a decrease to 1.6% by Day 4 (FIG. 4B, lower panel). In contrast to cps1-1, the absolute numbers of granulocytes responding to RH infection did not significantly increase until Day 4 where a 6.8-fold increase (p=0.001) over Day 0 was measured. This increase in granulocyte numbers continued through Day 6 with a 6.0-fold increase over Day 4 (p=0.001) followed by a significant reduction at Day 8 (p=0.001) (FIG. 4B, upper panel). This pattern was also observed in terms of the percent of total infiltrating cells being granulocytes, wherein at Day 2 post-infection 5.2% of the total cells were granulocytes, at Day 6 post-infection 15.3% of the total cells were granulocytes, and at Day 8 a 4-fold decrease was observed (FIG. 4C, lower panel). Recruitment of granulocytes after cps1-1 vaccination occurred more rapidly (peak by Day 2) as compared to RH infection (peak by Day 6) as indicated by both absolute numbers and percentages of total events (FIG. 4B). After Day 2, RH infection induced significantly greater granulocyte infiltration than did cps1-1 vaccination and these differences may have been due to a difference in initial antigen load, a delay in granulocyte infiltration by virulent RH infection, or granulocyte infiltration in response to RH infection associated host tissue destruction.

Macrophages. The level and kinetics of macrophage infiltration after infection with RH or vaccination with cps1-1 was also determined. Macrophages encompass the greatest percentage of resident PECs (~50%) in the uninfected steady state (FIG. 4C). There is evidence that macrophages are preferentially targeted for invasion by *T. gondii*. Either $Gr-1^+$ or $Gr-1^-$ macrophages respond to infection, provide a host cell environment amenable to parasite growth and replication, and provide a first line of host defense (Mordue & Sibley (2003) *J. Leukoc. Biol.* 74:1015-1025; Robben, et al. (2005) *J. Exp. Med.* 201:17611769). To measure the absolute number and percent of macrophages in total PECs, an intracellular stain for CD68 or macrosialin was employed. In addition to CD68, PECs were also stained with the surface marker Gr-1 to detect the *T. gondii*-specific double-positive staining $Gr-1^+ CD68^+$ inflammatory macrophage population. The absolute numbers of $CD68^+$ macrophages infiltrating into the peritoneum with cps1-1 vaccination significantly increased 1.5-fold (p<0.001) by Day 4 post-inoculation compared to Day 0 (FIG. 4C, upper panel). The maximum number of $CD68^+$ cells had infiltrated by Day 6 with a 2.1-fold increase (p=0.001) in absolute numbers over Day 0 controls. This population remained present at Day 8 post-infection with no significant change. When this pattern of influx was analyzed as a percent of total PECs, it was observed that the percentage of $CD68^+$ cells did not significantly change until Day 6 and Day 8, where unexpectedly $CD68^+$ cell numbers decreased (p=0.011) compared to Day 0 (FIG. 4C, lower panel). Although absolute numbers of $CD68^+$ macrophages increased with time in both RH infection and cps1-1 immunization, other cell populations were infiltrating at a more rapid rate by Day 6 post-inoculation.

$CD68^+ Gr-1^+$ Macrophages. Analysis was also carried out to determine the absolute number and percentage of the total PECs that were $Gr-1^+ CD68^+$ inflammatory macrophages infiltrating into the site of inoculation. At Day 0, or in uninfected naïve controls, less than 1% of the $CD68^+$ cells were also $Gr-1^+$ (FIG. 4D). When mice were immunized i.p. with cps1-1, a significant 168-fold increase (p<0.001) in the absolute numbers of $Gr-1^+ CD68^+$ cells was observed by Day 2 post-infection (FIG. 4D, upper panel). A significant 2.5-fold decrease (p<0.001) in the numbers of $Gr-1^+ CD68^+$ macrophages at Day 4 post-inoculation was then observed. It was surprising to also observe a second population or wave of $Gr-1^+ CD68^+$ macrophages infiltrating into the site of cps1-1 inoculation at Day 6, wherein a significant 2.5-fold increase (p=0.002) in absolute cell number (compared to Day 4 and Day 6) was observed, which was then followed by a significant 3.8-fold decrease (p=0.004) in the number of inflammatory macrophages by Day 8 post-vaccination (compared to Day 6 and Day 8). This analysis of the percent of total PECs identified as $Gr-1^+ CD68^+$ inflammatory macrophages over the course of inoculation with cps1-1 followed the pattern observed for absolute numbers (FIG. 4D, lower panel). In contrast, the percentage of $CD68^+$ macrophages decreased between Day 0 and Day 8 (FIG. 4C, lower panel). These observations indicate that of the $CD68^+$ resident macrophages that are present in the peritoneum at Day 0, >99% have been replaced by the *T. gondii*-specific inflammatory $Gr-1^+$ CD68$^+$ macrophages by Day 2 post-inoculation. Not wishing to be bound by theory, this is most likely due to infiltration of new Gr-1$^+$ CD68$^+$ inflammatory macrophages because in vitro infection of peritoneal-derived macrophages with cps1-1 under replicating or non-replicating conditions in uracil does not result in the expression of Gr-1. By Day 4 post-inoculation many of these Gr-1$^+$ CD68$^+$ inflammatory macrophages are cleared down to 27.5% of all CD68$^+$ macrophages. By Day 6 post-inoculation, 68% of the CD68$^+$ macrophages are Gr-1$^+$ CD68$^+$ followed by a decrease to 14.8% of all CD68$^+$ cells by Day 8 post-inoculation (Mordue & Sibley (2003) *J. Leukoc. Biol.* 74:1015-1025; Robben, et al. (2005) *J. Exp. Med.* 201:17611769).

In contrast to non-replicating cps1-1 vaccine, the total CD68$^+$ macrophages decreased 4-fold (p<0.001) by Day 2 post-active RH infection when compared to Day 0 (FIG. 4C, upper panel). The number of CD68$^+$ macrophages then increase significantly 7-fold (p<0.001) by Day 4 post-infection compared to Day 2. By Day 6 post-infection with RH, CD68$^+$ cells had increased 2-fold (p=0.032) over Day 4 and reached their highest absolute numbers at this time. By Day 8 post-infection absolute numbers of CD68$^+$ macrophages remained elevated but are not significantly lower (p=0.093) than Day 6 post-infection. A similar pattern of CD68$^+$ macrophages as a percent of total PECs after RH or cps1-1 inoculation was observed, indicating that CD68$^+$ macrophages were recruited at the same rate regardless of replicating (RH) or non-replicating (cps1-1) parasites. Other cells types were being recruited more rapidly to the site of parasite inoculation.

When the PECs were analyzed for the absolute numbers of *T. gondii*-specific Gr-1$^+$ CD68$^+$ inflammatory macrophages during RH infection, a delay in the recruitment of these cells to the site of RH infection was observed, i.e., cells were only observed at Day 4. By Day 6, the Gr-1$^+$ CD68$^+$ cells had significantly increased 2-fold (p=0.041) over Day 4. The absolute numbers of Gr-1$^+$ CD68$^+$ cells did not significantly change between Day 6 and Day 8. The analysis of the Gr-1$^+$ CD68$^+$ percent composition of the total events in response to RH infection revealed a similar, but delayed pattern to that observed for cps1-1 vaccination. Upon further analysis, a similar ratio of macrophage cell types infiltrating during infection with RH was not observed as compared to cps1-1 vaccination. By Day 4 and through Day 8 post-RH infection, Gr-1$^+$ CD68$^+$ macrophages made up greater than 99% of the total CD68$^+$ cells observed to infiltrate during the course of infection, indicating that although there may have been a similar pattern of Gr-1$^+$ CD68$^+$ entering and leaving the site of infection, there was a lack of balance between normal CD68$^+$ activated or non-activated resident peritoneal macrophages with the activated inflammatory *T. gondii*-specific Gr-1$^+$ CD68$^+$ macrophages. This imbalance could have been in part due to the inflammatory contribution caused by virulent RH infection associated host cell and tissue destruction.

B cells. B lymphocytes play a role in mediating the outcome of infection with *T. gondii* because cps1-1 vaccinated μMT mice showed a delayed time to death phenotype, but uniformly did not survive a high lethal dose RH challenge (FIG. 3B). Whether this role was significant for anti-*toxoplasma* antibody production or enhancing memory CD8$^+$ T cell responses remains under investigation (Sayles, et al. (2000) *Infect. Immun.* 68:1026-1033; Langhorne, et al. (1998) *Proc. Natl. Acad. Sci. USA* 95:1730-1734; Johnson, et al. (2002) *Infect. Immun.* 70:185-191). Accordingly, cell-specific differences in the host inflammatory cell infiltrate response to cps1-1 vaccination or RH infection was analyzed by measuring the absolute numbers and percentage of total PECs that were CD19$^+$ B cells. Unexpectedly, 2 days after cps1-1 inoculation a significant decrease (p=0.022) in the absolute numbers (30% decrease) from naïve controls was observed (FIG. 4E, upper panel). This was followed by a significant increase in CD19$^+$ B cell numbers at Day 4 (1.8-fold) and Day 6 (2-fold) with p-values equal to 0.001 and 0.003, respectively. The absolute numbers of CD19$^+$ B cells then remained steady through Day 8 post-inoculation. When the percent of CD19$^+$ B cells contained in total PECs after cps1-1 vaccination was assessed, 32.5% of the total PECS were CD19$^+$ B cells at Day 0 (FIG. 4E, lower panel). The percentage then significantly decreased 1.9-fold to 17.2% of the total PECs, and did not significantly change through Day 8. Analysis of PECs after RH infection revealed that while the absolute numbers of CD19$^+$ B cells followed a similar pattern as with cps1-1 inoculation only until Day 4, RH infection induced a significant 2-fold decrease (p=0.012) in CD19$^+$ B cells by Day 6. This clearance of the CD19$^+$ B cells markedly accelerated through Day 8 post-RH infection. When the percent of CD19$^+$ B cells in the total number of events was measured, it was observed that the percentage of B cells in PECs in response to RH infection significantly increased (p=0.018) by Day 2 post-infection from 32.5% to 42.9% of the total (FIG. 4E, lower panel). However, by Day 4 post-infection, the percentage of B cells had significantly decreased 2.2-fold (p<0.001) below Day 0 naïve controls. By Day 6 and Day 8 post-RH infection, the percent of CD19$^+$ B cells was reduced 14-fold and 35-fold, respectively, compared to Day 0 (FIG. 4E, lower panel). The retention or continual recruitment of CD19$^+$ B cells during cps1-1 vaccination could be an important component in the development of CD8$^+$ T cell memory through enhanced co-stimulation, antigen presentation, or by acting in an innate function if the CD19$^+$ B cells were proportionally higher for B1 B cells over B2 B cells.

Figure 4F:
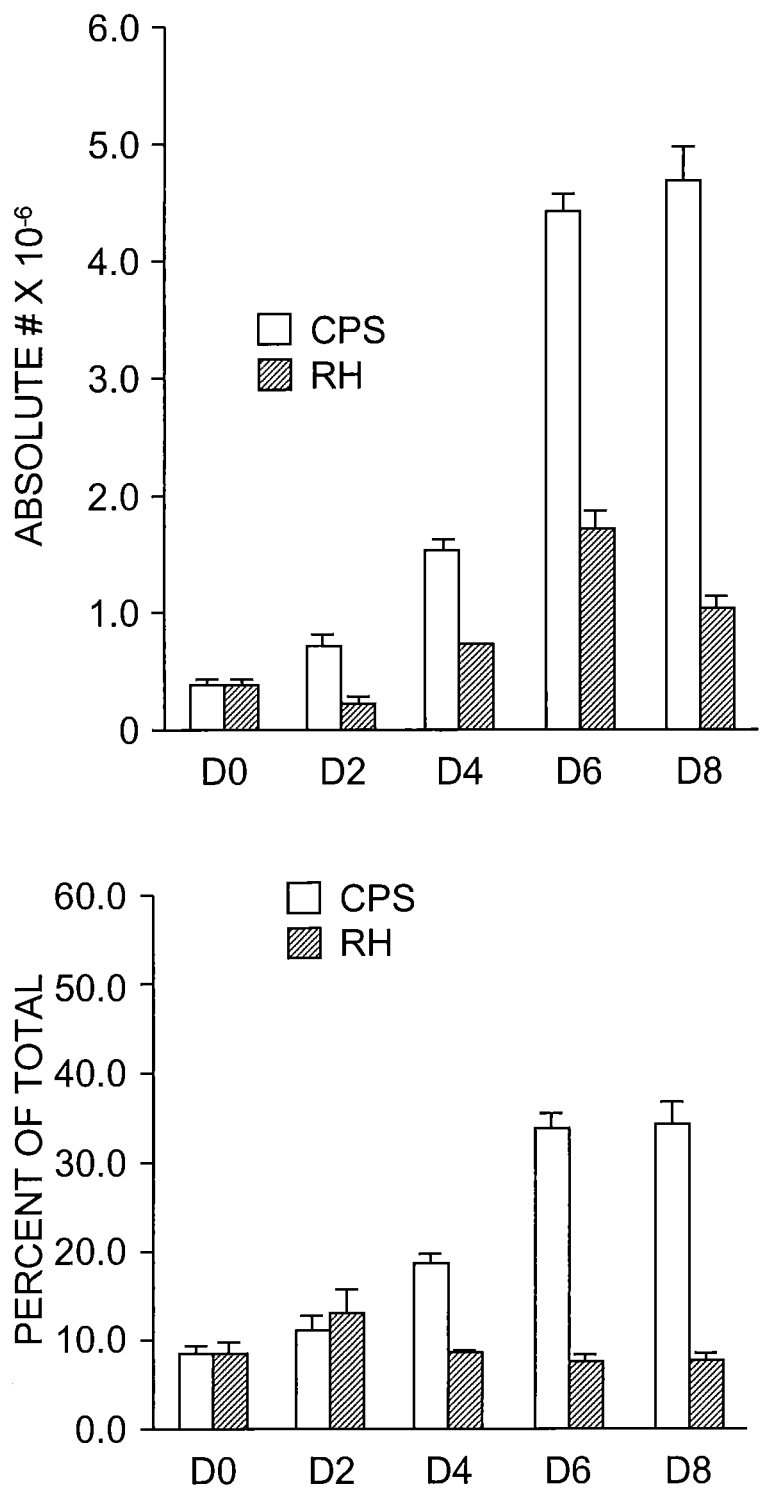

T cells. Resolution of infection by *T. gondii* requires a potent CD8$^+$ T cell response. A synergistic role of both CD4$^+$ and CD8$^+$ T cells is required to develop this cell mediated protection (Snzuki & Remington (1988) *J. Immunol.* 140: 3943-3946; Gazzinelli, et al. (1991) *J. Immunol.* 146:286-292; Subauste, et al. (1991) *J. Immunol.* 147:3955-3959). Due to the key role that both CD4$^+$ and CD8$^+$ T cells play in the outcome of *T. gondii* infection and development of protective immunity, the kinetics of cell infiltration to the site of inoculation was analyzed by measuring the absolute number and percent of the total PECs that were T cells (CD3$^+$) and how many of those T cells were CD3$^+$ CD4$^+$ or CD3$^+$ CD8$^+$ over the course of RH infection compared to cps1-1 vaccination. This analysis indicated that, when measuring CD3 alone, the absolute number of T lymphocytes infiltrating to the site of cps1-1 inoculation significantly increased 1.9-fold (P=0.022) by Day 2 post-infection (FIG. 4F, upper panel). The increase in absolute numbers of CD3$^+$ T cells continued to Day 4 and Day 6 post-infection with 4- and 11-fold increases, respectively, over Day 0. CD3$^+$ T cells were at their highest number at Day 8 post-cps1-1 inoculation. The same pattern was observed when measuring the percent of CD3$^+$ T cells in total PECs, wherein at Day 0 that there were less than 10% T lymphocytes, but by Day 4 post-infection this amount increased to 18.7% and at Day 6 and Day 8 the percent increased to 33.7% and 34.3%, respectively, of total PECs (FIG. 4F, lower panel). In contrast to cps1-1 vaccination, RH infection delayed an increase in total CD3$^+$ T cells until Day 4 post-infection, a 1.8-fold increase was observed (FIG. 4F, upper panel). The highest numbers of CD3$^+$ T cells were present by Day 6 which was then followed by a decrease in number at Day 8. The absolute numbers of T cells infiltrating into the site of infection were significantly lower (P=0.004, p<0.001, p<0.001, p<0.001) in response to RH infection than with cps1-1 vaccination for each time point beginning at Day 2 post-inoculation. When measuring the percent of CD3$^+$ T cells of total PECs, it was observed that only at Day 2 was there a significant increase (P=0.035) in the percentage of total T cells after RH infection (FIG. 4F, lower panel). Soon after this peak at Day 2 post-RH infection, the percentage of CD3$^+$ T cells decreased back to Day 0 levels. Overall the recruitment of CD3$^+$ T cells by the host in response to cps1-1 inoculation was very robust and the presence of significant RH replication and growth-associated host tissue destruction may severely restrict CD3$^+$ T cell recruitment.

Figure 4G:
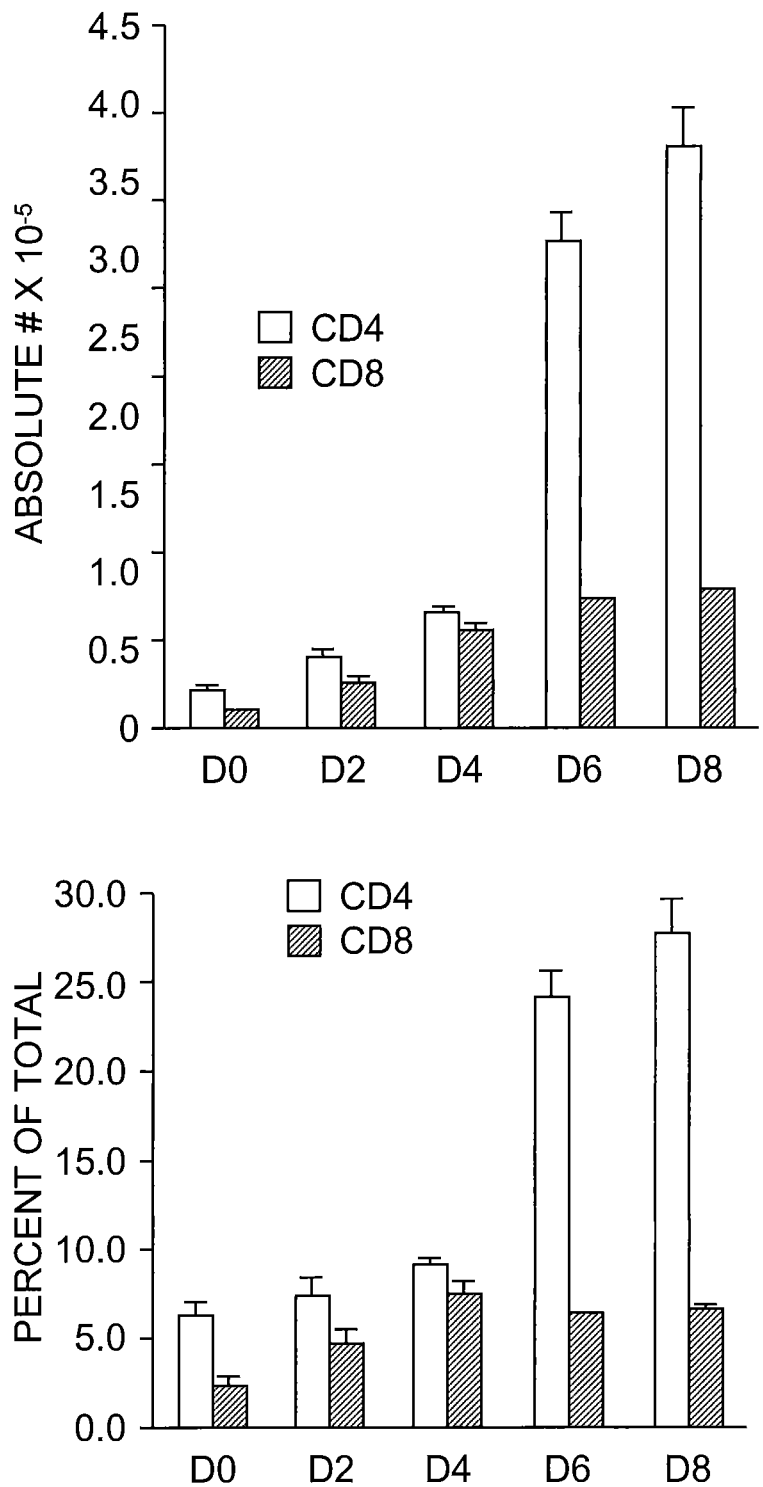

As both CD4$^+$ and CD8$^+$ T cells play a role in controlling T. gondii infection, the kinetics and numbers of either CD4$^+$ or CD8$^+$ T cells infiltrating into the site of inoculation was analyzed. The CD3$^+$ T cell analysis was extended to include cells that would stain double-positive for either CD3$^+$ CD4$^+$ or CD3$^+$ CD8$^+$. It was observed that after cps1-1 vaccination, both CD4$^+$ and CD8$^+$ T cell numbers increased significantly (p=0.029 and 0.007, respectively) 1.7- and 2.8-fold, respectively, by Day 2 post-infection (FIG. 4G, upper panel). Both CD4$^+$ and CD8$^+$ T cell numbers increased continuously over time and reached maximal numbers by Day 8 post-infection with absolute numbers of CD4$^+$ T cells significantly greater than CD8$^+$ T cells from Day 6 through Day 8 (p<0.001). However, when the different T cell populations were analyze as percentage of total PECs, the percent of CD3$^+$ CD8$^+$ T cells was found to increase significantly (p=0.03) early by Day 2 post-inoculation (FIG. 4G, lower panel). The CD3$^+$ CD4$^+$ T cell population did not significantly increase in percentage until Day 4 as compared to Day 0 (p=0.01), indicating that CD8$^+$ T cells infiltrated earlier in response to cps1-1 vaccination than the CD4$^+$ T cells. In contrast to vaccination with cps1-1, the absolute numbers of either CD4$^+$ or CD8$^+$ T cells in response to RH infection did not significantly increase until Day 4 post-infection with CD4$^+$ T cells undergoing 1.4-fold and CD8$^+$ T cells undergoing 2.3-fold increases (FIG. 4H, upper panel). Maximal increases in absolute numbers of both CD4$^+$ and CD8$^+$ T cells occurred by Day 6 post-RH infection followed by an acute and significant reduction (p=0.001 CD4; p=0.001 CD8) by Day 8 post-infection. There was no significant differences in absolute numbers between either T cell type, unlike the response to cps1-1 vaccination (compare FIGS. 4G and 4H). Percent of total event analysis revealed that only CD4$^+$ T cells significantly increased at Day 2 post-RH infection (p=0.01), while CD8$^+$ T cells did not significantly change as a percentage of total PECs for the entire course of infection (FIG. 4H, lower panel). The initial increase in the percent of CD4$^+$ T cells in the total PEC population was reversed by Day 4 with a significant decrease (p=0.001) to below Day 0 levels. These results indicate that CD8$^+$ T cells respond more rapidly than CD4$^+$ T cells to vaccination with cps1-1. However, CD4$^+$ T cells eventually infiltrate in greater numbers (and percentages) over CD8$^+$ T cells by Day 6 and Day 8 after cps1-1 vaccination. Despite a robustly enhanced level of cellular infiltration by Day 6 in the context of RH replication and growth-associated host tissue destruction (FIG. 4A), both CD4$^+$ and CD8$^+$ T lymphocytes were significantly impaired in their ability to infiltrate into the site of RH infection (FIG. 4H).

The Attenuated Type I cps1-1 Vaccine Induces Early Systemic Production of IFN-γ, IL-12p40 and IL-12p70. Previous studies establish that infections with viable and replicating T. gondii parasites induce potent Th-1-biased inflammatory responses highlighted by high-level production of IFN-γ and variable levels of IL-12p70 production depending on parasite genotype (Type I, II, II) (Scharton-Kersten, et al. (1996) Exp. Parasitol. 84:102-114; Robben, et al. (2004) J. Immunol. 172:3686-3694; Scharton-Kersten, et al. (1996) J. Immunol. 157:4045-4054). In contrast, studies utilizing replicating parasites are confounded by extensive infection-associated host tissue destruction from parasite replication and growth and the resulting tissue destruction may enhance the overproduction of potentially lethal inflammatory cytokines (Gavrilescu & Denkers (2001) J. Immunol. 167:902-909). Accordingly, systemic levels of pro-inflammatory Th-1 cytokines were measured in sera at Day 0, 2, 4, 6, and 8 post-inoculation of cps1-1-vaccinated mice. In this regard, cytokine produced solely in response to this attenuated Type I parasite could be measured in the absence of growth and replication-associated host tissue destruction and compared to C57Bl/6 mice that were infected with the virulent parental Type I strain RH. The production of IL-12p40, IL-12p70, and IFN-γ was measured by ELISA.

Figure 5A:
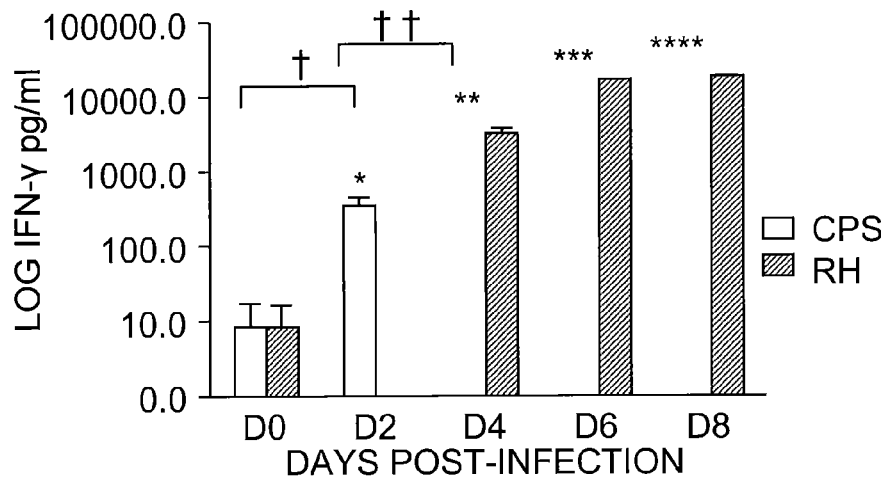
FIG. 5A, p=*0.03, 0.001, *0.0001, ****0.0001, †0.03, ††0.0001.

Systemic IFN-γ and IL-12p40 in serum of mice infected with RH did not significantly increase until Day 4 post-infection and quickly rose to maximum levels by Day 6 and 8. Systemic IFN-γ at Day 0 decreased by Day 2 compared to naïve Day 0 controls (FIG. 5A). Type I RH infection induced exceedingly low levels of systemic IL-12p70 only detectable on Day 2 and Day 4 (FIG. 5B) consistent with previous reports that IL-12p70 production may only be induced by Type II parasite strains (Robben, et al. (2004) J. Immunol. 172:3686-3694). Poor IL-12p70 induction in sera of mice was proposed to be one of the reasons Type I parasite infections are universally lethal (Robben, et al. (2004) supra).

Kinetics of production of systemic IFN-γ, IL-12p40, and IL-12p70 after vaccination with the Type I cps1-1 vaccine strain derived from parental RH was completely opposite to that observed with RH infection (FIG. 5). Systemic levels of IFN-γ from mice after cps1-1 vaccination were early (p=0.03) at Day 2 post-inoculation (FIG. 5A). This systemic IFN-γ production was transient and was significantly decreased (p=0.03) by Day 4 (<10 pg/ml IFN-γ) and remained below detectable levels for the remainder of the 8-day kinetic evaluation.

Figure 5B:
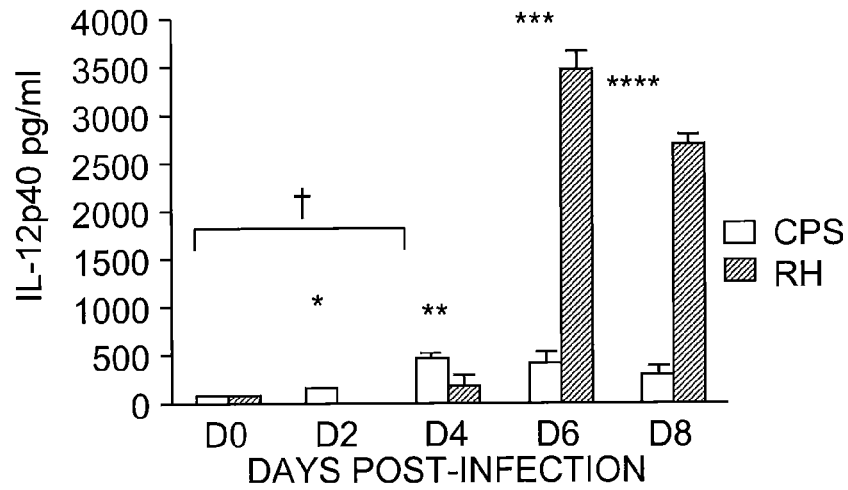
FIG. 5B, p=*0.0001, 0.04, *0.0001, ****0.0001, †0.001.

In contrast to RH infection, induction of systemic IL-12p40 after cps1-1 vaccination was low with a significant systemic increase (p=0.001) detected at Day 4 (4-fold increase over Day 0 naïve mice). Levels of IL-12p40 held steady through Day 6 and Day 8 (FIG. 5B). The level of early systemic IL-12p40 production was significantly lower in response to RH infection than cps1-1 vaccination at Day 2 and Day 4 post-infection with p-values equal to 0.0001 and 0.04, respectively.

Figure 5C:
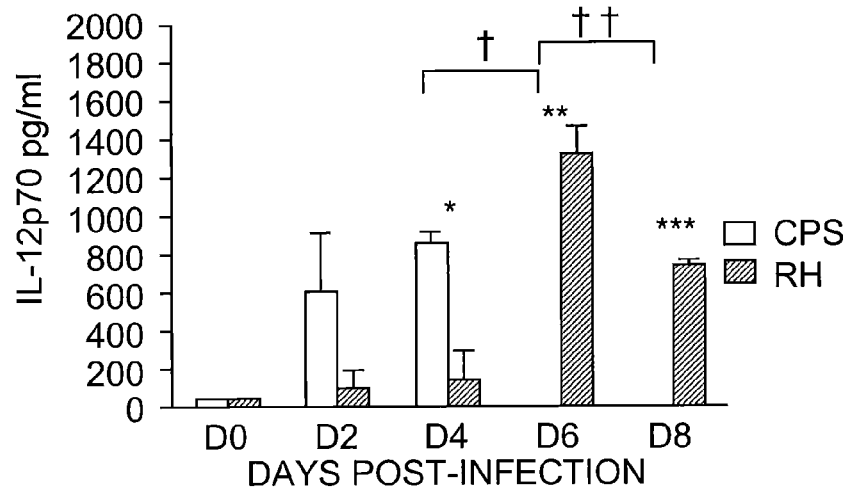
FIG. 5C, p=*0.001, 0.0001, *0.0001, †0.04, ††0.02.

Significant systemic IL-12p70 production was induced after vaccination with the Type I attenuated cps1-1 (FIG. 5C). Cps1-1 induced systemic IL-12p70 rapidly by Day 2 post-inoculation over undetectable levels in Day 0 naïve mice. IL-12p70 levels then showed a significant increase (p=0.036) by Day 4 with a further increase by Day 6 post-inoculation and a significant decrease by Day 8 (p=0.015). When comparing the IL-12p70 production in response to Type I-matched strains, cps1-1 compared to RH, significantly greater amounts (p=0.0001) were observed for the time points of Day 4, Day 6, and Day 8 collected from mice infected with cps1-1. This was a remarkable finding because the cps1-1 parasite is an attenuated Type I parasite and production of IL-12p70 has been reported to be suppressed in response to Type I infections (Robben, et al. (2004) supra) (see also FIG. 5C).

Vaccination with cps1-1 induced more rapid systemic production of IFN-γ and Il-12p40 than observed with RH infection. Significant IL-12p70 was produced with cps1-1 vaccination but not in RH infection. It has been reported that an immune evasion may be occurring in RH infection leading to a loss of control of the virulent Type I parasite with systemic overproduction of inflammatory cytokines and lethal pathology (Gavrilescu & Denkers (2001) *J. Immunol.* 167:902-909; Aliberti, et al. (2003) *Nat. Immunol.* 4:485-490). Both IL-12-dependent and -independent IFN-γ production has been shown to be required for the development of long term protective immunity leading to control of the chronic infection (Scharton-Kersten, et al. (1996) *Exp. Parasitol.* 84:102-114). IL-12 dependent IFN-γ production in particular is thought to be required for the development of long lasting protection (Gazzinelli, et al. (1994) *J. Immunol.* 153:2533-2543). The results presented herein indicate the lack of production of IL12p70 in response to RH would likely add to the inability of the host to directly control the RH infection. As observed during cps1-1 vaccination, IL-12p70 is produced systemically early and maintained, thereby potentially enhancing the overall immune response and leading to the development of more effective long lasting protective immunity.

The Immune Response of IFN-γ, IL-12p40, and IL-12p70 Production is Primarily a Local Response at the Site of cps1-1 Vaccination. As demonstrated herein, a unique pattern of inflammatory cell infiltration occurs during cps1-1 vaccination compared to RH infection. It was important then to measure the kinetics and magnitude of Th-1 cytokine production locally at the site of inoculation and at a peripheral site to ascertain how the local immune response may contribute to control of infection and the development of long lasting immune protection. C57Bl/6 mice were vaccinated i.p. with cps1-1 or infected i.p. with RH, and PECs and splenocytes were harvested at Day 0, Day 2, Day 4, Day 6, and Day 8 post-infection. Harvested PECs and splenocytes were cultured 24 hours at $1 \times 10^6$ and $5 \times 10^6$ cells/ml, respectively, and supernatants recovered from individual cell cultures were used for ELISA to measure the production of IFN-γ, IL-12p40, and IL-12p70.

Figure 6A:
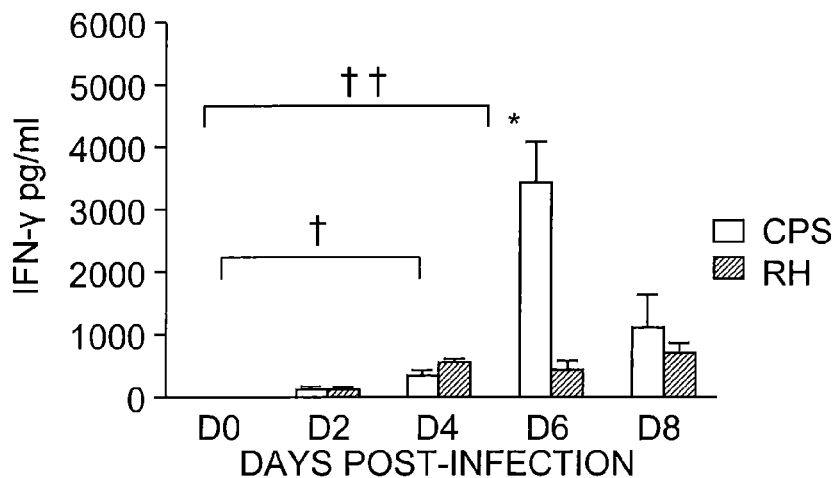
FIG. 6A, p=*0.005, †0.001, ††0.04.

PECs from mice infected with RH produced significantly more IFN-γ ($p<0.001$) at Day 4 post-infection than at Day 0 and Day 2 post-infection and remained at a similar level through Day 6 and Day 8 post-infection (FIG. 6A). IL-12p40 (FIG. 6B) was produced by PECs most significantly ($p<0.001$) at Day 4 post-infection (8-fold increase) as compared to Day 0 and Day 2. IL-12p40 levels subsequently decreased at Day 6 and fell below detectable levels by Day 8 post-infection. Moderate but highly variable levels of IL-12p70 were produced by PECs from RH-infected mice beginning on Day 4 then waning on Day 6 and Day 8 (FIG. 6C).

In comparison to PECs, splenocytes from RH-infected mice produced IFN-γ at greater levels than PECs (FIG. 6D) (Mordue & Sibley (2003) *J. Leukoc. Biol.* 74:1015-1025; Gavrilescu & Denkers (2001) *J. Immunol.* 167:902-909). IFN-γ production by splenocytes was not significantly increased until Day 4 post-infection as compared to Day 2 post-infection with a $p=0.001$ and IFN-γ levels increased on Day 6 and again increased by Day 8. When comparing IL-12p40 production between PECs and splenocytes in RH infection (compare FIG. 6B and FIG. 6E), the production of IL-12p40 appeared equivalent or higher in PECs when taking into account total cell number. Splenocytes produced IL-12p40 in a similar pattern to IFN-γ, where a significant increase in production ($p<0.001$) in response to RH infection was observed by Day 4, a further increase by Day 6 post-infection, and subsequent decline (FIG. 6E). Minimal production of IL-12p70 by splenocytes in response to RH infection was observed only on Day 4 and Day 6 post-infection (FIG. 6F).

In the case of cps1-1 vaccination, a novel and primarily local pattern of cytokine production by PEC and splenocyte populations was seen as compared to RH infection (FIG. 6). After cps1-1 vaccination, PEC IFN-γ production was detected by Day 2 and increased to highest levels by Day 6 as compared to Day 2 post-infection ($p=0.04$). Subsequently, IFN-γ levels significantly decreased by Day 8. Unexpectedly, PECs from cps1-1 vaccinated mice produced significantly greater IFN-γ levels than PECs from RH-infected mice by Day 6 post-infection with $p=0.005$ (FIG. 6A).

Figure 6B:
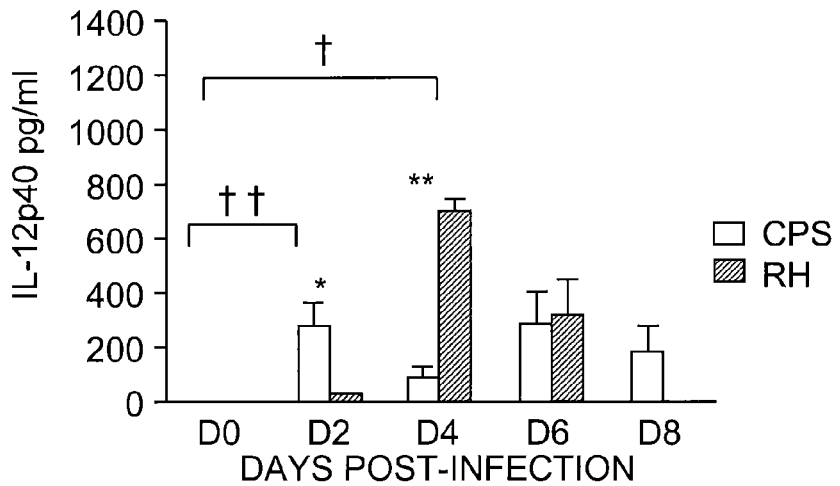
FIG. 6B, p=*0.03, **0.0001, †0.0001, ††0.04.
Figure 6C:
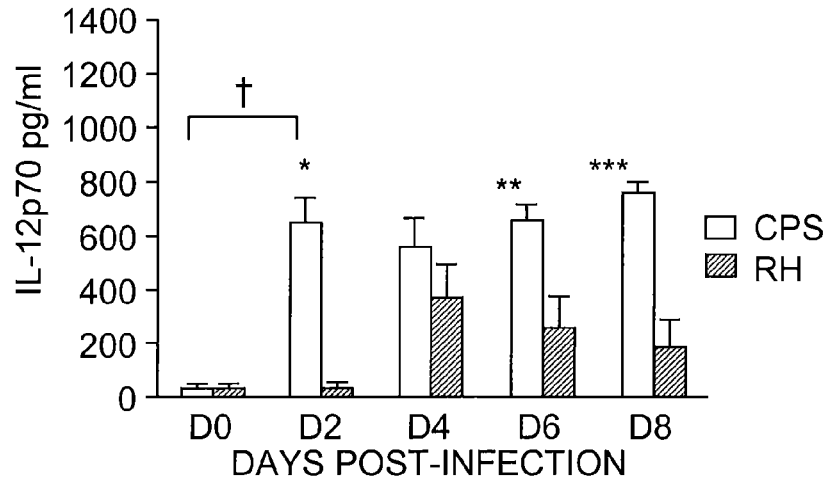
FIG. 6C, p=*0.007, 0.012, *0.001, †0.005.
Figure 6D:
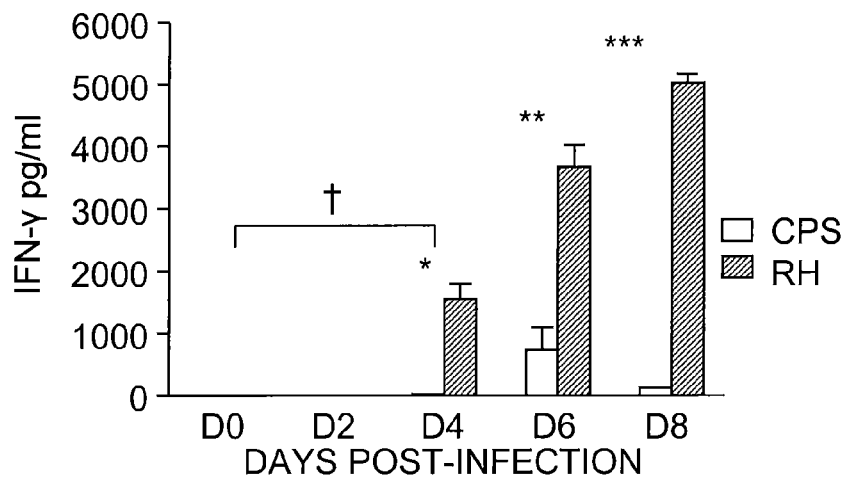
FIG. 6D, p=*0.001, 0.006, *0.0001, †0.001.
Figure 6E:
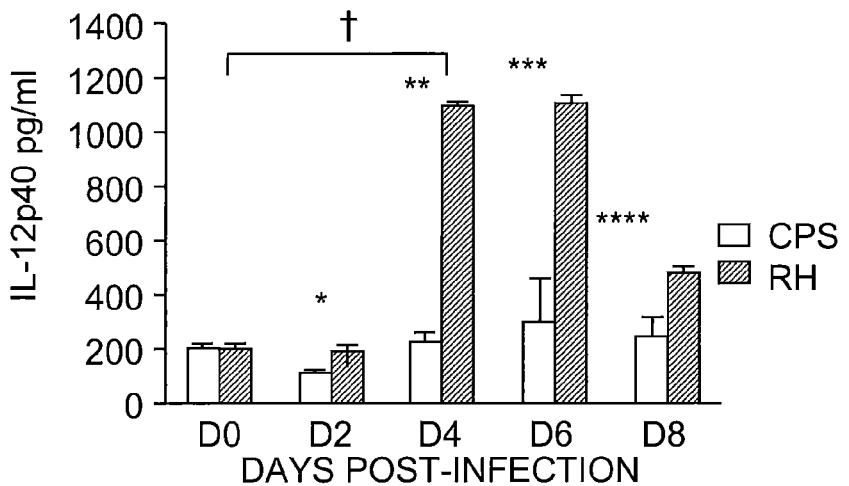
FIG. 6E, p=*0.02, 0.0001, *0.002, ****0.02, †0.0001.
Figure 6F:
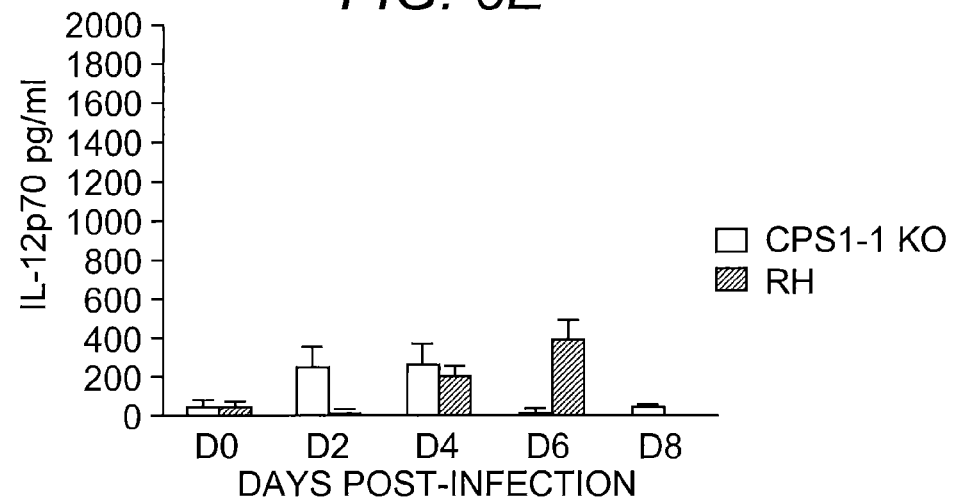
FIG. 6F, no significant differences.

As shown in FIG. 6B, cps1-1 vaccination induced a significant production of IL-12p40 by PECs by Day 2 post-infection as compared to that of Day 0 ($p=0.04$). Although PEC production of IL-12p40 from Day 2 through Day 8 did not significantly change, PEC from cps1-1-vaccinated mice more rapidly produced significant levels ($p=0.025$) than were observe in RH-infected mice at Day 2 post-infection (FIG. 6B). The opposite was true by Day 4, where PEC derived from RH-infected mice produced significantly more IL-12p40 ($p<0.001$) than PECs from cps1-1 vaccinated mice. In FIG. 6C it is revealed that PECs from cps1-1-vaccinated mice rapidly produce significantly greater levels of IL-12p70 by Day 2 post-infection as compared to RH with $p=0.007$. These IL-12p70 levels remained consistently high (Day 2 to Day 8) after cps1-1 vaccination, while Il-12p70 production from PECs after RH infection was delayed to Day 4 and was significantly lower by Day 6 and Day 8 with $p=0.012$ and $p=0.001$, respectively (FIG. 6C).

When comparing PECs cytokine production to that of splenocytes from cps1-1-vaccinated mice, higher PEC production (on a per cell basis) of IFN-γ (FIG. 6A and FIG. 6D) and IL-12p70 (FIG. 6C and FIG. 6F) was observed, while splenocyte production of IL12p40 from cps1-1-vaccinated mice was equivalent to that of PEC-production of this protein (FIG. 6B and FIG. 6E). These studies reveal that local production of Th-1 cytokines was more rapid and greater in response to cps1-1 vaccination. The data presented herein also indicates that the initial loss of control of the virulent RH infection may be due to a lack of an early potent cytokine response at the local site of infection. Significantly, it was observed that the immune response directed to a live and invasive parasite in the absence of replication-associated host cell and tissue damage is rapid and tightly controlled (FIGS. 4-6). These data indicate that transient and early (Day 2) systemic IFN-γ production and local IFN-γ production (Day 2 to Day 8), along with early and maintained (Day 2 to Day 8) IL-12p70 production both locally and systemically are sufficient to induce the development of long lasting protective immunity by the cps1-1 vaccine which is very effective at protecting against lethal challenge.

Model of a Local and Tightly Regulated Th-1 Immune Response to Vaccination With a Live, Non-Replicating Parasite in the Absence of Infection-Associated Host Tissue Destruction. Based on the results of analysis conducted herein, the following integrated kinetic model of the immune response to the attenuated non-replicating Type I parasite cps1-1 vaccine is contemplated. Inoculation i.p. with cps1-1 results in a rapid early recruitment of GR-1$^+$ CD68$^+$ granulocytes and GR-1$^+$ CD68$^+$ inflammatory macrophages into the local site of inoculation by Day 2. By Day 2 post-inoculation, some percentage of PEC-derived *T. gondii*-specific granulocytes and/or inflammatory macrophages has migrated peripherally to the spleen based on splenocyte production of IL-12p40 and IL-12p70 by Day 2 post-inoculation. It is possible that a small number of *T. gondii*-specific CD4+ and/or CD8+ T cells have also migrated to the spleen by Day 2. While the percentage of CD4+ T cells does not rise until Day 4, by Day 2, the absolute number of CD4+ T cells is slightly increased. Unexpectedly, the infiltration of CD8+ T cells is more significant compared to CD4+ T cells at Day 2. There is a transient systemic production of IFN-γ that is only detected at Day 2 that may be explained by the migration of *T. gondii* cells activated in the peritoneum to the spleen, or other lymphatic tissue. This indicates that by Day 2, the cps1-1 vaccine has already triggered immune surveillance to identify all locations and tissue where *T. gondii* parasites may have disseminated. However, because the vast majority of cps1-1-invaded cells remain at the original site of inoculation i.p., the Th-1-biased immune response amplifies locally in a tightly controlled manner, and at most, very minor peripheral or systemic responses develop. It appears that the cps1-1-vaccinated host has already committed to a Th-1-biased immune response by Day 2 based on cell infiltration and cytokine production profiles. In part, this early expansion via infiltration of inflammatory and adaptive Th-1 cell types is inversely proportional to a migration of B cell populations out of the peritoneum by Day 2. The retention of B cells is stable though reduced. The tightly controlled Th-1 response may explain the eventual production of *T. gondii*-specific IgG1 and IgG2a antibody subclasses. It is inferred that the Th-1 response is tightly controlled based on the stable production of systemic- and PEC-derived IL-12p70 from Day 2 to Day 8, along with the low levels of IFN-γ observed at Day 2 that is likely to be derived from the infiltrating granulocytes and/or inflammatory macrophages. While IFN-γ is not detectable (<10 pg/ml) systemically after Day 2, the PEC-derived IFN-γ slightly increases by Day 4, peaks at Day 6, then declines markedly at Day 8, indicating that IFN-γ in the peritoneum after Day 2 correlates closely to the same kinetic pattern as the percentage of CD8+ T cells present at the local site of vaccination. CD4+ T cells may contribute to PEC-derived IFN-γ although the continued rise in CD4+ T cells at Day 8 does not correlate with the significant decline in IFN-γ production between Day 6 and Day 8. The innate response subsides between Day 2 and Day 4 based on loss of systemic IFN-γ and the marked loss of granulocytes and inflammatory macrophages that infiltrate between Day 0 and Day 2. The slight increase in inflammatory macrophages between Day 4 and Day 6 indicates that some percentage of *T gondii*-specific Gr-1+ CD68+ cells that left the peritoneum on Day 2 to search peripheral organs has returned to the peritoneum where most of the originally vaccinated parasites remain locally positioned. These returning Gr-1+ CD68+ inflammatory macrophages or infiltrating T-reg cells may suppress the Th-1 response and explain the decline in IFN-γ between Day 6 and Day 8. The Day 4 to Day 6 Gr-1+ CD68+ increase cannot by itself explain the marked increase in IFN-γ between Day 4 and Day 6 and these inflammatory macrophages largely depart the peritoneum by Day 8. The cross-talk between CD4+ and CD8+ T cells may explain the peak of IFN-γ production on Day 6. The decline of IFN-γ by Day 8 indicates the local Th-1 inflammatory response is rapidly resolving. In regard to T cells, the data herein cannot discriminate between two models where the marked increase in CD4+ and CD8+ T cells at Day 6 (stable to day) is from continued infiltration of new T cells to the peritoneum or alternatively is due to IFN-γ-dependent expansion of previously peritoneum-activated *T gondii*-specific T cells. It is contemplated that the complete CD4+ and CD8+ T cell response is determined by cell infiltration, antigen presentation, and signaling events that have occurred by Day 2 post-vaccination with cps1-1. The Gr-1+ CD68+ inflammatory macrophage population may play a role in antigen presentation to CD4+ and CD8+ T cells. Infected epithelial cells or other cps1-1-invaded cell types are also likely to present antigen to T cells. The rapid production of IL-12p70 by Day 2 and its production maintained through Day 8 by PECs is likely important for tight regulation of the Th-1 immune response. The source of PEC-derived IL-12p70 is under investigation. Early production of IL-12p70 by Day 2 may originate from the Gr-1+ CD68+ granulocytes and Gr-1+ CD68+ inflammatory macrophages (Bennouna, et al. (2003) *J. Immunol.* 171: 6052-6058; Bliss, et al. (2000) *J. Immunol.* 165:4515-4521). However, IL-12p70 production rises significantly by Day 4 while the granulocyte population essentially disappears, and based on cell type profiles in the peritoneum the only profile that correlates precisely to production of IL12p70 is the CD19+ B cell. The immune response elicited to cps1-1 vaccination is local and rapid, and the inflammatory response is tightly regulated. This immune response leads to a very effective and long lasting immunity to *T. gondii*.

Example 6

*T. gondii* as a Delivery Vector for Heterologous Antigens

By way of illustration, gene specific primers are generated to amplify the coding sequence for *P. berghei* merozoite surface protein-1 (MSP-1), the sequence of which is known in the art under GENBANK Accession No. XP_678505. The amplified product fused to the SAG1 promoter (Striepen, et al. (1998) supra) and cloned into p53KOX3-1R, i.e., the CPSII deletion construct which harbors the DHFR-TK-TS marker sequences. The resulting construct is introduced into *T. gondii* using established methods and an attenuated uracil auxotroph which expresses MSP-1 is identified based on dependence upon pyrimidine supplementation for replication and expression of MSP-1. A suitable murine *Plasmodium* model is used to demonstrate protective immune responses of the *T. gondii*-based vaccine to *P. berghei* infection. Immune response to *Plasmodium* parasites is associated with reduction in patient infection intensity. With this invention, the potency of immune response against MSP-1 and other malarial antigens is expected.

Previous work has demonstrated the feasibility of using live vectors for immunization against malaria. Immunization of mice with Salmonella expressing CSP and MSP-1 protected against *P. berghei*, and induced immune responses against *P. falciparum* MSP-1 (Sadoff (1988) *Science* 240: 336-8; Toebe (1997) *Am. J. Trop. Med. Hyg.* 56:192-9; Wu (2000) *Biotechnol.* 83:125-35). The anti-MSP-1 immune response did not require secretion of antigen from the bacterium or surface display. These data indicate that use of *T. gondii* as a platform to deliver *P. berghei* antigens in vivo is highly likely to protect mice and other mammals against malaria. For use in humans, vaccines that work in the *P. berghei* mouse model can be reconstructed with homologous *P. falciparum* antigens. Safety and immunogenicity testing in mice and efficacy testing against infection in nonhuman primates can then lead to human trials.

Other antigens and animal models are well-known in the art and can be employed in accordance with the present invention. For example, the *B. anthracis* protective antigen can be expressed by the *T. gondii* cps1-1-based vector platform with protection against anthrax infection determined using either the well-established mouse or guinea pig model (Peterson et al. (2006) *Infect. Immun.* 74:1016-24).

Example 7

Essential Indels and Domains of CPSII

Plasmid Construction. A functional CPSII minigene encoding the authentic 1687 amino acids of carbamoyl phosphate synthetase was constructed by sequential coupling of defined cDNA segments generated by reverse transcriptase/PCR. First, a 1829 bp cDNA for the N-terminal GATase domain of CPSII was amplified from polyA+mRNA from the RH strain (5'-ACT AGT GGT GAT GAC GAC GAC AAG ATG CCT CAC AGT GGA GGG C-3', SEQ ID NO:12; and 5'-GAT ATC CAC GTG TCG CGG CCG CGC TCT C-3', SEQ ID NO:13). The 1829 bp cDNA was introduced (SpeI/EcoRV) into PET41b (SpeI/XhoI-blunted). Next an N-terminal section of the CPS domain cDNA including by 1829 to by 3532 was generated (5'-GAG AGC GCG GCC GCG AC-3', SEQ ID NO:14; and 5'-CAC GTG GAG GCG AGA CGT CGT CGT C-3', SEQ ID NO:15) and fused to the GATase domain (NotI/PmlI). The remainder of the CPS domain was constructed by amplifying two cDNA segments, by 3003-4097 (5'-AGT ACT TGA TGA ATT CAC CG-3', SEQ ID NO:16; and 5'-TTT CTG CGA GAT CTT CTT CAC G-3', SEQ ID NO:17) and by 4097-5065 (5'-GCG TGA AGA AGA TCT CGC AG-3', SEQ ID NO:18; and 5'-ATC GAT CAC GTG ATT TTT GAG GCC AGT ATT CAT CC-3', SEQ ID NO:19), and then the two C-terminal segments were fused in PCR4TOPO (EcoRI/BglII). Finally the C-terminal section of CPS was fused with the N-terminal section in PET41b (EcoRI/PmlI) and the complete 5063 bp CPSII minigene coding sequence was determined to verify authenticity.

5' UTR and 3' UTR were amplified from RH genomic DNA. 5' UTR to by −516 was amplified (5'-GCT AGC GTG GAC CCC CAT TAT CCT TCG C-3', SEQ ID NO:20; and 5'-ACT AGT CAC TCG TCG AAT GGT TGC GTC TG-3', SEQ ID NO:21), and 5' UTR to by −2057 was amplified (5'-GCT AGC GTG GAC CCC CAT TAT CCT TCG C-3', SEQ ID NO:22; and 5'-ACT AGT GAA ATC GCG ATC AAC GCG ACA G-3', SEQ ID NO:23). The 3' UTR (920 bp) was amplified (5'-AGT ACT TGC ACC ACC ACC ACC ACT AAT TTC CAA TAC TTT CGC CAA AAA CGT TCC-3', SEQ ID NO:24; and 5'-GCG CAC GTG GTT GAG AGC TTG ACC CGC ATG CA-3', SEQ ID NO:25). Finally 5' UTR segments (ScaI/SpeI) were fused into the CPSII minigene (SpeI), and then the 3' UTR (ScaI/PmlI) was fused to the above plasmid(s) (ScaI/PmlI).

Site-Directed Mutagenesis. Mutations were first introduced into the either the GATase or CPS domains using Stratagene's PCR based QUIKCHANGE® II XL Site-Directed Mutagenesis Kit. Products were DpnI digested, transformed into XL-10 GOLD® Ultracomp cells, and subsequently transferred into the full CPSII complementation vector. Forward and reverse complimentary primers containing the desired mutations were used to create the desired mutations and CPSII minigene mutations were verified prior to transfection experiments.

Parasite Culture and Transfection. Tachyzoites were maintained in human foreskin fibroblasts with or without uracil supplementation (300 mM). Wild-type or CPSII minigene plasmids containing defined mutations were transfected (20 mg) into the cps1-1 background and selections were performed without drug addition in the absence of uracil using previously described methods.

Parasite Growth Assays. The growth of tachyzoites in culture fibroblasts was measured at 36 hours post-transfection, as well as in standard 7 day pfu assays. To determine parasite growth rate (doubling time) tachyzoites per vacuole were scored from 50 randomly selected vacuoles containing 2 or more parasites 36 hours post-transfection. Transient complementation efficiency was measured at 36 hours by counting the number of vacuoles containing 2 or more parasites in 50 randomly selected areas of the culture. The wild-type CPSII minigene was used in control experiments in all transfections to compare efficiency of transient complementation. Stable complementation efficiency was determined in a standard 7 day plaque forming unit assays. Immediately following transfection duplicate cultures were inoculated with 2%, 0.5%, or 0.1% of transfected parasites and pfu were scored 7 days later.

Complementation of Uracil Auxotrophy with Functional CPSII cDNA. The cps1-1 mutant of *T. gondii* invades host cells, but due to pyrimidine starvation, exhibits no detectable growth rate in the absence of uracil supplementation. Consequently, providing a functional CPSII gene to the cps1-1 mutant can restore production of carbamoyl phosphate required for biosynthesis of UMP. To examine complementation, a cDNA minigene encoding the 1687 amino acid CPSII polypeptide was constructed under the control of authentic CPSII 5' UTR and 3' UTR regulatory regions. Plasmids representing a promoter-less minigene coding region construct as well as minigenes under the control of either 0.5 kb or 2.0 kb of 5' UTR were transfected into the cps1-1 uracil auxotrophic mutant and parasites were cultured in HFF cells in the absence or presence of uracil. Thirty-six hours after transfection, the number of tachyzoites per parasite vacuole was scored by counting 100 randomly chosen vacuoles. The 2 kb 5' UTR CPSII minigene Pc4 efficiently complemented the cps1-1 mutant and restored a normal tachyzoite growth rate in the absence of uracil. In contrast, both the promoter-less construct Pc0 as well as the 0.5 kb 5' UTR construct Pc2 failed to complement the cps1-1 mutant and did not restore any detectable growth rate in the absence of uracil. These results demonstrate functional complementation of uracil auxotrophy in *T. gondii*. By counting the number of vacuoles containing actively replicating tachyzoites in the absence versus the presence of uracil, the overall efficiency of complementation following transfection of the 2 kb 5' CPSII cDNA minigene was determined. In a 36 hour growth assay, uracil auxotrophy was complemented in ~34% of parasites surviving electroporation with plasmid Pc4, demonstrating a very high efficiency of complementation roughly equivalent to the efficiency of positive selection reported using plasmids bearing pyrimethamine resistant alleles of dihydrofolate reductase-thymidylate synthase as a selectable marker (Donald & Roos (1993) *Proc. Natl. Acad. Sci. USA* 90:11703-7). Pc4 transfectants showed a high frequency of stably complemented cps1-1 parasites that exhibited the high virulence phenotype of the parental RH strain in c57/b16 mice.

Functional Analysis of the Glutamine Amidotransferase Domain of CPSII. The requirement of the fused eukaryotic GATase domain to produce ammonia for CPS function in apicomplexan CPSII has not been previously examined in vivo. A mutation in plasmid Pc4 was constructed, wherein an essential catalytic triad residue of the GATase domain (Table 2), equivalent to Cys269 in *E. coli* Carbamoyl Phosphate Synthetase (Rubino, et al. (1987) *J. Biol. Chem.* 262:4382-6), was mutated to abolish activity. The resulting Cys345 to A1a345 mutation completely abolished complementation activity, indicating that *T. gondii* CPSII is dependent on a functional GATase domain for the production of ammonia in vivo (Table 3). The dependence of *T. gondii* CPSII activity on the amidotransferase domain validates the analysis of unique sites within this domain as parasite specific drug targets.

TABLE 2

| Mutation | Location in T. gondii CPS II | Effect on CPS or CPSII |
|---|---|---|
| E. c. C269A | C345 | Mutation in catalytic triad<br>Abolishes GATase activity |
| E. c. G359F | G435 | Mutation in tunnel wall<br>Ammonia leaks<br>Uncouples GATase & CPS |
| H. a. T456A | T533 | Mutation in MAPK site<br>Abolishes MAPK activation |
| E. c. E761A | E1316 | Mutation in K-loop<br>Abolishes ornithine activation<br>Abolishes UMP repression |
| E. c. H781K | H1336 | Mutation in K-loop<br>Reduces CPS activity<br>Reduces ornithine activation<br>Reduces UMP repression |
| E. c. T974A | T1530 | Mutation in regulatory-D<br>Reduces ornithine activation<br>Abolishes IMP activation<br>Abolishes UMP repression |
| H. a. S1345A | T1530 | Mutation in regulatory-D<br>Reduces PRPP activation |
| E. c. T1042A | T1649 | Mutation in regulatory-D<br>Reduces ornithine binding |

TABLE 3

| T. gondii CPSII GATase Mutation | Growth Rate (Hours) | Transient Efficiency (% of Wild-Type) | Stable Efficiency (% of Wild-Type) |
|---|---|---|---|
| Wild-Type | 7.4 | 100 | 100 |
| Δ172-229 | Nd | 0 | 0 |
| C345A | Nd | 0 | 0 |
| N348R | Nd | 0 | 0 |
| N348A | 8.2 | 96 | 91 |
| P385R | 11.5 | 18 | 1.3 |
| G435F | 12.4 | 8.4 | 0.6 |
| Δ455-457 | 7.5 | 98 | 103 |
| Δ454-470 | 8.9 | 64 | 11 |

Figure 7A:
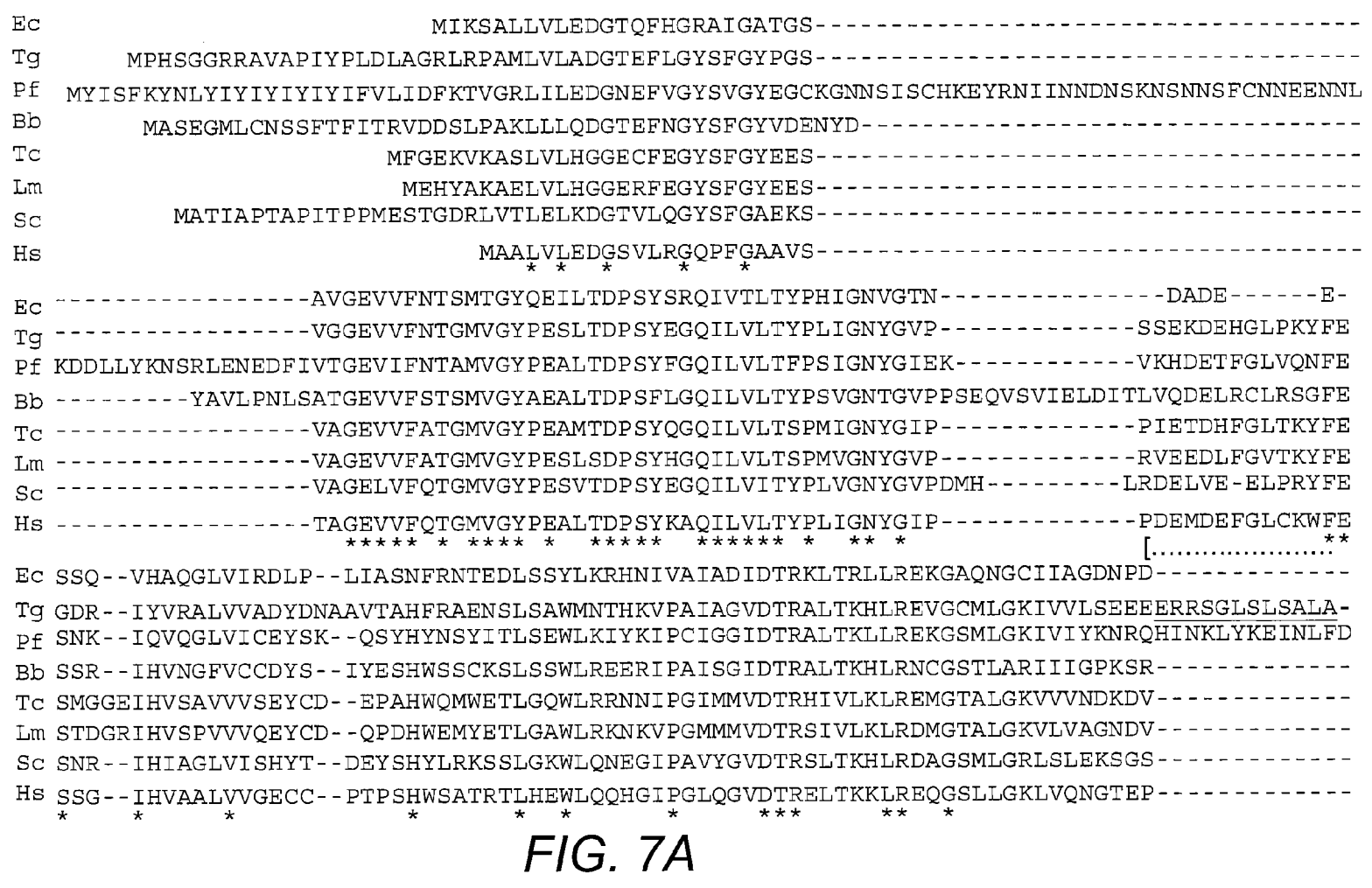

The proximal Asn348 residue, which is selectively present in most protozoan CPSII enzymes (FIG. 7), was subsequently targeted. Mutation of Asn348 to Arg348 abolished complementation activity, whereas mutation of Asn348 to Ala348 only moderately reduced the initial growth rate (from 7.4 to 8.4 hours) in the 36-hour growth assay, but did not significantly interfere with the efficiency of transient or stable complementation (Table 3). Amino acid 385 adjacent to residues encompassing the catalytic triad is uniquely a proline residue in T. gondii CPSII (FIG. 7). Changing amino acid P385 to R385 had a dramatic effect on reducing the initial parasite growth rate (from 7.4 to 11.5 hours, and reduced transient complementation efficiency to 18% and stable complementation efficiency to 1.3% of the control (Table 3). A reduced efficiency of transient complementation within the primary vacuole indicates that several copies of mutant R385 plasmid per parasite were required to restore growth. This was borne out in real-time PCR analysis of cloned progeny from the pfu assay indicating that between 3 and 7 plasmid copies were stably integrated in complemented parasites.

The requirements for ammonia production from GATase and channeling of ammonia are well-described for E. coli CPS (Huang & Raushel (2000) J. Biol. Chem. 275:26233-40; Huang & Raushel (2000) Biochemistry 39:3240-7; Miles, et al. (1998) Biochemistry 37:16773-9; Thoden, et al. (2002) J. Biol. Chem. 277:39722-7; Thoden, et al. (1999) Acta Crystallogr, D, 8-24). Perforation of the ammonia tunnel in E. coli CPS via mutation of G359 to F359 results in ammonia leakage from the tunnel and loss of CPS activity (Table 2). The Gly residue corresponding to E. coli G359 is universally conserved in all GATases that are coupled with CPS activity (FIG. 7). Mutation of T. gondii G435 to F435, corresponding to the E. coli G359 to F359 mutation, caused a marked reduction in the initial parasite growth rate (from 7.4 to 12.4 hours), and reduced transient complementation efficiency to 8.4% and stable complementation efficiency to 0.6% of the control. These results indicate that disruption of the putative ammonia tunnel markedly decreased CPSII activity in vivo (Table 3), again showing a strict dependence of the parasite CPS on ammonia produced by the fused GATase activity of CPSII.

Deletion of Indels. Apicomplexan CPSII enzymes contain locations where novel insertions of amino acids (indels) occur at several locations within the GATase and CPS domains (FIG. 7). While ribozyme targeting of a P. falciparum CPSII indel at the RNA level was previously shown to inhibit parasite proliferation (Flores, et al. (1997) J. Biol. Chem. 272: 16940-5), few studies have directly addressed the functional importance of indels in parasite proteins. The unusually frequent occurrence of novel insertions of low or high complexity within protozoan parasite proteins, particularly in Plasmodium sp. and T. gondii (Cherkasov, et al. (2006) Proteins 62:371-80; DePristo, et al. (2006) Gene 378:19-30), may provide parasite selective drug targets in certain instances where the indel provides a necessary function for biological activity of an essential parasite protein. Functional complementation of CPSII in T. gondii enabled a genetic test of essential indels. In the GATase domain the T. gondii CPSII indel location was targeted where other apicomplexan CPSII also exhibit a large amino acid insertion that other protozoans, fungi, mammals, and prokaryotes do not share (FIG. 7). Deletion of the GATase indel (E171-A229), relative to human GATase, completely abolished CPSII function as demonstrated by the inability of this mutant to complement the uracil auxotrophy of cps1-1 (Table 3), and established this indel as a parasite-selective drug target within the essential GATase domain.

The carboxy terminal region of the CPSII.A domain (domain A3) contains the oligomerization domain known to coordinate the formation of tetramers of E. coli CPS (Kim & Raushel (2001) Biochemistry 40:11030-6; Thoden, et al. (1997) Biochemistry 36:6305-16). On the N-terminal side of the putative CPSII oligomerization domain a novel indel of ~34 amino acids is present in T. gondii CPSII (FIG. 7). Deletion of this indel (C873-G910) caused a minor, but detectable, disruption in complementation activity based on a reduced initial growth rate (from 7.4 to 8.2 hours), similar transient complementation efficiency (113%), and slightly reduced stable complementation efficiency to 65% of the control (Table 4). The more subtle effect of this indel deletion in the T. gondii CPSII oligomerization domain is potentially similar to the minor effect on E. coli CPS activity previously observed in mutants blocked in oligomerization contact regions that prevent tetramer but not dimer formation (Kim & Raushel (2001) supra).

TABLE 4

| T. gondii CPS Mutation | Growth Rate (Hours) | Transient Efficiency (% of Wild-Type) | Stable Efficiency (% of Wild-Type) |
|---|---|---|---|
| Wild-Type | 7.4 | 100 | 100 |
| T533A | 7.4 | 105 | 98 |
| S581A | 7.3 | 109 | 104 |
| Δ873-910 | 8.2 | 113 | 65 |
| E1316A | Nd | 0 | 0 |
| E1318A | Nd | 0 | 0 |
| H1336K | Nd | 0 | 0 |
| T1430A | 7.7 | 86 | 82 |
| T1530A | 8.6 | 51 | 10 |
| T1530 fs | Nd | 0 | 0 |
| Δ1592-1628 | Nd | 0 | 0 |
| S1608A | Nd | 0 | 0 |
| T1649A | 8.5 | 65 | 37 |

Interaction of allosteric effectors with the C-terminal regulatory domain directly trigger conformational changes in CPS affecting activity and/or synchronization of active sites (Thoden, et al. (1999) *Acta Crystallogr. D Biol. Crystallogr.* 55:8-24). *T. gondii* and *B. bovis* CPSII share an indel location within the C-terminal regulatory domain (FIG. 7). To examine whether this novel indel was essential to CPSII function, a deletion of the C-terminal indel (G1592 to R1628) was constructed. This deletion completely abolished CPSII complementation activity (Table 4). Remarkably, only a point mutation at residue S1608 to A1608 in this indel was necessary to abrogate the ability of the CPSII minigene to complement the uracil auxotrophy of cps1-1. These results indicate that the C-terminal regulatory region indel represents a parasite-selective drug target.

CPSII Regulatory Domains. Suppression of mammalian CPSII activity is highly dependent on the presence or absence of regulated phosphorylation at a distinct MAP kinase site at (T456) in the carboxy phosphate CPSII.A domain by MAPK (Graves, et al. (2000) *Nature* 403:328-32). *T. gondii* and other lower eukaryotic forms of CPSII are distinct from mammalian CPSII in lacking this critical MAPK site (FIG. 7). However, since *T. gondii* CPSII shares the Threonine residue corresponding to the mammalian T456 position, this residue was mutated to exclude the possibility that a novel parasite MAP, or a novel, kinase may control CPSII activation. Mutation of T533 to A533 in *T. gondii* CPSII had no significant effect on complementation activity (Table 4). It was also determined whether the nearby putative MAPK core SP site present in *T. gondii* but absent in mammalian CPSII was necessary for activity. Mutation of 5581 to A581 also had no detectable effect on complementation activity (Table 4).

CPS is controlled via allosteric mechanisms acting through specific allosteric effectors and their binding interactions with the C-terminal domain of CPS.B (Braxton, et al. (2000) *Biochemistry* 38:1394-401; Fresquet, et al. (1999) *J. Mol. Biol.* 299:979-91; Pierrat, et al. (2002) *Arch. Biochem. Biophys.* 400:26-33; Thoden, et al. (1999) *J. Biol. Chem.* 274: 22502-7). Prokaryotic (*E. coli*) CPS activity is repressed by UMP, strongly activated by ornithine and weakly activated by IMP, whereas eukaryotic CPSII is typically activated by PRPP and is repressed by UTP (or UDP in kinetiplastids) (Jones (1980) *Ann. Rev. Biochem.* 49:253-79; Nara, et al. (1998) *Biochim. Biophys. Acta* 1387:462-8). Strikingly, *T. gondii* CPSII is insensitive to allosteric activation by PRPP, and relatively high levels of UTP are required for suppression (Asai, et al. (1983) *Mol. Biochem. Parasitol.* 7:89-100). To gain further insight into the importance of allosteric regulatory regions and the type of regulation occurring in *T. gondii* CPSII, mutations were constructed in several amino acid residues that were conserved between the *T. gondii* and *E. coli* C-terminal regulatory domains, and that were also known to mediate allosteric control in *E. coli* CPS (Table 2). While IMP induces only modest allosteric effects on *E. coli* CPS activity, ornithine potently activates the glutamine dependent ATPase and ATP synthesis reactions and thereby markedly upregulates activity by increasing the affinity of CPS for its nucleotide substrates while overriding the strong effect of UMP to suppress the catalytic activity of CPS (Braxton, et al. (1999) supra). Targeting of the conserved ornithine binding sites identified in *T. gondii* CPSII analogous to those previously identified in *E. coli* (Table 2) was carried out. The K loop coordinates the binding of a potassium ion and includes the conserved residue H781 that also coordinates the transmission of the allosteric regulatory signals from the C-terminal regulatory domain (Pierrat, et al. (2002) supra; Thoden, et al. (1999) supra). Mutation of H781 to K781 in *E. coli* CPS reduces the magnitude of the allosteric effects of both ornithine and UMP, decreases the allosteric response to IMP, and also diminishes the catalytic activity of CPS by one to two orders of magnitude in the absence of allosteric effectors (Pierrat, et al. (2002) supra). In *T. gondii*, it was found that a CPSII minigene with the analogous mutation (H1336 to K1336) failed to detectably complement the uracil auxotrophy of the cps1-1 mutant (Table 4). A second mutation (E761 to A761) also within the K loop of *E. coli* CPS was previously found to be crucial to the transmission of the allosteric activation signal by ornithine, but did not affect catalytic turnover in the absence of effectors. This mutation also eliminated feedback repression by UMP and decreased activation by IMP (Pierrat, et al. (2002) supra). In *T. gondii* CPSII, it was observed that the analogous mutation of E1316 to A1316 resulted in a complete loss of complementation activity by the mutant CPSII minigene (Table 4). Interestingly, a second mutation (E1318A to A1318) at a nonconserved residue two amino acids downstream of E1316 also resulted in a complete loss of complementation activity by the mutant CPSII minigene (Table 4).

To further define the extent of the impact of mutations within the allosteric regulatory region, a residue conserved between *T. gondii* and the *E. coli* CPS.B3 allosteric regulatory region (T974) that strongly influenced the allosteric response to ornithine in *E. coli* CPS (Table 2) was also targeted. The mutation T974 to A974 disrupts the IMP/UMP binding pocket in *E. coli* CPS and not only abolishes UMP inhibition and IMP activation, but also decreases activation by ornithine (Fresquet, et al. (2000) supra). Interestingly, this site also plays a role in allosteric control in mammalian CPSII as well since mutation of the corresponding hamster residue 51355 to A1355 nearly abolishes activation by PRPP and lowers overall CPSII activity ~5-fold (Simmons, et al. (2004) *Biochem. J.* 378:991-8). While *T. gondii* CPSII is nonresponsive to PRPP in vitro, mutation of the analogous residue in *T. gondii* CPSII (T1530 to A1530) significantly reduced CPSII complementation activity based on a reduced initial parasite growth rate (from 7.4 to 8.6 hours), and reduced transient complementation efficiency to 51% and stable complementation efficiency to 10% of the control suggesting several copies of this mutant allele are necessary to fully support parasite growth (Table 4). A second conserved residue (T1042) in the *E. coli* regulatory domain plays a direct role in ornithine binding (Pierrat, et al. (2002) supra). Mutation of T1042 to A1042 in *E. coli* CPS reduces the magnitude of the allosteric response to ornithine. The analogous mutation T1649 to A1649 in *T. gondii* had the more modest effect of slightly lowering the initial growth rate (from 7.4 to 8.5 hours), and reduced transient complementation efficiency to 65% and stable complementation efficiency to 37% of the control. Additionally, the overall importance of the relatively nonconserved *T. gondii* CPSII C-terminal regulatory region as a putative drug target could readily be seen through a frame-shift that was incorporated into T1530 that effectively deleted much of the regulatory region (Table 4). This mutation abolished complementation of cps1-1 by the CPSII minigene.

What is claimed is:

1. An attenuated uracil auxotroph mutant of *Toxoplasma gondii* comprising a nucleic acid molecule encoding an exogenous protein, wherein the exogenous protein is a non-*Toxoplasma gondii* bacterial, fungal, parasitic or tumor antigen, a protein that produces a non-*Toxoplasma gondii* antigen, a therapeutic antibody, an interferon, blood factor, insulin, erythropoietin, blood clotting factor, asparaginase, catalase, lipase, or tissue plasminogen activator.

2. The mutant of claim 1, wherein said mutant lacks a functional carbamoyl phosphate synthetase II enzyme.

3. A vaccine for protection against infection by *T. gondii* and a non-*T. gondii* disease comprising the mutant of claim 1 in admixture with a pharmaceutically acceptable carrier.

4. The vaccine of claim 3, wherein said vaccine is formulated for peritoneal, oral, topical, or intravenous administration.

5. A method for generating an immune response in an animal comprising administering to an animal an effective amount of the mutant of claim 1 so that an immune response to *Toxoplasma gondii* or non-*T. gondii* antigen is generated.

6. A method for identifying an effector of a human therapeutic target protein or enzyme comprising contacting the mutant of claim with an effector and determining whether the effector inhibits or activates the human therapeutic target protein or enzyme.

7. A method for sensing a host cell environment or specific molecules present or absent in the host cell environment comprising administering the mutant of claim 1 to a subject and determining the host cell environment or presence or absence of specific molecules in the host cell environment.

8. The method of claim 7, wherein the molecule is a pyrimidine.

* * * * *

UNITED STATES PATENT AND TRADEMARK OFFICE
CERTIFICATE OF CORRECTION

PATENT NO.        : 8,673,289 B2                                Page 1 of 1
APPLICATION NO.   : 12/808273
DATED             : March 18, 2014
INVENTOR(S)       : David Bzik It is certified that error appears in the above-identified patent and that said Letters Patent is hereby corrected as shown below:

In the Claims

Column 144, line 49, delete "claim with"
Column 144, line 49, add -- claim 1 with --

Signed and Sealed this
Third Day of June, 2014

Michelle K. Lee
*Deputy Director of the United States Patent and Trademark Office*

SEQUENCE LISTING

<160> NUMBER OF SEQ ID NOS: 32

<210> SEQ ID NO 1
<211> LENGTH: 27377
<212> TYPE: DNA
<213> ORGANISM: Toxoplasma gondii

<400> SEQUENCE: 1

```
caggcggagc ggcagaaacc gagagagacg cggtcgcgcg ggaaaactgg gggacagaag     60
gtcgcgatga tgcgacagag gccttcgaca ttcgagaatt caacacgttc tgccaagcaa    120
cagaaggcgc acaagggctg catgcagctg aagctcctgt ctgcaaaagc tcgatacgtg    180
acttgaccgg caccggatgc gacgggaggg aggaaatccc cgaaatcgca gaaaccccag    240
tttcgccgcg tcgtcctgag gaggcagtgg cggttcgcca ggcagttcgc tgttcgggaa    300
agcgttggac gtccagcgaa gcacaggcga agacggacga gaaaacccgg tgaaattcgt    360
caaggagccg agaaatcgcg atcaacgcga caggccccga aagcgcctct tgttggcgaa    420
ctggaaaaga aacagggtct gtctgcccgc gcggcggagc tgttcttttt gccgtggaca    480
ctcatgcgtg gacgcgaaaa ctcgagaaaa atcgagaact cgtcgagaaa actctttttg    540
cgtagaattc cggcctgctc tgtcgcgata aactctgtcg aatccgctcg ttcaaaagat    600
agtcgcttgc gctaaaaatg cagttgccca gctgccgtga gaacagcgtg gagaaaagaa    660
gactcggctt agatccggaa accgccgtct ctcccttccc gcccgggcgg actgccgttg    720
aggggtgtcg gcttcctcac acgcccgagc gcggtaggcg gcgactcgag gcgcgcttcg    780
cacaaagact tggtcacctc cgcgagggtc caaaaatgtg ctttcggaca gactgtggaa    840
agctgggctc tccggcactg ttgtaaaaaa tcccccgatt ccgcgctgca cactgtgcgc    900
ccaaccgcgg gcacatacga cgcgtcaagc gtggcgtttc tccctcgtcg ggtgtctctc    960
ctgctgagga aatagcgagg gaaaccgatc ttgtggaagg tagaagatct gcaggaaact   1020
tttgcagagt atgcacgcta tcgtcgcctc gtgaggaggt ggtggtaatt tctctgggaa   1080
actggtgacc cgcctctcta gccggctgga tggccagctg gcaagcctga gagctgtatc   1140
tgcctcgttg cggtgtctct ttacacgacc gtcaaactcg caggtgtggg tgtggcgtcg   1200
aaacacaatg tatttccaaa tgaaagaacg ctatcgccac atttgacgct tttcgaaaag   1260
gctccggcgc gaagcgcttc gccttccggg gggtgggaga cgagagtctg ccctctcttg   1320
ctcgggtgtc tatacacctc gattgtctac gggaggccgg agcggttcca gcacgtcctt   1380
gtttttagtt gttcgctgtt cgcttttaac gcaagtagta ggcgctcctt actctatttg   1440
gagtgaagct cccgtttttc ctgagaattg aggtccttaa attggtggcc cgccgttcct   1500
cccagagacc cccctctcgc gcttgccgcg tttcgcgctg cggtgtgtct gcccgtttcg   1560
cgaatcgctg tctcgcttcg cggcgagagt ctcgccgccc ctgtgtgact gagcctccac   1620
gcacgcgaca tctgccgtgt gaaatgaatt tttctgcttt tttcctgttt tcgtatccag   1680
agctgtttca aatcaaagac gtccgcaggt cccgtcggtt gtccctcgga agtacccctc   1740
cccgtgcatg cgttttgcgc gcatcgacga gcccgcagca cagagtcatg cggtctgcgg   1800
cgaagacctt tggggaaacc gtcgctcagc gctaatcggt ttgtccgttg atctgtcaga   1860
gaaaactccc accttttct cctttttgt ttctgcttca cggcaccccc cacactcgtc   1920
```

```
gatggttgcg tctgtgtctc cgtctttgag caagccgtga tttgctggcc ctccccgcg    1980
ccggttctcg cttcgcattt cttctctgca gcgcttcggc cctgaaacct tcgtcgttcc    2040
ccacttcgag tgtcgtttac agttcctctt ttcgcctctc attctgcgaa ccacgcccca    2100
actgctttcc cccatatcgg cggcgcctgt gcgacctccg gtctccacgc ccgcgcgact    2160
tctccgcctg ctgtccgctc ccgtgctgtc cttctgcacc ggatcttcct ctcgctgaac    2220
cttctgcccg tcttgtctct cgaattctcc tctaccctct tcttgtcttc ctctctgcat    2280
catccgtgtct ctcttgcgtg gggcagcggg tgctgttgag tctggcgcta cgtggctaag   2340
ttcgcggacg ccgcagagaa attccttgga gcgttttttg acggcgaagg ataatggggg    2400
tccaccatgc gctcgacgat gcgggggaga tgcctcacag tggagggcgg agagctgttg    2460
ctcccattta ccctctcgat ctggcaggtc agtccgccgt ttcgttcaga cttccttctc    2520
gtctgggttc tttgtttcac acgcctggcc gcgtctcctc tccgcttctt ggtgtgcagc    2580
ctcggttcct cccctttgat cagctgtctc ggttgcgctt ccgcccgtg cgtcgccttc     2640
cgtgtttgct tccaattttc tcctggcttg ctcgtgtgtt cgcgcccctc cggggagacc    2700
ggcctgtctg ctgccgacag agaggcagct gtgaagggcg tgatcatcaa ctgtctccga    2760
cggagagaca cgacgtctgt gatgcaagca aatgagcgcg tgtatgcaca ggtacccgcg    2820
catactgaaa tattttcgta tctgcagatc cacaggcgca tgcatgcgcc caactgtacc    2880
cacgcgtgtt tctacatagt tgtggagagg cacatgcgtc tgcatgtgtg cacgttgtct    2940
attcttgcga acgataaacc tggtggcgat ccgtgtgtta ttttcaagaa gtgatttcga    3000
cgcaggccat ctcgctcgtc gctcgtttcc tgtgtttgtc ggctgctcgc aggacgtctg    3060
agacctgcaa tgctggtgtt agccgatggg actgagtttc tcggatactc cttcggctac    3120
ccaggcagtg tgggaggcga ggtcgttttc aacactggta cgttttttctc gaatttgtcc   3180
agaaacgctg acgtttggcg tctctcctct ccagaaaggg tgcattcggt ctatccgctg    3240
tgtgctgcag cgattggtcc tcctcttaca agcgcgtaca ccaccctatg cagcctcatg    3300
caccgccatc tgtcaacgcg tgtggggacc gccaccacac gcccatgtat ctaccttcga    3360
taaacatatt tatgcatata tatatatata tatagcatat atatatatat atatatagca    3420
tatatatata tatatatatg catgtagata ctcaaaatgc atgcatattg gtacgtctgt    3480
tcacctgtat ttttctgcgt gataattaga tacccctggg ttgcgtcacc atgagctgtg    3540
tatcgttctg ggtgcatgcg ttgttgcggg agtgttcgtg cgtcgggaaa ggtagtggcc    3600
gacttcttgt cttttggcgtg gttaggtatg gtcggctacc ccgagtctct gacggatcct   3660
tcgtacgagg ggcagatcct cgttctcaca taccctctca tcggcaacta tggcgttccc    3720
tcttcggaaa aagtgagagc agacagcaag aaaacgaaga gactagcaga accccgtact    3780
tcgtggctga tccacatcag tgagagtcga ggagggagag tcggatttct cttgcgacgc    3840
aacgtcacag gaaagcaagt ctggcagggg tctccgcttt ctcacatgcc gaatgcgcac    3900
acaaatcatt catacgtcac tacaaaactg agtcctacgt gagaagagca acgtcacctc    3960
tccgtgagac atatacgtgt ttctatatac atatatacat attatgtata tatttatatt    4020
caaatatata tatatatata tatcaatg tgcatatcta agtttatata tgaacgttca      4080
tctgtctttc gggagagtat ttccctaaat ggcagatgct aagacgcctg tacacctgcg    4140
tgcaaaggtg tttacgcggg tgtctacacg tgagcgaagt gattgctaca cacatgtata    4200
tatatatata tatgtgatg tcgctttaca gtgtttgttt ttctgtacat ctaaagtcgt     4260
ctaggcatcg atatgcgatg tgcatttcag cgtatttcgt gtgtttcatt tccactcttc    4320
```

```
aggatgagca tggcctgccg aaatactttg agggcgaccg catttacgtt cgcgctctcg    4380
ttgtggcgga ctacgacaac gcagccgtga cggcacactt tcgtgcagag aacagcctca    4440
gtgcttggat gaacactcac aaagtcccgg cgattgcagg tgcgaaaaca tcgaggccga    4500
agtgtctgta gtgtcagatg cgcctctgga cacgacatcc tctttcgatg cttgtctttg    4560
attttcactt aattttctct tcgcaagtct gcgaaggaac gcctgtctgt acatctcgat    4620
gcccaggtgg ctttctcggc catttggagg aactgtcttg gatccgcgta gtaggcatgt    4680
atgagggagc agcttctctt tcttctgaat tgtgttccac ttgtaagtcg gttcgaccac    4740
gagcagtcaa gaggctctta ccgtgccacc gagtcaacgt cgcccatcac agaccggctt    4800
ttgaatgcct ttttcttcag gctccattaa tgcacgtctc actgaatccg tgctcgtcaa    4860
tttggacagc tagatctgtg tagtccctag agactaactt tggagggag actaacaata     4920
cagctaggtt gctctacctc ggctatgttt aacgcatagt tcacggatca ctgttgccac    4980
tggtccttac agagagagca cacgactgct cacgtgcttg tcatgagac acatctcgat     5040
cgtgtatgtt tcacttcagt tctgcagagc cgttcagtgt atgtctgcca tgacggggag    5100
gggtatctca agggtgtatt ttgaactgta tttccacggt gtacggggct tgaagtactg    5160
gcgcatctat gtctggagga cgggacgtgg tttagttcgt gtctcagtgc tcaacagcgt    5220
ccggatctct ggcatgctgt tgccatcctg ttagttgctg gccttcgcgg ctactctttc    5280
tcctttaggt gcacctccag tgtctccagt tcagctggtg ttcccttgcc gactgttgct    5340
gctctgtcag ggctttgtag gtccccgcct cactctcgtt tccgcttctc tgttttctgc    5400
gtccgtgtgt gtctcacctc ttcctcttcg tttccatctc ttttcttgtc tcgcctttcc    5460
acggctctcg tttgctcttg aaacgctgtc ggttgtcgtc gttccgcctc gttctctatt    5520
cggctctatc ttcgtcgttc gtcttttgct tcttttcgac ttcccgactc ctgcctgttt    5580
ccggctgtat cgtttctttt ttcaaggagt cgacacgcga gcgttgacca agcacctgcg    5640
cgaggtcggc tgcatgctgg gcaagatcgt cgtcctgagc gaagaagaag agcgtcgatc    5700
cggcttgtcg ctctcggctc tcgccgcgct tccctcagcg actgcagcag agcaacgagg    5760
agagaacgac gcgacggtga cgcccgacaa agcagaggcc cgcctaagag tggagaggcg    5820
acaagcagcg ctcacgatgt gggaggaggc gatccgcaac aaggcgaaga acctgccatg    5880
ggaagacccc aacaaagaca acctcgtcgc cctcgtttcg cgaaaagaag tgcgcgtgta    5940
caaatctact gtcgtggatc cggtgagtga cagagagccc agggaaagac gtttcacgtg    6000
cgaaagcgaa acgcagtttc cacagtcctt gtttagattt agcgtgggac atgcacaagt    6060
tgggattctg cggaatgccg ctatctgggg aggggagtat agacgccgag ttcaactcct    6120
ggcttcaatc tcccctcaat cgaggcgtag cgcaacgcgc tcgctttgca ctggtttcgc    6180
cgccccggag gtccgtgctg agctgtacgt acatccgggg tgtgtatgcc cgttgcgatc    6240
gcgtttgagt gttttcgggg tctgactgtg cgtgtccggg gcctcccggg cggcgcctgt    6300
cgaatgtgcg gctcggcttt gcccgccttc tttctccaaa gtgtgtctgg actgccttc     6360
tgtgttctgt cggaatctca agtctgggct gtcggtttcg ttgcctgaat ctgcagaatc    6420
tccgcgacgt cctcatcctc tgcgtggact gcgggatgaa atacaacatc taccgccagc    6480
ttctccatag caaattcgag cactgcaaca tcattctcaa ggtacagctg tcgctgctct    6540
gactgcattg actttgaaac tctcattcct gatctgttag ctctcccggc agttcgcttg    6600
tattttctgt ttcctgtggc gcccacccgt caattcccct ttctgcgcg ccgagcgctc     6660
ttcagctggt actgggaaat ggagatgtgt gtccagcagt atcaagacat acagaagtat    6720
```

```
actgatgtgt acacgtgaat ctccattctg tttatgcatg catgtctctc tctctctctc    6780
tctatatata tatatatatt tgtacatgta tttatgtgtg tgcgtgcgtt tgaatataag    6840
tacgtattat ctacaagttt gcatgtttcc gtacgaatgt ccgcaggcgt gtgtgtctgg    6900
ttacatgccg ctgaatctca ctattcaatt aaacagttga gtgtggagag gtaagcgaga    6960
ctgtgactgc gcaggtgtga aaccgttcag gagcgcatgc gctgtgcgtg tctctcaggt    7020
ggtgccgtgg gatttcgact ttggcaacga cgaatttgac gggctcttca tcagcaacgg    7080
tccaggcgac cctgagagat gcgaaaaaac agttgctaac attcggtgtg tgctgcagag    7140
aaaagccgat tcgttcgcca gagtcaggaa cagcacagtg gcgcatttcc atttccgtct    7200
tcgctgtaga cacgcaaaac catcgcgatt tgcagattgg ttgagcttgc tctctgagtc    7260
gcgggaaact gttccttccg ttccatggcg acccaggcac agagaagcgt gcatgcaaaa    7320
aacaacgtgg agtctctccg ttttgtctct gctaacttag tataacttta gacccggcaa    7380
acagcgacat gcacgagtta aacgcgtagt ccatctctta catgaaatgg actctttaga    7440
aagcgcaaga cggtgcacgc taccagcc tcgttcgtag gcttgcgtat tgagttcacg    7500
cgattgaaca ccgaattgtc gaggcgggaa gttcgcgtct accacatatt catctgagtt    7560
ccatctcggg ttgctccggt tcgggccaag gtgactggaa tgcccggtgg ctgccgggta    7620
ctatgtgctt ccccgcggat ctcccatgtt tcttgtgtg ggcagactgc gcagcactgc    7680
tggtggctgc gtaggttcat gcccttacaa tgtaaatccc ttttctaccg ttcgttcttc    7740
ctcccgtttt cagacgcgtc atggagcgaa agatccccat cttcggcatc tgcctaggaa    7800
accaacttct tgccctggct gccggcgcga gaacgtacaa aatgaaatac ggaaacagag    7860
gtaagcgttg tcgttcgtcg gtcacactga ttgtacgccg tttcaggtgt acgtacacct    7920
cttttaccgg cagcgaggcg ccggtccagg gagcgtcccg cgacgtgggt ggcaggccag    7980
tgactagcga cggcgaggcg aagagggaaa atagcatctc cggactctca tttctgtttt    8040
gccgttgcag gaatgaatca gccggtgatc gacttgcgaa cgtcgagatg ctacatcaca    8100
ccccagaacc atggctttgc cgtcgacgag agtaagcggc gacaacattc catctgcgaa    8160
atctaggtgc catgacctcc atatgccgtt atcgtagaca taatgttgat atgtagaatg    8220
catatggata cgtcgagaga ggtcagattc acttttgtag atgtagacgg ctataaatca    8280
aagtggttca tgcatctgct gttggttgta ttttgacagc attgtgaaag ggagtggtgt    8340
tcgatagaac gcaaatgtga cgcaattgta tccgtaagac cctgagtttc attataagta    8400
ggtattgcct ctgtacaaat gatccgcgag ccagaactgt ataactcaaa ccgaataaac    8460
agagtgtctg tcgctgtgaa tacgaatggt aacagtaatc catatattgc gcctagaacg    8520
taaccgatgt ggaataacgt aaaaatgcgt gtttgagccc tccacgtcag cggtctgtcg    8580
attgtgaatt agcgaagccg acccgtcgat gaagttcaac agtcagccag atattcagtc    8640
tctagaacct ccacaaagga tgatgtcctc caggtagcga agataccaac tgtggtgttg    8700
gagaatggcg tttcaaagcc ggtagcgttg cagacactct tgtgtcctcg tgggagtccg    8760
tgttcgaggc gggcagttgc tacagcaagt agatgcgtag aacgaagcga gacctccacg    8820
cggggattta cctttgaca tcagttctgg aagactgcag atcctttgca cagatgcaat    8880
atctgcttac ggtgtggcgc ttacaataca tggtcgagct atgctcctgt cggtctcagt    8940
gcggccttcg tcagatgaca gatgtggaca cctgcctata tgaccctgtg ttgaacctct    9000
cgccgttcct gcaggcacgc tgcctcgaga tttcctgccg ctctttgtaa atgcaaacga    9060
ccgttcgaac gaaggcatca tccatcgcac gctgccttt ttctctgcac agttccaccc    9120
```

```
agaggcgtca ggtaaggcgg gcgatacttc ttcgactgaa ataccgacgt tgcagatcag    9180
cgacatctct ttccgttggc gtcgtttcaa tgatcagtgc ttgaaggcat cttggcagcg    9240
tttcgtcgga ccaatacggc ggaactggag ctcgacggta caaggaatct gtgactgccg    9300
atgctcttct cgatgatgca ggggcgacag ttcctttcat gagggaaaca tgtgcttgtg    9360
tcatcagttc agttcctcat aactggaggc atctgttggg tcttaaataa agccgcccgc    9420
taagaaggat gctgccttgc gacgcaactc gtgtgtcacc aactgcatcg cgatgggaga    9480 gttttcctc tgagacaaaa cgaggatgga cctccgaagt tcgtgtacgc agtctgcgag    9540
tcagtggggt gccgacgcac gagacgaaga cgagccactc agagattatt gtttctcact    9600
tttctgcctc ggcgaagaag cagcgcatac ccatccggtgc ccctccgctg ggcgtctcgt    9660
gcgttccctg tcgctggcgc ggcttcgtca acacagtgca ccgattttt cttctgctcg    9720 tttgtgacaa cctagagagc tccagtgaga tcgaggagtg gcgcgagatg tgagtttcac    9780
gcggtggagg ccagatgatg tttcgtcaag agctgcgccg cagtctacca cgcagcgcag    9840
accccgtggg gtgtgtcctt cgcgcgattc tttcctggag tctgtggggt gtttatacac    9900
tcggcgtccc tctgtctgtg ccttctggct caggtggtcc gacagacacg ttttacttat    9960
ttggcgactt catcgcctcg attatgaagg cgcagacgct gaagcaggtc cacacgactc   10020
cgttctcctt tccgcagaag ttccagaaag ttctgcttct cggtaaggcc ggtgttcctc   10080
ccgcatcttg agggaaggcg agttcttta aagtgcagaa agcccttgc gggggtcatc   10140 agagaaggaa cgccatcggc tgcatccttc ttggtttctc gcaaatgcgt ctgtggcttg   10200
gccgtcgcgt ggttccttct gaacgcccgt gtggaggttt cccgacgctg tcatctctgc   10260
caaggtgtcg tcgtggacgt tcaagagtgc gagagcggcc ctgccgactg tcgcagagag   10320
cgcggctcat gtcatgtctc ccttgtgcat tctccctgag cttttcgcgg gctctctttc   10380
gacctctgtc tccgccggga tcatctgttt aggaggaccg tgtcgtggtg actgtgccgg   10440
aggctctgct cgctcaagtg aggaggtcgg ggtaaggcgg gaagtcggct gtgtgtgcgt   10500
ggtttatttg cttcgtaggg agcggaggcc tgagcatcgg ccaagccggg gagttcgact   10560
acagcggctc tcaggcgata aaggcgctga aagagcagaa catctttgtc gtcgtggtga   10620
accctaacat cgccacggtg cagaccagcc agcacatggc cgaccgggtg cgttgaccgc   10680
gcagacggat tgcgcagagt ggcgtcgagg gagcgcgaac gaaaaggag gacgcagacg   10740 ccagagaaga cacagagaat cagagagaca gcgagagaca gcgagagaca gacagcgaga   10800
cagaagatca atcgggaggc aaggaggaga gcgaggtaga gagaaaccgc gagaaacaca   10860
gagaggagca gagagctaac aagacagaaa caaagcgtgg tgcaggaaga cgcagatgag   10920
agggagagac ggagcccaga gcagagacag aaagacagag caaagagaga cacagacaga   10980
acagagagag agagataagg gtggaggtga aggaataaag gcggggcttg agcgaacggt   11040
gaagcattag gccgtggaag gtgacgaaag tgcgatggag gcaggatggt ctttgtgagg   11100
ccttctttgt cggaagaaga gagtggacac cacgtatttc cactgctgcg ttgcgtaacg   11160
cgtttatgag agagtactgc ggttccccag agactggcgg aaaccaagga gtcggcaggc   11220
tttctcgggt ctctctcccc ctgtcgttgt gagtttccta acgtctgtcg acttcgggaa   11280
gtccgaaact ctccggagaa gacacacgca actccaaact gcgagtggag tcgagccgat   11340
ccagtcgagt agtagcttgc atgaaatgtg tcgagccggg tgcatgcaat tcatttttc   11400 aggtgtactt cctgccgtc acggatgagt tcgtgacgaa agtcatcgaa aggaaatgc   11460 ccgacggcat tctctgcaca ttcggaggcc aggtgcgttt gcgtgtgtgc aacggctttt   11520
```

```
tcctcgatga acgtaactaa atgcgcgaag atataacgag gcctaggcac tcgcaaatgg   11580
acaatccatc catatgcata tatattcata tatatgcatg tttaatatat atatatatat   11640
atatatatat atataataat atgcgtatgg ggctggccat tgaggagata tgtatgcagc   11700
tgttcagagg agtagcgtag gcgaacacgt ttgcatgcat agagttctgg acgaagcacg   11760
tgatcgtgcg gatatatgta aatgaggttg tgggtgtatg tggggacagc gatatctgga   11820
cagggtacgg cttttttttt cactttatgg catgttcaga cggccctcaa ctgcgctgtg   11880
aaactccacg aacaaggcgt cctggcaaaa ttcggctgca aaatcctcgg cagtccaatc   11940
gaagtaagaa tgtattcata tatacatc catatatata tatatatata tatatatatt   12000
cgtaactgca taaatgcaca tattcatagt gatacatata tatatgcaca tagacatatg   12060
caagtacatc cgcgcacaca tatgtccata tatgtgtgta tatccatata taaatatata   12120
tccatatata tatatatata tatatatgta gagaaatgtg tgtgtgtatc agtgcacgtt   12180
acgatgcaca aatttgtata ctggtgtgta tttaggtatc cgcgcatttc gagtttcgtg   12240
ggaagcacgc ggtgtcttgt ttgtcttttt taggcgatca ttgcgactga ggatcgaaag   12300
gtgtttgcgg cgaagctgga agaaatcgga gaaaagtgg cggagagcgc ggccgcgaca   12360
aacacggaag aagctgtgca agcggcgaag gccattggct accccgtcct cattcgcgcc   12420
gccttcgcac tcggtcagcc aaagaagaga ccggggagtg aagacgagcg aagaaaaggg   12480
gcgcaaggtc gacgagagca atgagaggag acccagaaaa ggcgcacaca gaacggatgc   12540
agacggaaac agacgaggcg acaaaagagg cagtcgatga cagagaagaa tgcgagggag   12600
acggaagcac cgaagacgaa gggaagagaa ctggccagaa acgaaggata cggatttcac   12660
gttcaagtga tgtcaacttg cgtgtggact atcgcaggtg ggctcggatc tgggttcgcc   12720
gaggacgagg agaccgtccg acgcatttgc aaggaagcct tctcccattc ttctcaggtc   12780
cggtcaactt ctcgtagtgc atgcgtatac gcacatcaga gtaaaatttg catatatata   12840
tatatatata tataagtata tgtatgcaca catatatgtt tcagttctta tctgcgggtg   12900
tacttgtgca tgtccgcacc ggcgtcgtgt gggcagatgt gaacgtctgg agagagaggt   12960
cgcccgttct gaatgcgcgt gcatgcgttt ctgacaggcg tgtctgcatg gctgcggaag   13020
ccgaatgaaa ccccacactt ccgaaggaat ttcgcgtttc agccggttcg tttgcaggcc   13080
gagtgtcgtc ggggaggctt cctcgttgtg ttggtgtgtg ccggtccagt ggttctcgcg   13140 cgaagcccg agtgcgtccc ctataagact gaaaagcgcc aagtcgagct ggcggaactc   13200
tgagaattta cgttttttca ggttttcgtg gacaaaagcc tgaagggctg gaaggaggtg   13260
gagtacgaag tcgttcgcga ctgcaagaac aactgcatca ccgtctgcaa catggagaac   13320
ttggatcccc tcggtgcgtc tcgtctgtgt gcatttgccg tgtttgctct tcaactgtgg   13380
cttctcagct ctgtcgaggg gtgcgctgcg gaggctcgct gtacaccacg aattgtttct   13440
ggcctctctg ttaacgagcg ttctgaaacg aatccccaca caagtgcatg ctccctctcg   13500
tcctctcgct gcttgactct gtcgctgcgg gggaatccct cgtaccgtgc tctcgctgtg   13560
acgacctctg agtggacgcg tctctctcgg acttctcttt gtctctcgcc agacgcagtg   13620
attccaagtc tctctctttt tgtgcagcgc tgtctctgac gaacgctgtc tatcggcgta   13680
tctctccttc tccgcttctc cagagcttgg cacttctctg tataaagatt tacatatata   13740
tatatatata tatatatata tatatatata tatatatata tatttgaatg ttttttgtata   13800 tgcactccat ctggataatt cagtcgtcga actctattgt cacagcgttt tggtcactta   13860
aaccggcgtc cttcgtcgat ggtttgcgca tgcgcttttt gcgtccatgt ctgtacaccc   13920
```

```
gcgtgtggat ttttteccct caggcatcca cacgggagat tcgattgtcg ttgctccttc   13980
gcaggtgagc tgtcttcgct tgtgtttttc tgttttcat ctctctttat acatttctcg    14040
gtccgatatt tctgctctct catggcctct cttttgccat tttcctcgtt gttttctctt   14100
atccctcgtt cttcctcttg ttatgtcttc ttcttatcct ttgttatctt ttgtccgcgt   14160
tggtctattg ttgtctccgc ttcaaatccc ttcgtctccc acacaagcgc gcgttttctt   14220
ctttgctctc tctcttcaga cgctgtctaa cgaggactac taccgcctga gagataccgc   14280
gctgaaggtg attcgtcact tcggcatcgt cggcgaatgc aacatccaat acgcgctcga   14340
ccctaactcg gagaaatact acatcgtcga agtaggtgac aagagagtgc aaacgaaaaa   14400
ccacgggagg cgaagggaac gcggtcttac agaggatgat gccgcgagga aaggtggacg   14460
aacaccctga aacaggagag aggaaagcga gaaccggaca ggctcacacc aaagtcagac   14520
agaggccaca gagcgagaag gacagggagg tgcagaagcg gagagaccgg ccagaaaaga   14580
gagagacagg ggcggagata agtgctacag aaagtcgaga gaagctttct cgatcctagc   14640
tcaggttcga tgtcacctgc ctcgcgctgt gcggcatggc cacacgcatg ctgaaagtca   14700
acgagaaggt cgccaagcag ttctacaaat caagcactgt ccagacagct gctgacgggc   14760
attccgtttt tccttttgtg ggcgtttgtg tcgctgtctc cgacgttcgg acgtcccgcg   14820
actacagcgt ctctgacttt ccagacgcct cgctttctca tctcttctcc cgcttcgctg   14880
tcttgtgggc ctttttcctca ccgcaggtca acgcgcgtct ctctcggagc agcgccctcg   14940
cgtccaaagc cactgctac cctttggcct acattgcggc gaagctcgct ctcggtaacg   15000
tttgtctccc ttctgtttcg tcgaaacttc tgagtggctt ttccgaactg ttcgtcccag   15060
agtcgatccg catggcccgc tcaaagccca gcatccccctt tcattgctgc tctccttgat   15120
gcttcaagcg tgtctgcacg gccttccttc tgttcttaaa ttcgcggcgg tgatgtgcgt   15180
ttccgtctaa tcttctttgt ctcgtcggct gagtgaggtg gtgcttcggt cggttttcat   15240
cctcgagaac tggcagtgtg tgtcgcatgt tttctctctc catgtaggct cgactttggt   15300
ggagctcagt aactccgtga caaaagagac aaccgcctgc ttcgagcctt cgctggatta   15360
cgtcgtcacc aaggtgccga ggtgcgagga cacaacgcac acagatagaa gttccatagg   15420
gactcccagg acaccagtgg tttcttccct cttctctttg tggcccgact gctccctcgt   15480
tctctctttc ctgcctctct tcatctcttc ctctgtttct ctcttcgttg ttcctgtcct   15540
tcgccgtctc ttccgctgtt cactgttggg gtccgttcca gttcggccgt cgcttgcgtg   15600
tcaacgtgtg tatggttctc tctcctcaac gtcaccacgt cgccagcgtc cttgcccaaa   15660
attgtttctg ccttctgcag gagctcaacg ccttctgtta gatgcctctc tgacgcatgc   15720
tttgcatctc tgcactcgat agagacttgc cgttttgagg aagaagtttc cagagcgtct   15780
gagagagtgt cctcgcgcgt ctctcgacgt ccagcgaggc tcgcgcctcc tggcggtgaa   15840
cagattcgtg ttgaatatgt cttttctgctc tcaggtggga tctgcgaaaa ttcgagtcgt   15900
gcgaccccct gatgggcagc gcgatgaaga gtgtcggcga ggtcatggcc attggacgca   15960
ccttcgagga gtctctgcaa aaggcgctca ggtaaaccac aaagttccaa tcatcggcat   16020
ccgtcgacaa acagttgtcc cagttgaagt tattgtagcc acatctctct tctccgcatt   16080
tcctctctct tcctcttctc cctcttgttc tccctcttgg tctcccttgt gttctcttc    16140 ctgttctctg tttgcgacgt ttcttcgact gtgtctcgct gacgtccgtt ctggtggcct   16200
gcgttttcgc ctctgttctt cagaatggtg gacgagaagg ccggcggctt cgacgagtcg   16260
gtctgtcact ttttttccac ggacgaggac tgcgcgcctt cgctgcccgg gtcagacttc   16320
```

```
aagacgtcct cctctggaga atgcatgcgt ggcggctgcg gacgcacaga ctccggcgcc  16380
gagcggcagg ctgcgctgct ggaggcggaa cttcgccgtc cgtcaccgaa tcgaatctgg  16440
gcgctggcgc tcgccttcca gctcgggtgg acggtcgacg cgctccacga gaaaacgaaa  16500
atcgacaaat ggttttaag caaacttcaa aacatcaacg acatcaagcg acagctcacc  16560
cagctcaccc tcgatgacct cacgcgcgca gatttcttct acatcaagaa atacggtaaa  16620
cgccttcgcg cgctgtcgag acactggggc atgtggctcg ggtgtcttcg gggtggccgt  16680
caaacagtgg ggtgttccc agtcgcattt ctcactcgtt tgtacatctc gaaaacacg  16740 gcgacgatgc gcaagccgaa ggggacaaga gacaagcgat gctccatgtt ttcaaagctc  16800
ctgtctgttc cccgtctctt gtggcaatcg tcgaagatac gctaaccgca gactggtggt  16860
caaatgtttt ttttcgtttt gggatccact gtggttctca tcttctcgtc gtctcttgtc  16920
ttcgtctctc gctctcggct tctcgtcttc tactcggtct ccctgctcc gtttcttctc  16980 ctcgtccgtg tctcatgttc ctcttttctt ctcgccttct tcgcttcgtc tgtgcaacga  17040
ccagactgcg acaatccctc cccgttagta ggataggccg caggtttctc tctgtttccc  17100
aggattcagc gaccgtcaga ttgcgcagta cttgatgaat tcaccgagcg cggctgcgct  17160
gtcgcagttc gacgtgcgtc gtcggcgact gcacctgggc gtcagaccgt cggtgaagca  17220
aatcgacact ctcgcggccg agttcctgc tcacacgaat tacctttact tgacctacca  17280
aggaatcgac gacgacgtct cgcctctcgc cgccacgccg tccgtctcgg cggtcttcgc  17340
tggcgcgcga gccgagaaga gagaagaaga aaacgcagag acatgcagag acgacgagga  17400
cgaaagtctc ctccgccgcc tgagcaaaag ctccagcgcg cggcttagaa ccggcgaagg  17460
cgacgcaccc ggaaaacaat gttttgtggt tctaggtagg cgacgaaggc aagaaacttt  17520
gaggatggag agacgaagaa gcattgaagg gagagaaatg caaagacggg agagagatcg  17580
agaaccggag gagaagagag aggaatggcg acagagatca agggacgagt tggagacgat  17640
gcatgaagca aaggcgagca aaaaaggcga ttcacggaag accagaatca gacgacaaga  17700
acatgtcttt gtttatcgac gggcacacct ctttttcttt tctctcaagg acctgtcggt  17760
gcttgcgcac caggtactgc gatatatata tatatatata tatatataca tgaacatcca  17820
cagatatgct tgggtagata cagaagtaca tatatataca tatatatacg actattcatg  17880
catatgcatg tgtatatgct tttttgcacc tttttgtgcg ttggtatttt ttggtgtgtt  17940
tcggcaggct gcggctgcta ccgcatagga tccagcgtcg agttcgattg gtccgctgtt  18000
tcgtgtgtcc gtacacttcg ctctcttggc caccacgcga ttgtggtgag tattcgccgc  18060
ctctcagtgg tagatcactt cgcaaacgtt tcggtcctta ggtcaaggaa tttgcgacaa  18120
gcctctgcct caggttcctc gtgaatagcc tcagactatt tttaaacaaa tgcagcgatg  18180
cattaacgca tggggacact gcatgtgaga tgagccacgg ttccgcgaat atctttatgg  18240
atatgtatca atggatacat aaatatatat atatatatat acatatatta tgtacgcagt  18300
ggaggccatg tagaaatggg cattttacc tctattcacg aataagagta ggtctgtgca  18360
tgacgacgac ggacatgaaa gtgatgctag acagtatatg agcatttaaa aggtaattat  18420
tcataaaagt gtttattgaa cgttgttcgt cctgctcttg tcaattcgca ttccgtggaa  18480
caggtaaact gcaatcccga gactgtgtcg acggactacg acgtgagcga tcggctgtat  18540
ttcgaagact tgagcttgga aacagtcttg aacatctggt aggtttctca cgcgtagctg  18600
tccgattgtg ggctctccga atataagccg aatcgcggtg accagcctgg atgtcggcct  18660
tggacgtgtg tctggcccct cagattcccc gaacattcag agagagctca catggcccgt  18720
```

```
aggtttggtg tctctcagtg tgtcatgcag tgcatcaaag ttcgttcttt gaattcgcac   18780
atcccgtcga tgtctgtggg tccgccttgg atggcgccgc ctcgttggta tttgaagtcc   18840
caaataagag gcacagaaat cactgttttc gctgtgtgga agacacgttc ttttgtgtgt   18900
cccagatttc tctcttcttg tctttcttct cacgcttctc ttctgtcgtc atctgtgcct   18960
cgtgcacgcg tctctgaact cgtcgtattc tcctctcttg ctcgtgtctc tttccctcct   19020
gtttgacttt cttttccgtc tcgcttcgct tcccttgttc tcccgtcttg ccctcctgct   19080
tcacgcgttg tctgtcacgt ctggcttccg ttggtcgcct ctgttttccg gagttttctc   19140
ctcctccact ctcttcttta tctcagaaag actttgaaga tttaaacagg ggtccacctc   19200
ctattctaca ctccggagaa gaagtcatac cttcccgcgc ggtggtggat tccattcgct   19260
atcctgtgtc tcctgcctac tagtcaagag atgttgcgcg agtgtgtgct tctcgttcga   19320
gggtcctctg tcgtgcgttt ttcgttcgtt tccaggagaca ttgaagcccc ggcgggagtg   19380
attatttccg tgggcggcca gacaccaaac acgctgtgct ctgcactgga gaagcagggc   19440
gtgaggatcg tcgggacgag tgtggcggcg atcgactgct gcgaggacag acacaagttc   19500
tcccggctct gcgacgagct gaacatcgac cagccgaggt ggaaggagtt caccgacctt   19560
cgcacagcga aggccttctg ccaagaggta agcggaaaca catggttcat tcggggcgaa   19620
acaagagaaa acgggagatg gagatgggga cgaaaacgga gacgaacgag aagcaatcaa   19680
atggaaggca aagcagccga gaaatagaga gacacggaga cgcagaaatg tgcgcagagg   19740
acagcgaaac gcagatgaag cggggggaga cagagcggtc ttcaacagcg cgcagtcgag   19800
ttgaagaaga gacgaacgaa gaacggacgt caaaacacac aaggggagcg aaccttggag   19860
gactgataac agaagacgaa aagtcgaatt ggaagatagg aagtcgcagg agagatgaca   19920
caacctgtcg aggttccaaa ggggtagcgt gtgcccaaga gcaaaagcat tcgccggatg   19980
tccttacaac gtgcttgctg gcgcgacgac accatcaggt tacctcgaaa gtaaataccg   20040
tttctgcatt tttatcgaag aggtcttctg tctctgcttc tggcctacgt aaaataaaag   20100
gcttgctctg tgaaagcccc tgccggtcca catgttcgta ccgcacacgc ttacagtggt   20160
gtcttgcatg catttttcgc tggccgtttt tcttcctttc ccttcgcgac ggtctgtacg   20220
tacgcccgag accccgttgg tccacaggcg tccggcgcgg tggtgtctct ggtactccgg   20280
cctcgtcgaa cgtatgtttt ctcgcagttt gtctggcacg tgtttgaaag gctgtggatt   20340
cgcaagtcgc gttttctgcg ttcgttctcg ctcttctctg caggtcggct acccagtcct   20400
cgtgcgtcct tcctacgttt tgagtggtgc tgccatgcga gtggtgaccg acgacgagca   20460
gctcgacgcc ttcctcaaaa tcgcagctgt cgtcagtggc gaatctcccg tggtcatctc   20520
caagttcgtc gagaacgcca aggaagtaag aaaacgacct agacaggctc acgacttcca   20580
cgcttccacg catatccctg tatcgtgttc gtatctactt tcctgtgggc tacatgtctc   20640
cgtgttccta tgcagtgatg tcagagatct tcctcgaaat actctcttca gctgcgtata   20700
ggtgtatact tgcatgatat ccatttatct tttgcttgcg tatctatgta gatggaaatg   20760
catccgaatg ggatatatat atatatatat atatatatgc gtgtgttttc ttataattat   20820
gtatatatat atataatatc gatgtgtgca aacatgtgat ctccgcttag atggggaact   20880
cttgagcaat agtgaggcaa acgaaacgaa gttgtcaaaa tcagcaggaa ccaccggat   20940 gaacctggtg catgcttgcg taagcatagg cgtgcaagca tagtttcaca tggtaggcag   21000
gagccggcat tgttcggatg tatcgtcctc tcctcgttcc ttccgtggaa actgcctttt   21060
tggcttgcag gtggaatttg acagcgtcgc ttgccggggg gaaatcgtaa actttgcaat   21120
```

```
aagcgagcat gtggagaacg cgggtactca ctctggagac gcgactttga ttctccctgg   21180
acagaagctt tacgtggaaa cgattcggtg aggacgcatg aagagtgtgt tgtgacaccc   21240
gtccccagtg cgcgacagag aaaaagagac gaactttcca ggaacgcaga gagtcttcaa   21300
agattccgtt catgagtcgc ggctggtgca tctcgcgccc attgttttca aggacgctac   21360
gcgcccgaac gagtcgtgtt ctgtctcagc gtctccagtt gctgaatgcc gtggtgtcat   21420
cccagcaaac gcaactgtcg ctcttgtcga gagcgcgaga aagagaacat gcgaaaagag   21480
cgtttgaagg gagtggaggc ggcacctgca tgtaatcgag agaaagaata atggcttagt   21540
tgatgaagga cggtggagag aaagtgatcg aacttgaggc gcagtgaggg cgcagagaca   21600
gcgacaaaga catgtgagga tatccaggca agtgtgatgg gagagtcagg tagatatttg   21660
ccagtggaca atattgctag aaatggagac aagatggatg cagggtgaac ggacagttat   21720
cggtcggggt atacgagaaa taaatgcatg ttgaatgact tggatagatg agagagagag   21780
agggacgtag tggttccttg gccttgcgcc gccttgtcgt gaagggtcga caccagtcag   21840
atggagattc tgtcgcccac atcttcttta gaagaattga aaaagctgtt cttgtaagtt   21900
gtgaaggcac aaatgttttt tgcgtgcagt cgcgtgaaga agatctcgca gaaactcgcg   21960
cgcgcactcc aagtctcagg ttcgtttttc tcatacacta tctttcgttg attgctcttc   22020
ccctgcttct cctcaaaaac ctttctttgc gtcgtgcgtt cgatccggtg tcttctgcct   22080
ttctgtcagg tgccaactgt acacggttcg agtttctgtc ttctgagtcg agtgttcttc   22140
ttcaccattt tttcgtcgga cttcgtgtcg cttttgtgtta tccgacagtc gatagacctc   22200
ttttctccat cacgagaaag cgacgacgtt gcctttccta tcgcagctca cccagtggag   22260
gcaaaccgca ttggcggatc tgcaattcca aaccagagtt cagaggcgcc tgagactgcc   22320
ggacgttccc tcgagttcgt gtcagctgca tgcgttgcat gcgcatgcac agcgccaggg   22380
acggggcacc tgcgggtccg cttgcgagag ggcgtgctgt gcttttctgc ctttcttcag   22440
gtccgttcaa catccagttc atctgcaaac agaacgacgt gaaagtcatt gagtgcaact   22500
tgcgagcgtc gcgtactttc cccttcatca gcaaggcctt caatgtaaac ctcatcgacc   22560
tcgcgacaaa gtaagaagac caagggtatt ccacacgcgc ctcaagttcc cttttcaaca   22620
cactcttcga cacacatctc cgaataaaca taatctgcgt gcatgtttct ctagacaccg   22680
agagatctac acacgcgcat atgtatatac atatgtatat atatatatat atatacttac   22740
atatatacat acgtatgtgt gcgtatgatt ccactagagg caaagctacc ggtagggacc   22800
gattttgagg tggatttgtt tcgttctttc tcttcgtttc cttgtcgttt cgtctccagg   22860
gtgatgattg gcgcaccggt cactccgttg ccgattcact tgatggacct ttccttcgtc   22920
tgcgtgaaag ttccagtttt ctctttcgcg cgtcttcgcg gctgcgaccc ggtccttggc   22980
gtggaaatgc ggtcgactgg agaagtaagc aggctgctga agaaggagac gctattccgt   23040
tttcaagtcg ggaagcctgg cgtcgtttga ggcagatctg cattgccgtc tactcggctt   23100
ggaacgatag acagaggaag acacaagtgc gaggaagggg aaaggagga aaacagcgaa   23160 agaggaggaa agaagagtac ggcacaatgt gcgagcgaag cgagaagtga gtgagagtgt   23220
ttagaagaac aaagtgagaa acgaaaatga aacttctggg tatccttccc tcaagcgact   23280
gttcgtggac aaacgcagtt ttcactcgag acgtcaacgc gttccgtctc cattgcttgt   23340
ctcctcgcga ccgtgttgct tttccttttca caggttgcgt gcttcggagc cagcaaacat   23400 gaggcttttcc tcaaggctct catctcggct ggtgtgccgc tgcctcttga aagcgaacg   23460 attctcatca gcgcaggtac gcaacgttct gtaaactaag cgattctttc tgttcgcttt   23520
```

```
ctctctgtcg agcgacagca accttttcct gtctccttcc ctccctctcg agacagagca    23580
gcttccatgt tccccttagt gttttttaac agccgcgttt ctctgaagtc ggcgcatgca    23640
tctactattg cagatttcgc ttcgtgttcg tgcgagccga agaaatgctg cccgtcgccc    23700
tggcccttcg actctctctc ctcgtcagtt tcgctctctc catttccagc tggcgaagag    23760
tttctatgga catatgtctg tcggtcgcgt gtgatgcatg cactgcctct cggttgtgac    23820
attttatcct cttgtctttg caggccctct gtggtcgaag atggaactcg agccgtactt    23880
caaaatcctt ttggacctgg gcttacaat ctacgcaacg gaaggtaagt ggaggcgcac      23940
tccatgaatc cctttgcagt tctctcttct ttttcttctc acactaacag ttggtgttcc    24000
tatctatcta cctacctctc tatctatgtc tctctggttg tctgtctgcc tctcggtccg    24060
tgtatctgtg tatctgtcgg tgcagctctc taagccgcga acggtcgtgc gtatatatat    24120
gttcatctgc aacacaacga acgctctgta tgcacgtgcc atgtcgatat gactgtgtac    24180
gctggccgtc gttgtctgtg tgcaggtgta ttgcttcgcc gctgcagaac gtagcatatg    24240
tgtctttatt caacattttt gaagggatat tgccttcggt ttctttcagt ggcatttagc    24300 taggatttt tccttttttt tgaaaggtag tgaagaacgt gtgttgacgg ccagggccgc      24360
agcacatgct gcgatgtctt tcttttgccc atggtgtgtg tgtgtgtgtc ttgtgtggtc    24420
gctttggctt tcttcattg gactgttttt cgttttgtgt ttcttccatt tttccgttct      24480
tcaagtgcat gcgaaggttg tcaagcgtat tctctcggaa ttggctttca caaagctctt    24540 ctgcccgct cctcgtttgt ttccaccttt cggcttcttt ttgttcaacg ttcgcatgct      24600
cacacgcatg cacgcctcga tcttttcctg tcctgacgca gacaagtgct cttcgtttta    24660
ctgctgtccc cgtttccgct gccccgccgt gacttctctc gttttgcgag ttcacgtttc    24720
ttctttcttc gttttttctgg attttcttcg gtgcccaggt acctacagat tcctcatgaa    24780
cagcgtcgtt cgcgggcagg ggacccacct gcctgggaac gcgtcgccgg cgtccgacag    24840
cggccttcgg actcctacga cagccgagtc cgacgcagat gcgtgcattc gcgcgaaata    24900
cgcatcgcgc attattcgcg tgagaaagcc gattgtcgga tcgaatgagt cgcacaacgg    24960
aggtcaccag tcacctcacg ctctctccct cattgaaagt ggtaaggccc ggcagtgcgt    25020
tttcgggtgg ctgtgcagac ggggcatgcg attttttgcg tttctgagca acgaggcgcc    25080
agcatgtaca cacagcccag tggtttatgt cttgtttgct ttcgtgttgc agtcgcacat    25140
gcatgcactc ttatgtgtat gcgcatctat cgtgccaagg tccattcaca tgcctagtta    25200
tgtgcatgcg gaggttgaga tgcatactga ggatggtcga tgtttaaacg attgttgaca    25260
ggctcagcta ttgggagcga gcatggtttt tctctgtgag agttcactgg accctagacc    25320
gtaaacactt gcagagactg gctggacccc ctcgatcgaa accatgcatg cagcagtcaa    25380
gtcgaccaca gacagaaaca gacgcacagc agtgccacgg agatgtaggt gcggcgttca    25440
cggaggtaga ggtgaacatg tggtttcaca tggcttttg aattttttcg caagaaggaa      25500
agtacgagaa cttcctgcta tgcacgaatc gctcatcctt tcttgccgaa gaacgaaacg    25560
gtgtcttgtt tgttcacata gggaaggtcg aaatggtcat caatgtgcct gacagcatga    25620
accaccgagc ggccacaaac ggctacctga tgcgtcgcac tgcgaccgac tgcggaggtg    25680
cgttttgcct cagtgggcgc aacagacgaa ccaaagaaac gaaagaaaag acagaaaaaa    25740
atggtggaac tcgtgctcta gcaaaacgga ctacccgacg gaactgcaaa gcgtctgtct    25800
ggtccgaggg cgtcttgccg ttcccgactg ggcgttcgaa aaaagcaagt cttctccatt    25860
tcatgttttg gcggcccgcg caagcaacag taatcttcac tggcttggcc caccgactct    25920
```

```
cacgacctca gttcagtatg cgggcgcggg gaatcaagtg cgaaatactc gttttctaca    25980
taattatata tatatatata tatgtatata cgcgtacata gatataaata cggacatgta    26040
gacagatgta tgcatatgca tatatagtta caaacgtgta tagatttaga cagattcgta    26100
atattttgtg tatgtttcga tcaatacatt aacgtttcgc ttgcaatcag atgcgtcgat    26160
ggcctcaaca gtcgacagag catggggtac gctgttttct ggggtcggga acgtttcaga    26220
aatctcgtca gagagagcgg gcttctccgc gccattggcg tttgcgtgtc tgcaatatgt    26280
tgatcggcgt ttacgtcgtt ttcttgtttt tctcttcgca gttccccctcc tgacaaacgt    26340
caaagtggca agcatgttcg tcgaggccct caacaagaaa gaagcgaaag aagctcaggg    26400
tcgctccttc tgggacattc gcagctggga tgaatactgg cctcaaaaat aatttccaat    26460
actttcgcca aaaacgttcc atatctctcg ctctactgac gcatttgagt tacgcgacgg    26520
atttccagca gtggctccgc tgtatgcttc ttcctctctc tctaggcata atgatatcta    26580
tatatatata tatatatata tatgcatatg tatgtgtacg tgtgtgggaa caccggcttg    26640
agaaccggtt ttcaagacgt tggaagtcgt ctcatctttg ttcctccaca actgagcatt    26700
tgtctgtgta gatgcgcggc tttgttcaca tgtgtatcga catctcagct gttacgtgtg    26760
ttcatgtgaa tagagcagcg agcgtacaag tagtgaattt gcctcagggt cttttggcga    26820
cggttggtgt tgtctaagca acgcgcttgc agttgtgtgc atgcttgagc cgatttgaac    26880
caacaaccta tttgtgcggt gccagtgttc tgcaaagaga gcgtcacgca gggaatgctt    26940
caaagccgaa acaaatggca tcgaaactct cgtcggatgc gagacatgcc tgcacctcct    27000
gccgtcgcat tccatttcga aggaaagtca tcgcctcgga cgccgagttc tgattcacgg    27060
aaaatatgca gactgtggcg taaccattct ctcagaagaa acacagattt ctacaactcg    27120
aacttcgcct tcttccataa acgtttcgtc agcatatata tacatacata gatatatacg    27180
tgtataagta aaccctatac acgtatatgt atgactaaac ataaatatac atctatgcat    27240
atatatatat atatatgaat atacatttta ctgagacacc tgtgtcgtct ttttggattc    27300
acttgcacct gtttcagcga ggacgaatcc acggaaatca ttttttgttgc atgcgggtca    27360
agctctcaac gaagctt                                                   27377
```

<210> SEQ ID NO 2
<211> LENGTH: 1687
<212> TYPE: PRT
<213> ORGANISM: Toxoplasma gondii

<400> SEQUENCE: 2

```
Met Pro His Ser Gly Gly Arg Arg Ala Val Ala Pro Ile Tyr Pro Leu
1               5                   10                  15

Asp Leu Ala Gly Arg Leu Arg Pro Ala Met Leu Val Leu Ala Asp Gly
            20                  25                  30

Thr Glu Phe Leu Gly Tyr Ser Phe Gly Tyr Pro Gly Ser Val Gly Gly
        35                  40                  45

Glu Val Val Phe Asn Thr Gly Met Val Gly Tyr Pro Glu Ser Leu Thr
    50                  55                  60

Asp Pro Ser Tyr Glu Gly Gln Ile Leu Val Leu Thr Tyr Pro Leu Ile
65                  70                  75                  80

Gly Asn Tyr Gly Val Pro Ser Ser Glu Lys Asp Glu His Gly Leu Pro
                85                  90                  95

Lys Tyr Phe Glu Gly Asp Arg Ile Tyr Val Arg Ala Leu Val Val Ala
            100                 105                 110
```

```
Asp Tyr Asp Asn Ala Ala Val Thr Ala His Phe Arg Ala Glu Asn Ser
        115                 120                 125

Leu Ser Ala Trp Met Asn Thr His Lys Val Pro Ala Ile Ala Gly Val
130                 135                 140

Asp Thr Arg Ala Leu Thr Lys His Leu Arg Glu Val Gly Cys Met Leu
145                 150                 155                 160

Gly Lys Ile Val Val Leu Ser Glu Glu Glu Arg Arg Ser Gly Leu
                165                 170                 175

Ser Leu Ser Ala Leu Ala Ala Leu Pro Ser Ala Thr Ala Ala Glu Gln
                180                 185                 190

Arg Gly Glu Asn Asp Ala Thr Val Thr Pro Asp Lys Ala Glu Ala Arg
                195                 200                 205

Leu Arg Val Glu Arg Arg Gln Ala Ala Leu Thr Met Trp Glu Glu Ala
210                 215                 220

Ile Arg Asn Lys Ala Lys Asn Leu Pro Trp Glu Asp Pro Asn Lys Asp
225                 230                 235                 240

Asn Leu Val Ala Leu Val Ser Arg Lys Glu Val Arg Val Tyr Lys Ser
                245                 250                 255

Thr Val Val Asp Pro Asn Leu Arg Asp Val Leu Ile Leu Cys Val Asp
                260                 265                 270

Cys Gly Met Lys Tyr Asn Ile Tyr Arg Gln Leu Leu His Ser Lys Phe
                275                 280                 285

Glu His Cys Asn Ile Ile Leu Lys Val Val Pro Trp Asp Phe Asp Phe
290                 295                 300

Gly Asn Asp Glu Phe Asp Gly Leu Phe Ile Ser Asn Gly Pro Gly Asp
305                 310                 315                 320

Pro Glu Arg Cys Glu Lys Thr Val Ala Asn Ile Arg Arg Val Met Glu
                325                 330                 335

Arg Lys Ile Pro Ile Phe Gly Ile Cys Leu Gly Asn Gln Leu Leu Ala
                340                 345                 350

Leu Ala Ala Gly Ala Arg Thr Tyr Lys Met Lys Tyr Gly Asn Arg Gly
                355                 360                 365

Met Asn Gln Pro Val Ile Asp Leu Arg Thr Ser Arg Cys Tyr Ile Thr
370                 375                 380

Pro Gln Asn His Gly Phe Ala Val Asp Glu Ser Thr Leu Pro Arg Asp
385                 390                 395                 400

Phe Leu Pro Leu Phe Val Asn Ala Asn Asp Arg Ser Asn Glu Gly Ile
                405                 410                 415

Ile His Arg Thr Leu Pro Phe Phe Ser Ala Gln Phe His Pro Glu Ala
                420                 425                 430

Ser Gly Gly Pro Thr Asp Thr Phe Tyr Leu Phe Gly Asp Phe Ile Ala
                435                 440                 445

Ser Ile Met Lys Ala Gln Thr Leu Lys Gln Val His Thr Thr Pro Phe
450                 455                 460

Ser Phe Pro Gln Lys Phe Gln Lys Val Leu Leu Gly Ser Gly Gly
465                 470                 475                 480

Leu Ser Ile Gly Gln Ala Gly Glu Phe Asp Tyr Ser Gly Ser Gln Ala
                485                 490                 495

Ile Lys Ala Leu Lys Glu Gln Asn Ile Phe Val Val Val Asn Pro
                500                 505                 510

Asn Ile Ala Thr Val Gln Thr Ser Gln His Met Ala Asp Arg Val Tyr
                515                 520                 525

Phe Leu Pro Val Thr Asp Glu Phe Val Thr Lys Val Ile Glu Lys Glu
530                 535                 540
```

-continued

```
Met Pro Asp Gly Ile Leu Cys Thr Phe Gly Gln Thr Ala Leu Asn
545                 550                 555                 560

Cys Ala Val Lys Leu His Glu Gln Gly Val Leu Ala Lys Phe Gly Cys
                565                 570                 575

Lys Ile Leu Gly Ser Pro Ile Glu Ala Ile Ala Thr Glu Asp Arg
                580                 585                 590

Lys Val Phe Ala Ala Lys Leu Glu Glu Ile Gly Glu Lys Val Ala Glu
                595                 600                 605

Ser Ala Ala Ala Thr Asn Thr Glu Glu Ala Val Gln Ala Ala Lys Ala
610                 615                 620

Ile Gly Tyr Pro Val Leu Ile Arg Ala Ala Phe Ala Leu Gly Gly Leu
625                 630                 635                 640

Gly Ser Gly Phe Ala Glu Asp Glu Glu Thr Val Arg Arg Ile Cys Lys
                645                 650                 655

Glu Ala Phe Ser His Ser Ser Gln Val Phe Val Asp Lys Ser Leu Lys
                660                 665                 670

Gly Trp Lys Glu Val Glu Tyr Glu Val Val Arg Asp Cys Lys Asn Asn
                675                 680                 685

Cys Ile Thr Val Cys Asn Met Glu Asn Leu Asp Pro Leu Gly Ile His
690                 695                 700

Thr Gly Asp Ser Ile Val Val Ala Pro Ser Gln Thr Leu Ser Asn Glu
705                 710                 715                 720

Asp Tyr Tyr Arg Leu Arg Asp Thr Ala Leu Lys Val Ile Arg His Phe
                725                 730                 735

Gly Ile Val Gly Glu Cys Asn Ile Gln Tyr Ala Leu Asp Pro Asn Ser
                740                 745                 750

Glu Lys Tyr Tyr Ile Val Glu Val Asn Ala Arg Leu Ser Arg Ser Ser
                755                 760                 765

Ala Leu Ala Ser Lys Ala Thr Gly Tyr Pro Leu Ala Tyr Ile Ala Ala
                770                 775                 780

Lys Leu Ala Leu Gly Ser Thr Leu Val Glu Leu Ser Asn Ser Val Thr
785                 790                 795                 800

Lys Glu Thr Thr Ala Cys Phe Glu Pro Ser Leu Asp Tyr Val Val Thr
                805                 810                 815

Lys Val Pro Arg Trp Asp Leu Arg Lys Phe Glu Ser Cys Asp Pro Leu
                820                 825                 830

Met Gly Ser Ala Met Lys Ser Val Gly Glu Val Met Ala Ile Gly Arg
                835                 840                 845

Thr Phe Glu Glu Ser Leu Gln Lys Ala Leu Arg Met Val Asp Glu Lys
850                 855                 860

Ala Gly Gly Phe Asp Glu Ser Val Cys His Phe Ser Thr Asp Glu
865                 870                 875                 880

Asp Cys Ala Pro Ser Leu Pro Gly Ser Asp Phe Lys Thr Ser Ser
                885                 890                 895

Gly Glu Cys Met Arg Gly Gly Cys Arg Thr Asp Ser Gly Ala Glu
                900                 905                 910

Arg Gln Ala Ala Leu Leu Glu Ala Glu Leu Arg Arg Pro Ser Pro Asn
                915                 920                 925

Arg Ile Trp Ala Leu Ala Leu Ala Phe Gln Leu Gly Trp Thr Val Asp
                930                 935                 940

Ala Leu His Glu Lys Thr Lys Ile Asp Lys Trp Phe Leu Ser Lys Leu
945                 950                 955                 960

Gln Asn Ile Asn Asp Ile Lys Arg Gln Leu Thr Gln Leu Thr Leu Asp
```

-continued

```
                965                 970                 975
Asp Leu Thr Arg Ala Asp Phe Phe Tyr Ile Lys Lys Tyr Gly Phe Ser
                980                 985                 990
Asp Arg Gln Ile Ala Gln Tyr Leu Met Asn Ser Pro Ser Ala Ala Ala
            995                1000                1005
Leu Ser Gln Phe Asp Val Arg Arg Arg Leu His Leu Gly Val
        1010                1015                1020
Arg Pro Ser Val Lys Gln Ile Asp Thr Leu Ala Ala Glu Phe Pro
    1025                1030                1035
Ala His Thr Asn Tyr Leu Tyr Leu Thr Tyr Gln Gly Ile Asp Asp
    1040                1045                1050
Asp Val Ser Pro Leu Ala Ala Thr Pro Ser Val Ser Ala Val Phe
    1055                1060                1065
Ala Gly Ala Arg Ala Glu Lys Arg Glu Glu Asn Ala Glu Thr
    1070                1075                1080
Cys Arg Asp Asp Glu Asp Glu Ser Leu Leu Arg Arg Leu Ser Lys
    1085                1090                1095
Ser Ser Ser Ala Arg Leu Arg Thr Gly Glu Gly Asp Ala Pro Gly
    1100                1105                1110
Lys Gln Cys Phe Val Val Leu Gly Cys Gly Cys Tyr Arg Ile Gly
    1115                1120                1125
Ser Ser Val Glu Phe Asp Trp Ser Ala Val Ser Cys Val Arg Thr
    1130                1135                1140
Leu Arg Ser Leu Gly His His Ala Ile Val Val Asn Cys Asn Pro
    1145                1150                1155
Glu Thr Val Ser Thr Asp Tyr Asp Val Ser Asp Arg Leu Tyr Phe
    1160                1165                1170
Glu Asp Leu Ser Leu Glu Thr Val Leu Asn Ile Trp Asp Ile Glu
    1175                1180                1185
Ala Pro Ala Gly Val Ile Ile Ser Val Gly Gly Gln Thr Pro Asn
    1190                1195                1200
Thr Leu Cys Ser Ala Leu Glu Lys Gln Gly Val Arg Ile Val Gly
    1205                1210                1215
Thr Ser Val Ala Ala Ile Asp Cys Cys Glu Asp Arg His Lys Phe
    1220                1225                1230
Ser Arg Leu Cys Asp Glu Leu Asn Ile Asp Gln Pro Arg Trp Lys
    1235                1240                1245
Glu Phe Thr Asp Leu Arg Thr Ala Lys Ala Phe Cys Gln Glu Val
    1250                1255                1260
Gly Tyr Pro Val Leu Val Arg Pro Ser Tyr Val Leu Ser Gly Ala
    1265                1270                1275
Ala Met Arg Val Val Thr Asp Asp Glu Gln Leu Asp Ala Phe Leu
    1280                1285                1290
Lys Ile Ala Ala Val Val Ser Gly Glu Ser Pro Val Val Ile Ser
    1295                1300                1305
Lys Phe Val Glu Asn Ala Lys Glu Val Glu Phe Asp Ser Val Ala
    1310                1315                1320
Cys Arg Gly Glu Ile Val Asn Phe Ala Ile Ser Glu His Val Glu
    1325                1330                1335
Asn Ala Gly Thr His Ser Gly Asp Ala Thr Leu Ile Leu Pro Gly
    1340                1345                1350
Gln Lys Leu Tyr Val Glu Thr Ile Arg Arg Val Lys Lys Ile Ser
    1355                1360                1365
```

```
Gln Lys Leu Ala Arg Ala Leu Gln Val Ser Gly Pro Phe Asn Ile
    1370            1375                1380

Gln Phe Ile Cys Lys Gln Asn Asp Val Lys Val Ile Glu Cys Asn
    1385            1390                1395

Leu Arg Ala Ser Arg Thr Phe Pro Phe Ile Ser Lys Ala Phe Asn
    1400            1405                1410

Val Asn Leu Ile Asp Leu Ala Thr Lys Val Met Ile Gly Ala Pro
    1415            1420                1425

Val Thr Pro Leu Pro Ile His Leu Met Asp Leu Ser Phe Val Cys
    1430            1435                1440

Val Lys Val Pro Val Phe Ser Phe Ala Arg Leu Arg Gly Cys Asp
    1445            1450                1455

Pro Val Leu Gly Val Glu Met Arg Ser Thr Gly Glu Val Ala Cys
    1460            1465                1470

Phe Gly Ala Ser Lys His Glu Ala Phe Leu Lys Ala Leu Ile Ser
    1475            1480                1485

Ala Gly Val Pro Leu Pro Leu Glu Lys Arg Thr Ile Leu Ile Ser
    1490            1495                1500

Ala Gly Pro Leu Trp Ser Lys Met Glu Leu Glu Pro Tyr Phe Lys
    1505            1510                1515

Ile Leu Leu Asp Leu Gly Phe Thr Ile Tyr Ala Thr Glu Gly Thr
    1520            1525                1530

Tyr Arg Phe Leu Met Asn Ser Val Val Arg Gly Gln Gly Thr His
    1535            1540                1545

Leu Pro Gly Asn Ala Ser Pro Ala Ser Asp Ser Gly Leu Arg Thr
    1550            1555                1560

Pro Thr Thr Ala Glu Ser Asp Ala Asp Ala Cys Ile Arg Ala Lys
    1565            1570                1575

Tyr Ala Ser Arg Ile Ile Arg Val Arg Lys Pro Ile Val Gly Ser
    1580            1585                1590

Asn Glu Ser His Asn Gly Gly His Gln Ser Pro His Ala Leu Ser
    1595            1600                1605

Leu Ile Glu Ser Gly Lys Val Glu Met Val Ile Asn Val Pro Asp
    1610            1615                1620

Ser Met Asn His Arg Ala Ala Thr Asn Gly Tyr Leu Met Arg Arg
    1625            1630                1635

Thr Ala Thr Asp Cys Gly Val Pro Leu Leu Thr Asn Val Lys Val
    1640            1645                1650

Ala Ser Met Phe Val Glu Ala Leu Asn Lys Lys Glu Ala Lys Glu
    1655            1660                1665

Ala Gln Gly Arg Ser Phe Trp Asp Ile Arg Ser Trp Asp Glu Tyr
    1670            1675                1680

Trp Pro Gln Lys
    1685

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
```

```
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 3
ccnytnggna thcaycangg ngay                                            24

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 4
ytcytcmaan gtyctnccka tngacatnac                                      30

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Pro Leu Gly Ile His Thr Gly Asp Ser Ile
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Gly Glu Val Met Ser Ile Gly Arg Thr Phe Glu Glu
1               5                   10

<210> SEQ ID NO 7
<211> LENGTH: 22
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (2)..(2)
<223> OTHER INFORMATION: Xaa denotes an aliphatic amino acid residue

<400> SEQUENCE: 7

Glu Xaa Asn Ala Arg Leu Ser Arg Ser Ser Ala Leu Ala Ser Lys Ala
1               5                   10                  15

Thr Gly Tyr Pro Leu Ala
            20

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa denotes Ser or Ala.
<220> FEATURE:
<221> NAME/KEY: MISC_FEATURE
<222> LOCATION: (12)..(12)
<223> OTHER INFORMATION: Xaa denotes a positively charged amino acid
      residue.
<220> FEATURE:
<221> NAME/KEY: MISC_FEATURE
<222> LOCATION: (17)..(17)
<223> OTHER INFORMATION: Xaa denotes Ser or Ala

<400> SEQUENCE: 8

Met Lys Ser Val Gly Glu Val Met Xaa Ile Gly Xaa Thr Phe Glu Glu
1               5                   10                  15

Xaa

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Val or Ala.
<220> FEATURE:
<221> NAME/KEY: MISC_FEATURE
<222> LOCATION: (11)..(12)
<223> OTHER INFORMATION: Xaa denotes Ser or Ala.

<400> SEQUENCE: 9

Leu Xaa Arg Pro Ser Tyr Val Leu Ser Gly Xaa Xaa Met
1               5                   10

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10
gggagatcta tggcttcgta ccccggccat caa                               33

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide
```

<400> SEQUENCE: 11 gggatcctc agttagcctc ccccatctcc cg                        32

<210> SEQ ID NO 12
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 12
actagtggtg atgacgacga caagatgcct cacagtggag ggc           43

<210> SEQ ID NO 13
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 13
gatatccacg tgtcgcggcc gcgctctc                            28

<210> SEQ ID NO 14
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 14
gagagcgcgg ccgcgac                                        17

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
cacgtggagg cgagacgtcg tcgtc                               25

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
agtacttgat gaattcaccg                                     20

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 17
tttctgcgag atcttcttca cg                                  22

<210> SEQ ID NO 18
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 18
gcgtgaagaa gatctcgcag                                              20

<210> SEQ ID NO 19
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 19
atcgatcacg tgattttga ggccagtatt catcc                              35

<210> SEQ ID NO 20
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 20
gctagcgtgg accccatta tccttcgc                                      28

<210> SEQ ID NO 21
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 21
actagtcact cgtcgaatgg ttgcgtctg                                    29

<210> SEQ ID NO 22
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 22
gctagcgtgg accccatta tccttcgc                                      28

<210> SEQ ID NO 23
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 23
actagtgaaa tcgcgatcaa cgcgacag                                     28

<210> SEQ ID NO 24
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 24
agtacttgca ccaccaccac caccactaat ttccaatact ttcgccaaaa acgttcc      57
```

<210> SEQ ID NO 25
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 25
gcgcacgtgg ttgagagctt gacccgcatg ca                          32

<210> SEQ ID NO 26
<211> LENGTH: 1455
<212> TYPE: PRT
<213> ORGANISM: Escherichia coli

<400> SEQUENCE: 26

```
Met Ile Lys Ser Ala Leu Leu Val Leu Glu Asp Gly Thr Gln Phe His
1               5                   10                  15

Gly Arg Ala Ile Gly Ala Thr Gly Ser Ala Val Gly Glu Val Val Phe
                20                  25                  30

Asn Thr Ser Met Thr Gly Tyr Gln Glu Ile Leu Thr Asp Pro Ser Tyr
            35                  40                  45

Ser Arg Gln Ile Val Thr Leu Thr Tyr Pro His Ile Gly Asn Val Gly
        50                  55                  60

Thr Asn Asp Ala Asp Glu Glu Ser Ser Gln Val His Ala Gln Gly Leu
65                  70                  75                  80

Val Ile Arg Asp Leu Pro Leu Ile Ala Ser Asn Phe Arg Asn Thr Glu
                85                  90                  95

Asp Leu Ser Ser Tyr Leu Lys Arg His Asn Ile Val Ala Ile Ala Asp
            100                 105                 110

Ile Asp Thr Arg Lys Leu Thr Arg Leu Leu Arg Glu Lys Gly Ala Gln
        115                 120                 125

Asn Gly Cys Ile Ile Ala Gly Asp Asn Pro Asp Ala Ala Leu Ala Leu
    130                 135                 140

Glu Lys Ala Arg Ala Phe Pro Gly Leu Asn Gly Met Asp Leu Ala Lys
145                 150                 155                 160

Glu Val Thr Thr Ala Glu Ala Tyr Ser Trp Thr Gln Gly Ser Trp Thr
                165                 170                 175

Leu Thr Gly Gly Leu Pro Glu Ala Lys Lys Glu Asp Glu Leu Pro Phe
            180                 185                 190

His Val Ala Tyr Asp Phe Gly Ala Lys Arg Asn Ile Leu Arg Met
        195                 200                 205

Leu Val Asp Arg Gly Cys Arg Leu Thr Ile Val Pro Ala Gln Thr Ser
    210                 215                 220

Ala Glu Asp Val Leu Lys Met Asn Pro Asp Gly Ile Phe Leu Ser Asn
225                 230                 235                 240

Gly Pro Gly Asp Pro Ala Pro Cys Asp Tyr Ala Ile Thr Ala Ile Gln
                245                 250                 255

Lys Phe Leu Glu Thr Asp Ile Pro Val Phe Gly Ile Cys Leu Gly His
            260                 265                 270

Gln Leu Leu Ala Leu Ala Ser Gly Ala Lys Thr Val Lys Met Lys Phe
        275                 280                 285

Gly His His Gly Gly Asn His Pro Val Lys Val Glu Lys Asn Val
    290                 295                 300

Val Met Ile Thr Ala Gln Asn His Gly Phe Ala Val Asp Glu Ala Thr
305                 310                 315                 320
```

```
Leu Pro Ala Asn Leu Arg Val Thr His Lys Ser Leu Phe Asp Gly Thr
                325                 330                 335

Leu Gln Gly Ile His Arg Thr Asp Lys Pro Ala Phe Ser Phe Gln Gly
            340                 345                 350

His Pro Glu Ala Ser Pro Gly Pro His Asp Ala Ala Pro Leu Phe Asp
        355                 360                 365

His Phe Ile Glu Leu Ile Glu Gln Tyr Arg Lys Thr Ala Lys Met Pro
    370                 375                 380

Lys Arg Thr Asp Ile Lys Ser Ile Leu Ile Leu Gly Ala Gly Pro Ile
385                 390                 395                 400

Val Ile Gly Gln Ala Cys Glu Phe Asp Tyr Ser Gly Ala Gln Ala Cys
                405                 410                 415

Lys Ala Leu Arg Glu Glu Gly Tyr Arg Val Ile Leu Val Asn Ser Asn
            420                 425                 430

Pro Ala Thr Ile Met Thr Asp Pro Glu Met Ala Asp Ala Thr Tyr Ile
        435                 440                 445

Glu Pro Ile His Trp Glu Val Arg Lys Ile Ile Glu Lys Glu Arg
    450                 455                 460

Pro Asp Ala Val Leu Pro Thr Met Gly Gly Gln Thr Ala Leu Asn Cys
465                 470                 475                 480

Ala Leu Glu Leu Glu Arg Gln Gly Val Leu Glu Glu Phe Gly Val Thr
                485                 490                 495

Met Ile Gly Ala Thr Ala Asp Ala Ile Asp Lys Ala Glu Asp Arg Arg
            500                 505                 510

Arg Phe Asp Val Ala Met Lys Lys Ile Gly Leu Glu Thr Ala Arg Ser
        515                 520                 525

Gly Ile Ala His Thr Met Glu Glu Ala Leu Ala Val Ala Ala Asp Val
    530                 535                 540

Gly Phe Pro Cys Ile Ile Arg Pro Ser Phe Thr Met Gly Gly Ser Gly
545                 550                 555                 560

Gly Gly Ile Ala Tyr Asn Arg Glu Glu Phe Glu Ile Cys Ala Arg
                565                 570                 575

Gly Leu Asp Leu Ser Pro Thr Lys Glu Leu Leu Ile Asp Glu Ser Leu
            580                 585                 590

Ile Gly Trp Lys Glu Tyr Glu Met Glu Val Val Arg Asp Lys Asn Asp
        595                 600                 605

Asn Cys Ile Ile Val Cys Ser Ile Glu Asn Phe Asp Ala Met Gly Ile
    610                 615                 620

His Thr Gly Asp Ser Ile Thr Val Ala Pro Ala Gln Thr Leu Thr Asp
625                 630                 635                 640

Lys Glu Tyr Gln Ile Met Arg Asn Ala Ser Met Ala Val Leu Arg Glu
                645                 650                 655

Ile Gly Val Glu Thr Gly Gly Ser Asn Val Gln Phe Ala Val Asn Pro
            660                 665                 670

Lys Asn Gly Arg Leu Ile Val Ile Glu Met Asn Pro Arg Val Ser Arg
        675                 680                 685

Ser Ser Ala Leu Ala Ser Lys Ala Thr Gly Phe Pro Ile Ala Lys Val
    690                 695                 700

Ala Ala Lys Leu Ala Val Gly Tyr Thr Leu Asp Glu Leu Met Asn Asp
705                 710                 715                 720

Ile Thr Gly Gly Arg Thr Pro Ala Ser Phe Glu Pro Ser Ile Asp Tyr
                725                 730                 735

Val Val Thr Lys Ile Pro Arg Phe Asn Phe Glu Lys Phe Ala Gly Ala
```

-continued

```
                   740                 745                 750
Asn Asp Arg Leu Thr Thr Gln Met Lys Ser Val Gly Glu Val Met Ala
              755                 760                 765
Ile Gly Arg Thr Gln Gln Glu Ser Leu Gln Lys Ala Leu Arg Gly Leu
          770                 775                 780
Glu Val Gly Ala Thr Gly Phe Asp Pro Lys Val Ser Leu Asp Asp Pro
785                 790                 795                 800
Glu Ala Leu Thr Lys Ile Arg Arg Glu Leu Lys Asp Ala Gly Ala Asp
              805                 810                 815
Arg Ile Trp Tyr Ile Ala Asp Ala Phe Arg Ala Gly Leu Ser Val Asp
          820                 825                 830
Gly Val Phe Asn Leu Thr Asn Ile Asp Arg Trp Phe Leu Val Gln Ile
          835                 840                 845
Glu Glu Leu Val Arg Leu Glu Glu Lys Val Ala Glu Val Gly Ile Thr
      850                 855                 860
Gly Leu Asn Ala Asp Phe Leu Arg Gln Leu Lys Arg Lys Gly Phe Ala
865                 870                 875                 880
Asp Ala Arg Leu Ala Lys Leu Ala Gly Val Arg Glu Ala Glu Ile Arg
              885                 890                 895
Lys Leu Arg Asp Gln Tyr Asp Leu His Pro Val Tyr Lys Arg Val Asp
          900                 905                 910
Thr Cys Ala Ala Glu Phe Ala Thr Asp Thr Ala Tyr Met Tyr Ser Thr
          915                 920                 925
Tyr Glu Glu Glu Cys Glu Ala Asn Pro Ser Thr Asp Arg Glu Lys Ile
      930                 935                 940
Met Val Leu Gly Gly Gly Pro Asn Arg Ile Gly Gln Gly Ile Glu Phe
945                 950                 955                 960
Asp Tyr Cys Cys Val His Ala Ser Leu Ala Leu Arg Glu Asp Gly Tyr
              965                 970                 975
Glu Thr Ile Met Val Asn Cys Asn Pro Glu Thr Val Ser Thr Asp Tyr
          980                 985                 990
Asp Thr Ser Asp Arg Leu Tyr Phe Glu Pro Val Thr Leu Glu Asp Val
          995                 1000                1005
Leu Glu Ile Val Arg Ile Glu Lys Pro Lys Gly Val Ile Val Gln
      1010                1015                1020
Tyr Gly Gly Gln Thr Pro Leu Lys Leu Ala Arg Ala Leu Glu Ala
      1025                1030                1035
Ala Gly Val Pro Val Ile Gly Thr Ser Pro Asp Ala Ile Asp Arg
      1040                1045                1050
Ala Glu Asp Arg Glu Arg Phe Gln His Ala Val Glu Arg Leu Lys
      1055                1060                1065
Leu Lys Gln Pro Ala Asn Ala Thr Val Thr Ala Ile Glu Met Ala
      1070                1075                1080
Val Glu Lys Ala Lys Glu Ile Gly Tyr Pro Leu Val Val Arg Pro
      1085                1090                1095
Ser Tyr Val Leu Gly Gly Arg Ala Met Glu Ile Val Tyr Asp Glu
      1100                1105                1110
Ala Asp Leu Arg Arg Tyr Phe Gln Thr Ala Val Ser Val Ser Asn
      1115                1120                1125
Asp Ala Pro Val Leu Leu Asp His Phe Leu Asp Asp Ala Val Glu
      1130                1135                1140
Val Asp Val Asp Ala Ile Cys Asp Gly Glu Met Val Leu Ile Gly
      1145                1150                1155
```

```
Gly Ile Met Glu His Ile Glu Gln Ala Gly Val His Ser Gly Asp
        1160                1165                1170

Ser Ala Cys Ser Leu Pro Ala Tyr Thr Leu Ser Gln Glu Ile Gln
    1175                1180                1185

Asp Val Met Arg Gln Val Gln Lys Leu Ala Phe Glu Leu Gln
1190                1195                1200

Val Arg Gly Leu Met Asn Val Gln Phe Ala Val Lys Asn Asn Glu
    1205                1210                1215

Val Tyr Leu Ile Glu Val Asn Pro Arg Ala Ala Arg Thr Val Pro
    1220                1225                1230

Phe Val Ser Lys Ala Thr Gly Val Pro Leu Ala Lys Val Ala Ala
    1235                1240                1245

Arg Val Met Ala Gly Lys Ser Leu Ala Glu Gln Gly Val Thr Lys
    1250                1255                1260

Glu Val Ile Pro Pro Tyr Tyr Ser Val Lys Val Val Leu Pro
    1265                1270                1275

Phe Asn Lys Phe Pro Gly Val Asp Pro Leu Leu Gly Pro Glu Met
    1280                1285                1290

Arg Ser Thr Gly Glu Val Met Gly Val Gly Arg Thr Phe Ala Glu
    1295                1300                1305

Ala Phe Ala Lys Ala Gln Leu Gly Ser Asn Ser Thr Met Lys Lys
    1310                1315                1320

His Gly Arg Ala Leu Leu Ser Val Arg Glu Gly Asp Lys Glu Arg
    1325                1330                1335

Val Val Asp Leu Ala Ala Lys Leu Leu Lys Gln Gly Phe Glu Leu
    1340                1345                1350

Asp Ala Thr His Gly Thr Ala Ile Val Leu Gly Glu Ala Gly Ile
    1355                1360                1365

Asn Pro Arg Leu Val Asn Lys Val His Glu Gly Arg Pro His Ile
    1370                1375                1380

Gln Asp Arg Ile Lys Asn Gly Glu Tyr Thr Tyr Ile Ile Asn Thr
    1385                1390                1395

Thr Ser Gly Arg Arg Ala Ile Glu Asp Ser Arg Val Ile Arg Arg
    1400                1405                1410

Ser Ala Leu Gln Tyr Lys Val His Tyr Asp Thr Thr Leu Asn Gly
    1415                1420                1425

Gly Phe Ala Thr Ala Met Ala Leu Asn Ala Asp Ala Thr Glu Lys
    1430                1435                1440

Val Ile Ser Val Gln Glu Met His Ala Gln Ile Lys
    1445                1450                1455

<210> SEQ ID NO 27
<211> LENGTH: 2391
<212> TYPE: PRT
<213> ORGANISM: Plasmodium falciparum

<400> SEQUENCE: 27

Met Tyr Ile Ser Phe Lys Tyr Asn Leu Tyr Ile Tyr Ile Tyr
1                5                  10                  15

Ile Tyr Ile Phe Val Leu Ile Asp Phe Lys Thr Val Gly Arg Leu Ile
                20                  25                  30

Leu Glu Asp Gly Asn Glu Phe Val Gly Tyr Ser Val Gly Tyr Glu Gly
            35                  40                  45

Cys Lys Gly Asn Asn Ser Ile Ser Cys His Lys Glu Tyr Arg Asn Ile
        50                  55                  60
```

```
Ile Asn Asn Asp Asn Ser Lys Asn Ser Asn Asn Ser Phe Cys Asn Asn
65                  70                  75                  80

Glu Glu Asn Asn Leu Lys Asp Asp Leu Leu Tyr Lys Asn Ser Arg Leu
            85                  90                  95

Glu Asn Glu Asp Phe Ile Val Thr Gly Glu Val Ile Phe Asn Thr Ala
        100                 105                 110

Met Val Gly Tyr Pro Glu Ala Leu Thr Asp Pro Ser Tyr Phe Gly Gln
    115                 120                 125

Ile Leu Val Leu Thr Phe Pro Ser Ile Gly Asn Tyr Gly Ile Glu Lys
130                 135                 140

Val Lys His Asp Glu Thr Phe Gly Leu Val Gln Asn Phe Glu Ser Asn
145                 150                 155                 160

Lys Ile Gln Val Gln Gly Leu Val Ile Cys Glu Tyr Ser Lys Gln Ser
                165                 170                 175

Tyr His Tyr Asn Ser Tyr Ile Thr Leu Ser Glu Trp Leu Lys Ile Tyr
            180                 185                 190

Lys Ile Pro Cys Ile Gly Gly Ile Asp Thr Arg Ala Leu Thr Lys Leu
        195                 200                 205

Leu Arg Glu Lys Gly Ser Met Leu Gly Lys Ile Val Ile Tyr Lys Asn
    210                 215                 220

Arg Gln His Ile Asn Lys Leu Tyr Lys Glu Ile Asn Leu Phe Asp Pro
225                 230                 235                 240

Gly Asn Ile Asp Thr Leu Lys Tyr Val Cys Asn His Phe Ile Arg Val
                245                 250                 255

Ile Lys Leu Asn Asn Ile Thr Tyr Asn Tyr Lys Asn Lys Glu Glu Phe
            260                 265                 270

Asn Tyr Thr Asn Glu Met Ile Thr Asn Asp Ser Ser Met Glu Asp His
        275                 280                 285

Asp Asn Glu Ile Asn Gly Ser Ile Ser Asn Phe Asn Asn Cys Pro Ser
    290                 295                 300

Ile Ser Ser Phe Asp Lys Ser Glu Ser Lys Asn Val Ile Asn His Thr
305                 310                 315                 320

Leu Leu Arg Asp Lys Met Asn Leu Ile Thr Ser Ser Glu Glu Tyr Leu
                325                 330                 335

Lys Asp Leu His Asn Cys Asn Phe Ser Asn Ser Ser Asp Lys Asn Asp
            340                 345                 350

Ser Phe Phe Lys Leu Tyr Gly Ile Cys Glu Tyr Asp Lys Tyr Leu Ile
        355                 360                 365

Asp Leu Glu Glu Asn Ala Ser Phe His Tyr Asn Asn Val Asp Glu Tyr
    370                 375                 380

Gly Tyr Tyr Asp Val Asn Lys Asn Thr Asn Ile Leu Ser Asn Asn Lys
385                 390                 395                 400

Ile Glu Gln Asn Asn Asn Glu Asn Asn Lys Asn Asn Lys Asn Asn
                405                 410                 415

Asn Asn Asn Glu Val Asp Tyr Ile Lys Lys Asp Glu Asp Asn Asn Val
            420                 425                 430

Asn Ser Lys Val Phe Tyr Ser Gln Tyr Asn Asn Ala Gln Asn Asn
        435                 440                 445

Glu His Thr Glu Phe Asn Leu Asn Asn Asp Tyr Ser Thr Tyr Ile Arg
    450                 455                 460

Lys Lys Met Lys Asn Glu Glu Phe Leu Asn Leu Val Asn Lys Arg Lys
465                 470                 475                 480

Val Asp His Lys Glu Lys Ile Ile Val Ile Val Asp Cys Gly Ile Lys
                485                 490                 495
```

```
Asn Ser Ile Ile Lys Asn Leu Ile Arg His Gly Met Asp Leu Pro Leu
                500                 505                 510

Thr Tyr Ile Ile Val Pro Tyr Tyr Asn Phe Asn His Ile Asp Tyr
            515                 520                 525

Asp Ala Val Leu Leu Ser Asn Gly Pro Gly Asp Pro Lys Lys Cys Asp
        530                 535                 540

Phe Leu Ile Lys Asn Leu Lys Asp Ser Leu Thr Lys Asn Lys Ile Ile
545                 550                 555                 560

Phe Gly Ile Cys Leu Gly Asn Gln Leu Leu Gly Ile Ser Leu Gly Cys
                565                 570                 575

Asp Thr Tyr Lys Met Lys Tyr Gly Asn Arg Gly Val Asn Gln Pro Val
            580                 585                 590

Ile Gln Leu Val Asp Asn Ile Cys Tyr Ile Thr Ser Gln Asn His Gly
        595                 600                 605

Tyr Cys Leu Lys Lys Lys Ser Ile Leu Lys Arg Lys Glu Leu Ala Ile
            610                 615                 620

Ser Tyr Ile Asn Ala Asn Asp Lys Ser Ile Glu Gly Ile Ser His Lys
625                 630                 635                 640

Asn Gly Arg Phe Tyr Ser Val Gln Phe His Pro Glu Gly Asn Asn Gly
                645                 650                 655

Pro Glu Asp Thr Ser Phe Leu Phe Lys Asn Phe Leu Leu Asp Ile Phe
            660                 665                 670

Asn Lys Lys Lys Gln Tyr Arg Glu Tyr Leu Gly Tyr Asn Ile Ile Tyr
        675                 680                 685

Ile Lys Lys Lys Val Leu Leu Leu Gly Ser Gly Leu Cys Ile Gly
690                 695                 700

Gln Ala Gly Glu Phe Asp Tyr Ser Gly Thr Gln Ala Ile Lys Ser Leu
705                 710                 715                 720

Lys Glu Cys Gly Ile Tyr Val Ile Leu Val Asn Pro Asn Ile Ala Thr
                725                 730                 735

Val Gln Thr Ser Lys Gly Leu Ala Asp Lys Val Tyr Phe Leu Pro Val
            740                 745                 750

Asn Cys Glu Phe Val Glu Lys Ile Ile Lys Glu Lys Pro Asp Phe
        755                 760                 765

Ile Leu Cys Thr Phe Gly Gly Gln Thr Ala Leu Asn Cys Ala Leu Met
        770                 775                 780

Leu Asp Gln Lys Lys Val Leu Lys Lys Asn Cys Gln Cys Leu Gly
785                 790                 795                 800

Thr Ser Leu Glu Ser Ile Arg Ile Thr Glu Asn Arg Thr Leu Phe Ala
            805                 810                 815

Glu Lys Leu Lys Glu Ile Asn Glu Arg Ile Ala Pro Tyr Gly Ser Ala
        820                 825                 830

Lys Asn Val Asn Gln Ala Ile Asp Ile Ala Asn Lys Ile Gly Tyr Pro
        835                 840                 845

Ile Leu Val Arg Thr Thr Phe Ser Leu Gly Gly Leu Asn Ser Ser Phe
        850                 855                 860

Ile Asn Asn Glu Glu Leu Ile Glu Lys Cys Asn Lys Ile Phe Leu
865                 870                 875                 880

Gln Thr Asp Asn Glu Ile Phe Ile Asp Lys Ser Leu Gln Gly Trp Lys
            885                 890                 895

Glu Ile Glu Tyr Glu Leu Leu Arg Asp Asn Lys Asn Cys Ile Ala
            900                 905                 910

Ile Cys Asn Met Glu Asn Ile Asp Pro Leu Gly Ile His Thr Gly Asp
```

```
               915                 920                 925
Ser Ile Val Val Ala Pro Ser Gln Thr Leu Ser Asn Tyr Glu Tyr Tyr
    930                 935                 940
Lys Phe Arg Glu Ile Ala Leu Lys Val Ile Thr His Leu Asn Ile Ile
945                 950                 955                 960
Gly Glu Cys Asn Ile Gln Phe Gly Ile Asn Pro Gln Thr Gly Glu Tyr
                965                 970                 975
Cys Ile Ile Glu Val Asn Ala Arg Leu Ser Arg Ser Ser Ala Leu Ala
            980                 985                 990
Ser Lys Ala Thr Gly Tyr Pro Leu Ala Tyr Ile Ser Ala Lys Ile Ala
        995                 1000                1005
Leu Gly Tyr Asp Leu Ile Ser Leu Lys Asn Ser Ile Thr Lys Lys
    1010                1015                1020
Thr Thr Ala Cys Phe Glu Pro Ser Leu Asp Tyr Ile Thr Thr Lys
    1025                1030                1035
Ile Pro Arg Trp Asp Leu Asn Lys Phe Glu Phe Ala Ser Asn Thr
    1040                1045                1050
Met Asn Ser Ser Met Lys Ser Val Gly Glu Val Met Ser Ile Gly
    1055                1060                1065
Arg Thr Phe Glu Glu Ser Ile Gln Lys Ser Leu Arg Cys Ile Asp
    1070                1075                1080
Asp Asn Tyr Leu Gly Phe Ser Asn Thr Tyr Cys Ile Asp Trp Asp
    1085                1090                1095
Glu Lys Lys Ile Ile Glu Glu Leu Lys Asn Pro Ser Pro Lys Arg
    1100                1105                1110
Ile Asp Ala Ile His Gln Ala Phe His Leu Asn Met Pro Met Asp
    1115                1120                1125
Lys Ile His Glu Leu Thr His Ile Asp Tyr Trp Phe Leu His Lys
    1130                1135                1140
Phe Tyr Asn Ile Tyr Asn Leu Gln Asn Lys Leu Lys Thr Leu Lys
    1145                1150                1155
Leu Glu Gln Leu Ser Phe Asn Asp Leu Lys Tyr Phe Lys Lys His
    1160                1165                1170
Gly Phe Ser Asp Lys Gln Ile Ala His Tyr Leu Ser Phe Asn Thr
    1175                1180                1185
Ser Asp Asn Asn Asn Asn Asn Asn Ile Ser Ser Cys Arg Val
    1190                1195                1200
Thr Glu Asn Asp Val Met Lys Tyr Arg Glu Lys Leu Gly Leu Phe
    1205                1210                1215
Pro His Ile Lys Val Ile Asp Thr Leu Ser Ala Glu Phe Pro Ala
    1220                1225                1230
Leu Thr Asn Tyr Leu Tyr Leu Thr Tyr Gln Gly Gln Glu His Asp
    1235                1240                1245
Val Leu Pro Leu Asn Met Lys Arg Lys Lys Ile Cys Thr Leu Asn
    1250                1255                1260
Asn Lys Arg Asn Ala Asn Lys Lys Lys Val His Val Lys Asn His
    1265                1270                1275
Leu Tyr Asn Glu Val Val Asp Asp Lys Asp Thr Gln Leu His Lys
    1280                1285                1290
Glu Asn Asn Asn Asn Asn Met Asn Ser Gly Asn Val Glu Asn
    1295                1300                1305
Lys Cys Lys Leu Asn Lys Glu Ser Tyr Gly Tyr Asn Asn Ser Ser
    1310                1315                1320
```

-continued

```
Asn Cys Ile Asn Thr Asn Asn Ile Asn Ile Glu Asn Asn Ile Cys
1325                1330                1335
His Asp Ile Ser Ile Asn Lys Asn Ile Lys Val Thr Ile Asn Asn
1340                1345                1350
Ser Asn Asn Ser Ile Ser Asn Asn Glu Asn Val Glu Thr Asn Leu
1355                1360                1365
Asn Cys Val Ser Glu Arg Ala Gly Ser His His Ile Tyr Gly Lys
1370                1375                1380
Glu Glu Lys Ser Ile Gly Ser Asp Asp Thr Asn Ile Leu Ser Ala
1385                1390                1395
Gln Asn Ser Asn Asn Asn Phe Ser Cys Asn Asn Glu Asn Met Asn
1400                1405                1410
Lys Ala Asn Val Asp Val Asn Val Leu Glu Asn Asp Thr Lys Lys
1415                1420                1425
Arg Glu Asp Ile Asn Thr Thr Thr Val Phe Met Glu Gly Gln Asn
1430                1435                1440
Ser Val Ile Asn Asn Lys Asn Lys Glu Asn Ser Ser Leu Leu Lys
1445                1450                1455
Gly Asp Glu Glu Asp Ile Val Met Val Asn Leu Lys Lys Glu Asn
1460                1465                1470
Asn Tyr Asn Ser Val Ile Asn Val Asp Cys Arg Lys Lys Asp
1475                1480                1485
Met Asp Gly Lys Asn Ile Asn Asp Glu Cys Lys Thr Tyr Lys Lys
1490                1495                1500
Asn Lys Tyr Lys Asp Met Gly Leu Asn Asn Asn Ile Val Asp Glu
1505                1510                1515
Leu Ser Asn Gly Thr Ser His Ser Thr Asn Asp His Leu Tyr Leu
1520                1525                1530
Asp Asn Phe Asn Thr Ser Asp Glu Glu Ile Gly Asn Asn Lys Asn
1535                1540                1545
Met Asp Met Tyr Leu Ser Lys Glu Lys Ser Ile Ser Asn Lys Asn
1550                1555                1560
Pro Gly Asn Ser Tyr Tyr Val Val Asp Ser Val Tyr Asn Asn Glu
1565                1570                1575
Tyr Lys Ile Asn Lys Met Lys Glu Leu Ile Asp Asn Glu Asn Leu
1580                1585                1590
Asn Asp Glu Tyr Asn Asn Asn Val Asn Met Asn Cys Ser Asn Tyr
1595                1600                1605
Asn Asn Ala Ser Ala Phe Val Asn Gly Lys Asp Arg Asn Asp Asn
1610                1615                1620
Leu Glu Asn Asp Cys Ile Glu Lys Asn Met Asp His Thr Tyr Lys
1625                1630                1635
His Tyr Asn Arg Leu Asn Asn Arg Arg Ser Thr Asn Glu Arg Met
1640                1645                1650
Met Leu Met Val Asn Asn Glu Lys Glu Ser Asn His Glu Lys Gly
1655                1660                1665
His Arg Arg Asn Gly Leu Asn Lys Lys Asn Lys Glu Lys Asn Met
1670                1675                1680
Glu Lys Asn Lys Gly Lys Asn Lys Asp Lys Lys Asn Tyr His Tyr
1685                1690                1695
Val Asn His Lys Arg Asn Asn Glu Tyr Asn Ser Asn Asn Ile Glu
1700                1705                1710
Ser Lys Phe Asn Asn Tyr Val Asp Asp Ile Asn Lys Lys Glu Tyr
1715                1720                1725
```

```
Tyr Glu Asp Glu Asn Asp Ile Tyr Tyr Phe Thr His Ser Ser Gln
    1730            1735                1740
Gly Asn Asn Asp Asp Leu Ser Asn Asp Asn Tyr Leu Ser Ser Glu
    1745            1750                1755
Glu Leu Asn Thr Asp Glu Tyr Asp Asp Tyr Tyr Tyr Asp Glu
    1760            1765                1770
Asp Glu Glu Asp Asp Tyr Asp Asp Asp Asn Asp Asp Asp Asp Asp
    1775            1780                1785
Asp Asp Asp Asp Gly Glu Asp Glu Glu Asp Asn Asp Tyr Tyr Asn
    1790            1795                1800
Asp Asp Gly Tyr Asp Ser Tyr Asn Ser Leu Ser Ser Ser Arg Ile
    1805            1810                1815
Ser Asp Val Ser Ser Val Ile Tyr Ser Gly Asn Glu Asn Ile Phe
    1820            1825                1830
Asn Glu Lys Tyr Asn Asp Ile Gly Phe Lys Ile Ile Asp Asn Arg
    1835            1840                1845
Asn Glu Lys Glu Lys Glu Lys Lys Lys Cys Phe Ile Val Leu Gly
    1850            1855                1860
Cys Gly Cys Tyr Arg Ile Gly Ser Ser Val Glu Phe Asp Trp Ser
    1865            1870                1875
Ala Ile His Cys Val Lys Thr Ile Arg Lys Leu Asn His Lys Ala
    1880            1885                1890
Ile Leu Ile Asn Cys Asn Pro Glu Thr Val Ser Thr Asp Tyr Asp
    1895            1900                1905
Glu Ser Asp Arg Leu Tyr Phe Asp Glu Ile Thr Thr Glu Val Ile
    1910            1915                1920
Lys Phe Ile Tyr Asn Phe Glu Asn Ser Asn Gly Val Ile Ile Ala
    1925            1930                1935
Phe Gly Gly Gln Thr Ser Asn Asn Leu Val Phe Ser Leu Tyr Lys
    1940            1945                1950
Asn Asn Val Asn Ile Leu Gly Ser Val His Lys Val Leu Ile Val
    1955            1960                1965
Val Lys Ile Gly Ile Asn Phe Arg Thr Tyr Val Ile Leu Lys Ile
    1970            1975                1980
Asp Gln Pro Lys Trp Asn Lys Phe Thr Lys Leu Ser Lys Ala Ile
    1985            1990                1995
Gln Phe Ala Asn Glu Val Lys Phe Pro Val Leu Val Arg Pro Ser
    2000            2005                2010
Tyr Val Leu Ser Gly Ala Ala Met Arg Val Val Asn Cys Phe Glu
    2015            2020                2025
Glu Leu Lys Asn Phe Leu Met Lys Ala Ala Ile Val Ser Lys Asp
    2030            2035                2040
Asn Pro Val Val Ile Ser Lys Phe Ile Glu Asn Ala Lys Glu Ile
    2045            2050                2055
Glu Ile Asp Cys Val Ser Lys Asn Gly Lys Ile Ile Asn Tyr Ala
    2060            2065                2070
Ile Ser Glu His Val Glu Asn Ala Gly Val His Ser Gly Asp Ala
    2075            2080                2085
Thr Leu Ile Leu Pro Ala Gln Asn Ile Tyr Val Glu Thr His Arg
    2090            2095                2100
Lys Ile Lys Lys Ile Ser Glu Lys Ile Ser Lys Ser Leu Asn Ile
    2105            2110                2115
Ser Gly Pro Phe Asn Ile Gln Phe Ile Cys His Gln Asn Glu Ile
```

```
    2120                2125                2130

Lys Ile  Ile Glu Cys Asn Leu  Arg Ala Ser Arg Thr  Phe Pro Phe
    2135                2140                2145

Ile Ser  Lys Ala Leu Asn Leu  Asn Phe Ile Asp Leu  Ala Thr Arg
    2150                2155                2160

Ile Leu  Met Gly Tyr Asp Val  Lys Pro Ile Asn Ile  Ser Leu Ile
    2165                2170                2175

Asp Leu  Glu Tyr Thr Ala Val  Lys Ala Pro Ile Phe  Ser Phe Asn
    2180                2185                2190

Arg Leu  His Gly Ser Asp Cys  Ile Leu Gly Val Glu  Met Lys Ser
    2195                2200                2205

Thr Gly  Glu Val Ala Cys Phe  Gly Leu Asn Lys Tyr  Glu Ala Leu
    2210                2215                2220

Leu Lys  Ser Leu Ile Ala Thr  Gly Met Lys Leu Pro  Lys Lys Ser
    2225                2230                2235

Ile Leu  Ile Ser Ile Lys Asn  Leu Asn Asn Lys Leu  Ala Phe Glu
    2240                2245                2250

Glu Pro  Phe Gln Leu Leu Phe  Leu Met Gly Phe Thr  Ile Tyr Ala
    2255                2260                2265

Thr Glu  Gly Thr Tyr Asp Phe  Tyr Ser Lys Phe Leu  Glu Ser Phe
    2270                2275                2280

Asn Val  Asn Lys Gly Ser Lys  Phe His Gln Arg Leu  Ile Lys Val
    2285                2290                2295

His Asn  Lys Asn Ala Glu Asn  Ile Ser Pro Asn Thr  Thr Asp Leu
    2300                2305                2310

Ile Met  Asn His Lys Val Glu  Met Val Ile Asn Ile  Thr Asp Thr
    2315                2320                2325

Leu Lys  Thr Lys Val Ser Ser  Asn Gly Tyr Lys Ile  Arg Arg Leu
    2330                2335                2340

Ala Ser  Asp Phe Gln Val Pro  Leu Ile Thr Asn Met  Lys Leu Cys
    2345                2350                2355

Ser Leu  Phe Ile Asp Ser Leu  Tyr Arg Lys Phe Ser  Arg Gln Lys
    2360                2365                2370

Glu Arg  Lys Ser Phe Tyr Thr  Ile Lys Ser Tyr Asp  Glu Tyr Ile
    2375                2380                2385

Ser Leu  Val
    2390

<210> SEQ ID NO 28
<211> LENGTH: 1645
<212> TYPE: PRT
<213> ORGANISM: Babesia bovis
<400> SEQUENCE: 28

Met Ala Ser Glu Gly Met Leu Cys Asn Ser Ser Phe Thr Phe Ile Thr
1               5                   10                  15

Arg Val Asp Asp Ser Leu Pro Ala Lys Leu Leu Leu Gln Asp Gly Thr
            20                  25                  30

Glu Phe Asn Gly Tyr Ser Phe Gly Tyr Val Asp Glu Asn Tyr Asp Tyr
        35                  40                  45

Ala Val Leu Pro Asn Leu Ser Ala Thr Gly Glu Val Val Phe Ser Thr
    50                  55                  60

Ser Met Val Gly Tyr Ala Glu Ala Leu Thr Asp Pro Ser Phe Leu Gly
65                  70                  75                  80

Gln Ile Leu Val Leu Thr Tyr Pro Ser Val Gly Asn Thr Gly Val Pro
```

```
                    85                  90                  95
Pro Ser Glu Gln Val Ser Val Ile Glu Leu Asp Ile Thr Leu Val Gln
                100                 105                 110
Asp Glu Leu Arg Cys Leu Arg Ser Gly Phe Glu Ser Arg Ile His
                115                 120                 125
Val Asn Gly Phe Val Cys Cys Asp Tyr Ser Ile Tyr Glu Ser His Trp
            130                 135                 140
Ser Ser Cys Lys Ser Leu Ser Ser Trp Leu Arg Glu Glu Arg Ile Pro
145                 150                 155                 160
Ala Ile Ser Gly Ile Asp Thr Arg Ala Leu Thr Lys His Leu Arg Asn
                165                 170                 175
Cys Gly Ser Thr Leu Ala Arg Ile Ile Gly Pro Lys Ser Arg Gly
                180                 185                 190
Leu Val Ser Pro Arg Leu Leu Glu Ser Ser Phe Tyr Asp Thr Asn
                195                 200                 205
Asn Pro Asp Leu Met Arg Ser Leu Pro Asp Pro His Pro Val Leu Tyr
                210                 215                 220
Thr Met Ser Glu Ile Asp Gly Glu Arg Tyr Val Thr Ser Tyr Glu Phe
225                 230                 235                 240
Thr Val Ala Glu Leu Asp Asp Ile Leu Ser Arg Asp Pro Cys Ala Cys
                245                 250                 255
His Ser Ser Asp Leu Asp Val His Phe Ala Ser Lys Lys Lys Phe Cys
                260                 265                 270
Gly Tyr Pro Asn Lys Pro Val Asn Asp Cys Ala Ser Gly Ser Gly Ser
                275                 280                 285
Leu Tyr Ser Ser Ser Leu Ser Leu Lys Gly Val Thr Leu Val Val Ile
                290                 295                 300
Val Asp Cys Gly Ile Lys Ser Asn Ile Ile Arg Leu Phe Leu Arg Met
305                 310                 315                 320
Ser Pro Val Gln Val Arg Ala Leu Val Val Pro His Asn Phe Asp Phe
                325                 330                 335
Asn Arg Ile Pro Tyr Asp Gly Leu Ile Ile Ser Asn Gly Pro Gly Asp
                340                 345                 350
Pro Ser Asp Ala Thr Val Thr Ile Ala Asn Leu Arg Arg Ala Met Glu
                355                 360                 365
Arg Thr Thr Pro Ile Phe Gly Ile Cys Leu Gly His Gln Leu Met Gly
                370                 375                 380
Leu Ala Ala Gly Ala Lys Thr Tyr Lys Met Arg Tyr Gly His Arg Gly
385                 390                 395                 400
Phe Asn Gln Pro Cys Val Asp Leu Arg Thr Ser Lys Cys Tyr Met Thr
                405                 410                 415
Ser Gln Asn His Gly Tyr Ala Ile Asp Glu Glu Thr Leu Pro Ser Glu
                420                 425                 430
Trp Leu Arg Tyr Cys Asp Ala Asn Asp Gly Cys Val Glu Gly Ile Ile
                435                 440                 445
His Met Thr Tyr Pro Trp Phe Ser Leu Gln Phe His Pro Glu Ala Ser
                450                 455                 460
Gly Gly Pro Thr Asp Thr Leu Phe Leu Met Arg Asp Phe Ile Tyr Ser
465                 470                 475                 480
Leu Gly Lys Ser Gly Ser Ile Pro Leu His Ile Arg Arg His Phe Thr
                485                 490                 495
Ser Arg Ser Met Glu Gly Gly Ile Leu Leu Leu Ser Gly Gly Ile
                500                 505                 510
```

-continued

```
Ser Ile Gly Gln Ala Gly Glu Phe Asp Tyr Ser Gly Ser Gln Ala Ile
        515                 520                 525

Leu Ala Leu Lys Glu Ser Gly Ala Glu Val Ile Leu Val Asn Pro Asn
530                 535                 540

Val Ala Thr Val Gln Thr Asn His Gly Leu Ala Asp Val Val Tyr Phe
545                 550                 555                 560

Glu Leu Leu Leu Leu Ile Val Ser Asn Ile Ile Glu Lys Glu Arg Pro
                565                 570                 575

Asp Gly Ile Met Cys Ser Phe Gly Gly Gln Thr Ala Leu Asn Cys Gly
            580                 585                 590

Ile Asp Leu Tyr Lys Ser Gly Ile Leu Ser Lys Tyr Asn Cys Glu Val
        595                 600                 605

Leu Gly Thr Pro Ile Glu Thr Ile Asn Thr Glu Asp Arg Ala Leu
        610                 615                 620

Phe Asn Arg Lys Leu Ala Glu Ile Gly Glu Arg Cys Ala Pro Ser Lys
625                 630                 635                 640

Val Gly Thr Asp Val Gly Ser Cys Ile Ser Ala Ala Gln Glu Leu Gly
                645                 650                 655

Tyr Pro Val Leu Val Arg Thr Asn Tyr Ala Leu Gly Gly Phe Gly Ser
            660                 665                 670

Gly Leu Ala Ser Asp Glu Ser Glu Leu Arg Ser Ile Leu Ser Asn Ile
        675                 680                 685

Phe Ser Thr Ser Ser Cys Arg Lys Gly Gly Ser Asp Thr Thr Glu Ala
690                 695                 700

Gly Ser Gly Ser Ser Phe Pro Val Glu Asp Val Cys Val Tyr Ile Asp
705                 710                 715                 720

Lys Ala Leu Lys Gly Trp Lys Glu Ile Glu Phe Glu Ile Ile Arg Asp
                725                 730                 735

Asn Asn Asp Asn Cys Ile Ser Pro Ala Ser Met Glu Asn Phe Asp Pro
            740                 745                 750

Leu Gly Ile His Thr Gly Asp Ser Ile Val Val Ala Pro Ala Gln Thr
        755                 760                 765

Leu Thr Asn Gly Glu Leu Tyr Lys Tyr Arg Glu Ile Ala Phe Lys Ile
    770                 775                 780

Val Arg Tyr Leu Gly Ser Val Gly Glu Cys Asn Val Gln Phe Ala Val
785                 790                 795                 800

Asn Pro Asp Thr Asp Asp Tyr Phe Ile Val Glu Leu Asn Ala Arg Leu
                805                 810                 815

Ser Arg Ser Ser Ala Leu Ala Ser Lys Ala Thr Gly Tyr Pro Leu Ala
            820                 825                 830

Tyr Phe Ala Ala Arg Ile Ala Leu Gly Phe Asp Leu Val Gln Met Arg
        835                 840                 845

Asn Ala Ile Thr Leu Val Thr Thr Ala Cys Phe Glu Pro Ser Leu Asp
850                 855                 860

Tyr Ile Val Val Lys Ile Pro Lys Trp Asp Leu Arg Lys Phe Glu Tyr
865                 870                 875                 880

Ala Asp Asn Leu Leu Gly Ser Ser Met Lys Ser Val Gly Glu Val Met
                885                 890                 895

Ser Ile Gly Arg Thr Phe Glu Glu Ala Met Gln Lys Ala Leu Arg Met
            900                 905                 910

Gln Val Arg Val Leu Gly Phe Asn Ser Gly Val Met Ser Gly Ala Asp
        915                 920                 925

Ser Glu Ala Ile Thr Glu Ala Leu Arg His Pro Thr Pro Asp His Val
930                 935                 940
```

-continued

Ala Ala Ile Ala Arg Ala Phe Glu Leu Gly Met Thr Val Ser Asp Ile
945                 950                 955                 960

His Gly Leu Thr Lys Ile Asp Pro Trp Phe Leu His Arg Leu His His
            965                 970                 975

Leu His Ile Leu Asn Ala His Leu Ser Ile Leu Pro Ser Leu Ser Ser
            980                 985                 990

Phe Thr Pro Ala Met Met Arg Tyr Tyr Lys Val Tyr Gly Phe Ser Asp
        995                 1000                1005

Arg Gln Ile Ser Arg Glu Ile Val Lys Ser Thr Val Ser Glu Asp
    1010                1015                1020

Asp Val Arg Glu Leu Arg Lys Ser Trp Gly Ile Val Pro Phe Val
    1025                1030                1035

Lys Val Ile Asp Thr Met Ala Ala Glu Tyr Pro Ala Lys Thr Asn
    1040                1045                1050

Tyr Cys Tyr Leu Thr Tyr Asn Gly Ile Glu Ser Asp Val Leu Pro
    1055                1060                1065

Cys Gly Pro Ile Asp Ser Lys Asp Ser Val Ser Ala Thr Ser Ile
    1070                1075                1080

Val Val Leu Gly Cys Gly Pro Tyr Arg Ile Gly Ser Ser Ile Glu
    1085                1090                1095

Phe Asp Trp Val Cys Cys Ser Cys Val Lys Ala Leu Arg Ser Leu
    1100                1105                1110

Gly His Ala Ala Val Ile Val Asn Cys Asn Pro Glu Thr Val Ser
    1115                1120                1125

Thr Asp Tyr Asp Val Arg Asp Arg Leu Tyr Phe Asp Glu Leu Thr
    1130                1135                1140

Val Glu Ile Val Asp Ala Ile Tyr His Phe Glu Asn Pro Lys Gly
    1145                1150                1155

Ile Val Ile Ser Val Gly Gly Gln Thr Ala Asn Asn Leu Ala Leu
    1160                1165                1170

Gln Phe His Ser Leu Gly Leu Pro Ile Leu Gly Thr Ser Val Glu
    1175                1180                1185

Ser Ile Asp Ser Cys Glu Asp Arg Tyr Ser Phe Ser Glu Val Val
    1190                1195                1200

Cys Ser Phe Gly His Asp Gln Thr Cys Met Glu Glu Phe Thr Ser
    1205                1210                1215

Phe Glu Gly Ala Lys Gln Phe Cys Thr Lys Val Ser Phe Pro Val
    1220                1225                1230

Leu Val Arg Pro Ser Tyr Val Leu Ser Gly Ala Ser Met Arg Val
    1235                1240                1245

Ile Val Ser Phe Glu Glu Leu Glu Lys Tyr Leu Gln Thr Ser Ala
    1250                1255                1260

Val Val Asn Arg Glu His Pro Val Val Ile Ser Lys Phe Ile Glu
    1265                1270                1275

Lys Ala Asn Glu Val Glu Val Glu Thr Val Trp His Leu Gly Tyr
    1280                1285                1290

Tyr Thr Glu Thr Thr Pro Leu Val Glu His Val Glu His Ala Gly
    1295                1300                1305

Thr His Ser Gly Asp Ala Thr Leu Ile Leu Pro Ala Gln Asn Ile
    1310                1315                1320

Phe Val Gly Thr His Arg Ala Val Lys Lys Ile Thr Arg Glu Phe
    1325                1330                1335

Ser Arg Tyr Leu Asn Tyr Asp Gly Pro Phe Asn Val Gln Tyr Leu

-continued

```
                 1340            1345             1350

Cys Lys Asn Asn Glu Ile Lys Ile Ile Glu Cys Asn Leu Arg Ala
    1355            1360            1365

Ser Arg Thr Leu Pro Phe Ile Ser Lys Thr Leu Asn Val Asn Phe
    1370            1375            1380

Ile Asp Gln Ala Thr Arg Val Met Val Gly Ser Pro Ala Arg Val
    1385            1390            1395

His Asn Ile Gln Leu Met Asp Ile Asp Tyr Val Ala Val Lys Val
    1400            1405            1410

Pro Val Phe Ser Phe His Arg Leu Ser Pro Ser His Pro Val Val
    1415            1420            1425

Gly Val Asp Met Lys Ser Thr Gly Glu Val Val Gly Phe Gly Ala
    1430            1435            1440

Asn Lys Tyr Glu Ala Leu Leu Lys Ala Met Met Ala Ser Asn Val
    1445            1450            1455

Arg Leu Pro Thr Ser Gly Met Leu Ile Ser Leu Asp Ser Asp Val
    1460            1465            1470

Arg Gln Val Phe Asp Phe Ser Tyr Cys Lys Asp Asp Ile Gly Ile
    1475            1480            1485

Arg Leu Arg Arg Leu Cys Tyr Lys Gly Tyr Ile Arg Ile Pro Phe
    1490            1495            1500

Leu Ile Asn Glu Val Pro Ala Ser Gly Ala Ser Ile Thr Lys Gly
    1505            1510            1515

Leu Asp Val Gln Ser Leu Leu Ala Cys Ser Leu Gln Phe Phe Glu
    1520            1525            1530

Asp Thr Ile Gly Asp Ser Leu Leu His Val Gly Ser Ser His Lys
    1535            1540            1545

Cys Gly Arg Leu Leu Cys Cys Thr Asn Leu Val Arg Lys Val Ser
    1550            1555            1560

Pro Arg Pro Val Glu Leu Met Lys Ser Val Val Val His Met Phe
    1565            1570            1575

Ile Asn Ala Ala Gly Cys Ala Ile Pro Asn Arg Leu Ser Asp Gly
    1580            1585            1590

Tyr Val Met Arg Arg Ala Ala Val Asp Asn Lys Val Thr Leu Ile
    1595            1600            1605

Thr Cys Met Lys Leu Ala Lys Leu Phe Ile Asp Ala Leu Val Met
    1610            1615            1620

Arg His Ile Arg Thr Ser Lys Gly Lys Leu Phe Phe His Asn Lys
    1625            1630            1635

Ser Gln Gln Glu Tyr Leu Asn
    1640            1645

<210> SEQ ID NO 29
<211> LENGTH: 1522
<212> TYPE: PRT
<213> ORGANISM: Trypanosoma cruzi

<400> SEQUENCE: 29

Met Phe Gly Glu Lys Val Lys Ala Ser Leu Val Leu His Gly Gly Glu
1               5                   10                  15

Cys Phe Glu Gly Tyr Ser Phe Tyr Glu Glu Ser Val Ala Gly Glu
                20                  25                  30

Val Val Phe Ala Thr Gly Met Val Gly Tyr Pro Glu Ala Met Thr Asp
            35                  40                  45

Pro Ser Tyr Gln Gly Gln Ile Leu Val Leu Thr Ser Pro Met Ile Gly
```

```
                50                   55                   60
Asn Tyr Gly Ile Pro Pro Ile Glu Thr Asp His Phe Gly Leu Thr Lys
 65                  70                  75                  80

Tyr Phe Glu Ser Met Gly Gly Glu Ile His Val Ser Ala Val Val Val
                 85                  90                  95

Ser Glu Tyr Cys Asp Glu Pro Ala His Trp Gln Met Trp Glu Thr Leu
                100                 105                 110

Gly Gln Trp Leu Arg Arg Asn Asn Ile Pro Gly Ile Met Met Val Asp
                115                 120                 125

Thr Arg His Ile Val Leu Lys Leu Arg Glu Met Gly Thr Ala Leu Gly
130                 135                 140

Lys Val Val Asn Asp Lys Asp Val Pro Phe Phe Asp Pro Asn Val
145                 150                 155                 160

Arg His Leu Val Ala Glu Val Ser Thr Lys Thr Arg Ser Thr Tyr Gly
                165                 170                 175

His Gly Thr Leu Val Ile Leu Val Ile Asp Met Gly Val Lys Leu Asn
                180                 185                 190

Ser Leu Arg Cys Leu Leu Lys Tyr Asp Val Thr Leu Ile Val Val Pro
                195                 200                 205

His Asp Trp Asp Ile Thr Lys Glu Thr Tyr Asp Gly Leu Phe Ile Ser
210                 215                 220

Asn Gly Pro Gly Asn Pro Gln Met Cys Thr Lys Thr Ile Glu His Val
225                 230                 235                 240

Arg Trp Ala Ile Thr Gln Asp Lys Pro Ile Phe Gly Ile Cys Met Gly
                245                 250                 255

Asn Gln Ile Leu Ala Leu Ala Ala Gly Gly Ser Thr Tyr Lys Met Lys
                260                 265                 270

Tyr Gly His Arg Gly Gln Asn Gln Pro Ser Thr Ser Arg Ser Asp Gly
                275                 280                 285

His Val Phe Ile Thr Thr Gln Asn His Gly Phe Ala Val Asp Phe Lys
                290                 295                 300

Ser Val Ser Gln Asp Glu Trp Glu Glu Cys Phe Tyr Asn Pro Asn Asp
305                 310                 315                 320

Asp Ser Asn Glu Gly Leu Arg His Arg Thr Lys Pro Phe Phe Ser Val
                325                 330                 335

Gln Phe His Pro Glu Gly Arg Cys Gly Pro Gln Asp Thr Glu Tyr Leu
                340                 345                 350

Phe Gly Gly Val Ile Ala His Val Lys Glu Ser Lys Val Lys Glu Ala
                355                 360                 365

Ser Lys Tyr Lys Pro Arg Lys Val Leu Val Leu Gly Ala Gly Gly Ile
                370                 375                 380

Val Ile Ala Gln Ala Gly Glu Phe Asp Tyr Ser Gly Ser Gln Cys Leu
385                 390                 395                 400

Lys Ala Leu Ser Glu Glu Gly Ile Glu Thr Val Leu Val Asn Pro Asn
                405                 410                 415

Ile Ala Thr Val Gln Thr Asp Asp Glu Met Ala Asp Gln Ile Tyr Phe
                420                 425                 430

Val Pro Ile Thr Ala Glu Ala Val Glu Arg Val Ile Glu Lys Glu Arg
                435                 440                 445

Pro Asp Gly Ile Met Leu Ala Trp Gly Gly Gln Thr Ala Leu Asn Cys
                450                 455                 460

Gly Leu Glu Met Asp Arg Leu Gly Ile Leu Lys Lys Tyr Asn Val Gln
465                 470                 475                 480
```

```
Val Leu Gly Thr Pro Ile Ser Thr Ile Thr Val Glu Asp Arg Asp
                485                 490                 495

Leu Phe Arg Asn Ala Leu Leu Gln Ile Asn Glu His Val Ala Lys Ser
            500                 505                 510

Leu Ala Val Thr Ser Ile Glu Glu Ala Val Gly Ala Ser Lys Val Ile
            515                 520                 525

Gly Phe Pro Leu Met Leu Arg Ala Ala Tyr Cys Leu Gly Gly Gln Gly
            530                 535                 540

Ser Gly Ile Val Tyr Asn Glu Glu Leu Arg His Lys Val Gly Val
545                 550                 555                 560

Ala Leu Ala Val Ser Pro Gln Val Leu Glu Glu Ser Val Ala Gly
                565                 570                 575

Trp Lys Glu Val Glu Tyr Glu Val Val Arg Asp Ile Tyr Asp Asn Cys
            580                 585                 590

Ile Thr Val Cys Asn Met Glu Asn Phe Asp Pro Met Gly Thr His Thr
            595                 600                 605

Gly Glu Ser Ile Val Val Ala Pro Leu Gln Thr Leu Thr Ser Asp Glu
            610                 615                 620

Tyr His Met Leu Arg Ser Ala Ser Ile Lys Ile Ile Arg His Leu Gly
625                 630                 635                 640

Ile Val Gly Glu Cys Asn Ile Gln Tyr Gly Leu Asp Pro Thr Ser His
                645                 650                 655

Arg Tyr Val Val Ile Glu Val Asn Ala Arg Leu Ser Arg Ser Ser Ala
                660                 665                 670

Leu Ala Ser Lys Ala Thr Gly Tyr Pro Leu Ala Leu Val Ala Ala Lys
            675                 680                 685

Ile Ala Leu Gly Lys Gly Leu Phe Glu Ile Ala Asn Gly Val Thr Lys
            690                 695                 700

Thr Thr Met Ala Cys Phe Glu Pro Ser Leu Asp Tyr Ile Val Val Lys
705                 710                 715                 720

Val Pro Arg Trp Asp Leu Ser Lys Phe Asn Met Val Ser Gln Asn Ile
                725                 730                 735

Gly Ser Met Met Lys Ser Val Gly Glu Val Met Ala Ile Gly Arg Thr
            740                 745                 750

Phe Glu Glu Ala Leu Gln Lys Ala Leu Arg Met Val Asp Pro Ser His
            755                 760                 765

Thr Gly Phe Asp Val Pro Pro Arg Leu Glu Ala Lys Lys Asn Trp Asp
            770                 775                 780

His Met Gln Asp Leu Lys Val Pro Thr Pro Asp Arg Ile Phe Ala Ile
785                 790                 795                 800

Cys Arg Ala Leu His Glu Gly Val Ser Val Glu Thr Ile His Glu Met
                805                 810                 815

Thr Arg Ile Asn Leu Phe Phe Leu Asn Lys Leu His Lys Leu Ile Leu
            820                 825                 830

Leu Gln Asn His Met Leu Gly Gln Tyr Lys Gly Lys Met Asn Thr Met
            835                 840                 845

Pro Arg Asp Cys Leu Leu Lys Met Lys Ala Asn Gly Phe Ser Asp Ala
            850                 855                 860

Gln Ile Ala Lys Tyr Phe Leu Cys Thr Ala Asp Asp Val Arg Glu Ser
865                 870                 875                 880

Arg Met Glu Leu Lys Ile Thr Pro Lys Val Lys Gln Ile Asp Thr Val
                885                 890                 895

Ala Gly Glu Ile Pro Ala Ser Gln Cys Gly Phe Leu Tyr Thr Ser Tyr
                900                 905                 910
```

```
Asn Ala Tyr His Asp Asp Val Glu Phe Thr Glu Tyr Ala Val Phe Gly
        915                 920                 925

Cys Gly Val Tyr Arg Ile Gly Asn Ser Val Glu Phe Asp Tyr Gly Gly
        930                 935                 940

Val Leu Val Ala Arg Glu Leu Arg Arg Leu Gly Lys Lys Val Ile Leu
945                 950                 955                 960

Ile Asn Tyr Asn Pro Glu Thr Val Ser Thr Asp Tyr Asp Glu Cys Asp
            965                 970                 975

Arg Leu Tyr Phe Glu Glu Val Ser Glu Glu Thr Val Leu Asp Ile Leu
                980                 985                 990

Leu Lys Glu Arg Ile Gln Gly Val Val Ile Ser Leu Gly Gly Gln Ile
            995                 1000                1005

Val Gln Asn Met Ala Leu Arg Leu Lys Gln His Gly Leu Pro Ile
    1010                1015                1020

Leu Gly Thr Asp Pro Val Asn Val Asp Lys Ala Glu Asn Arg His
    1025                1030                1035

Lys Phe Ser Lys Met Cys Asp Glu Leu Gly Val Leu Gln Pro Glu
    1040                1045                1050

Trp Ile Leu Ser Thr Ile Val Glu Gln Val His Glu Phe Cys Lys
    1055                1060                1065

Gln Val Gly Phe Pro Thr Leu Val Arg Pro Ser Tyr Val Leu Ser
    1070                1075                1080

Gly Ser Ala Met Ala Val Ile Ala Ser Ala Ala Asp Ile Asn Arg
    1085                1090                1095

Tyr Leu Glu Glu Ala Ala Leu Val Ser Gly Glu His Pro Val Val
    1100                1105                1110

Val Ser Lys Tyr Tyr Glu Gly Ala Met Glu Tyr Asp Val Asp Ile
    1115                1120                1125

Val Ala His His Gly Arg Val Leu Cys Tyr Ala Ile Cys Glu His
    1130                1135                1140

Val Glu Asn Ala Gly Val His Ser Gly Asp Ala Thr Met Phe Leu
    1145                1150                1155

Pro Pro Gln Asn Thr Glu Lys Glu Val Met Lys Arg Ile Tyr Asn
    1160                1165                1170

Thr Thr Ala Leu Ile Ala Glu Glu Leu Asp Val Val Gly Pro Met
    1175                1180                1185

Asn Ile Gln Phe Leu Phe Thr Lys Asp Lys Gln Leu Arg Val Ile
    1190                1195                1200

Glu Ala Asn Ile Arg Ser Ser Arg Ser Val Pro Phe Val Ser Lys
    1205                1210                1215

Thr Leu Gly Ile Ser Phe Pro Ala Val Met Val Ser Ala Phe Leu
    1220                1225                1230

Ser Gln His Asp Ser Asn Leu Val Pro Ile Lys Arg Ala Arg Met
    1235                1240                1245

Thr His Ile Gly Cys Lys Ala Ser Val Phe Ser Phe Asn Arg Leu
    1250                1255                1260

Ala Gly Ala Asp Pro Ile Leu Gly Val Glu Met Ala Ser Thr Gly
    1265                1270                1275

Glu Ile Gly Val Phe Gly Arg Asp Lys Lys Glu Val Phe Leu Lys
    1280                1285                1290

Ala Met Leu Cys Gln Asn Phe Arg Tyr Pro Gln Arg Gly Val Phe
    1295                1300                1305

Ile Ser Cys Asp Val Asp Ala Met Ala Glu Asp Leu Cys Pro Thr
```

```
                  1310              1315              1320

Leu Ser  Ala Ser Asp Arg Phe  Pro Val Phe Thr Ser  Lys Gln Thr
    1325              1330              1335

Ser Arg  Val Leu Ala Asp Tyr  Gly Ile Pro His Thr  Val Leu Thr
    1340              1345              1350

Gln Arg  His Glu Asp Ser Glu  Pro Thr Phe Asp Thr  Ala Val Ala
    1355              1360              1365

Val Lys  Glu Lys Phe Asp Leu  Val Ile Gln Leu Arg  Asp Lys Arg
    1370              1375              1380

Gln Asp  Phe Met Leu Arg Arg  Cys Thr Gln Glu Asn  Ala Thr Ala
    1385              1390              1395

Asp Tyr  Trp Ile Arg Arg Leu  Ala Val Asp Tyr Asn  His Ser Leu
    1400              1405              1410

Leu Thr  Glu Pro Asn Val Val  Arg Met Phe Cys Glu  Thr Leu Asp
    1415              1420              1425

Val Asp  Val Lys Glu Ile Glu  Ile Glu Pro Phe Arg  Leu Tyr Val
    1430              1435              1440

Pro Arg  Val Tyr Asn Lys Met  Glu Asn Asp Asn Tyr  Thr Met Leu
    1445              1450              1455

His Arg  His Lys Val Gly Leu  Cys Ile Thr Ser Thr  Asn Asp Ser
    1460              1465              1470

Lys Val  Leu Ala Ile Ser Leu  Arg Glu Glu Lys Ile  Ala Leu Thr
    1475              1480              1485

Cys Phe  His Ala Cys Leu Gly  Gly Ile Lys Asn Asn  Ser Glu Glu
    1490              1495              1500

Ile Ala  Glu Gln Phe Arg Ser  Ile Gly Ser Thr Ser  Arg Ala His
    1505              1510              1515

Arg Pro  Pro His
    1520

<210> SEQ ID NO 30
<211> LENGTH: 1520
<212> TYPE: PRT
<213> ORGANISM: Leishmania major

<400> SEQUENCE: 30

Met Glu  His Tyr Ala Lys Ala  Glu Leu Val Leu His  Gly Gly Glu Arg
1                 5                  10                  15

Phe Glu  Gly Tyr Ser Phe Gly  Tyr Glu Glu Ser Val  Ala Gly Glu Val
              20                  25                  30

Val Phe  Ala Thr Gly Met Val  Gly Tyr Pro Glu Ser  Leu Ser Asp Pro
          35                  40                  45

Ser Tyr  His Gly Gln Ile Leu  Val Leu Thr Ser Pro  Met Val Gly Asn
    50                  55                  60

Tyr Gly  Val Pro Arg Val Glu  Glu Asp Leu Phe Gly  Val Thr Lys Tyr
65                  70                  75                  80

Phe Glu  Ser Thr Asp Gly Arg  Ile His Val Ser Pro  Val Val Val Gln
              85                  90                  95

Glu Tyr  Cys Asp Gln Pro Asp  His Trp Glu Met Tyr  Glu Thr Leu Gly
              100                 105                 110

Ala Trp  Leu Arg Lys Asn Lys  Val Pro Gly Met Met  Val Asp Thr
          115                 120                 125

Arg Ser  Ile Val Leu Lys Leu  Arg Asp Met Gly Thr  Ala Leu Gly Lys
    130                 135                 140

Val Leu  Val Ala Gly Asn Asp  Val Pro Phe Met Asp  Pro Asn Thr Arg
```

```
            145                 150                 155                 160
Asn Leu Val Ala Glu Val Ser Thr Lys Thr Arg Val Thr His Gly His
                165                 170                 175
Gly Thr Leu Arg Ile Leu Val Ile Asp Met Gly Val Lys Leu Asn Gln
                180                 185                 190
Leu Arg Cys Leu Leu Lys His Asp Val Thr Leu Ile Val Val Pro His
                195                 200                 205
Asp Trp Asp Ile Thr Thr Glu Leu Tyr Asp Gly Leu Phe Ile Thr Asn
        210                 215                 220
Gly Pro Gly Asn Pro Gln Met Cys Thr Ser Thr Ile Arg Ser Val Arg
225                 230                 235                 240
Trp Ala Leu Gln Gln Asp Lys Pro Ile Phe Gly Ile Cys Met Gly Asn
                245                 250                 255
Gln Met Leu Cys Pro Pro Ala Gly Gly Thr Thr Tyr Lys Met Lys Tyr
                260                 265                 270
Gly His Arg Gly Gln Asn Gln Pro Cys Lys Cys Asn Ile Asp Asp Arg
                275                 280                 285
Val Val Ile Thr Thr Gln Lys Pro Gly Phe Ala Val Asp Phe Lys Thr
        290                 295                 300
Leu Pro Ser Asp Glu Trp Glu Glu Tyr Phe Thr Asn Ser Asn Asp Gly
305                 310                 315                 320
Ser Asn Glu Gly Leu Trp His Lys Thr Lys Pro Phe Cys Ser Val Gln
                325                 330                 335
Phe His Pro Glu Gly Arg Cys Gly Pro Gln Asp Thr Glu Tyr Leu Phe
                340                 345                 350
Ser Glu Tyr Val Cys Arg Val Lys Gly Ser Lys Val Lys Glu Val Ala
                355                 360                 365
Lys Phe Lys Pro Arg Lys Val Leu Val Leu Gly Ala Gly Gly Ile Val
                370                 375                 380
Ile Ala Gln Ala Gly Glu Phe Asp Tyr Ser Gly Ser Gln Cys Leu Lys
385                 390                 395                 400
Ser Leu Arg Glu Glu Gly Met Glu Thr Val Leu Ile Asn Pro Asn Ile
                405                 410                 415
Ala Thr Val Gln Thr Asp Asp Glu Met Ala Asp His Ile Tyr Phe Val
                420                 425                 430
Pro Leu Thr Val Glu Ala Val Glu Arg Val Ile Glu Lys Glu Arg Pro
                435                 440                 445
Asp Gly Ile Leu Leu Gly Trp Gly Gly Gln Thr Ala Leu Asn Cys Gly
        450                 455                 460
Val Lys Leu Asp Glu Leu Gly Val Leu Lys Lys Tyr Asn Val Gln Val
465                 470                 475                 480
Leu Gly Thr Pro Val Ser Val Ile Ala Val Thr Glu Asp Arg Glu Leu
                485                 490                 495
Phe Arg Asp Thr Leu Leu Gln Ile Asn Glu Gln Val Ala Lys Ser Ala
                500                 505                 510
Ala Val Thr Ser Val Glu Glu Ala Val Ala Ser Lys Asp Ile Gly
                515                 520                 525
Phe Pro Met Met Val Arg Ala Ala Tyr Cys Leu Gly Gly Gln Gly Ser
        530                 535                 540
Gly Ile Val Glu Asn Met Ala Glu Leu Arg His Lys Val Glu Val Ala
545                 550                 555                 560
Leu Ala Ala Ser Pro Gln Val Leu Leu Glu Glu Ser Val Ala Gly Trp
                565                 570                 575
```

-continued

```
Lys Glu Ile Glu Tyr Glu Val Arg Asp Ile Tyr Asp Asn Cys Ile
            580                 585                 590

Thr Val Cys Asn Met Glu Asn Phe Asp Pro Met Gly Val His Thr Gly
        595                 600                 605

Glu Ser Ile Val Val Ala Pro Ser Gln Thr Leu Ser Asn Asp Glu Phe
    610                 615                 620

His His Leu Arg Ser Ala Ser Ile Lys Ile Arg His Leu Gly Ile
625                 630                 635                 640

Val Gly Glu Cys Asn Ile Gln Tyr Gly Leu Asp Pro Phe Ser His Arg
                645                 650                 655

Tyr Val Val Ile Glu Val Asn Ala Arg Leu Ser Arg Ser Ser Ala Leu
            660                 665                 670

Ala Ser Lys Ala Thr Gly Tyr Pro Leu Ala His Val Ala Thr Lys Ile
        675                 680                 685

Ala Leu Gly Lys Gly Leu Phe Glu Ile Thr Asn Gly Val Thr Lys Thr
    690                 695                 700

Thr Met Ala Cys Phe Glu Pro Ser Met Asp Tyr Ile Ala Val Lys Met
705                 710                 715                 720

Pro Arg Trp Asp Leu His Lys Phe Asn Met Val Ser Gln Glu Ile Gly
                725                 730                 735

Ser Met Met Lys Ser Val Gly Glu Val Met Ser Ile Gly Arg Thr Phe
            740                 745                 750

Glu Glu Ala Met Gln Lys Ala Ile Arg Met Val Asp Pro Ser Tyr Thr
        755                 760                 765

Gly Phe Ser Ile Pro Asp Arg Phe Ala Gly Ala Asp Phe Asp Tyr Met
    770                 775                 780

Glu His Ile Arg His Pro Thr Pro Tyr Arg Leu Phe Ala Ile Cys Arg
785                 790                 795                 800

Ala Leu Leu Asp Gly His Ser Ala Glu Glu Leu Tyr Gln Met Thr Lys
                805                 810                 815

Ile Thr Arg Val Phe Leu Tyr Lys Leu Glu Lys Leu Val Arg Leu Ser
            820                 825                 830

Met Ala Thr Ser Thr Leu Tyr Ala Asn Arg Leu Thr Glu Met Pro Arg
        835                 840                 845

Glu Asn Leu Leu Ser Met Lys Ala His Gly Phe Ser Asp Arg Gln Leu
    850                 855                 860

Ala Gln Leu Leu Asn Thr Thr Ala Ala Asp Val Arg Ala Arg Arg Val
865                 870                 875                 880

Glu Leu Asn Val Met Pro Leu Ile Lys Gln Ile Asp Thr Val Ala Gly
                885                 890                 895

Glu Tyr Pro Ala Ala Gln Cys Cys Tyr Leu Tyr Ser Thr Tyr Asn Ala
            900                 905                 910

Gln Arg Asp Asp Val Pro Phe Thr Glu Tyr Ala Val Leu Gly Cys Gly
        915                 920                 925

Val Tyr Arg Ile Gly Asn Ser Val Glu Phe Asp Tyr Gly Gly Val Leu
    930                 935                 940

Val Ala Arg Glu Leu Arg Arg Leu Gly Asn Lys Val Ile Leu Ile Asn
945                 950                 955                 960

Tyr Asn Pro Glu Thr Val Ser Thr Asp Tyr Asp Glu Cys Asp Arg Leu
                965                 970                 975

Tyr Phe Asp Glu Val Ser Glu Glu Thr Val Leu Asp Ile Leu Thr Lys
            980                 985                 990

Glu Arg Val Arg Gly Val Val Ile  Ser Leu Gly Gly Gln  Ile Val Gln
        995                 1000                 1005
```

```
Asn Met Val Leu Ser Leu Lys Lys Ser Gly Leu Pro Ile Leu Gly
    1010                1015                1020

Thr Asp Pro Ala Asn Ile Asp Met Ala Glu Asp Arg Asn Lys Phe
    1025                1030                1035

Ser Lys Met Cys Asp Asn Leu Gly Val Pro Gln Pro Glu Trp Ile
    1040                1045                1050

Ser Ala Thr Ser Val Glu Gln Val His Glu Phe Cys Asp Arg Val
    1055                1060                1065

Gly Tyr Pro Ala Leu Val Arg Pro Ser Tyr Val Leu Ser Gly Ser
    1070                1075                1080

Ala Met Ala Val Ile Ala Asn Lys Glu Asp Val Thr Arg Tyr Leu
    1085                1090                1095

Lys Glu Ala Ser Phe Val Ser Gly Glu His Pro Val Val Val Ser
    1100                1105                1110

Lys Tyr Tyr Glu Asp Ala Thr Glu Tyr Asp Val Asp Ile Val Ala
    1115                1120                1125

His His Gly Arg Val Leu Cys Tyr Gly Ile Cys Glu His Val Glu
    1130                1135                1140

Asn Ala Gly Val His Ser Gly Asp Ala Thr Met Phe Leu Pro Pro
    1145                1150                1155

Gln Asn Thr Asp Lys Asp Thr Met Lys Arg Ile Tyr Asp Ser Val
    1160                1165                1170

Asn Arg Ile Ala Glu Lys Leu Asp Val Val Gly Pro Met Asn Val
    1175                1180                1185

Gln Phe Leu Leu Thr Ala Glu Gly His Leu Arg Val Ile Glu Ala
    1190                1195                1200

Asn Val Arg Lys Phe Arg Ser Val Pro Phe Val Ser Lys Thr Leu
    1205                1210                1215

Gly Ile Ser Phe Pro Ser Val Met Val Ser Ala Phe Leu Ala Arg
    1220                1225                1230

Lys Asp Gln Asn Leu Val Pro Ile Lys Arg Ala Lys Met Thr His
    1235                1240                1245

Ile Gly Cys Lys Ala Ser Met Phe Ser Phe Ile Pro Leu Ala Gly
    1250                1255                1260

Ala Asp Pro Ile Leu Gly Val Glu Met Ala Ser Thr Gly Glu Ile
    1265                1270                1275

Gly Val Phe Gly Arg Asp Lys His Glu Val Phe Leu Lys Ala Met
    1280                1285                1290

Leu Cys Gln Asn Phe Arg Ile Pro Lys Lys Gly Val Phe Phe Ser
    1295                1300                1305

Ile Asp Val Asp Ser Gln Thr Glu Ala Leu Cys Pro Tyr Ile Gln
    1310                1315                1320

His Leu Val Gly Arg Gly Leu Lys Val Tyr Gly Thr Ala Asn Thr
    1325                1330                1335

Ala Ala Val Leu His Glu Tyr Gly Ile Glu Cys Glu Val Leu Leu
    1340                1345                1350

Gln Arg Ser Glu Leu Pro Ser Gly Asp Ala Cys Glu Ser Asn Arg
    1355                1360                1365

Pro Ala Val Tyr Asp Glu Glu Val Ala Lys Lys Glu Lys Phe Asp
    1370                1375                1380

Leu Val Ile Gln Leu Arg Asp Lys Arg Arg Asp Phe Val Leu Arg
    1385                1390                1395

Arg Cys Thr Arg Glu Thr Ala Pro Pro Asp Tyr Trp Val Arg Arg
```

```
                1400              1405              1410

Leu Ala Val Asp Tyr Asn Ile Pro Leu Leu Thr Glu Pro Ser Leu
    1415              1420              1425

Val Lys Met Phe Cys Glu Phe Met Asp Leu Pro Ala Ser Ser Ile
    1430              1435              1440

Glu Val Glu Pro Phe Arg His Tyr Val Pro Lys Ile Tyr His Lys
    1445              1450              1455

Val Glu Asn Asn Asn Cys Ala Met Leu Leu Met Arg Cys His Lys
    1460              1465              1470

Val Gly Leu Met Ile Thr Asp Asn Asn Gly Ser Lys Val Leu Ala
    1475              1480              1485

Leu Arg Leu Ser Gln Glu Gly Leu Asn Ile Thr Cys Phe His Gly
    1490              1495              1500

Tyr Leu Gly Gly Ser Asp Ile Gly Gln Phe Glu Gln Ala Phe Gln
    1505              1510              1515

Arg Pro
    1520

<210> SEQ ID NO 31
<211> LENGTH: 1498
<212> TYPE: PRT
<213> ORGANISM: Saccharomyces cerevisiae

<400> SEQUENCE: 31

Met Ala Thr Ile Ala Pro Thr Ala Pro Ile Thr Pro Pro Met Glu Ser
1               5                   10                  15

Thr Gly Asp Arg Leu Val Thr Leu Glu Leu Lys Asp Gly Thr Val Leu
                20                  25                  30

Gln Gly Tyr Ser Phe Gly Ala Glu Lys Ser Val Ala Gly Glu Leu Val
            35                  40                  45

Phe Gln Thr Gly Met Val Gly Tyr Pro Glu Ser Val Thr Asp Pro Ser
        50                  55                  60

Tyr Glu Gly Gln Ile Leu Val Ile Thr Tyr Pro Leu Val Gly Asn Tyr
65                  70                  75                  80

Gly Val Pro Asp Met His Leu Arg Asp Glu Leu Val Glu Glu Leu Pro
                85                  90                  95

Arg Tyr Phe Glu Ser Asn Arg Ile His Ile Ala Gly Leu Val Ile Ser
                100                 105                 110

His Tyr Thr Asp Glu Tyr Ser His Tyr Leu Arg Lys Ser Ser Leu Gly
            115                 120                 125

Lys Trp Leu Gln Asn Glu Gly Ile Pro Ala Val Tyr Gly Val Asp Thr
        130                 135                 140

Arg Ser Leu Thr Lys His Leu Arg Asp Ala Gly Ser Met Leu Gly Arg
145                 150                 155                 160

Leu Ser Leu Glu Lys Ser Gly Ser Asp Arg Thr Ile Ser Arg Ser Ser
                165                 170                 175

Ser Trp Arg Ser Ala Phe Asp Val Pro Glu Trp Val Asp Pro Asn Val
                180                 185                 190

Gln Asn Leu Val Ser Lys Val Ser Ile Asn Glu Pro Lys Leu Tyr Val
            195                 200                 205

Pro Pro Ala Asp Asn Lys His Ile Glu Leu Gln Thr Gly Pro Asp Gly
        210                 215                 220

Lys Val Leu Arg Ile Leu Ala Ile Asp Val Gly Met Lys Tyr Asn Gln
225                 230                 235                 240

Ile Arg Cys Phe Ile Lys Arg Gly Val Glu Leu Lys Val Val Pro Trp
```

-continued

```
                    245                 250                 255
Asn Tyr Asp Phe Thr Lys Glu Asp Tyr Asp Gly Leu Phe Ile Ser Asn
                260                 265                 270

Gly Pro Gly Asp Pro Ser Val Leu Asp Asp Leu Ser Gln Arg Leu Ser
            275                 280                 285

Asn Val Leu Glu Ala Lys Lys Thr Pro Val Phe Gly Ile Cys Leu Gly
        290                 295                 300

His Gln Leu Ile Ala Arg Ala Ala Gly Ala Ser Thr Leu Lys Leu Lys
305                 310                 315                 320

Phe Gly Asn Arg Gly His Asn Ile Pro Cys Thr Ser Thr Ile Ser Gly
                325                 330                 335

Arg Cys Tyr Ile Thr Ser Gln Asn His Gly Phe Ala Val Asp Val Asp
                340                 345                 350

Thr Leu Thr Ser Gly Trp Lys Pro Leu Phe Val Asn Ala Asn Asp Asp
                355                 360                 365

Ser Asn Glu Gly Ile Tyr His Ser Glu Leu Pro Tyr Phe Ser Val Gln
            370                 375                 380

Phe His Pro Glu Ser Thr Pro Gly Pro Arg Asp Thr Glu Phe Leu Phe
385                 390                 395                 400

Asp Val Phe Ile Gln Ala Val Lys Glu Phe Lys Tyr Thr Gln Val Leu
                405                 410                 415

Lys Pro Ile Ala Phe Pro Gly Gly Leu Leu Glu Asp Asn Val Lys Ala
                420                 425                 430

His Pro Arg Ile Glu Ala Lys Lys Val Leu Val Leu Gly Ser Gly Gly
                435                 440                 445

Leu Ser Ile Gly Gln Ala Gly Glu Phe Asp Tyr Ser Gly Ser Gln Ala
            450                 455                 460

Ile Lys Ala Leu Lys Glu Glu Gly Ile Tyr Thr Ile Leu Ile Asn Pro
465                 470                 475                 480

Asn Ile Ala Thr Ile Gln Thr Ser Lys Gly Leu Ala Asp Lys Val Tyr
                485                 490                 495

Phe Val Pro Val Thr Ala Glu Phe Val Arg Lys Val Ile Leu His Glu
                500                 505                 510

Arg Pro Asp Ala Ile Tyr Val Thr Phe Gly Gly Gln Thr Ala Leu Ser
            515                 520                 525

Val Gly Ile Ala Met Lys Asp Glu Phe Glu Ala Leu Gly Val Lys Val
        530                 535                 540

Leu Gly Thr Pro Ile Asp Thr Ile Ile Thr Thr Glu Asp Arg Glu Leu
545                 550                 555                 560

Phe Ser Asn Ala Ile Asp Glu Ile Asn Glu Lys Cys Ala Lys Ser Gln
                565                 570                 575

Ala Ala Asn Ser Val Asp Glu Ala Leu Ala Ala Val Lys Glu Ile Gly
            580                 585                 590

Phe Pro Val Ile Val Arg Ala Ala Tyr Ala Leu Gly Gly Leu Gly Ser
            595                 600                 605

Gly Phe Ala Asn Asn Glu Lys Glu Leu Val Asp Leu Cys Asn Val Ala
        610                 615                 620

Phe Ser Ser Ser Pro Gln Val Leu Val Glu Lys Ser Met Lys Gly Trp
625                 630                 635                 640

Lys Glu Val Glu Tyr Glu Val Val Arg Asp Ala Phe Asp Asn Cys Ile
                645                 650                 655

Thr Val Cys Asn Met Glu Asn Phe Asp Pro Leu Gly Ile His Thr Gly
                660                 665                 670
```

Asp Ser Ile Val Val Ala Pro Ser Gln Thr Leu Ser Asp Glu Asp Tyr
            675                 680                 685

Asn Met Leu Arg Thr Thr Ala Val Asn Val Ile Arg His Leu Gly Val
    690                 695                 700

Val Gly Glu Cys Asn Ile Gln Tyr Ala Leu Asn Pro Val Ser Lys Asp
705                 710                 715                 720

Tyr Cys Ile Ile Glu Val Asn Ala Arg Leu Ser Arg Ser Ser Ala Leu
                725                 730                 735

Ala Ser Lys Ala Thr Gly Tyr Pro Leu Ala Tyr Thr Ala Ala Lys Leu
            740                 745                 750

Gly Leu Asn Ile Pro Leu Asn Glu Val Lys Asn Ser Val Thr Lys Ser
            755                 760                 765

Thr Cys Ala Cys Phe Glu Pro Ser Leu Asp Tyr Cys Val Val Lys Met
770                 775                 780

Pro Arg Trp Asp Leu Lys Lys Phe Thr Arg Val Ser Thr Glu Leu Ser
785                 790                 795                 800

Ser Ser Met Lys Ser Val Gly Glu Val Met Ser Ile Gly Arg Thr Phe
                805                 810                 815

Glu Glu Ala Ile Gln Lys Ala Ile Arg Ser Thr Glu Tyr Ala Asn Leu
            820                 825                 830

Gly Phe Asn Glu Thr Asp Leu Asp Ile Asp Tyr Glu Leu Asn
            835                 840                 845

Asn Pro Thr Asp Met Arg Val Phe Ala Ile Ala Asn Ala Phe Ala Lys
850                 855                 860

Lys Gly Tyr Ser Val Asp Lys Val Trp Glu Met Thr Arg Ile Asp Lys
865                 870                 875                 880

Trp Phe Leu Asn Lys Leu His Asp Leu Val Gln Phe Ala Glu Lys Ile
                885                 890                 895

Ser Ser Phe Gly Thr Lys Glu Glu Leu Pro Ser Leu Val Leu Arg Gln
            900                 905                 910

Ala Lys Gln Leu Gly Phe Asp Asp Arg Gln Ile Ala Arg Phe Leu Asp
            915                 920                 925

Ser Asn Glu Val Ala Ile Arg Arg Leu Arg Lys Glu Tyr Gly Ile Thr
930                 935                 940

Pro Phe Val Lys Gln Ile Asp Thr Val Ala Ala Glu Phe Pro Ala Tyr
945                 950                 955                 960

Thr Asn Tyr Leu Tyr Met Thr Tyr Asn Ala Asp Ser His Asp Leu Ser
                965                 970                 975

Phe Asp Asp Val Met Val Leu Gly Ser Gly Val Tyr Arg Ile Gly Ser
            980                 985                 990

Ser Val Glu Phe Asp Trp Cys Ala Val Thr Ala Val Arg Thr Leu Arg
            995                 1000                 1005

Ala Asn Asn Ile Lys Thr Ile Met Val Asn Tyr Asn Pro Glu Thr
    1010                1015                 1020

Val Ser Thr Asp Tyr Asp Glu Ala Asp Arg Leu Tyr Phe Glu Thr
    1025                1030                 1035

Ile Asn Leu Glu Arg Val Leu Asp Ile Tyr Glu Ile Glu Asn Ser
    1040                1045                 1050

Ser Gly Val Val Val Ser Met Gly Gly Gln Thr Ser Asn Asn Ile
    1055                1060                 1065

Ala Met Thr Leu His Arg Glu Asn Val Lys Ile Leu Gly Thr Ser
    1070                1075                 1080

Pro Asp Met Ile Asp Ser Ala Glu Asn Arg Tyr Lys Phe Ser Arg
    1085                1090                 1095

-continued

```
Met Leu Asp Gln Ile Gly Val Asp Gln Pro Ala Trp Lys Glu Leu
    1100            1105                1110
Thr Ser Met Asp Glu Ala Glu Ser Phe Ala Glu Lys Val Gly Tyr
    1115            1120                1125
Pro Val Leu Val Arg Pro Ser Tyr Val Leu Ser Gly Ala Ala Met
    1130            1135                1140
Asn Thr Val Tyr Ser Lys Asn Asp Leu Glu Ser Tyr Leu Asn Gln
    1145            1150                1155
Ala Val Glu Val Ser Arg Asp Tyr Pro Val Val Ile Thr Lys Tyr
    1160            1165                1170
Ile Glu Asn Ala Lys Glu Ile Glu Met Asp Ala Val Ala Arg Asn
    1175            1180                1185
Gly Glu Leu Val Met His Val Val Ser Glu His Val Glu Asn Ala
    1190            1195                1200
Gly Val His Ser Gly Asp Ala Thr Leu Ile Val Pro Pro Gln Asp
    1205            1210                1215
Leu Ala Pro Glu Thr Val Asp Arg Ile Val Val Ala Thr Ala Lys
    1220            1225                1230
Ile Gly Lys Ala Leu Lys Ile Thr Gly Pro Tyr Asn Ile Gln Phe
    1235            1240                1245
Ile Ala Lys Asp Asn Glu Ile Lys Val Ile Glu Cys Asn Val Arg
    1250            1255                1260
Ala Ser Arg Ser Phe Pro Phe Ile Ser Lys Val Val Gly Val Asn
    1265            1270                1275
Leu Ile Glu Leu Ala Thr Lys Ala Ile Met Gly Leu Pro Leu Thr
    1280            1285                1290
Pro Tyr Pro Val Glu Lys Leu Pro Asp Asp Tyr Val Ala Val Lys
    1295            1300                1305
Val Pro Gln Phe Ser Phe Pro Arg Leu Ala Gly Ala Asp Pro Val
    1310            1315                1320
Leu Gly Val Glu Met Ala Ser Thr Gly Glu Val Ala Thr Phe Gly
    1325            1330                1335
His Ser Lys Tyr Glu Ala Tyr Leu Lys Ser Leu Leu Ala Thr Gly
    1340            1345                1350
Phe Lys Leu Pro Lys Lys Asn Ile Leu Leu Ser Ile Gly Ser Tyr
    1355            1360                1365
Lys Glu Lys Gln Glu Leu Leu Ser Ser Val Gln Lys Leu Tyr Asn
    1370            1375                1380
Met Gly Tyr Lys Leu Phe Ala Thr Ser Gly Thr Ala Asp Phe Leu
    1385            1390                1395
Ser Glu His Gly Ile Ala Val Gln Tyr Leu Glu Val Leu Asn Lys
    1400            1405                1410
Asp Asp Asp Asp Gln Lys Ser Glu Tyr Ser Leu Thr Gln His Leu
    1415            1420                1425
Ala Asn Asn Glu Ile Asp Leu Tyr Ile Asn Leu Pro Ser Ala Asn
    1430            1435                1440
Arg Phe Arg Arg Pro Ala Ser Tyr Val Ser Lys Gly Tyr Lys Thr
    1445            1450                1455
Arg Arg Leu Ala Val Asp Tyr Ser Val Pro Leu Val Thr Asn Val
    1460            1465                1470
Lys Cys Ala Lys Leu Leu Ile Glu Ala Ile Ser Arg Asn Ile Thr
    1475            1480                1485
Leu Asp Val Ser Glu Arg Asp Ala Gln Thr
```

<210> SEQ ID NO 32
<211> LENGTH: 1453
<212> TYPE: PRT
<213> ORGANISM: Homo sapiens

<400> SEQUENCE: 32

```
Met Ala Ala Leu Val Leu Glu Asp Gly Ser Val Leu Arg Gly Gln Pro
 1               5                  10                  15

Phe Gly Ala Ala Val Ser Thr Ala Gly Glu Val Val Phe Gln Thr Gly
            20                  25                  30

Met Val Gly Tyr Pro Glu Ala Leu Thr Asp Pro Ser Tyr Lys Ala Gln
        35                  40                  45

Ile Leu Val Leu Thr Tyr Pro Leu Ile Gly Asn Tyr Gly Ile Pro Pro
    50                  55                  60

Asp Glu Met Asp Glu Phe Gly Leu Cys Lys Trp Phe Glu Ser Ser Gly
65                  70                  75                  80

Ile His Val Ala Ala Leu Val Val Gly Glu Cys Cys Pro Thr Pro Ser
                85                  90                  95

His Trp Ser Ala Thr Arg Thr Leu His Glu Trp Leu Gln Gln His Gly
            100                 105                 110

Ile Pro Gly Leu Gln Gly Val Asp Thr Arg Glu Leu Thr Lys Lys Leu
        115                 120                 125

Arg Glu Gln Gly Ser Leu Leu Gly Lys Leu Val Gln Asn Gly Thr Glu
    130                 135                 140

Pro Ser Ser Leu Pro Phe Leu Asp Pro Asn Ala Arg Pro Leu Val Pro
145                 150                 155                 160

Glu Val Ser Ile Lys Thr Pro Arg Val Phe Asn Thr Gly Gly Ala Pro
                165                 170                 175

Arg Ile Leu Ala Leu Asp Cys Gly Leu Lys Tyr Asn Gln Ile Arg Cys
            180                 185                 190

Leu Cys Gln Arg Gly Ala Glu Val Thr Val Val Pro Trp Asp His Ala
        195                 200                 205

Leu Asp Ser Gln Glu Tyr Glu Gly Leu Phe Leu Ser Asn Gly Pro Gly
    210                 215                 220

Asp Pro Ala Ser Tyr Pro Ser Val Val Ser Thr Leu Ser Arg Val Leu
225                 230                 235                 240

Ser Glu Pro Asn Pro Arg Pro Val Phe Gly Ile Cys Leu Gly His Gln
                245                 250                 255

Leu Leu Ala Leu Ala Ile Gly Ala Lys Thr Tyr Lys Met Arg Tyr Gly
            260                 265                 270

Asn Arg Gly His Asn Gln Pro Cys Leu Leu Val Gly Ser Gly Arg Cys
        275                 280                 285

Phe Leu Thr Ser Gln Asn His Gly Phe Ala Val Glu Thr Asp Ser Leu
    290                 295                 300

Pro Ala Asp Trp Ala Pro Leu Phe Thr Asn Ala Asn Asp Gly Ser Asn
305                 310                 315                 320

Glu Gly Ile Val His Asn Ser Leu Pro Phe Phe Ser Val Gln Phe His
                325                 330                 335

Pro Glu His Gln Ala Gly Pro Ser Asp Met Glu Leu Leu Phe Asp Ile
            340                 345                 350

Phe Leu Glu Thr Val Lys Glu Ala Thr Ala Gly Asn Pro Gly Gly Gln
        355                 360                 365

Thr Val Arg Glu Arg Leu Thr Glu Arg Leu Cys Pro Pro Gly Ile Pro
```

```
            370                 375                 380
Thr Pro Gly Ser Gly Leu Pro Pro Arg Lys Val Leu Ile Leu Gly
385                 390                 395                 400

Ser Gly Gly Leu Ser Ile Gly Gln Ala Gly Glu Phe Asp Tyr Ser Gly
                405                 410                 415

Ser Gln Ala Ile Lys Ala Leu Lys Glu Glu Asn Ile Gln Thr Leu Leu
                420                 425                 430

Ile Asn Pro Asn Ile Ala Thr Val Gln Thr Ser Gln Gly Leu Ala Asp
                435                 440                 445

Lys Val Tyr Phe Leu Pro Ile Thr Pro His Tyr Val Thr Gln Val Ile
            450                 455                 460

Arg Asn Glu Arg Pro Asp Gly Val Leu Leu Thr Phe Gly Gly Gln Thr
465                 470                 475                 480

Ala Leu Asn Cys Gly Val Glu Leu Thr Lys Ala Gly Val Leu Ala Arg
                485                 490                 495

Tyr Gly Val Arg Val Leu Gly Thr Thr Val Glu Thr Ile Glu Leu Thr
            500                 505                 510

Glu Asp Arg Arg Ala Phe Ala Ala Arg Met Ala Glu Ile Gly Glu His
            515                 520                 525

Val Ala Pro Ser Glu Ala Gly Asn Ser Leu Glu Gln Ala Gln Ala Ala
530                 535                 540

Ala Glu Arg Leu Gly Tyr Pro Val Leu Val Arg Ala Ala Phe Ala Val
545                 550                 555                 560

Gly Gly Leu Gly Ser Gly Phe Ala Ser Asn Arg Glu Glu Leu Ser Ala
                565                 570                 575

Leu Val Ala Pro Ala Phe Ala His Thr Ser Gln Val Leu Val Asp Lys
                580                 585                 590

Ser Leu Lys Gly Trp Lys Glu Ile Glu Tyr Glu Val Val Arg Asp Ala
            595                 600                 605

Tyr Gly Asn Cys Val Thr Val Cys Asn Met Glu Asn Leu Asp Pro Leu
            610                 615                 620

Gly Ile His Thr Gly Glu Ser Ile Val Val Ala Pro Ser Gln Thr Leu
625                 630                 635                 640

Asn Asp Arg Glu Tyr Gln Leu Leu Arg Gln Thr Ala Ile Lys Val Thr
                645                 650                 655

Gln His Leu Gly Ile Val Gly Glu Cys Asn Val Gln Tyr Ala Leu Asn
                660                 665                 670

Pro Glu Ser Glu Gln Tyr Tyr Ile Ile Glu Val Asn Ala Arg Leu Ser
                675                 680                 685

Arg Ser Ser Ala Leu Ala Ser Lys Ala Thr Gly Tyr Pro Leu Ala Tyr
690                 695                 700

Val Ala Ala Lys Leu Ala Leu Gly Ile Pro Leu Pro Glu Leu Arg Asn
705                 710                 715                 720

Ser Val Thr Gly Gly Thr Ala Ala Phe Glu Pro Ser Val Asp Tyr Cys
                725                 730                 735

Val Val Lys Ile Pro Arg Trp Asp Leu Ser Lys Phe Leu Arg Val Ser
                740                 745                 750

Thr Lys Ile Gly Ser Cys Met Lys Ser Val Gly Glu Val Met Gly Ile
            755                 760                 765

Gly Arg Ser Phe Glu Glu Ala Phe Gln Lys Ala Leu Arg Met Val Asp
            770                 775                 780

Glu Asn Cys Val Gly Phe Asp His Thr Val Lys Pro Val Ser Asp Met
785                 790                 795                 800
```

-continued

```
Glu Leu Glu Thr Pro Thr Asp Lys Arg Ile Phe Val Ala Ala Ala
                805             810                 815

Leu Trp Ala Gly Tyr Ser Val Asp Arg Leu Tyr Glu Leu Thr Arg Ile
            820             825                 830

Asp Arg Trp Phe Leu His Arg Met Lys Arg Ile Ile Ala His Ala Gln
            835             840                 845

Leu Leu Glu Gln His Arg Gly Gln Pro Leu Pro Pro Asp Leu Leu Gln
        850             855             860

Gln Ala Lys Cys Leu Gly Phe Ser Asp Lys Gln Ile Ala Leu Ala Val
865             870             875             880

Leu Ser Thr Glu Leu Ala Val Arg Lys Leu Arg Gln Glu Leu Gly Ile
            885             890                 895

Cys Pro Ala Val Lys Gln Ile Asp Thr Val Ala Ala Glu Trp Pro Ala
            900             905                 910

Gln Thr Asn Tyr Leu Tyr Leu Thr Tyr Trp Gly Thr Thr His Asp Leu
            915             920                 925

Thr Phe Arg Thr Val Leu Val Leu Gly Ser Gly Val Tyr Arg Ile Gly
        930             935             940

Ser Ser Val Glu Phe Asp Trp Cys Ala Val Gly Cys Ile Gln Gln Leu
945             950             955             960

Arg Lys Met Gly Tyr Lys Thr Ile Met Val Asn Tyr Asn Pro Glu Thr
            965             970                 975

Val Ser Thr Asp Tyr Asp Met Cys Asp Arg Leu Tyr Phe Asp Glu Ile
            980             985                 990

Ser Phe Glu Val Val Met Asp Ile Tyr Glu Leu Glu Asn Pro Glu Gly
            995             1000                1005

Val Ile Leu Ser Met Gly Gly Gln Leu Pro Asn Asn Met Ala Met
            1010            1015                1020

Ala Leu His Arg Gln Gln Cys Arg Val Leu Gly Thr Ser Pro Glu
            1025            1030                1035

Ala Ile Asp Ser Ala Glu Asn Arg Phe Lys Phe Ser Arg Leu Leu
            1040            1045                1050

Asp Thr Ile Gly Ile Ser Gln Pro Gln Trp Arg Glu Leu Ser Asp
            1055            1060                1065

Leu Glu Ser Ala Arg Gln Phe Cys Gln Thr Val Gly Tyr Pro Cys
            1070            1075                1080

Val Val Arg Pro Ser Tyr Val Leu Ser Gly Ala Ala Met Asn Val
            1085            1090                1095

Ala Tyr Ala Asp Gly Asp Leu Glu Arg Phe Leu Ser Ser Ala Ala
            1100            1105                1110

Ala Val Ser Lys Glu His Pro Val Val Ile Ser Lys Phe Ile Gln
            1115            1120                1125

Glu Ala Lys Glu Ile Asp Val Asp Ala Val Ala Ser Asp Gly Val
            1130            1135                1140

Val Ala Ala Ile Ala Ile Ser Glu His Val Glu Asn Ala Gly Val
            1145            1150                1155

His Ser Gly Asp Ala Thr Leu Val Thr Pro Pro Gln Asp Ile Thr
            1160            1165                1170

Ala Lys Thr Leu Glu Arg Ile Lys Ala Ile Val His Ala Val Gly
            1175            1180                1185

Gln Glu Leu Gln Val Thr Gly Pro Phe Asn Leu Gln Leu Ile Ala
            1190            1195                1200

Lys Asp Asp Gln Leu Lys Val Ile Glu Cys Asn Val Arg Val Ser
            1205            1210                1215
```

```
Arg Ser Phe Pro Phe Val Ser Lys Thr Leu Gly Val Asp Leu Val
    1220            1225            1230

Ala Leu Ala Thr Arg Val Ile Met Gly Glu Glu Val Glu Pro Val
    1235            1240            1245

Gly Leu Met Thr Gly Ser Gly Val Val Gly Val Lys Val Pro Gln
    1250            1255            1260

Phe Ser Phe Ser Arg Leu Ala Gly Ala Asp Val Val Leu Gly Val
    1265            1270            1275

Glu Met Thr Ser Thr Gly Glu Val Ala Gly Phe Gly Glu Ser Arg
    1280            1285            1290

Cys Glu Ala Tyr Leu Lys Ala Met Leu Ser Thr Gly Phe Lys Ile
    1295            1300            1305

Pro Lys Lys Asn Ile Leu Leu Thr Ile Gly Ser Tyr Lys Asn Lys
    1310            1315            1320

Ser Glu Leu Leu Pro Thr Val Arg Leu Leu Glu Ser Leu Gly Tyr
    1325            1330            1335

Ser Leu Tyr Ala Ser Leu Gly Thr Ala Asp Phe Tyr Thr Glu His
    1340            1345            1350

Gly Val Lys Val Thr Ala Val Asp Trp His Phe Glu Glu Ala Val
    1355            1360            1365

Asp Gly Glu Cys Pro Pro Gln Arg Ser Ile Leu Glu Gln Leu Ala
    1370            1375            1380

Glu Lys Asn Phe Glu Leu Val Ile Asn Leu Ser Met Arg Gly Ala
    1385            1390            1395

Gly Gly Arg Arg Leu Ser Ser Phe Val Thr Lys Gly Tyr Arg Thr
    1400            1405            1410

Arg Arg Leu Ala Ala Asp Phe Ser Val Pro Leu Ile Ile Asp Ile
    1415            1420            1425

Lys Cys Thr Lys Leu Phe Val Glu Ala Leu Gly Gln Ile Gly Pro
    1430            1435            1440

Ala Pro Pro Leu Lys Val His Val Asp Cys
    1445            1450
```